(12) United States Patent
Schreiber et al.

(10) Patent No.: US 6,448,443 B1
(45) Date of Patent: Sep. 10, 2002

(54) SYNTHESIS OF COMBINATORIAL LIBRARIES OF COMPOUNDS REMINISCENT OF NATURAL PRODUCTS

(75) Inventors: Stuart L. Schreiber, Boston; Matthew D. Shair, Somerville, both of MA (US); Derek S. Tan, Rochester, NY (US); Michael A. Foley, Somerville; Brent R. Stockwell, Boston, both of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/121,922

(22) Filed: Jul. 25, 1998

Related U.S. Application Data

(63) Continuation-in-part of application No. 08/951,930, filed on Oct. 15, 1997.
(60) Provisional application No. 60/029,128, filed on Oct. 16, 1996, and provisional application No. 60/049,864, filed on Jun. 6, 1997.

(51) Int. Cl.[7] .................. G01N 33/53; G01N 33/566; G01N 33/543; C07C 233/00; C07C 235/00

(52) U.S. Cl. .................. 564/191; 435/7.1; 435/7.2; 435/DIG. 22; 435/DIG. 34; 436/501; 436/518; 564/123

(58) Field of Search .................. 435/7.1, 7.2, DIG. 22, 435/DIG. 34; 436/501, 518; 564/123, 191

(56) References Cited

PUBLICATIONS

Bastos et al. Inhibitors of Human Heart Chymase Based on a Peptide Library. Proc. Natl. Acad. Sci. USA, vol. 92, pp. 6738–6742, Jul. 1995.*

* cited by examiner

*Primary Examiner*—Bennett Celsa
*Assistant Examiner*—Maurie E. Garcia
(74) *Attorney, Agent, or Firm*—Choate, Hall & Stewart; Karoline K.M. Shair; Brenda Herschbach Jarrell

(57) ABSTRACT

The present invention provides complex compounds reminiscent of natural products and libraries thereof, as well as methods for their production. The inventive compounds and libraries of compounds are reminiscent of natural products in that they contain one or more stereocenters, and a high density and diversity of functionality. In general, the inventive libraries are synthesized from diversifiable scaffold structures, which are synthesized from readily available or easily synthesizable template structures. In certain embodiments, the inventive compounds and libraries are generated from diversifiable scaffolds synthesized from a shikimic acid based epoxyol template. In other embodiments, the inventive compounds and libraries are generated from diversifiable scaffolds synthesized from the pyridine-based template isonicotinamide. The present invention also provides a novel ortho-nitrobenzyl photolinker and a method for its synthesis. Furthermore, the present invention provides methods and kits for determining one or more biological activities of members of the inventive libraries. Additionally, the present invention provides pharmaceutical compositions containing one or more library members.

8 Claims, 68 Drawing Sheets

*Diversity Expansion Can Be Achieved by Functional Group Manipulation*

The boxed regions provide a high density of potential diversity nucleation points without the use of protecting groups.

Each chemical step will deliver a new monomer while concurrently generating a new position for functionalization.

Seven potential monomer sites radially arrayed.

*Reaction Sequence Yields Diverse Products in High Purity*

Binding of human growth hormone to its symmetrical extracellular receptor induces homodimerization of the receptor and initiates the intracellular growth hormone signalling pathway. The "hot spot" a small patch of residues which were identified as being responsible for > 85% of the binding energy between hGH and its receptor, is an excellent target for the library.

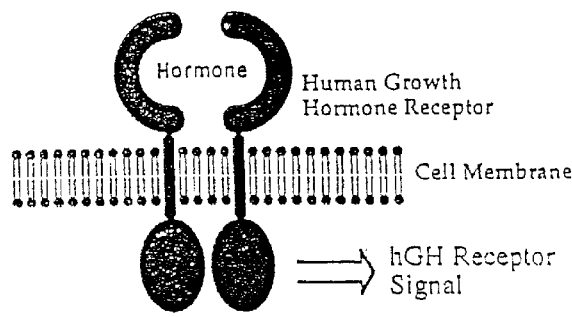

The radical small molecule library will be assayed for binding to the human growth hormone receptor. High affinity binders will be covalently homodimerized at the position where the solid phase was attached and tested for their ability to induce hGH receptor signalling. This would constitute the first example of direct dimerization by a small molecule dimer system. Applications to other signalling systems may also be possible based on our radial library.

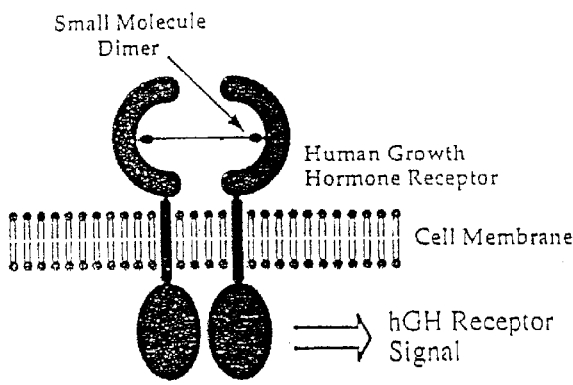

Figure 3

*Diversity Expansion Can Be Achieved by Functional Group Manipulation*
The boxed regions provide a high density of potential diversity nucleation points without the use of protecting groups.
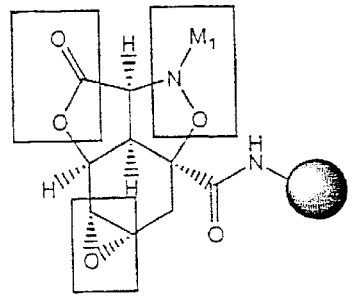
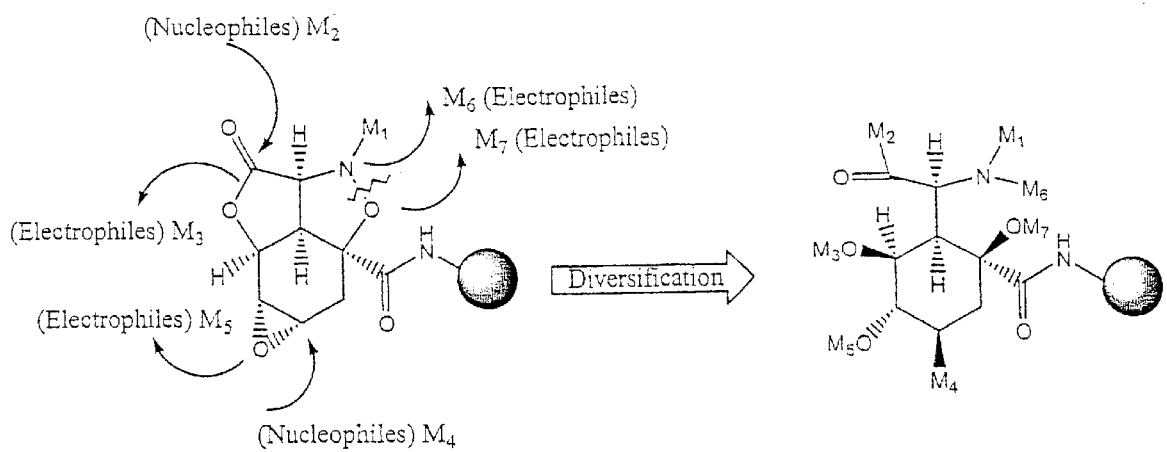
Each chemical step will deliver a new monomer while concurrently generating a new position for functionalization.
Seven potential monomer sites radially arrayed.
Figure 4

*ortho*-Nitrobenzyl Photolinkers
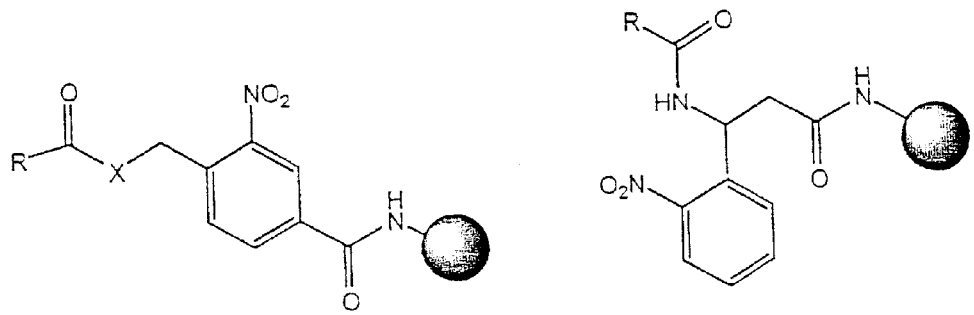
Rich Linker (Nba) 350 nm
Rich, Guwara
*JACS*, 1975, *97*, 1575
Geysen Linker (Anp) 365 nm
Brown, Wagner, Geysen
*Mol. Div.*, 1995, *1*, 4-12
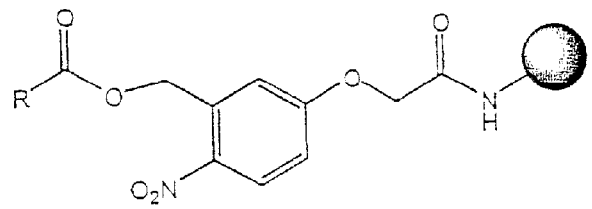
Linker A
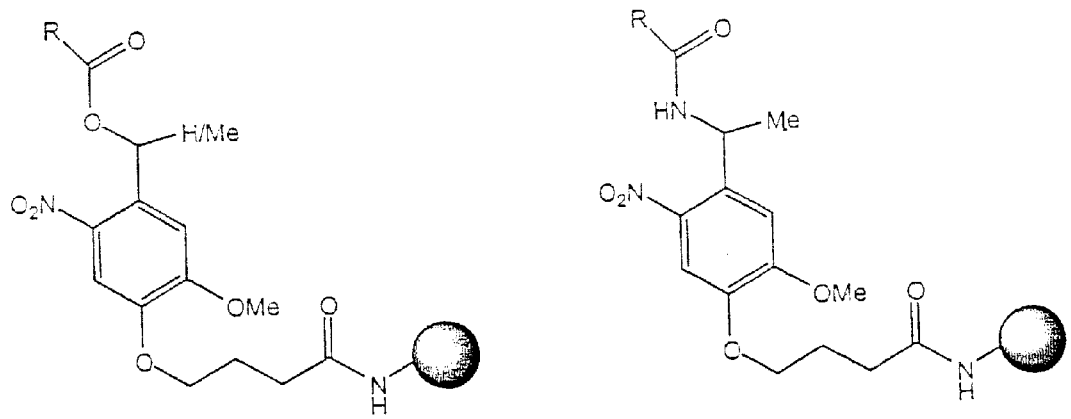
Affymax Linkers (Hep, Hmp, Aep) 365 nm
Holmes, Jones *JOC*, 1995, *60*, 2138
Holmes, *JOC*, 1997, *62*, 2370-2380
*Figure 10*

A Dithiane-Protected Benzoin Photolinker

*Addition of an $R_0$ Diversity Position via Fukuyama Sulfonamide Alkylation*

Development of the Parent Benzyl Tetracycle Synthesis and Tandem Reaction of the Nitrone Portion

*Acetoacetate as a Synthetic Intermediate*

Photolytic Cleavage Reveals a Novel Rearrangement

Cleavage from the Solid Phase under UV Conditions (354 nm) Causes Photochemical Rearrangement of the Allyl Functionality

*Nitrogen Deprotection: Further Functionality*

Removal of the Teoc N-protection reveals a homo-allylic amine, subsequent tandem acylation and (3+2) cycloaddition yield a polycyclic alkaloid.

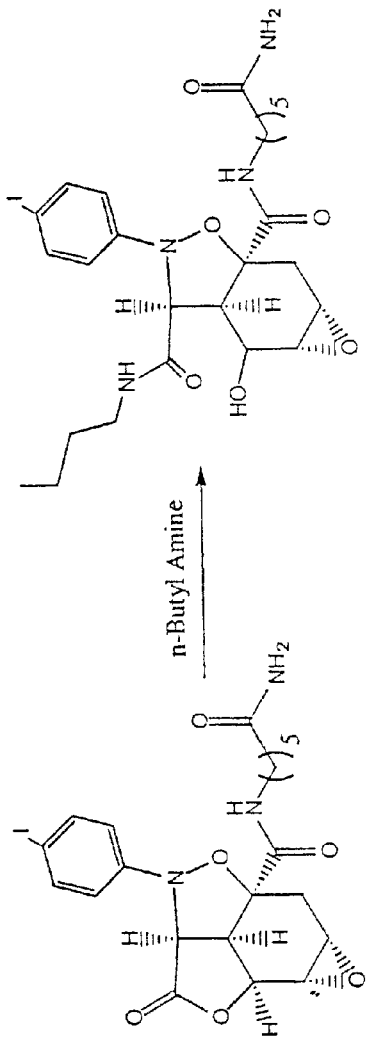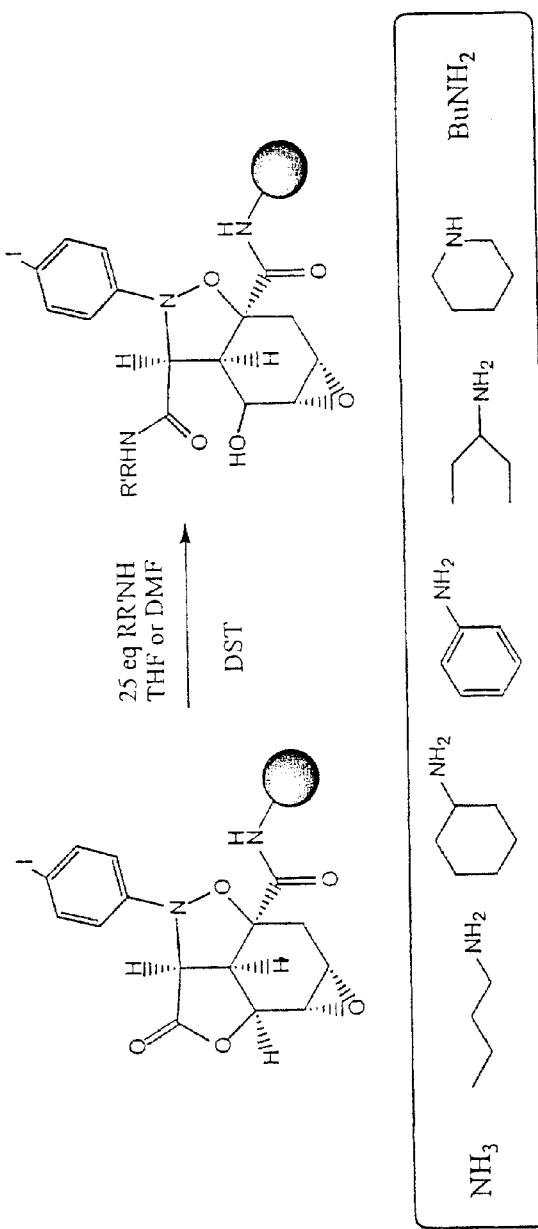
Figure 26

Epoxide Opening Reactions
Ytterbium triflate-catalyzed Ritter reaction

A New/Old Epoxide Opening Reaction
Chemoselective solvolysis with AcSH and AcOH
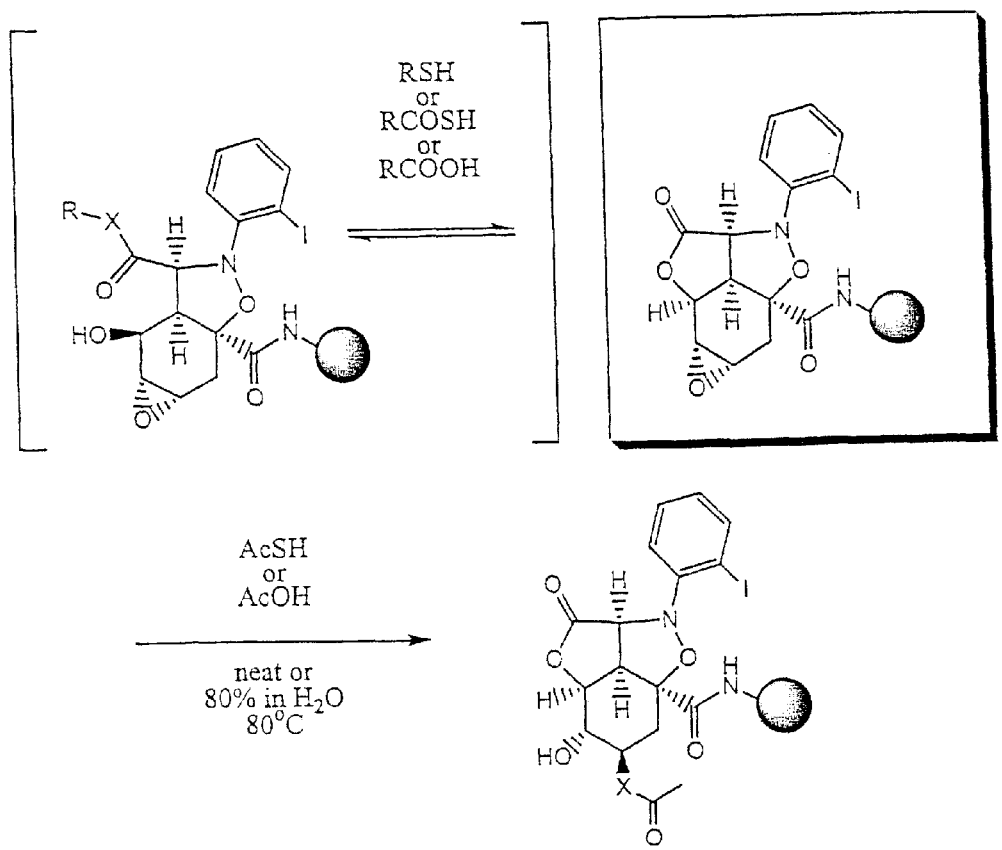
*Epoxide solvolysis exposes hydroxyl and leaves an orthogonally protected thioacetate*
Gowan, D.A.; Berchtold, G.A. *J. Org. Chem.* 1981, 2381-2383.
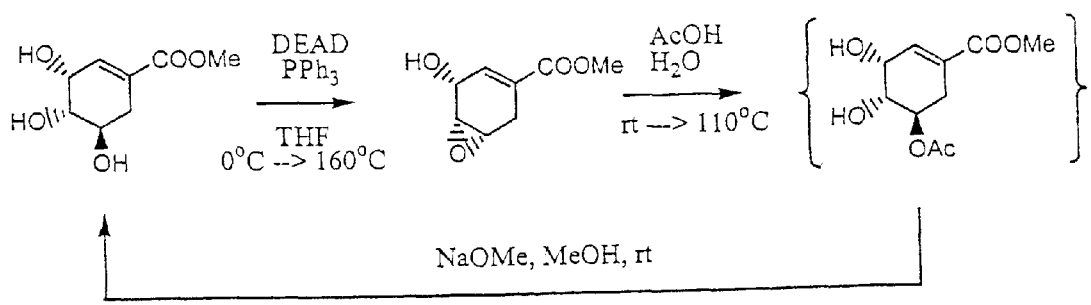
Figure 31

Nitrone and Nitrile Oxide, Alkyne Cycloadditions

Representative Potential Nucleation Points

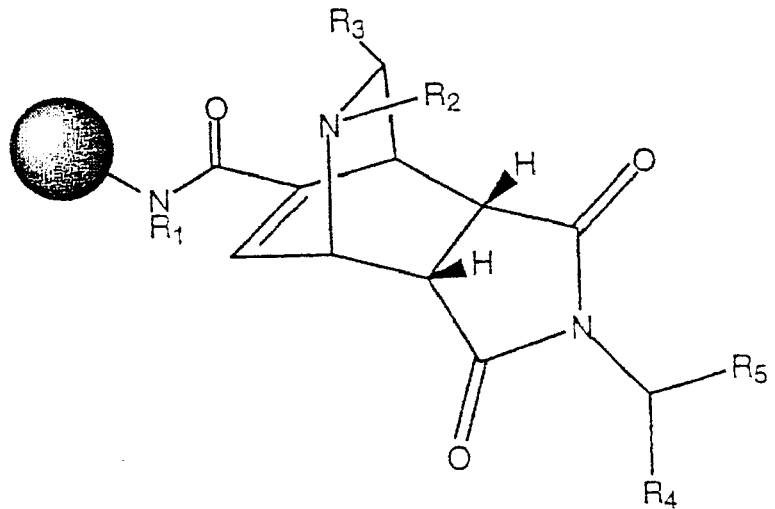

$R_1$ = from aliphatic alcohols which will be attached by a Mitsunobu reaction. Straight chain, branched, and cyclic alcohol. The key requirement is that the alcohol not have an unprotected site that could be acylated. An amine, thiol, etc.

$R_2$ = Chloroformates (alcohols reacted with phosgene), and anything that can acylate or alkylate an amine, i.e., alkyl bromides, mesylates, aldehydes, etc.

$R_3$ = allyl, any allyl derivative of allyltributyltin, thiazole, indole $R_4$ = all amines and amino acids $R_5$ = all amines and alcohols

*Figure 37*

Efficient Synthesis of N-Arylimide Derivatives
*3 positions provide multiple functionality. A wide variety of monomers can be accommodated, including amino acids.*
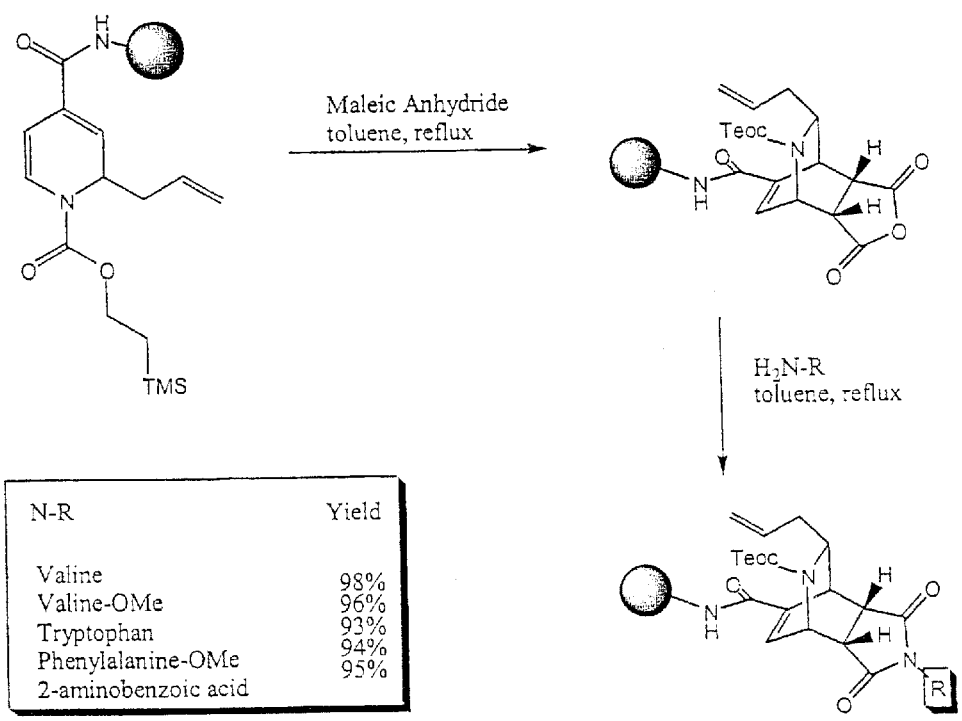
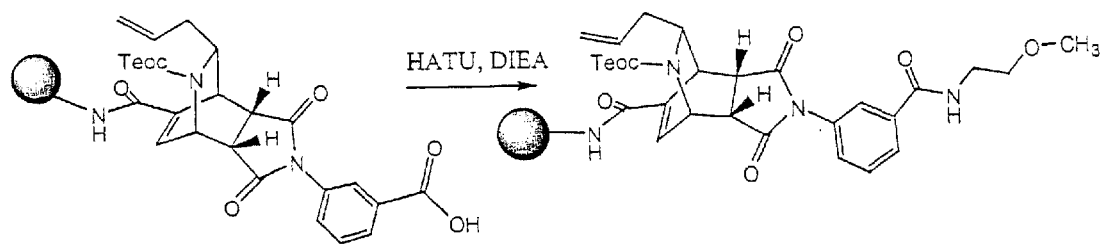
Side chain extensions provide additional functionality
*Figure 38*

R₀ = aliphatic groups
R₁ = any alpha-haloketone
R₂ = acyclic and cyclic α,β-unsaturated esters or amides and maleimide which can undergo a Mitsunobu reaction after the next step is complete
R₃ = same as R₂

Synthetic Plan for Generation of 46.5 Million Complex Molecules

Synthetic Plan for Generation of 30 Million Complex Molecules
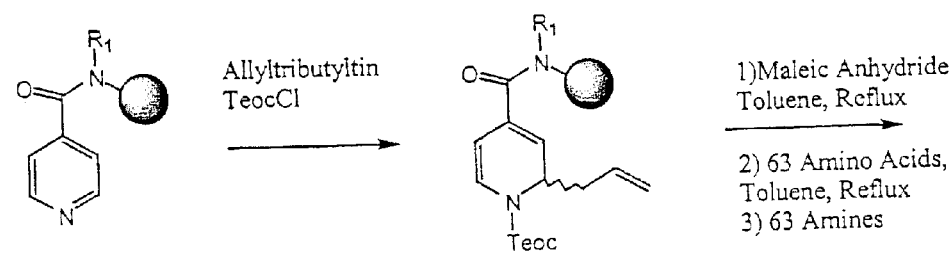
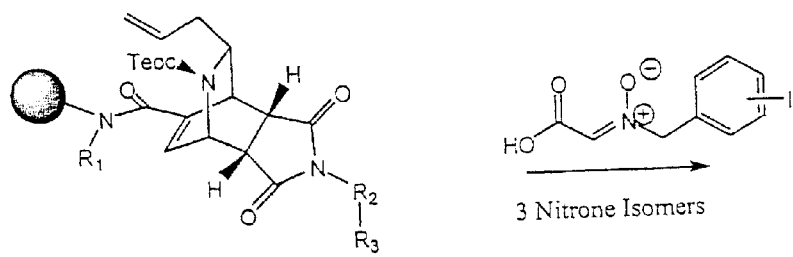
500,094 compounds
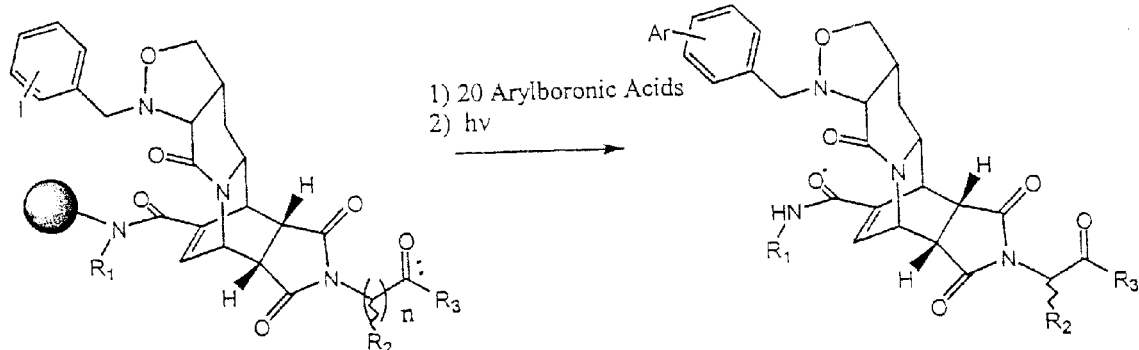
1,500,282 compounds
30,056,640
Figure 41

Library Quality Control-Test Library Synthesis
*Final pools analyzed by LC-MS for 456 unique masses*

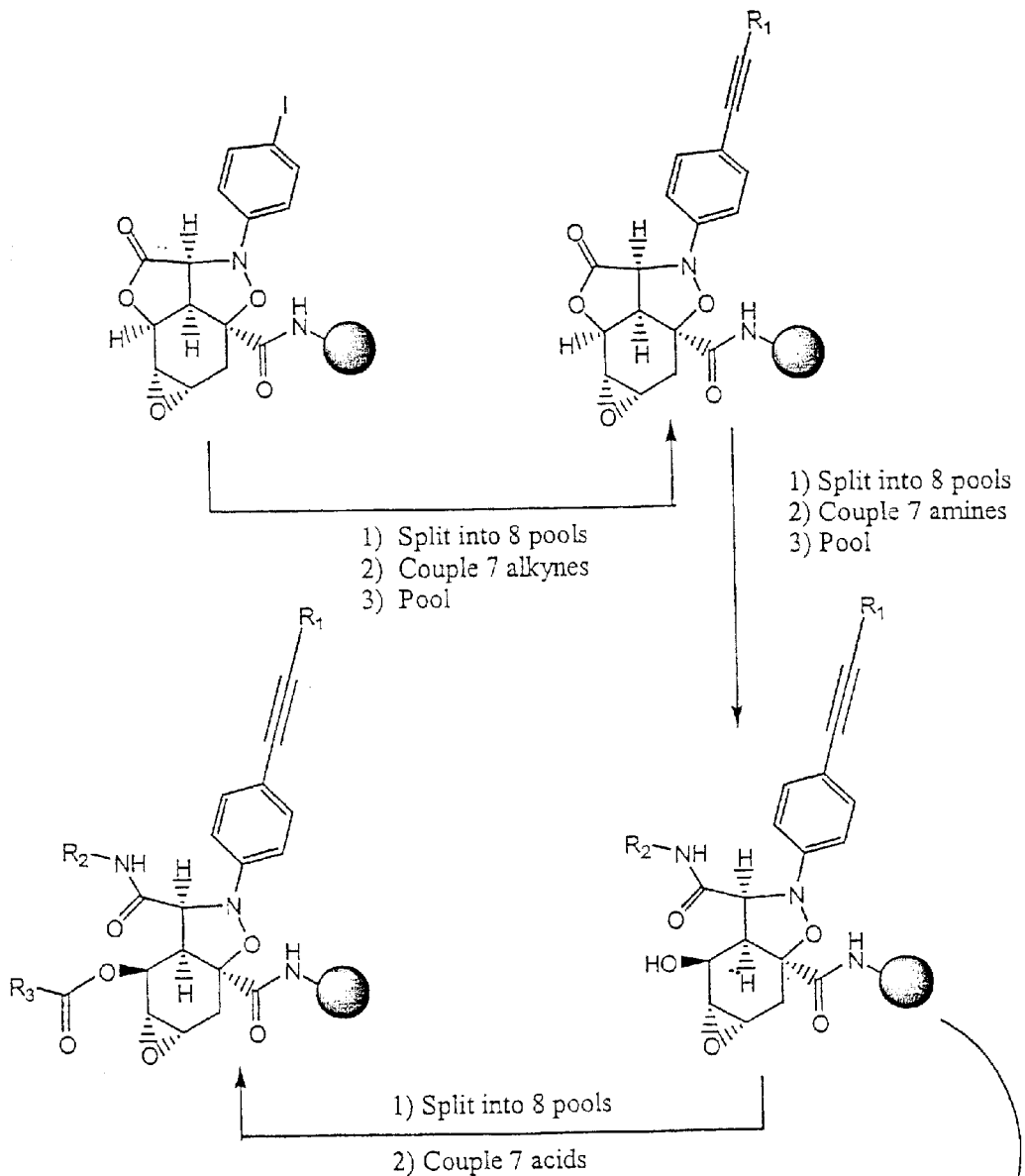

Functionalized monomers chosen to examine interactions between positions.
Alkynes and amines selected so all products have unique molecular weights.

Analyze each of 8 pools for 64 unique masses by LC-MS with mass scanning

456/456 (100%) detected at some level.
418/456 (92%) detected at >1)% average intensity.
400/456 (88%) detected at >20% average intensity.

*Figure 42*

*Library Quality Control-Demonstration Compounds*
*Reaction sequence yields diverse products in high purity*

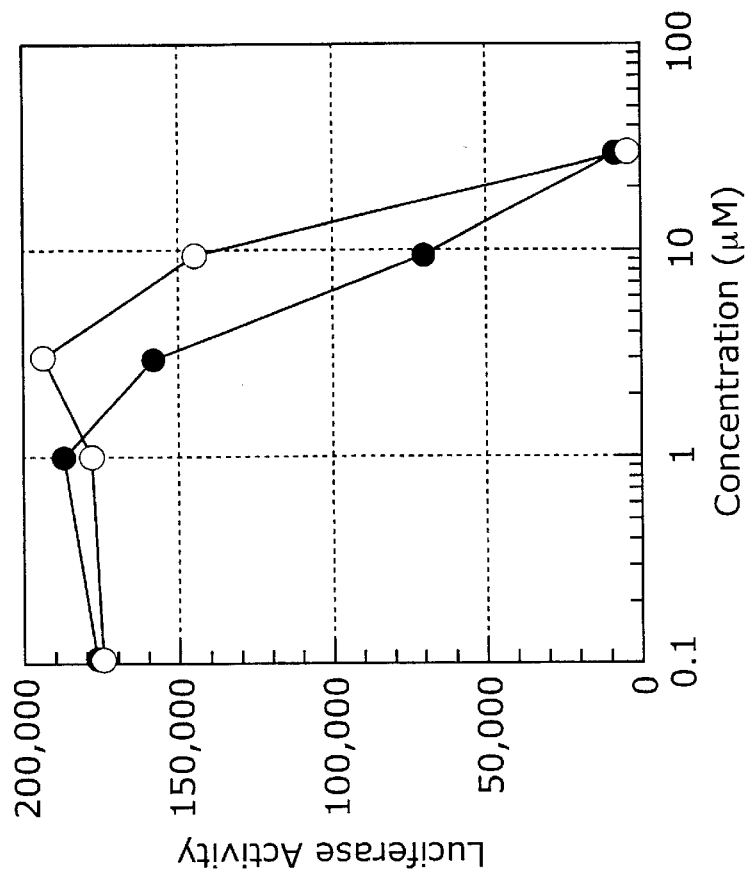
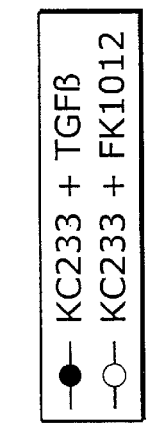
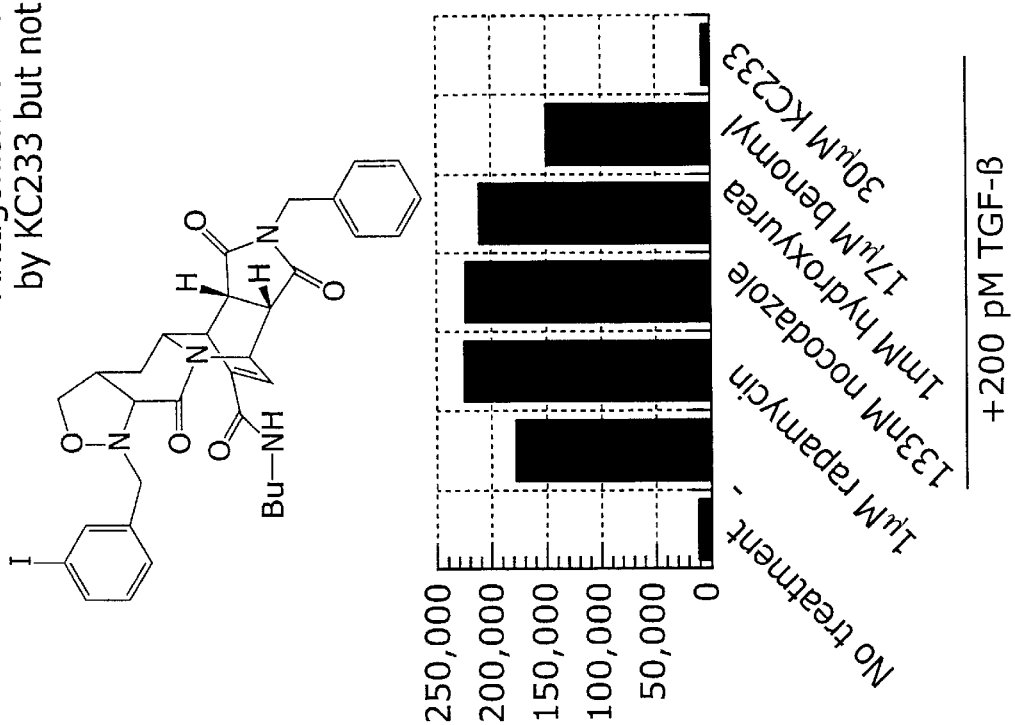
Figure 48 a) Alkyne building blocks
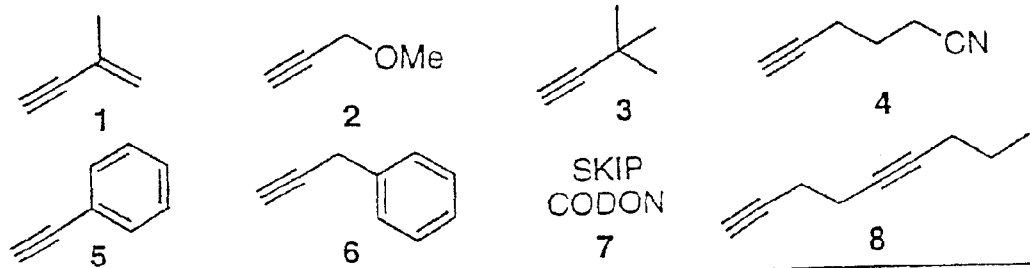
b) Amine building blocks
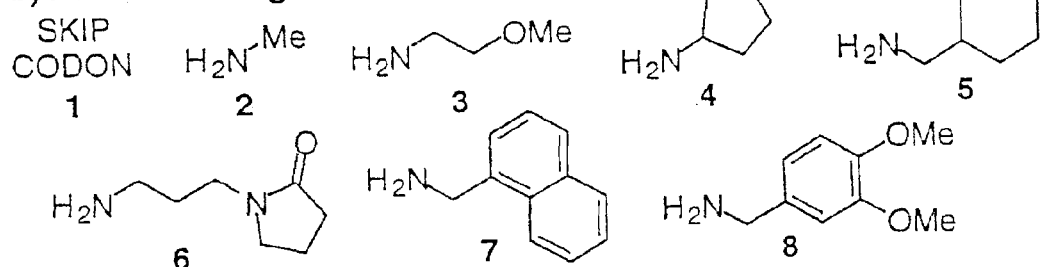
c) Acid building blocks
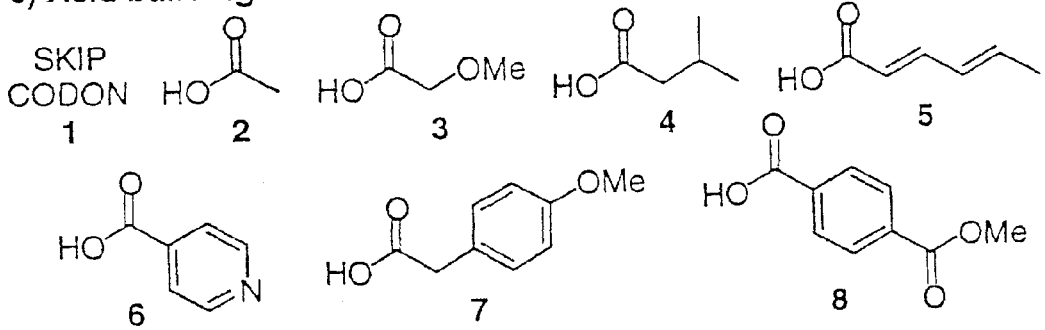
Tetracycle and building blocks used in test library.
*Figure 55*

|   | Amines | | | | | | | |
|---|---|---|---|---|---|---|---|---|
|   | 1 | 2 | 3 | 4 | 5 | 6 | 7 | 8 |
| MW | 0 | 31 | 75 | 85 | 113 | 142 | 157 | 167 |

| Alkynes | MW | 1 | 2 | 3 | 4 | 5 | 6 | 7 | 8 |
|---|---|---|---|---|---|---|---|---|---|
| 1 | 66 | 381 | 412 | 456 | 466 | 494 | 523 | 538 | 548 |
| 2 | 70 | 385 | 416 | 460 | 470 | 498 | 527 | 542 | 552 |
| 3 | 82 | 397 | 428 | 472 | 482 | 510 | 539 | 554 | 564 |
| 4 | 93 | 408 | 439 | 483 | 493 | 521 | 550 | 565 | 575 |
| 5 | 102 | 417 | 448 | 492 | 502 | 530 | 559 | 574 | 584 |
| 6 | 116 | 431 | 462 | 506 | 516 | 544 | 573 | 588 | 598 |
| 7 | 128 | 443 | 474 | 518 | 528 | 556 | 585 | 600 | 610 |
| 8 | 134 | 449 | 480 | 524 | 534 | 562 | 591 | 606 | 616 |

Alkyne and amine building block masses and the resulting 64 unique γ-hydroxyamide product masses. Acylation of the C-6 alcohol with a carboxylic acid shifts all of the product masses for that pool by the same value (mass of the acid minus water).

*Figure 56*

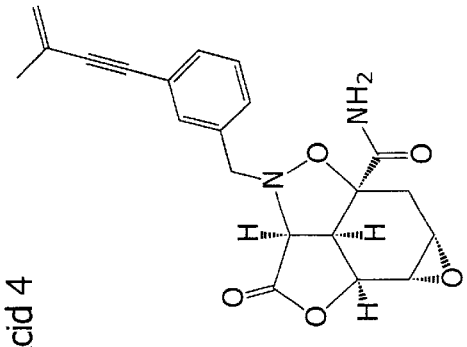
Alkyne 1, Amine 15, (Acid 4)
[M+H]+ = 381
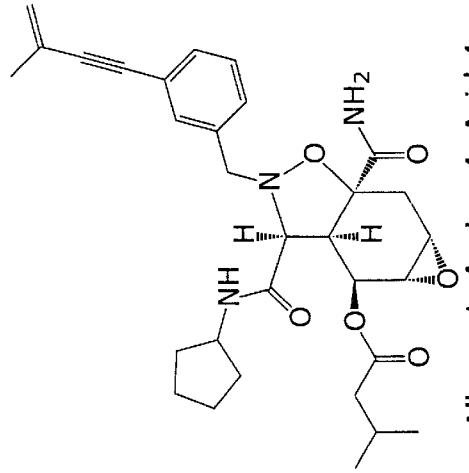
Alkyne 1, Amine 4, Acid 4
[M+H]+ = 550
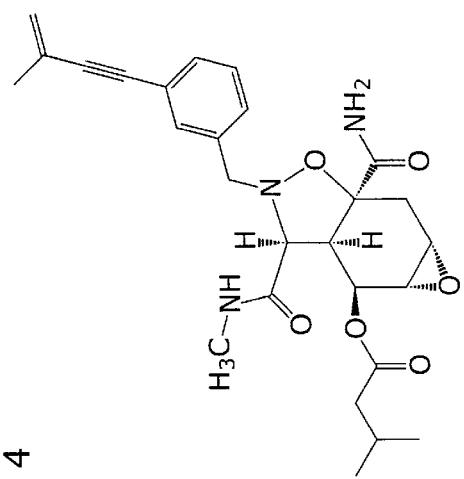
Alkyne 1, Amine 2, Acid 4
[M+H]+ = 496
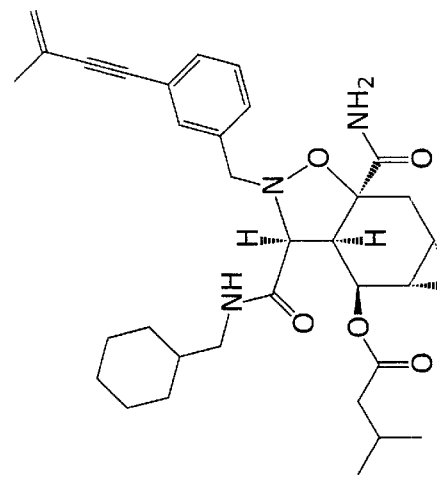
Alkyne 1, Amine 5, Acid 4
[M+H]+ = 578
*Figure 57B*

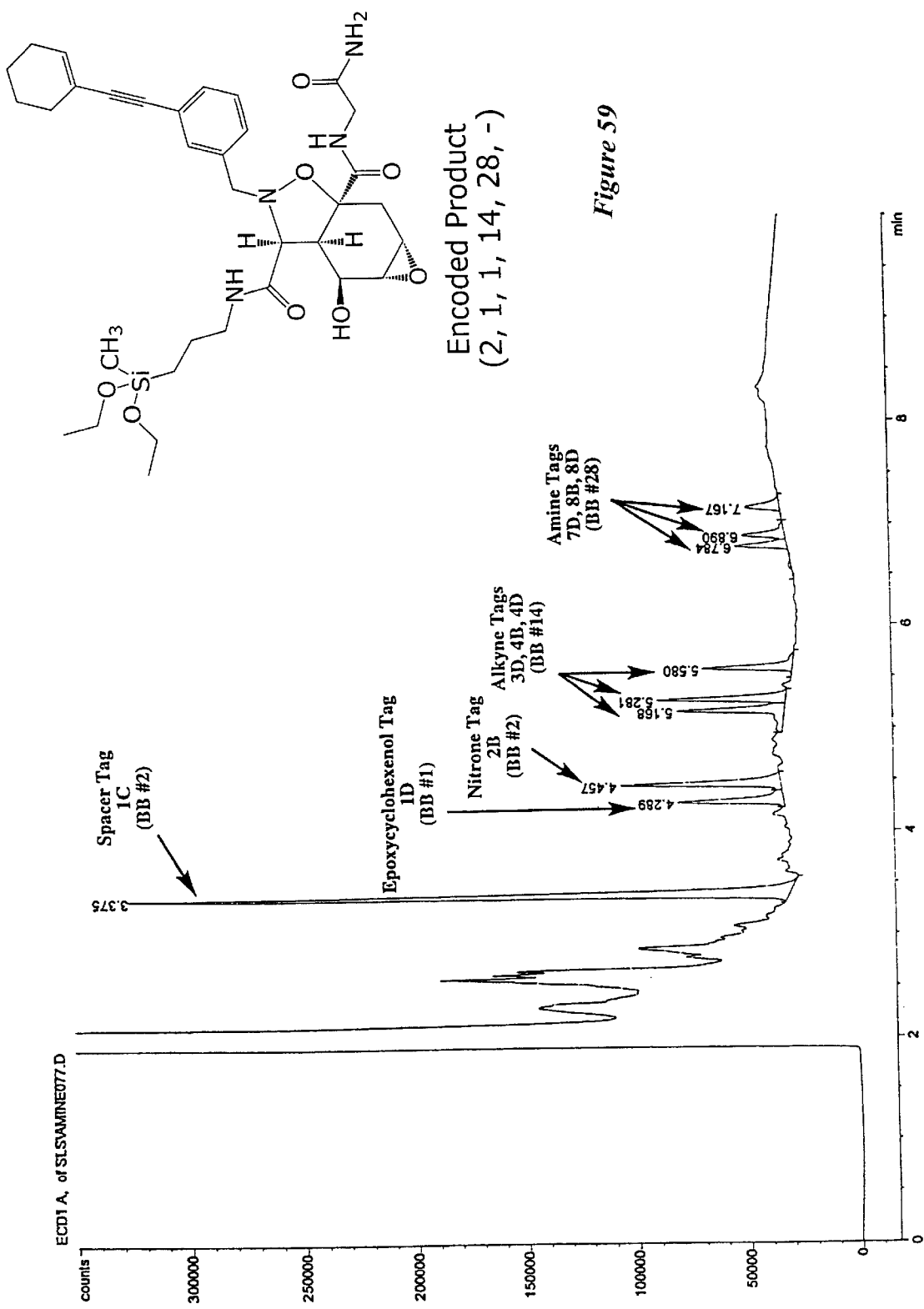

SYNTHESIS OF COMBINATORIAL LIBRARIES OF COMPOUNDS REMINISCENT OF NATURAL PRODUCTS

RELATED APPLICATIONS

This application is a continuation-in-part of U.S. application Ser. No. 08/951,930, filed Oct. 15, 1997, which claims the benefit of priority of U.S. provisional application No. 60/029,128, filed Oct. 16, 1996 and U.S. provisional application No. 60/049,864 filed Jun. 6, 1997, the entire contents of which are hereby incorporated in their entirety.

GOVERNMENT SUPPORT

This invention was supported by NIH grant No. AI39619 and therefore the government has certain rights in this invention.

BACKGROUND OF THE INVENTION

The identification of small organic molecules that affect specific biological functions is an endeavor that impacts both biology and medicine. Such molecules are useful as therapeutic agents and as probes of biological function. In but one example from the emerging field of chemical genetics, in which small molecules can be used to alter the function of biological molecules to which they bind, these molecules have been effective at elucidating signal transduction pathways by acting as chemical protein knockouts, thereby causing a loss of protein function. (Schreiber et al. *J. Am. Chem. Soc.* 1990, 112, 5583; Mitchison, *Chem. and Biol.* 1994, 1, 3) Additionally, due to the interaction of these small molecules with particular biological targets and their ability to affect specific biological functions, they may also serve as candidates for the development of therapeutics.

Because it is difficult to predict which small molecules will interact with a biological target. intense efforts have been directed towards the generation of large numbers, or "libraries", of small organic compounds. These libraries can then be linked to sensitive screens to identify the active molecules. In many cases, researchers have developed "biased" libraries, in which all members share a particular characteristic, such as an ability to interact with a particular target ligand, or a characteristic structural feature designed to mimic a particular aspect of a class of natural compounds. For example, a number of libraries have been designed to mimic one or more features of natural peptides. Such peptidomimetic libraries include phthalimido libraries (WO 97/22594), thiophene libraries (WO 97/40034), benzodiazopene libraries (U.S. Pat. No. 5,288,514), libraries formed by the sequential reaction of dienes (WO 96/03424), thiazolidinone libraries, libraries of metathiazanones and their derivatives (U.S. Pat. No. 5,549,974), and azatide libraries (WO 97/35199) (for review of peptidomimetic technologies, see Gante, J., *Angew. Chem. Int. Ed. Engl.* 1994, 33, 1699–1720 and references cited therein).

Each of these libraries has provided solid phase synthetic strategies for compounds possessing specific core functionalities, but none achieves the complexity of structure found in natural products, or in other lead compounds prepared through traditional chemical synthetic routes. Complex natural products commonly contain several different functionalities and often are rich in stereochemical complexity. Such diversity and complexity are difficult to achieve if the synthesis is restricted to a specific class of compounds.

Recognizing the need for development of synthetic strategies that produce large numbers of complex molecules, Boger et al. (EP 0774 464) have recently developed a solution-phase synthetic strategy for producing a library of compounds based on a functionalizable template core, to which various reagents can be added. However, there remains a need for development of solid-phase strategies, where the more rapid production methods such as split-and-pool strategies can be employed to generate larger (>1,000,000), more complex libraries. Additional solution-phase strategies would, of course, also be valuable.

SUMMARY OF THE INVENTION

The present invention provides methods for the production of compounds and libraries of complex compounds reminiscent of natural products from diversifiable scaffold structures. In particular, the present invention provides synthetic strategies that allow production of complex compounds and preferably large collections of complex compounds that are reminiscent of natural products in that they contain one or more stereocenters, and a high density and diversity of functionality. In preferred embodiments, the compounds of the present inventive libraries are structurally related to a natural product. Alternatively or additionally, the compounds of the inventive libraries possess the capability of acting as a ligand in a biological system to produce a desired inhibitory or promoter effect, and thus may also be functionally reminiscent of natural products.

According to the present invention, the inventive compounds and combinatorial libraries are synthesized from diversifiable solid support bound scaffolds, which are synthesized from readily available or easily synthesizable template structures. In certain embodiments, the inventive compounds and libraries are generated from diversifiable scaffolds synthesized from a shikimic acid based epoxyol template. In other embodiments, the inventive compounds and libraries are generated from diversifiable scaffolds synthesized from the pyridine-based template isonicotinamide.

In addition to providing complex compounds reminiscent of natural products, combinatorial libraries thereof, and methods of their production, the present invention also provides a novel ortho-nitrobenzyl photolinker, and a method for its synthesis, that can be used in the preparation of solid support bound compounds and combinatorial libraries.

The present invention further provides a method for determining one or more biological activities of a library member. In a preferred embodiment, the method for determining one or more biological activities of the inventive compounds comprises contacting the inventive compounds with a biological target, such as a binding target or transcription based assay, and determining a statistically significant change in a biochemical activity relative to the level of biochemical activity in the absence of the compound.

The present invention further provides a kit comprising a library of compounds and reagents for determining one or more biological activities of the library member. To give but one example, the biological activity can be determined by providing a kit containing a binding reagent, such as a direct reagent (binding target) or an indirect reagent (transcription based assay) and a library of compounds.

The present invention additionally provides pharmaceutical compositions containing one or more library members. In a preferred embodiment, the pharmaceutical composition preferably comprises one or more of the inventive compounds and a pharmaceutically acceptable carrier.

DEFINITIONS

"Combinatorial library": As used herein, a "combinatorial library" is a plurality of complex compounds reminiscent of natural products synthesized from diversifiable scaffold structures by employing different reactants, or monomers, at each stage of the diversification of the scaffold structures. The combinatorial libraries of the present invention may be prepared in solution or on the solid phase.

"Diversifiable scaffold structures": As used herein, a "diversifiable scaffold structure" is a compound synthesized from a template structure, which contains unique latent or active functionalities capable of being further reacted with synthetic reagents to generate at least one new functionality, but, particularly in the case of a latent functionality, may generate more than one. As used herein, a "latent functionality" is one that is present, but is temporarily inactive. Upon release with an activator or reagent, the latent functionality becomes active, and is thus available for further diversification. For example, a diversifiable scaffold structure may contain an epoxide moiety, which, upon reaction with a nucleophile releases a latent alcohol functionality and generates an additional functionality at the site of nucleophilic attack.

Furthermore, the alcohol functionality can be subsequently diversified using electrophites to yield other functionalities including, but not limited to, ether, ester, carbamate and thioester.

"Complex compounds reminiscent of natural products": As used herein, a complex compound reminiscent of a natural product is a compound that, similarly to complex natural products which nature has selected through evolution, contains more than one stereocenter, a high density and diversity of functionality, and a diverse range of atoms within one structure. This term can also, for the purposes of the present invention, be used interchangeably with the term "natural product-like" compound. In this context, diversity of functionality can be defined as varying the topology, charge, size, hydrophilicity, hydrophobicity, and reactivity, to name a few, of the functional groups present in the compounds. The term, "high density of functionality", as used herein, can preferably be used to define any molecule that contains at least four latent or active diversifiable functional moieties. These structural characteristics may additionally render the inventive compounds functionally reminiscent of complex natural products, in that they may interact specifically with a particular biological receptor, and thus may also be functionally natural product-like.

"Small Molecule": As used herein, the term "small molecule" refers to an organic compound either synthesized in the laboratory or found in nature. Typically, a small molecule is characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small. molecules" that are synthesized in the laboratory include, but are not limited to, the inventive compounds incorporated herein.

"Linker": The term "linker", as used herein, refers to a molecule or group of molecules connecting a solid support and a combinatorial library member. The linker may be comprised of a single linking molecule or may comprise a linking molecule and a spacer molecule, intended to separate the linking molecule and the library member by a specific distance.

"Radially Arrayed": The term "radially arrayed" as used herein, refers to a spatial arrangement of functionality that projects outwardly in all directions, from the synthesized scaffold structure.

"Protecting Group": The term "protecting group" as used herein, refers to a chemical group that reacts selectively with a desired functionality in good yield to give a derivative that is stable to further reactions for which protection is desired, can be selectively removed from the particular functionality that it protects to yield the desired functionality, and is removable in good yield by reagents compatible with the other functional group(s) generated during the reactions.

"Support": The term "support", as used herein interchangeably as beads, solid surfaces, substrates, particles, supports, etc. These terms are intended to include 1) solid supports such as beads, pellets, disks, capillaries, pore-glass beads, silica gels, polystyrene beads optionally cross-linked with divinylbenzene, grafted co-poly beads, polyacrylamide beads, latex beads, dimethylacrylamide beads optionally cross-linked with N,N'-bis acryloyl ethylene diamine, glass particles coated with a hydrophobic polymer, or any other material having a rigid or semi-rigid surface; and 2) soluble supports such as low molecular weight non-cross-linked polystyrene. These materials also contain functionalities such that identifiers and/or templates, scaffolds, and inventive compounds can be attached to them. It is particularly preferred for the purposes of the present invention that the solid support Tentagel is used.

"Identifier Tag": The term "identifier tag" as used herein, refers to a means for recording a step in a series of reactions used in the synthesis of a chemical library. For the purposes of this application, the terms encoded chemical library and tagged chemical library both refer to libraries containing a means for recording each step in the reaction sequence for the synthesis of the chemical library.

DESCRIPTION OF THE DRAWING

FIG. 3 depicts the use of a small molecule to bind the Human Growth Hormone receptor.

FIG. 4 depicts the inventive method for the shikimic acid based combinatorial library.

FIG. 10 depicts alternative ortho-nitrobenzyl photolinkers.

FIG. 26 depicts aminolysis of the tetracycle with n-butylamine.

FIG. 31 depicts chemoselective solvolysis with AcSH and AcOH.

FIG. 37 depicts representative potential nucleation points of the isoquinuclidine scaffold.

FIG. 38 depicts the efficient synthesis of N-arylimide derivatives.

FIG. 41 depicts a synthetic plan for the generation of 30 million complex molecules.

FIG. 42 depicts a test library synthesis library quality control.

FIG. 48 depicts the antagonism of TGF-$\beta$-induced reporter gene activity.

FIG. 55 depicts building blocks used in test library.

FIG. 56 depicts alkyne and amine building block masses and the resulting 64 unique g-hydroxyamide product masses. Acylation of the C-6 alcohol with a carboxylic acid shifts all of the product masses for that pool by the same value (mass of the acid minus water).

FIGS. 57A and 57B depict representative LC-MS data for test library final pool 4: fully averaged mass spectrum, total ion count trace, single mass traces, and corresponding structures. The 550 and 496 single mass traces represent typical "clean" product signals. Smaller peaks (6.02 min. 6.58 min) in the 578 single mass trace arise from isotopic compositions of lower mass products (FW=575, 576). The 381 single mass trace is representative of a "weak" product signal.

FIG. 59 depicts representative EC-GC trace for binary encoding tag analysis. The sample analyzed was from the tag coupling, reaction encoding amine building block 28. The product structure corresponding to the binary code is shown.

DESCRIPTION OF CERTAIN PREFERRED EMBODIMENTS

Figure 1:
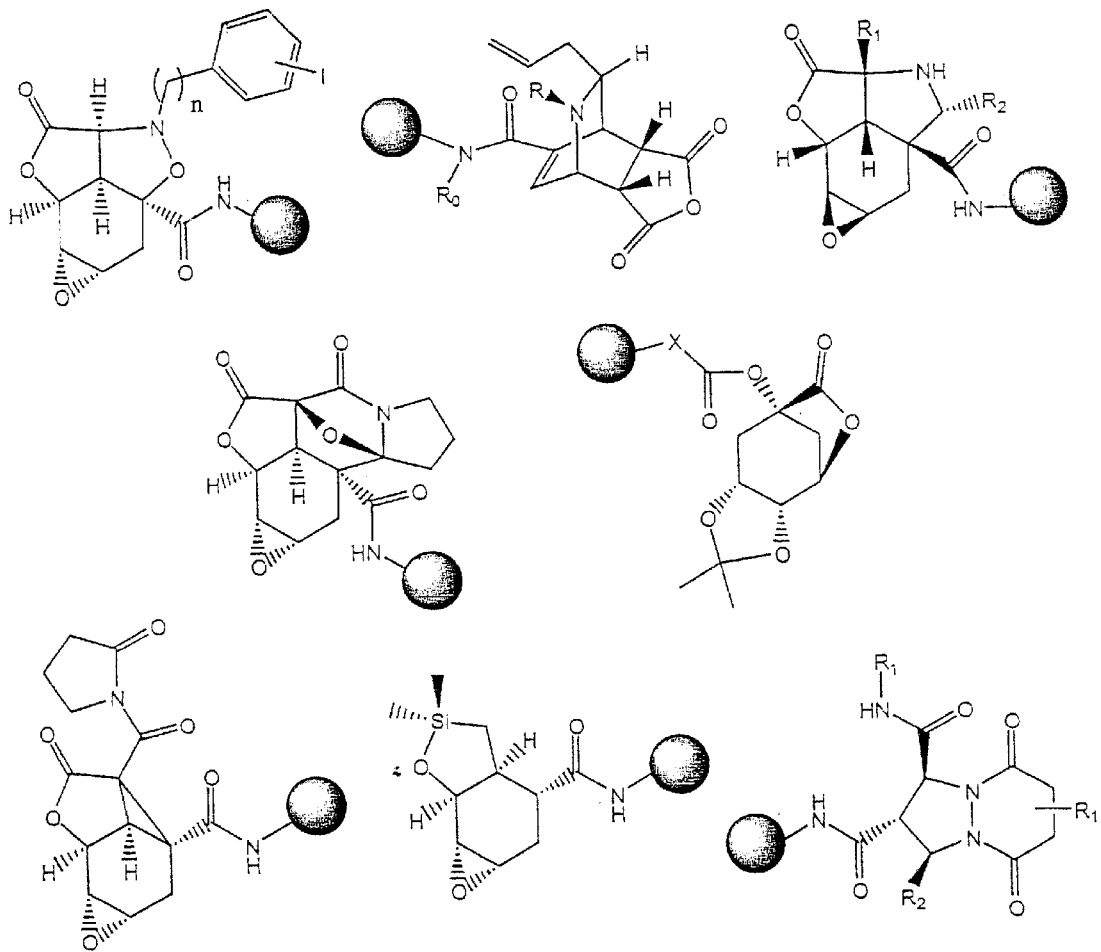
FIG. 1 depicts several examples of natural product-like compounds.
Figure 2:
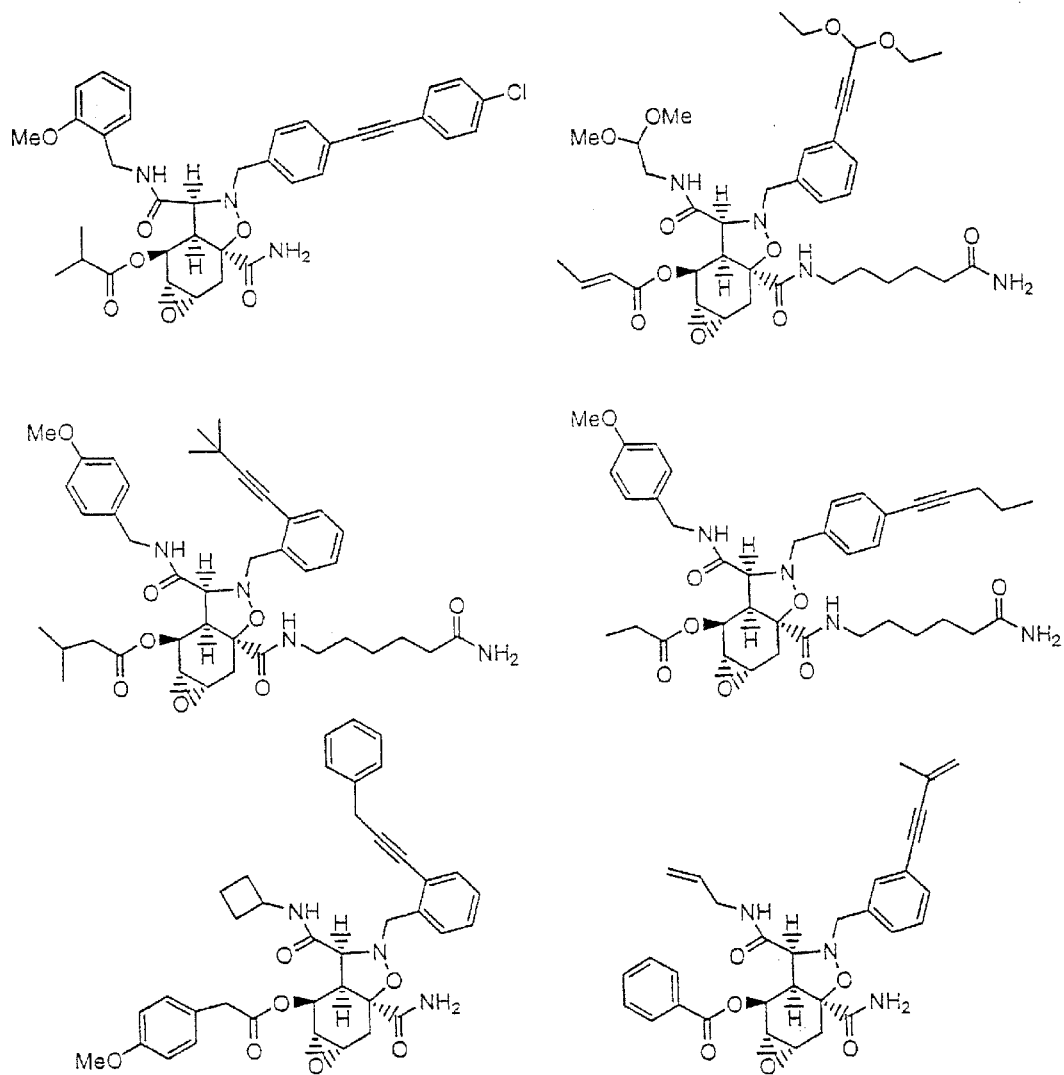
FIG. 2 depicts the diverse reaction products of one embodiment of the inventive method.

As described herein, the present invention provides complex radially arrayed compounds and libraries of compounds, and methods for making such libraries. In general, the present invention provides synthetic strategies that allow production of compounds and large collections of compounds that are reminiscent of complex natural products in that they contain at least one stereocenter, a high density and diversity of functionality displayed in a radial array, and a diverse range of atoms within one structure. In this context, diversity of functionality can be defined as varying a specific characteristic or set of characteristics of the functional groups present in the molecule including, but not limited to, topology, size, charge, hydrophilicity, hydrophobicity, and reactivity. Examples of ways in which functional groups may differ from one another include, but are not limited to, variations in either the shape or chain length of a particular collection of atoms or variations in the particular atoms present in the functional groups. Additionally, functional groups may also differ from one another by variations in both the shape or chain length and variations in the particular atoms present in the functional groups. In the context of the present invention, a highdensity of functionality can be defined as a large number of chemical moieties present in an inventive compound or library member. In preferred embodiments the inventive compounds and library members contain at least four chemical moieties. For example, in a preferred embodiment, an inventive compound or library member may contain substituted aryl, epoxide, amine and ester functionalities, and will contain at least one stereocenter. FIG. 1 depicts examples of inventive compounds containing stereochemical complexity and a high density and diversity of functionality, qualities that render them reminiscent of natural products or "natural product-like". FIG. 2 depicts examples of some of the inventive compounds. Furthermore, as discussed previously, the functionality is displayed in a radial array, which, unlike many polymers or chains of peptides or other molecules, enables diversification in all directions, thus adding to the complexity of the inventive compounds and providing them with a greater likelihood of interacting with biological molecules. In certain embodiments, this complexity is achieved by designing the inventive compounds and libraries of compounds based on an existing natural product, such as ibogamine or catharanthine, or based on a receptor for a particular protein, such as the "hot spot" of human growth hormone (FIG. 3). In other embodiments, the present invention also provides compounds and libraries of compounds that, although not based on an existing natual product, are reminiscent of natural products because of their stereochemical and functional complexity and diversity, and thus may be thought of as "non-natural" natural products. Whether the compounds are "non-natural" or are based on an existing natural product, the compounds and libraries of compounds are expected to be useful as therapeutics and biological probes because of their ability to interact with biomolecules, such as proteins, carbohydrates, and nucleic acids.

In particular, the inventive method involves the synthesis of combinatorial libraries from solution phase or solid support bound scaffolds, which are synthesized from readily available or easily synthesizable template structures. The synthesis of the scaffolds and combinatorial libraries from solid support bound templates is particularly preferred because of the ease with which large numbers (>1,000,000) of compounds can be synthesized. The template structures are preferably selected for the inventive method because they are easily synthesizable or readily available, they contain multiple reactive sites where individual combinatorial units can be added to generate scaffold structures in preferably four steps or fewer, and possess the potential for stereochemical diversity. The resulting scaffold structures are characterized by their rigidity, stereochemical and functional group complexity, high density and diversity of functionality radially arrayed (e.g., at least four functionalizable sites) from which to generate highly diversified libraries, and by the minimal need to employ protecting groups (e.g., no more than one functionality in the molecule contains a protecting group, or in the case of certain scaffold structures, no protecting groups need be employed) during the synthesis of the scaffold structures and combinatorial libraries. Preferred template and scaffold structures also include those that are capable of reacting with reagents without the need for a catalyst. Importantly, the diversity of these highly complex compounds and libraries of compounds reminiscent of natural products, as discussed above, results both from the ability to diversify the templates and combinatorializable units used to synthesize the scaffold structures, and from the diversity generated upon reaction with the latent and non-latent functionalities in the scaffold structure. This diversity, as discussed above, results from the changing of the shape, size, hydrophilicity, hydrophobicity, charge and reactivity to name a few, when introducing new functionality. In the method of the presently claimed invention, solution phase or solid phase techniques may be employed to generate combinatorial libraries containing as many as or more than one million members of complex radially arrayed compounds reminiscent of natural products, and more preferably libraries containing as many as or more than two million members of complex compounds reminiscent of natural products.

Particularly preferred embodiments of the present invention include the synthesis of compounds and libraries of compounds starting from a shikimic acid based epoxyol template and the synthesis of compounds and libraries of compounds starting from a pyridine based template, isonicotinamide. FIG. 4 depicts the inventive method for the shikimic acid based combinatorial library, in which the boxed regions depict the potential diversity nucleation points. Each chemical step thus performed in the inventive method will deliver a new monomer while concurrently generating a new position for functionality.

Various characteristics of the templates and resulting scaffolds and reactions utilized in certain preferred embodiments of the present invention are discussed in more detail below; certain examples of inventive reactions and compounds are also presented.

Synthesis of Template Structures

In one particularly preferred embodiment, the present invention provides a method for the synthesis of complex compounds and combinatorial libraries generated from scaffold structures that are synthesized from shikimic acid based epoxyol templates. In another particularly preferred embodiment, the present invention provides a method for the synthesis of complex compounds and combinatorial libraries generated from scaffold structures synthesized from a readily available isonicotinamide template. These epoxyol and isonicotinamide templates are subjected to different reaction conditions to yield different highly complex diversifiable scaffold structures from which the complex compounds and libraries of the present invention are generated.

As discussed above, the epoxyol and isonicotinamide templates are selected for the inventive method because they are easily synthesizable or readily available, contain multiple reactive sites from which to synthesize complex diversifiable structures in a minimal number of steps, preferably four steps or fewer, and possess the potential for stereochemical diversity. As will be appreciated by one of ordinary skill in the art, the method of the present invention is intended to encompass all possible stereoisomers and diastereomers for each of the reaction conditions employed.

Figure 5:
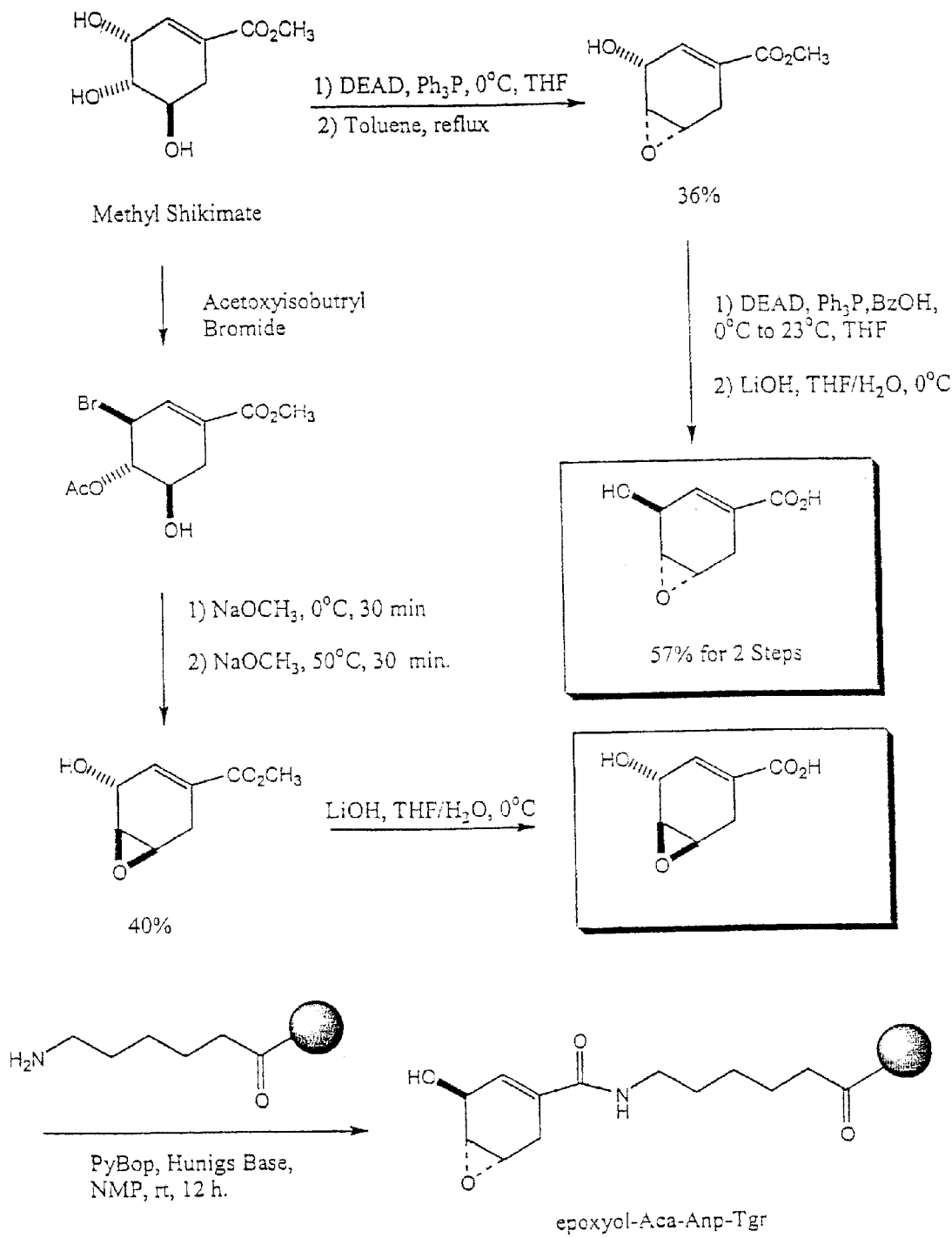
FIG. 5 depicts the synthesis of different enantiomers of the epoxyol templates.

In one particularly preferred embodiment, the synthesis of desired epoxyol templates is achieved. Additionally, employing different reaction conditions in the presence of methyl shikimate enables the synthesis of enantiomers of the desired epoxyol templates as shown in FIG. 5. For example, reaction under Berchtold reaction conditions, subsequent reaction with DEAD (diethylazo dicarboxylate), triphenylphosphine and benzoic acid, and reaction with LiOH yields the R, S, S acid. The other enantiomer is readily synthesized using acetoxyisobutyryl bromide, subsequent epoxidation with NaOCH$_3$ and Payne rearrangement, and finally reaction with LiOH to yield the S, R, R acid. These epoxyol templates can be utilized for further reaction in solution, or may subsequently be attached to a solid support.

Figure 6:
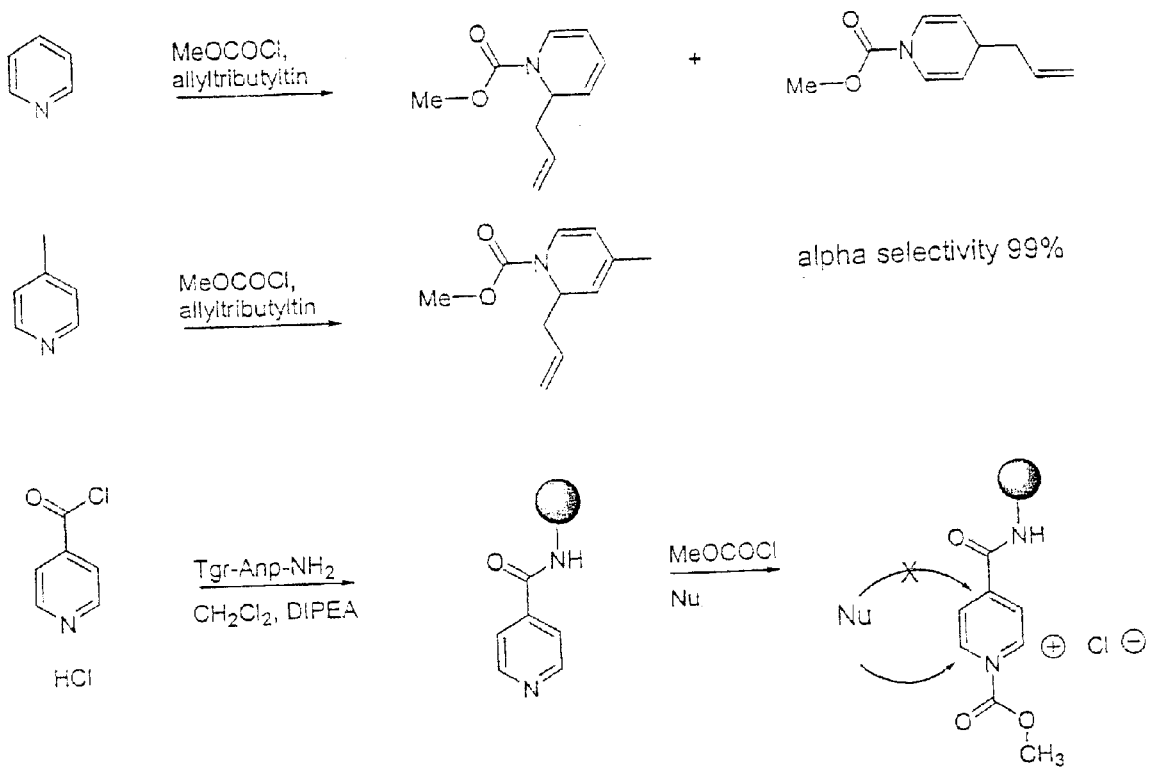
FIG. 6 depicts the synthesis of an isonicotinamide template. Isonicotinoyl chloride provides a handle for solid phase attachment and blocks 4-position in tandem reaction. See also Yamaguchi et al. *J. Org. Chem.* 1985, 50, 287 and Yamaguchi et al. *J. Org. Chem.* 1988, 53, 3507.

In another particularly preferred embodiment, an isonicotinamide template is easily synthesized from the commercially available reagent isonicotinoyl chloride and an amine. The use of isonicotinoyl chloride as a starting material is preferred because it provides a handle for solid phase attachment, if desired, and also because it blocks the 4-position in a tandem reaction as shown in FIG. 6. In yet another particulary preferred embodiment, an alternative isonicotinamide template is synthesized via Fukuyama sulfonamide alkylation, in which a diversifiable amide functionality is created by alkylation of the nitrogen under Mitsunobu conditions. Nitrobenzenesulfonylchloride is reacted with a solid support to generate a solid support-bound sulfonamide. Subsequent reaction with triphenylphosphine or tributylphosphine and DEAD or TMAD generates a solid support bound sulfonamide containing a diversity position. Subsequent cleavage of the sulfonamide with thiophenylate, or more generally a thiophenoxide, wherein the counterion includes, but is not limited to, sodium, potassium, cesium or amine bases, wherein said amine bases include, but are not limited to, DBU, MTBD, DIPEA, or triethylamine, yields a functionalized moiety available for further reaction with isonicotinoyl chloride to yield the functionalized isonicotinamide template. In preferred embodiments, the diversifiable functionality present on the nitrogen includes but is not limited to branched or unbranched, substituted or unsubstituted alkyl, aryl, and arylalkyl moieties.

Once the synthesis of either a desired solution phase or solid support bound template has been completed, the template is then available for further reaction to yield the desired solution phase or solid support bound scaffold structure. The use of solid support bound templates is particuarly preferred because it enables the use of more rapid split and pool techniques to generate libraries containing as many as or more than 1,000,000 members.

Figure 7:
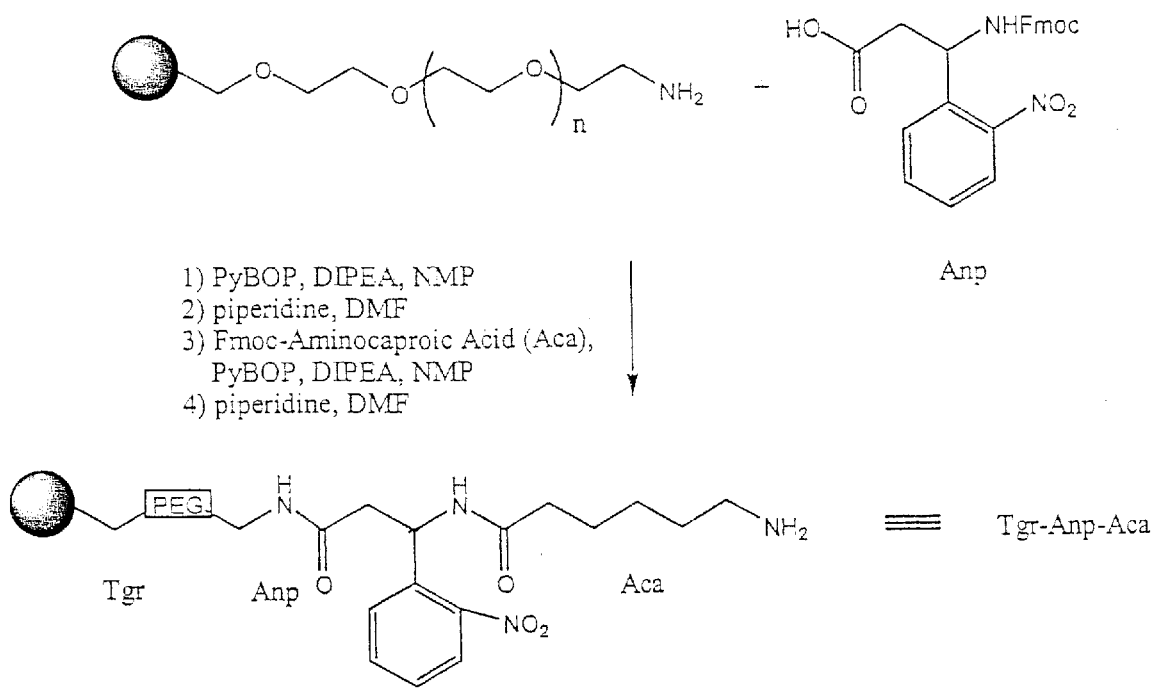
FIG. 7 depicts the use of a preferred Tentagel amino resin.

A solid support, for the purposes of this invention, is defined as an insoluble material to which compounds are attached during a synthesis sequence. The use of a solid support is advantageous for the synthesis of libraries because the isolation of support-bound reaction products can be accomplished simply by washing away reagents from the support-bound material and therefore the reaction can be driven to completion by the use of excess reagents. Additionally, the use of a solid support also enables the use of specific encoding techniques to "track" the identity of the inventive compounds in the library. A solid support can be any material which is an insoluble matrix and can have a rigid or semi-rigid surface. Exemplary solid supports include but are not limited to pellets, disks, capillaries, hollow fibers, needles, pins, solid fibers, cellulose beads, pore-glass beads, silica gels, polystyrene beads optionally cross-linked with divinylbenzene, grafted co-poly beads, poly-acyrlamide beads, latex beads, dimethylacrylamide beads optionally crosslinked with N-N'-bis-acryloylethylenediamine, and glass particles coated with a hydrophobic polymer. One of ordinary skill in the art will realize that the choice of a particular solid support will be limited by the compatibility of the support with the reaction chemistry being utilized. In one particularly preferred embodiment, a Tentagel amino resin, a composite of 1) a polystyrene bead crosslinked with a divinylbenzene and 2) PEG (polyethylene glycol), is employed for use in the present invention, as shown in FIG. 7. Tentagel is a particulary useful solid support because it provides a versatile support for use in on-bead or off-bead assays, and it also undergoes excellent swelling in solvents ranging from toluene to water.

The compounds of the present invention may be attached directly to the solid support or may be attached to the solid support through a linking reagent, as shown in FIG. 7. Direct attachment to the solid support may be useful if it is desired not to detach the library member from the solid support. For example, for direct on-bead analysis of biological activity or analysis of the compound structure, a stronger interaction between the library member and the solid support may be desirable. Alternatively, the use of a linking reagent may be useful if more facile cleavage of the inventive library members from the solid support is desired.

Figure 8:
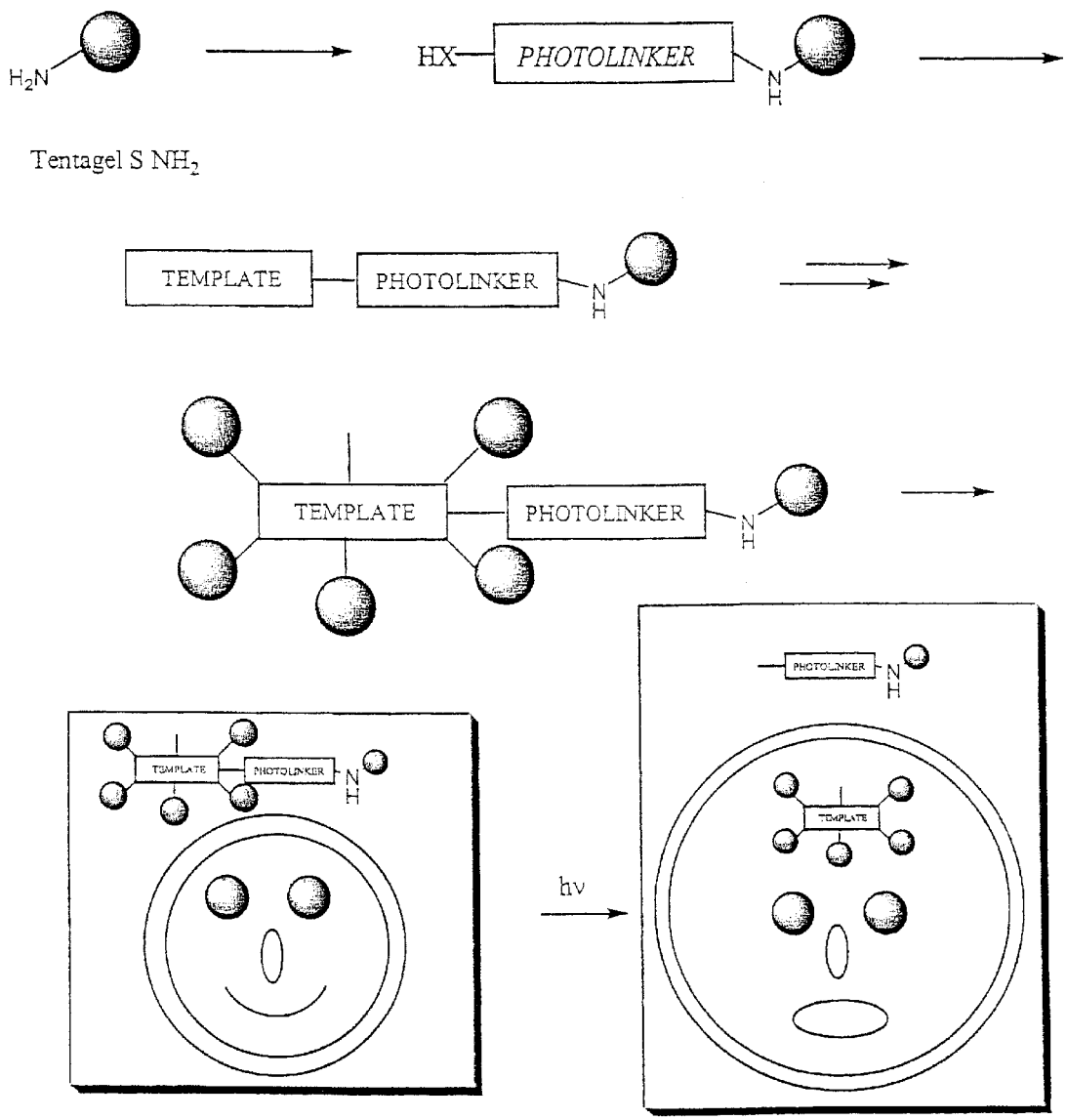
FIG. 8 depicts the use of a photocleavable linker to attach the solid phase resin to the desired template structure.

Furthermore, any linking reagent used in the present invention may comprise a single linking molecule, or alternatively may comprise a linking molecule and one or more spacer molecules, as depicted in FIG. 7. A spacer molecule is particularly useful when the particular reaction conditions require that the linking molecule be separated from the library member, or if additional distance between the solid support/linking unit and the library member is desired. In one particularly preferred embodiment, photocleavable linkers are employed to attach the solid phase resin to the desired template structure. as shown in FIG. 8. Photocleavable linkers are particularly advantageous for the presently claimed invention because of the ability to use these linkers in in vivo screening strategies. Once the template is released from the solid support via photocleavage, the complex small molecule is able to enter the cell.

Figure 9:
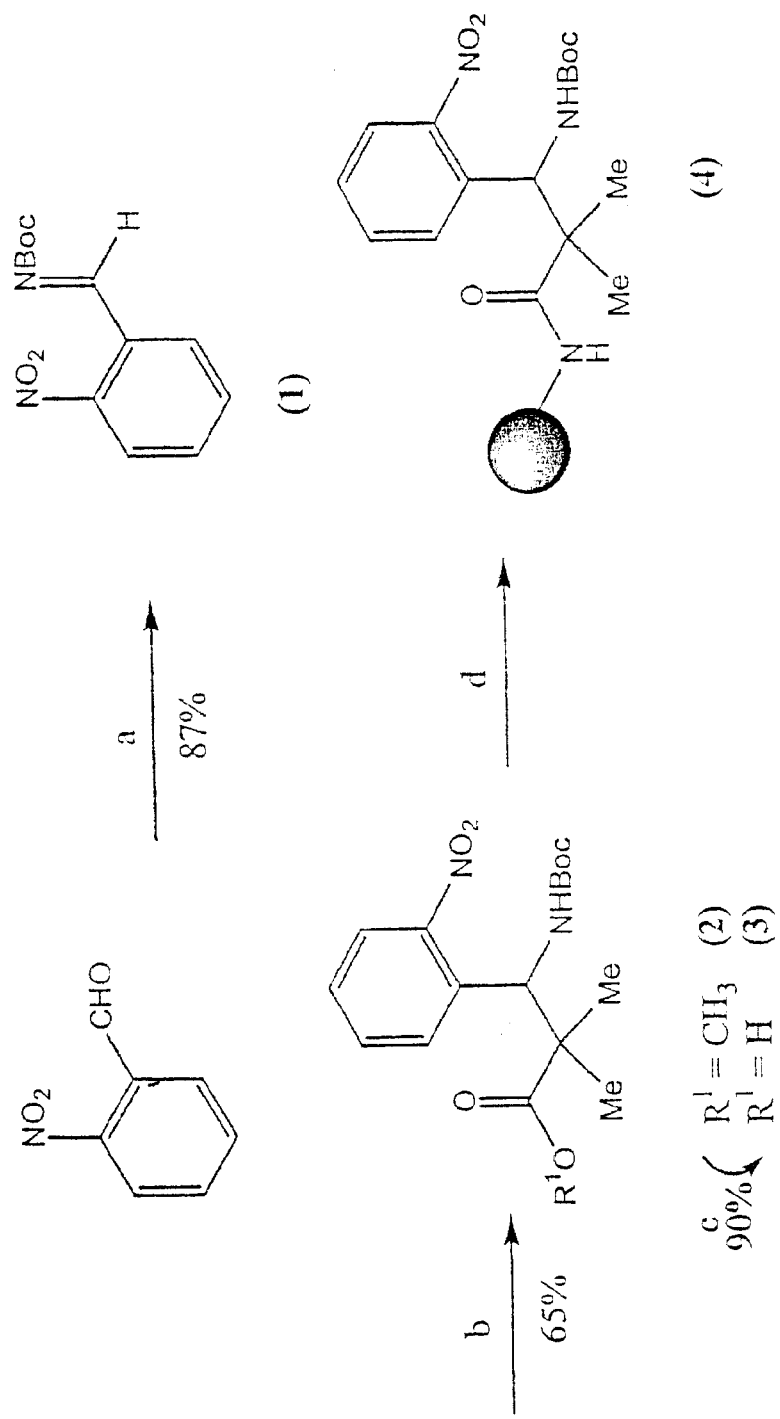
FIG. 9 depicts the synthesis of a novel ortho-nitrobenzyl photolabile linker. (a) t-BuOCONH$_2$ (1.5 eq), NaSO$_2$Ph (2.5 eq), HCOOH (2 eq.), 2:1 H$_2$O/MeOH, 3 crops over 60 h, ii. K$_2$CO$_3$, THF, reflux 12 h; (b) i. i-Pr$_2$NH, BuLi, THF, −78° C., then methyl isobutyrate, 30 min. ii. 3, −78° C., 2 min. then AcOH/THF; (c) LiOH (10 eq), MeOH/H$_2$O, 60° C.; (d) Tentagel S NH$_2$, 5 (1.6 eq), HATU (1.5 eq.), i-Pr$_2$NEt (4 eq), 3:1 DMF/CH$_2$Cl$_2$, 12h.

In addition to providing for the synthesis of scaffold structures, compounds and libraries of compounds, in another aspect, the present invention provides a novel ortho-nitrobenzyl photolabile linker (3-amino-3-(2'-nitrophenyl)-2,2-dimethylpropionic acid (FIG. 1) and a method for the synthesis of the photolabile linker, as shown in FIG. 9. As shown in FIG. 9, the imine (1) is synthesized in two steps from commercially available 2-nitrobenzaldehyde by modification of a published procedure. (Kanazawa, A. M. et al., *J. Org. Chem.* 1994, 59, 1238). The amino ester (2) is then formed by the addition of a pre-cooled solution of (1) to the lithium enolate of methyl isobutyrate. Subsequent recrystallization from 40:60 ether/petroleum ether, hydrolysis of the synthesized ester with lithium hydroxide (LiOH), and coupling to Tentagel S NH$_2$ using HATU yields the support bound linker (4). Importantly, this linker is incapable of β-elimination, a common decomposition pathway for photolinkers, and is stable to acid, base and Lewis acid/amine conditions.

Compound 1

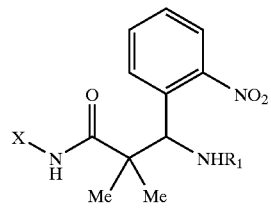

Referring to Compound 1, R$_1$ includes, but is not limited to a protecting group, a complex compound reminiscent of a natural product, a spacer, a biomolecule, or a polymer; and X is a solid support unit.

Figure 11:
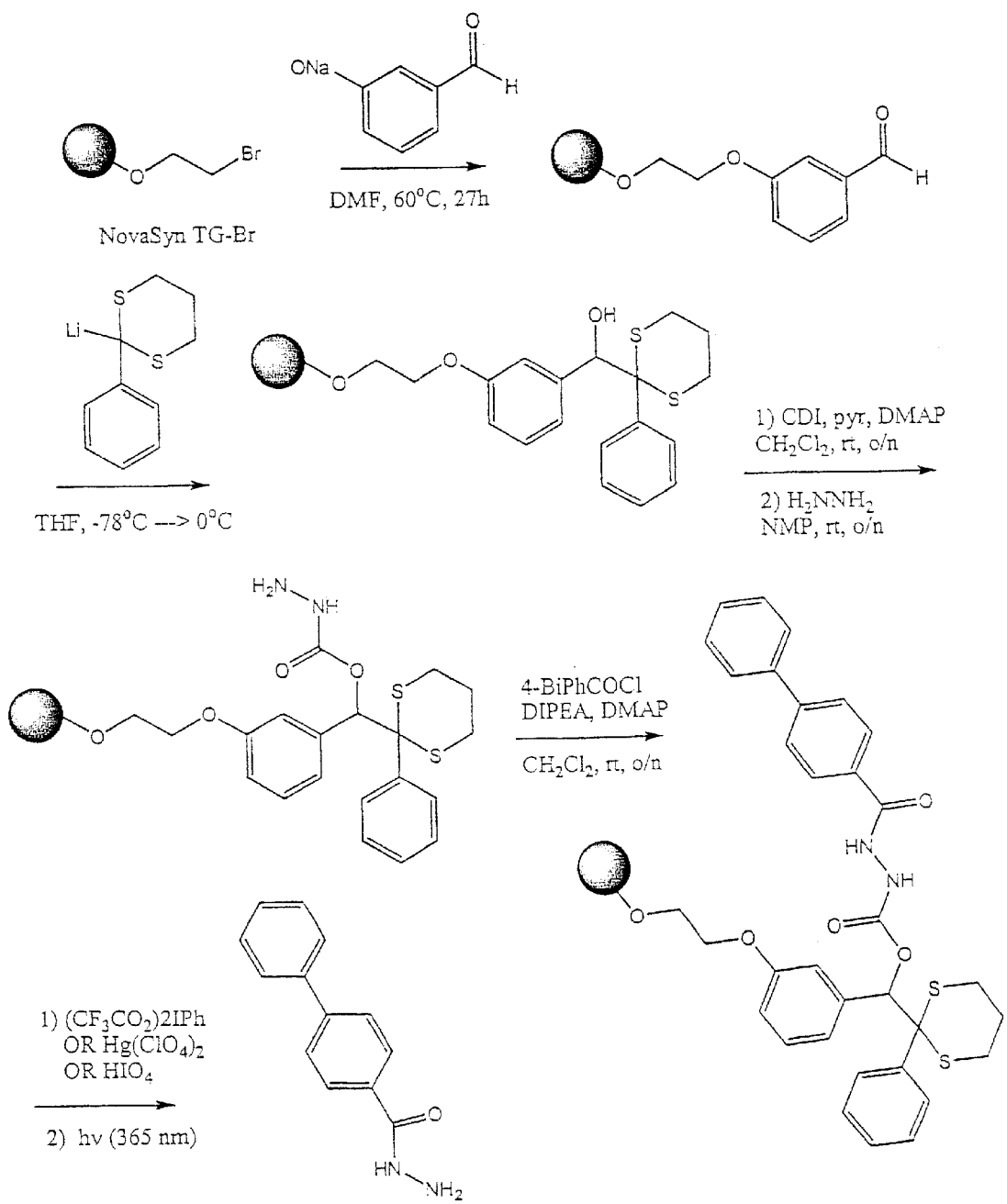
FIG. 11 depicts a dithiane-protected benzoin photolinker.

In other particularly preferred embodiments, alternative ortho-Nitrobenzyl photolinkers are employed, such as the Rich Linker (Nba), Geysen Linker (Anp), Linker (A), and Affymax Linkers (Hep, Hmp, Aep) as shown in FIG. 10. Additionally, a dithiane-protected benzoin photolinker, as shown in FIG. 11 may be employed. One of ordinary skill in the art will also realize that any of these photolinkers as well as other photolinkers can be employed with the limitation that they will not degrade in the presence of the complex reaction steps employed in the synthesis of the compounds and combinatorial libraries. Furthermore, the method of the present invention is not limited to the use of photocleavable linkers; rather other linkers may be employed, preferably those that are capable of delivering the desired compounds in vivo.

Furthermore, as mentioned above, it may also be desirable, or even necessary, to utilize a spacer unit, to ensure that the photolinker is sufficiently distanced from the desired compound. Representative spacer units include but are not limited to aminocaproic acid (Aca), glycine, and any amino acid that does not contain a functionality capable of being acylated.

In certain embodiments, the completed template may be attached to the solid phase, through a linking unit, or directly, and subsequently used in the synthesis of desired scaffold structures. In particularly preferred embodiments, attachment of the completed templates of the present invention to the solid phase is achieved by reaction under standard amide coupling conditions. In one example, FIG. 5 depicts the attachment of completed epoxyol templates to the solid phase by reaction with PyBOP, Hunig's Base and NMP, to yield a support bound epoxyol template. One of ordinary skill in the art will realize that attachment of templates to the solid phase may also be effected through alternative means, such as, but not limited to, ether linkages. This choice of linkage will depend upon the reactivity of the functionalities available in the compounds and the solid support units (including any combination of a solid support, and linking reagent) and the stability of these linkages.

Figure 12:
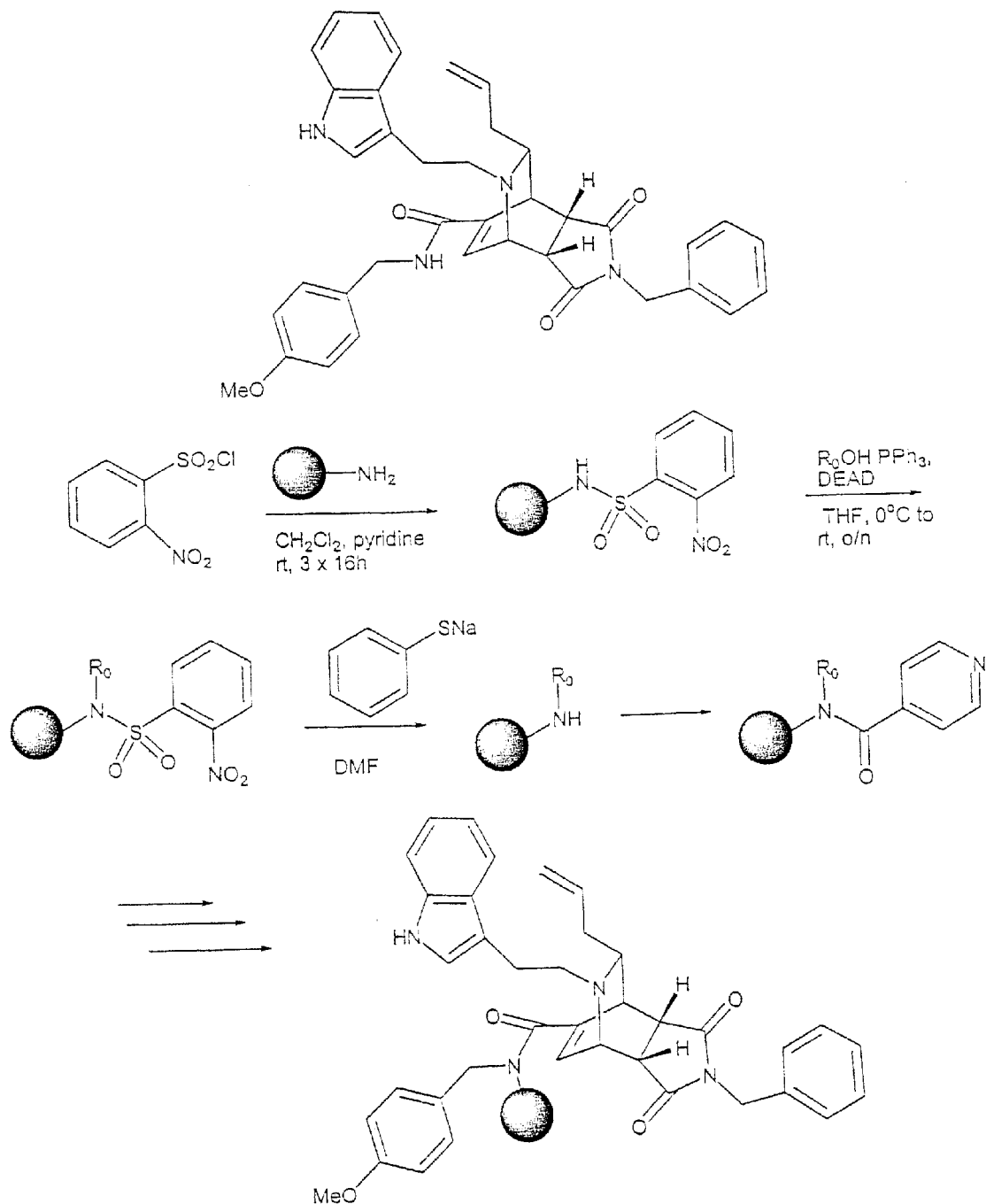
FIG. 12 depicts addition of a diversity position via Fukuyama sulfonamide alkylation. See, Fukuyama et al. *Tet. Lett.* 1995, 36, 6373.

In other embodiments, one of the reagents used in the synthesis of the desired template may be attached to the solid support and the template synthesis completed while on the solid support. For example, as shown in FIG. 6, attachment of isonicotinoyl chloride to the solid phase to yield a support bound isonicotinamide, is achieved by reaction with Anp-Tgl and DIPEA. Furthermore, as shown in FIG. 12, alkylation of the nitrogen via Fukuyama sulfonamide alkylation, wherein nitrobenzenesulfonylchloride is reacted with a solid support to generate a solid support-bound sulfonamide, and subsequent reaction with triphenylphosphine or tributylphosphine and DEAD or TMA, generates a solid support bound sulfonamide containing a diversity position. Subsequent cleavage of the sulfonamide with thiophenylate, or more generally thiophenoxide, wherein the counterion includes, but is not limited to, sodium, potassium, cesium or amine bases, and wherein said amine bases include, but are not limited to, DBU, MTBD, DIPEA, or triethylamine, yields the alkylated support bound moiety available for further reaction with isonicotinoyl chloride to yield an alkylated isonicotinamide derivative. In preferred embodiments, the diversifiable functionality, $R_0$, includes but is not limited to branched or unbranched, substituted or unsubstituted alkyl, aryl, and arylalkyl moieties.

Each of the templates synthesized according to the method of the present invention, whether in the solution phase or attached to a solid support, can then be subsequently used in the synthesis of desired scaffold structures.

Shikimic Acid Based Scaffold Structures

Figure 13:
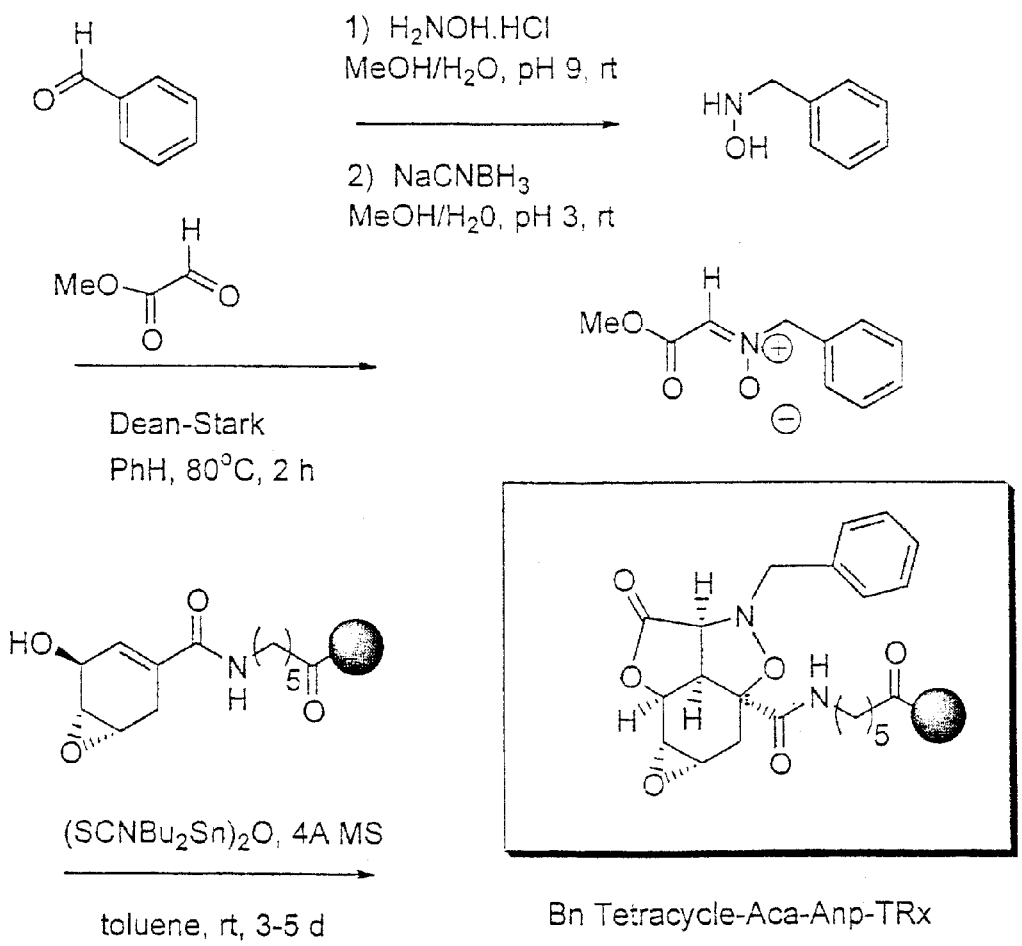
FIG. 13 depicts the synthesis and tandem reaction of the nitrone portion.
Figure 14:
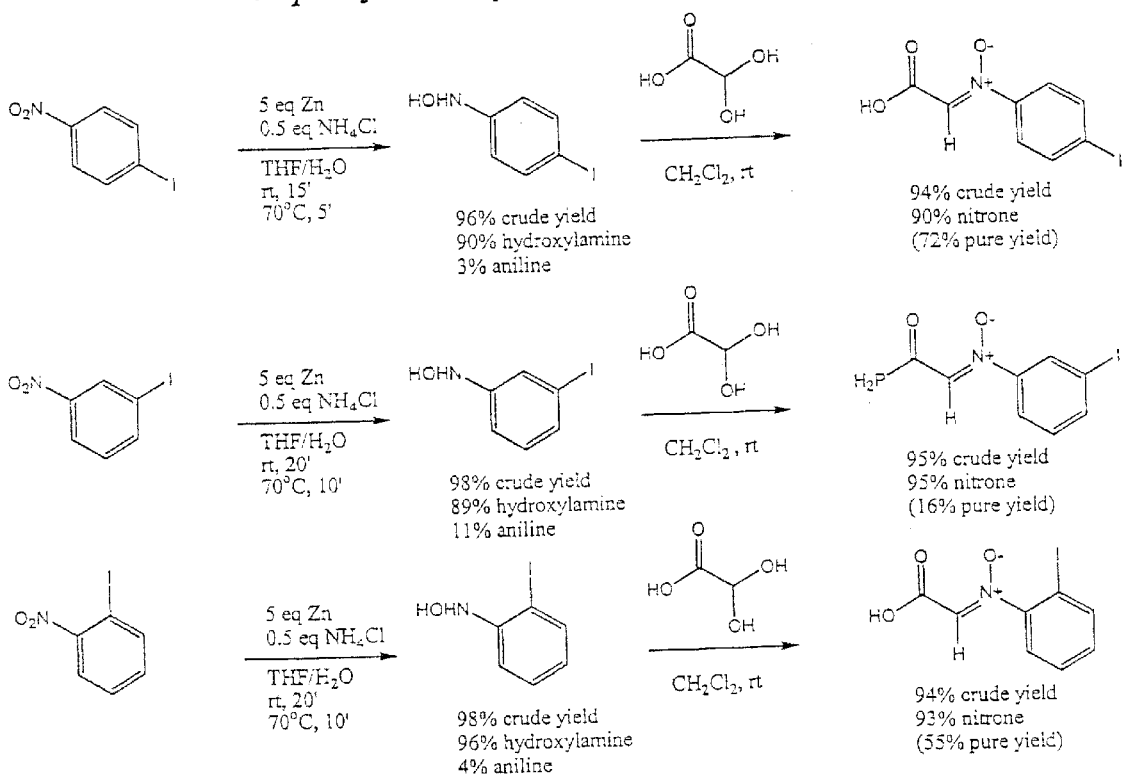
FIG. 14 depicts the synthesis of iodophenyl nitrones.

The above-described epoxyol templates provide useful starting materials for the synthesis of diversifiable scaffold structures. In one particularly preferred embodiment, the synthesis of a tetracyclic scaffold is achieved by reaction of the epoxyol bound template with a nitrone under transesterification conditions to yield a tetracycle as shown in FIG. 13. One of ordinary skill in the art will realize that any commonly used transesterifiction reagent may be employed to yield the desired tetracycle structure, such as the Otera catalyst, $(SCNBu_2Sn)_2O$. Moreover, the nitrone employed in the reaction can also be varied to yield different derivatives of the tetracyclic scaffold. As shown in FIG. 13, a. benzyl nitrone is synthesized from a benzaldehyde precursor. In other embodiments, other aldehydes, such as any aromatic or aliphatic aldehyde, can be substituted to yield different nitrones. Alternatively, FIG. 14 depicts the synthesis of different iodophenyl nitrones from the nitrophenyliodides. These nitrophenyliodides are reduced, preferably with $Zn/NH_4Cl$, to the N-iodophenylhydroxylamine, followed by condensation with glyoxylic acid monohydrate to form the N-iodophenylnitrones. Any of the abovementioned nitrones, or derivatives thereof can be subsequently reacted with the epoxyol template to yield a desired tetracycle, such as the tetracycle shown in Compound 2 below.

Compound 2

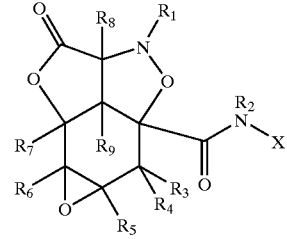

Referring to Compound 2, $R_1$–$R_9$ each independently includes, but is not limited to hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, any functionality incorporating phosphorous, and any substituted or unsubstituted heterocycle wherein said substituted heterocycle is preferably substituted with 1–5 substitutents selected from the group consisting of lower alkyl, halo, hydroxy, amino, thio, lower alkoxy, lower alkylthio, lower alkylamino, nitro, phenoxy, benzyloxy; and X includes, but is not limited, to any of the above, a solid support, a biomolecule or polymer. Furthermore, each of the above functionalities may be unsubstituted or substituted with appropriate chemical moieties. In a particularly preferred embodiment, $R_2$–$R_9$ are each hydrogen, $R_1$ is an substituted or unsubstitued alkyl, aryl, or alkylaryl, and X is a solid support unit or hydrogen.

Figure 15:
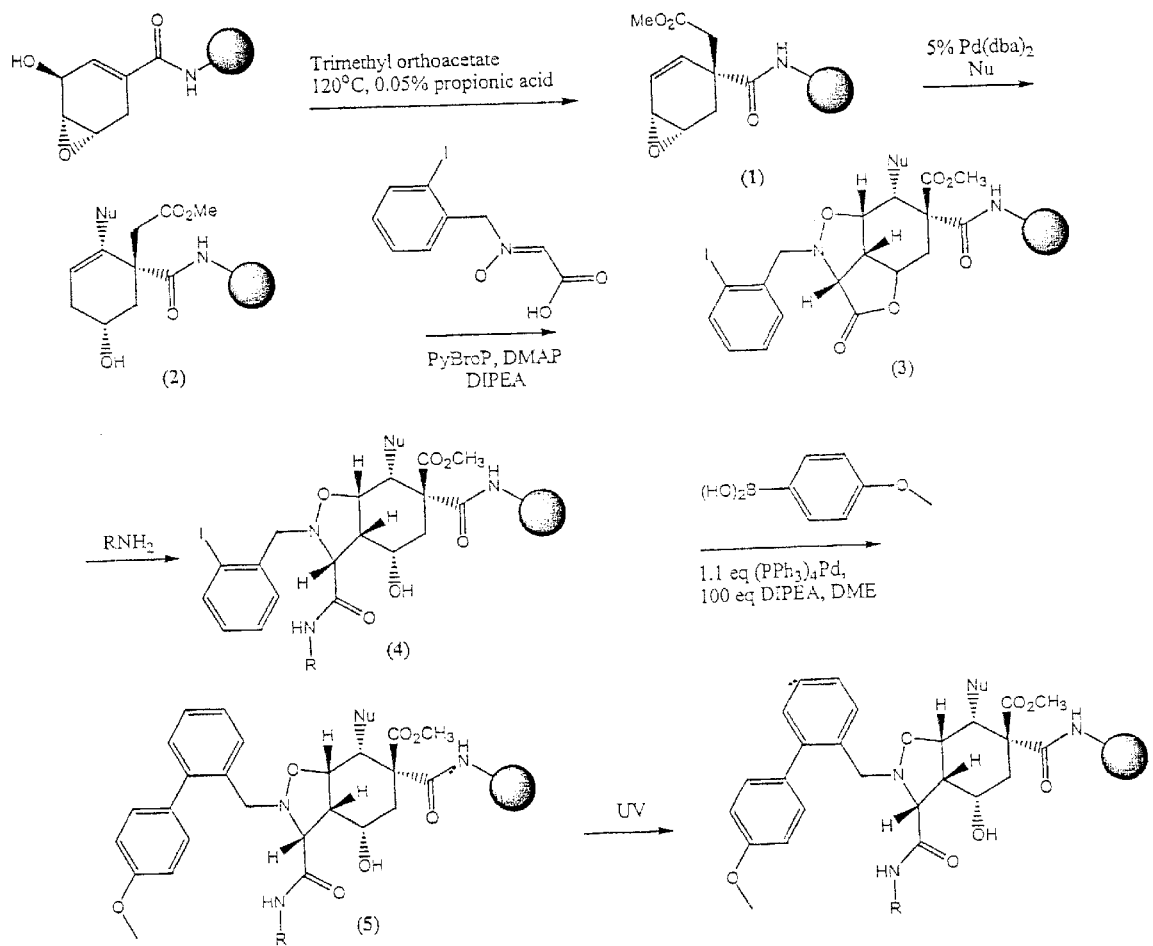
FIG. 15 depicts the synthesis of alternative scaffold structures.

In another particularly preferred embodiment, alternative scaffold structures can be obtained in which the epoxyol bound template is treated with an orthoacetate, such as trimethylorthoacetate to undergo a Johnson ortho-ester-like Claisen rearrangement to yield the ester (1), as shown in FIG. 15 and in Compound 3 below.

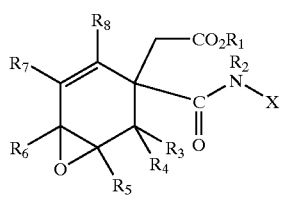

Compound 3

Referring to Compound 3, $R_1$–$R_8$ each independently includes, but is not limited to, hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, any functionality incorporating phosphorous, and substituted or unsubstituted heterocycle wherein said substituted heterocycle is preferably substituted with 1–5 substitutents selected from the group consisting of lower alkyl, halo, hydroxy, amino, thio, lower alkoxy, lower alkylthio, lower alkylamino, nitro, phenoxy, and benzyloxy; and X includes, but is not limited to, any of the above, a solid support, a biomolecule or polymer. Furthermore, each of the above functionalities may be unsubstituted or substituted with appropriate chemical moieties. In a particularly preferred embodiment, $R_2$–$R_8$ are each hydrogen and $R_1$ is a lower alkyl group, such as methyl, and X is a hydrogen or a solid support unit.

Reaction of this scaffold structure with other reagents also yields alternative diversifiable scaffold structures, as shown in FIG. 15. For example, reaction with a palladium allylation catalyst such as $Pd(dba)_2$ and a nucleophile (Y), yields an alternative epoxide opened structure (2), as shown in Compound 4 below.

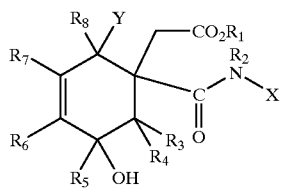

Compound 4

Referring to Compound 4, $R_1$–$R_8$ each independently includes, but is not limited to hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, any functionality incorporating phosphorous, and substituted or unsubstituted heterocycle wherein said substituted heterocycle is preferably substituted with 1–5 substitutents selected from the group consisting of lower alkyl, halo, hydroxy, amino, thio, lower alkoxy, lower alkylthio, lower alkylamino, nitro, phenoxy, and benzyloxy; X includes, but is not limited to, any of the above, a solid support, a biomolecule or polymer; and Y includes, but is not limited to nucleophiles selected from the group consisting of amine, phenol, maleonate, thiol, carboxylic acid, and azide. Furthermore, each of the above functionalities may be unsubstituted or substituted with appropriate chemical moieties. In a particulary preferred embodiment, $R_2$–$R_8$ are each hydrogen and $R_1$ is a lower alkyl group, such as methyl, X is a hydrogen or a solid support unit, and Y is an amine, phenol, maleonate, thiol, carboxylic acid, or azide.

Subsequent reaction with a nitrone, under standard conditions, yields an alternative diversifiable scaffold structure (3), as shown in Compound 5 below, where the addition of reagents, such as but not limited to, amines or boronic acid, yields diversified structures, as shown in FIG. 15.

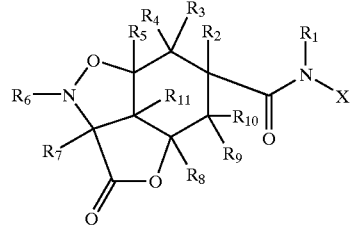

Compound 5

Referring to Compound 5, $R_1$–$R_{11}$ each independently includes, but is not limited to, hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, any functionality incorporating phosphorous, and substituted or unsubstituted heterocycle wherein said substituted heterocycle is preferably substituted with 1–5 substituents selected from the group consisting of lower alkyl, halo, hydroxy, amino, thio, lower alkoxy, lower alkylthio, lower alkylamino, nitro, phenoxy, and benzyloxy; and X includes, but is not limited to, any of the above, a solid support unit, a biomolecule or polymer. Furthermore, each of the above functionalities may be unsubstituted or substituted with appropriate chemical moieties. In a particularly preferred embodiment, $R_1$–$R_5$ and $R_7$–$R_{11}$ are each hydrogen, $R_6$ is a substituted or unsubstituted aryl, alkyl, arylalkyl; and X is hydrogen or a solid support unit.

Figure 16:
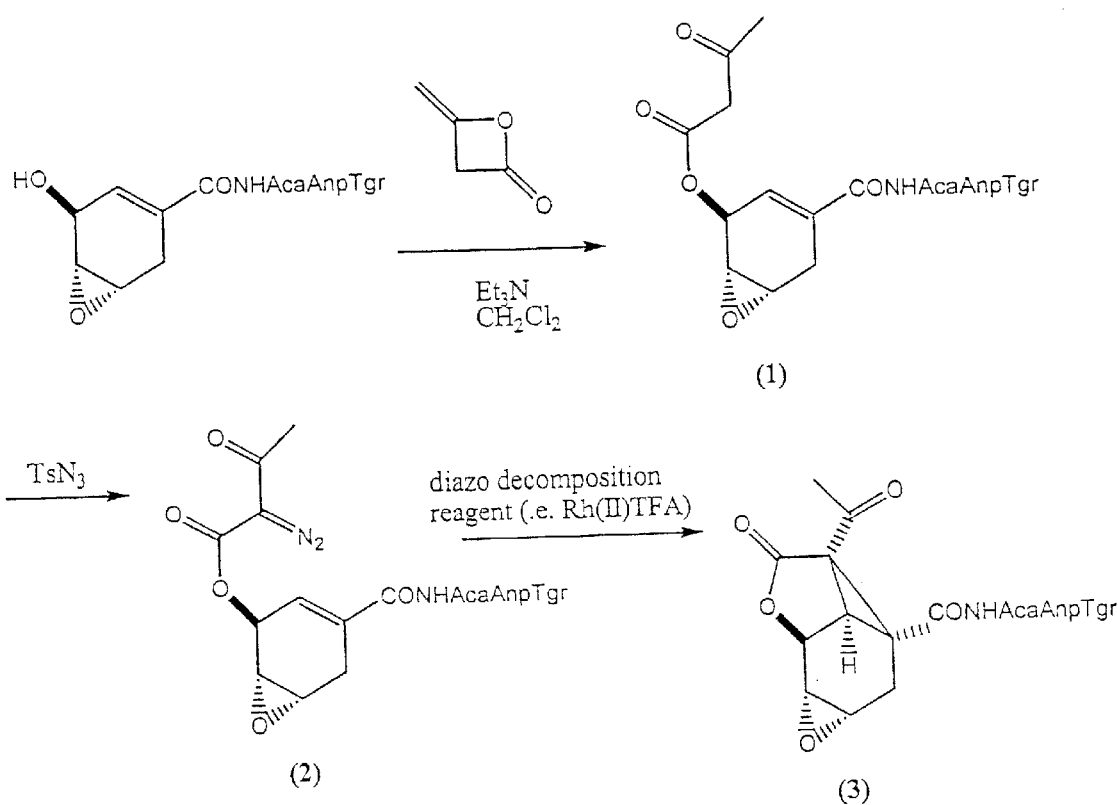
FIG. 16 depicts acetoacetate as a synthetic intermediate.

Additionally, in another particularly preferred embodiment, a different scaffold can be constructed whereby the inventive epoxyol template is treated with an acylating agent including, but not limited to a diketene, to yield the diketone, as shown in FIG. 16. Subsequent reaction with tosyl azide yields the diazo β-keto ester (2). Finally, cyclopropanation with a rhodium or copper catalyst yields the cyclic scaffold structure (3), as shown in Compound 6 below, which contains several radially diversifiable moieties.

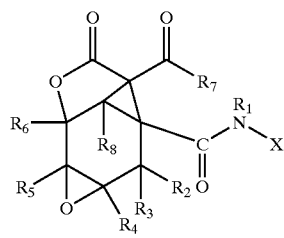

Compound 6

Referring to Compound 6, $R_1$–$R_8$ each independently includes, but is not limited to, hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, any functionality incorporating phosphorous, and substituted or unsubstituted heterocycle wherein said substituted heterocycle is preferably substituted with 1–5 substituents selected from the group consisting of lower alkyl, halo, hydroxy, amino, thio, lower alkoxy, lower alkylthio, lower alkylamino, nitro, phenoxy, and benzyloxy; and X includes, but is not limited to any of the above, a solid support unit, a biomolecule or polymer. Furthermore, each of the above functionalities may be unsubstituted or substituted with appropriate chemical moieties. In particularly preferred embodiments, $R_1$–$R_6$ and $R_9$ are each hydrogen, $R_7$ is a lower alkyl, such as methyl, and X is a hydrogen or a solid support unit.

One of ordinary skill in the art will appreciate that the particular functional groups available at any site in the template structures must be compatible with the particular reaction chemistry being utilized in the synthesis of the scaffold structures. Additionally, the compounds described herein contain one or more centers of asymmetry and may thus give rise to enantiomers, diastereomers and other stereoisomeric forms. The present invention is meant to include all such possible stereoisomers as well as their racemic and optically pure forms. Optically active (R) and (S) isomers may be prepared using chiral synthesis, chiral reagents, or resolved using conventional techniques. When the compounds disclosed herein contain olefinic double bonds, it is intended to include both E and Z geometric isomers. Furthermore, the examples and scaffolds, and the functional groups contained therein, presented above are not intended to be exclusive; rather all equivalents thereof are intended to be within the scope of the present invention.

Synthesis of Pyridine Based Scaffold Structures

The present invention also provides a method for the synthesis of compounds and complex combinatorial libraries based on isonicotinamide in the solution phase or on the solid support, as discussed previously.

Figure 17:
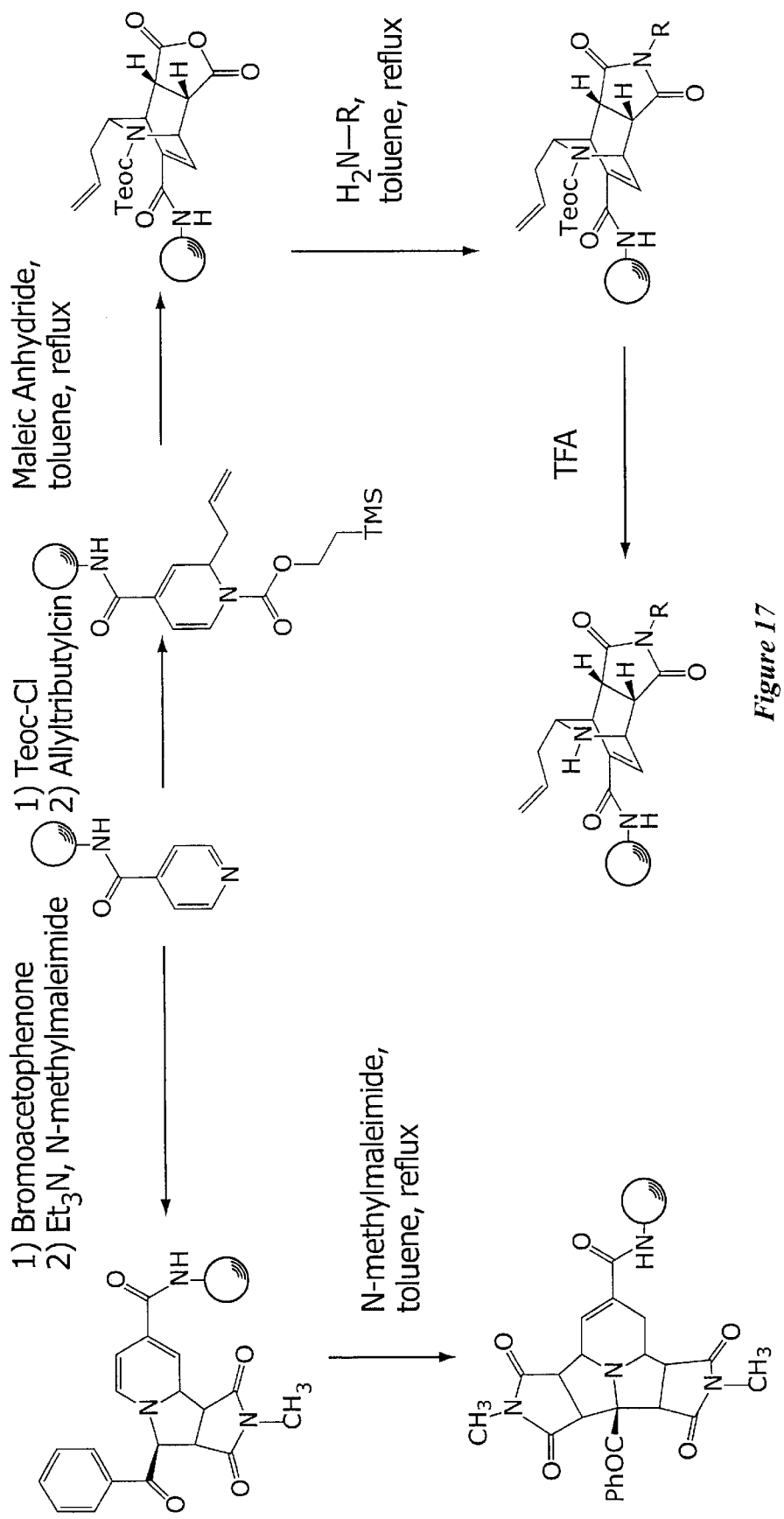
FIG. 17 depicts the solid phase synthesis of rigid polycyclic core structures.

In particularly preferred embodiments, the solid support bound isonicotinamide can be first converted into an azomethine ylide in the synthesis of diversifiable scaffold structures. For example, in one particularly preferred embodiment, the cup-like pentacyclic piperidine scaffold (1), as shown in FIG. 17, can be obtained by reaction of the template with bromoacetopheone, triethylamine and N-methylmaleimide to yield the azomethine ylide. Subsequently, reaction with N-methylmalimide under reflux conditions yields the desired pentacycle, as shown in FIG. 7a below, wherein Z is N—R, and wherein R is preferably a substituted or unsubstituted alky or aryl mioety and which contains several sites of latent functionality for diversification. One of ordinary skill in the art will realize that the synthesis of the scaffold is not limited to the pentacyclic structure and may also be diversified by employing any double substituted or unsubstituted bond containing an electron withdrawing group, to yield alternative piperidine structures for Compound 7a, in which Z is $CH_2$, O or S, or structures as shown in Compound 7b.

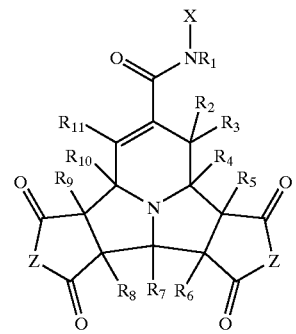

Compound 7a

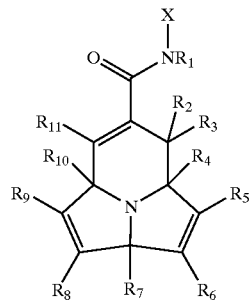

Compound 7b

Referring to Compounds 7a and 7b, $R_1$–$R_{11}$ each independently includes hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, any functionality incorporating phosphorous, and substituted or unsubstituted heterocycle wherein said substituted heterocycle is preferably substituted with 1–5 substituents selected from the group consisting of lower alkyl, halo, hydroxy, amino, thio, lower alkoxy, lower alkylthio, lower alkylamino, nitro, phenoxy, and benzyloxy; X is any of the above, a solid support, a biomolecule or polymer; and Z is NR, wherein R includes but is not limited to any substituted or unsubstituted alkyl or aryl mioety, $CH_2$, O, or S. In particularly preferred embodiments, $R_1$ is hydrogen or any aliphatic group, $R_2$–$R_6$ and $R_8$–$R_{11}$ are each hydrogen, $R_7$ is a benzoyl moiety, X is a hydrogen, or a solid support unit; and in the case of Compound 7a, Z is NR, wherein R includes but is not limited to any substituted or unsubstituted alkyl or aryl mioety.

Figure 18:
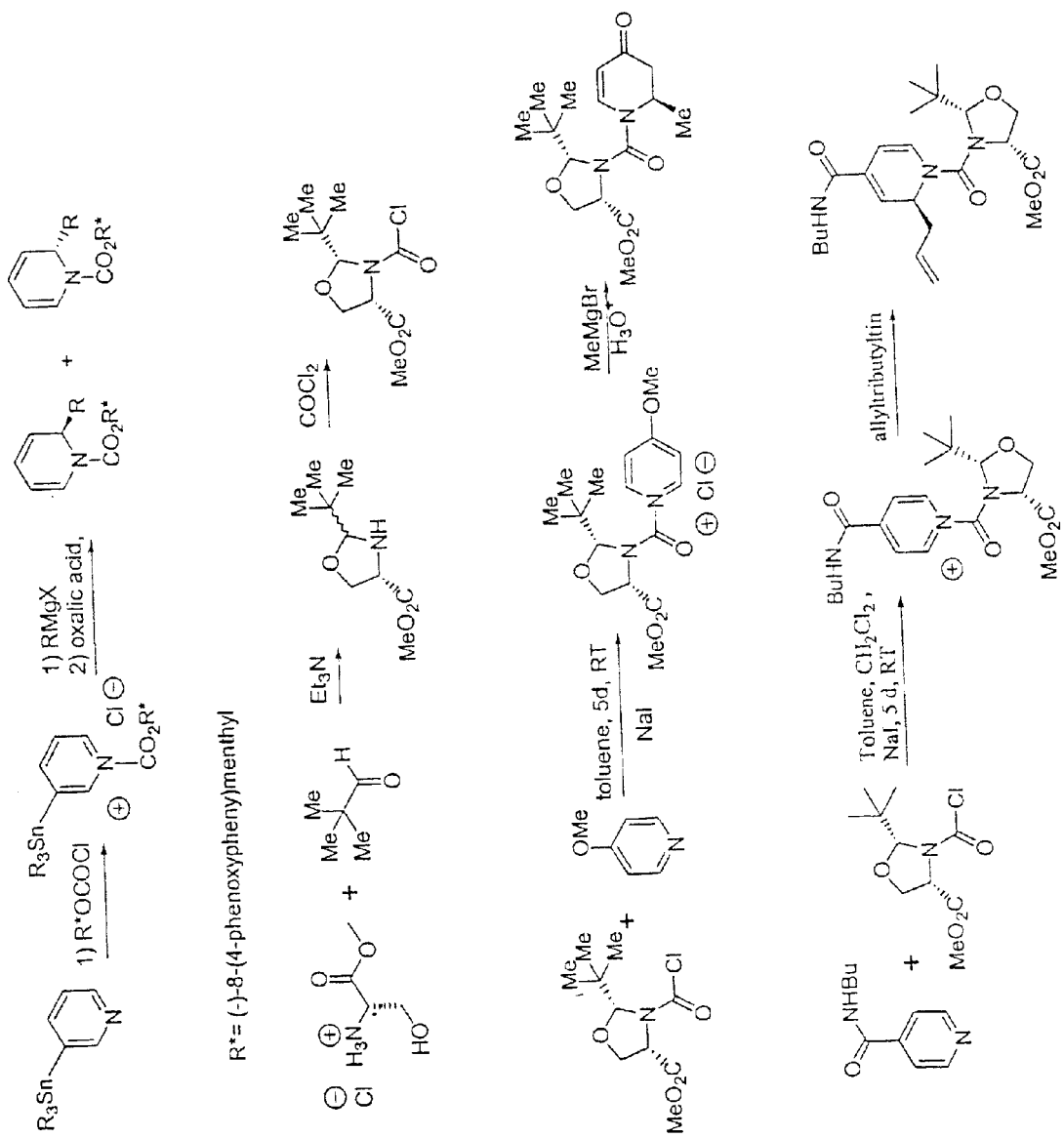
FIG. 18 depicts the asymmetric synthesis of 1,2-dihydropyridines. See, Comins et al. *J. Org. Chem.* 1991, 56, 7197; Comins et al. *J. Am. Chem. Soc.* 1993, 115, 8851; Streith et al. *Tet. Lett.* 1994, 35, 3927; Seebach et al. *Tet. Lett.* 1984, 25, 2545.
Figure 19:
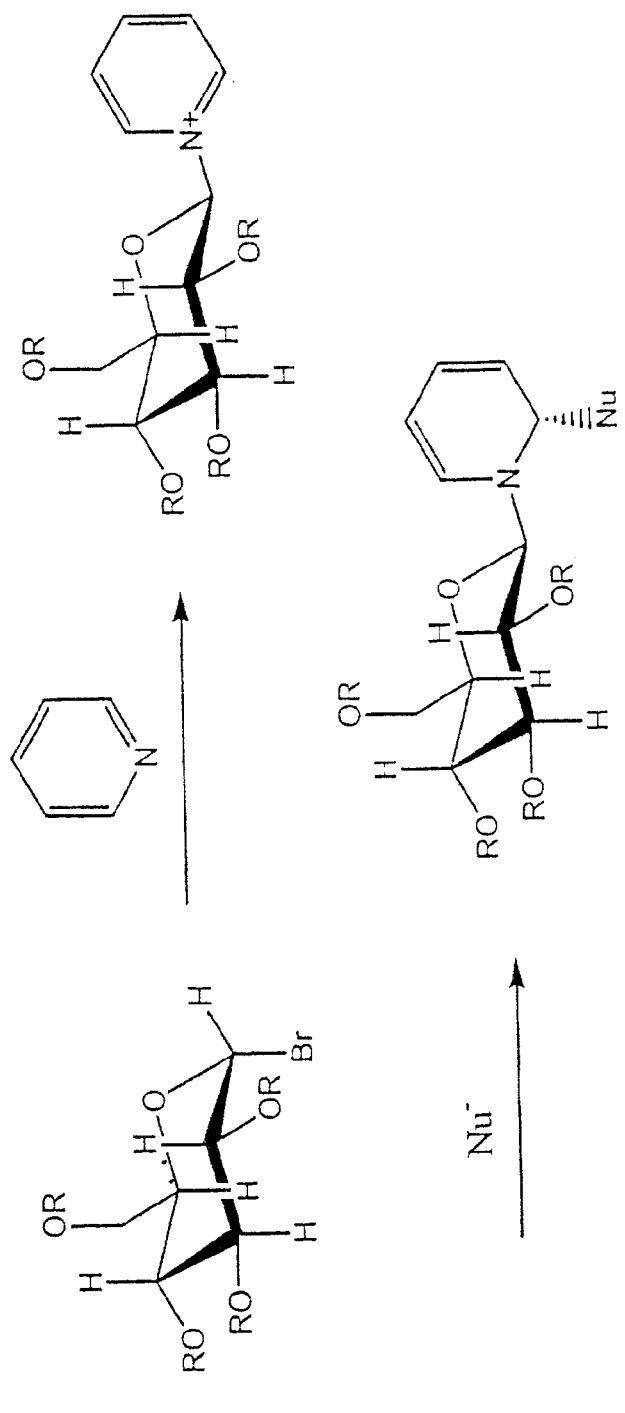
FIG. 19 depicts the use of a sugar based chiral auxiliary.
Figure 20:
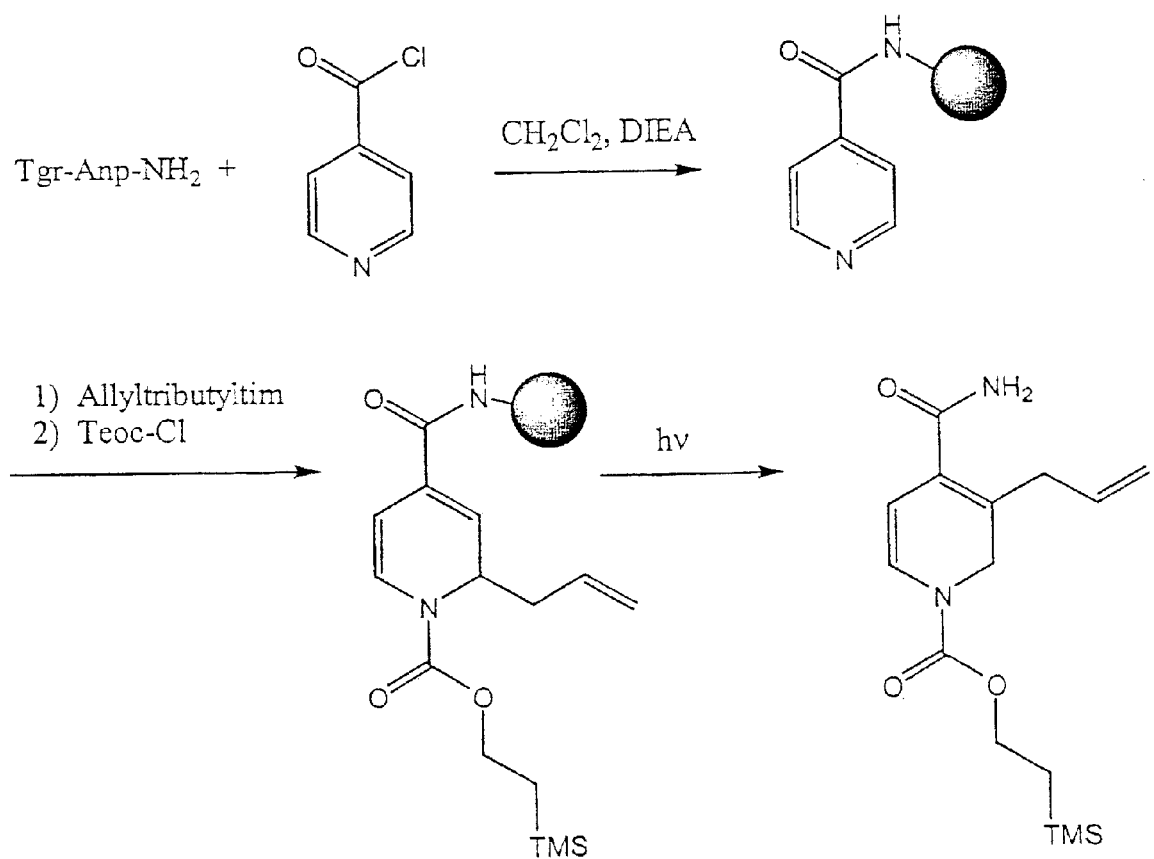
FIG. 20 depicts a novel rearrangement from photolytic cleavage.
Figure 21:
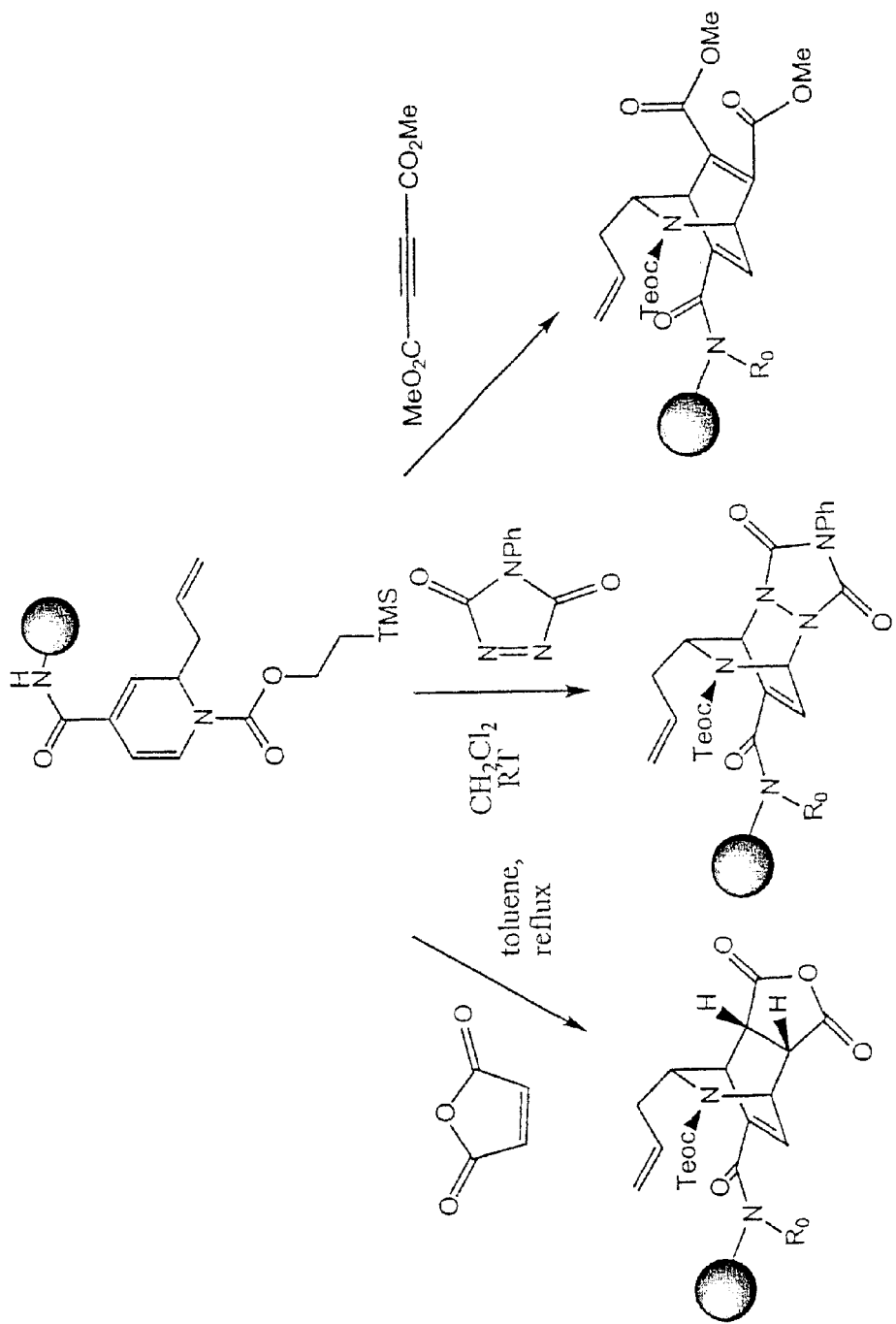
FIG. 21 depicts examples of solid phase cycloaddition chemistry.

In another particularly preferred embodiment, the resin bound isonicotinamide template is converted to the allyl derivative, from which isoquinuclidine scaffolds are synthesized, as shown in FIG. 17. First, the resin bound template is treated with allyltributyltin to yield the allyl intermediate. One of ordinary skill in the art will realize that this reaction may also be effected stereoselectively to yield stereochemically pure scaffold structures. For example, in one particularly preferred embodiment, the synthesis of an enantiomerically pure compound may be effected by the asymmetric synthesis of 1,2 dihydropyridine as shown in FIG. 18, which can then be used in the synthesis of enantiomerically pure scaffold structures and combinatorial libraries. FIG. 19 also depicts a method for the stereoselective synthesis of 1,2-dihydropyridines utilizing a sugar based chiral auxiliary. Alkylation of the pyridine with glucosyl bromide yields the pyridinium salt which is then capable of directing the addition of nucleophiles stereoselectively. In addition to providing stereochemically pure compounds, the inventive method also provides a novel rearrangement of the allyl intermediate as shown in FIG. 20. Upon exposure to light, the allyl intermediate undergoes a rearrangement to yield a new intermediate which can subsequently be utilized in the synthesis of the scaffold, thus providing further diversity. The intermediate, as shown in FIG. 17, or any of the intermediates discussed above, may be subsequently reacted with dienophiles, including, but not limited to maleic anhydride, aza-dicarboximide, and dimethylacetylenedicarboxylate, in a Diels-Alder reaction to yield various tricyclic intermediates, as shown in FIG. 21 and more generally in Compounds 8a and 8b. Subsequent reaction of the imide intermediate with a primary amine, and removal of the protecting group yields alternative isoquinuclidine scaffolds, as shown in FIG. 17, and more generally in Compound 8b.

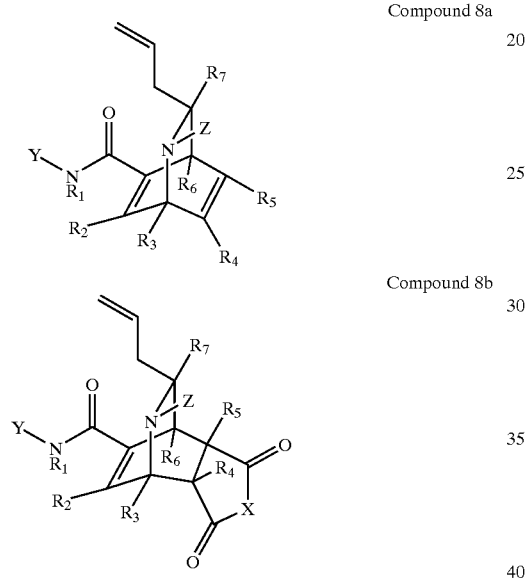

Compound 8a

Compound 8b

Figure 22:
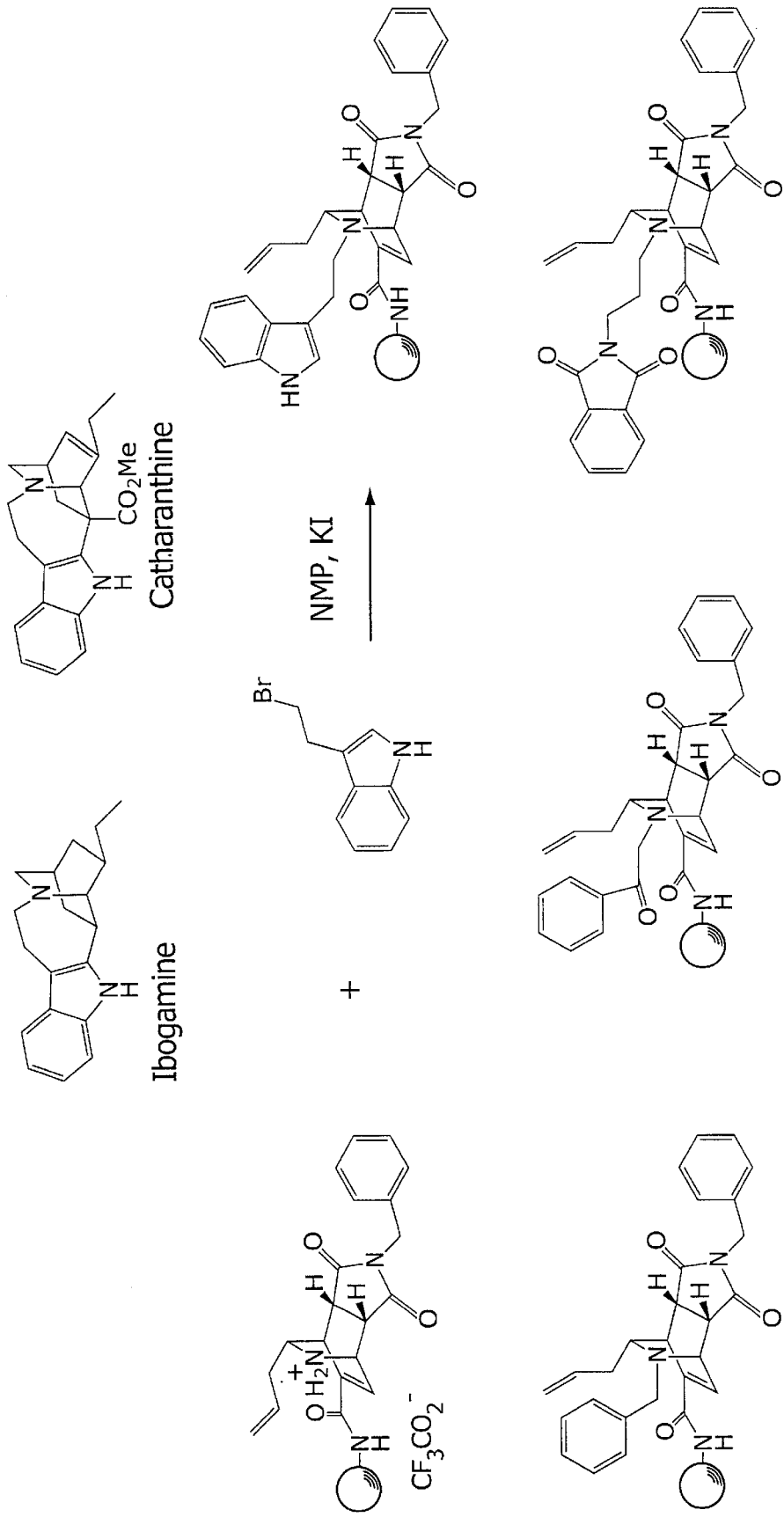
FIG. 22 depicts the stereoselective synthesis of ibogamine-like compounds compatible with nanodroplet assays.
Figure 23:
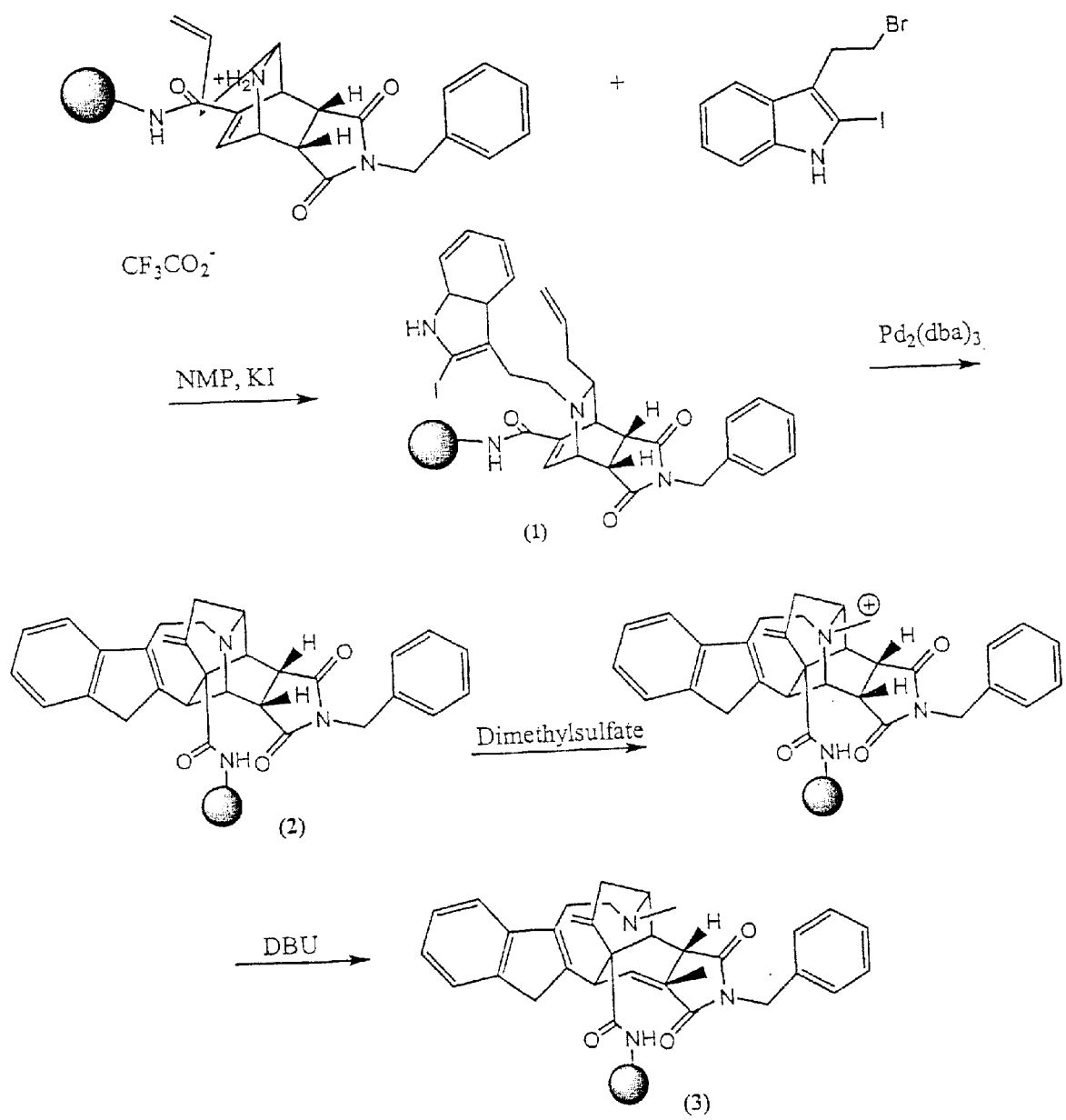
FIG. 23 depicts further reactions of isoquinuclidine scaffolds.

Referring to Compounds 8a and 8b, $R_1$–$R_7$ each independently includes, but is not limited to hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, hydrogen, alkynyl, halogen, cyano, sulfhydryl, carbamoyl, nitro, trifluoromethyl, any functionality incorporating phosphorous, and substituted or unsubstituted heterocycle wherein said substituted heterocycle is preferably substituted with 1–5 substituents selected from the group consisting of lower alkyl, halo, hydroxy, amino, thio, lower alkoxy, lower alkylthio, lower alkylamino, nitro, phenoxy, and benzyloxy; X includes, but is not limited to NR, wherein R includes but is not limited to any substituted or unsubstituted alkyl or aryl mioety, CH$_2$, O or S; Y includes, but is not limited to hydrogen, a solid support unit, a polymer or biomolecule; and Z includes, but is not limited to, hydrogen or indole. Furthermore, each of the above functionalities may be unsubstituted or substituted with appropriate chemical moieties. In particularly preferred embodiments, $R_1$–$R_7$ are each hydrogen, X is NR, wherein R includes but is not limited to any substituted or unsubstituted alkyl or aryl moiety, Y is a solid support unit, and Z is an indole to generate an ibogamine-like compound, as shown in FIG. 22. Furthermore, as shown in FIG. 23, an indole substituted allyl scaffold (1) is also capable of undergoing palladium insertion to yield the cyclic structure (2). Reaction with dimethyl sulfate and DBU yields an alternative structure (3) depicted in FIG. 23.

Figure 24:
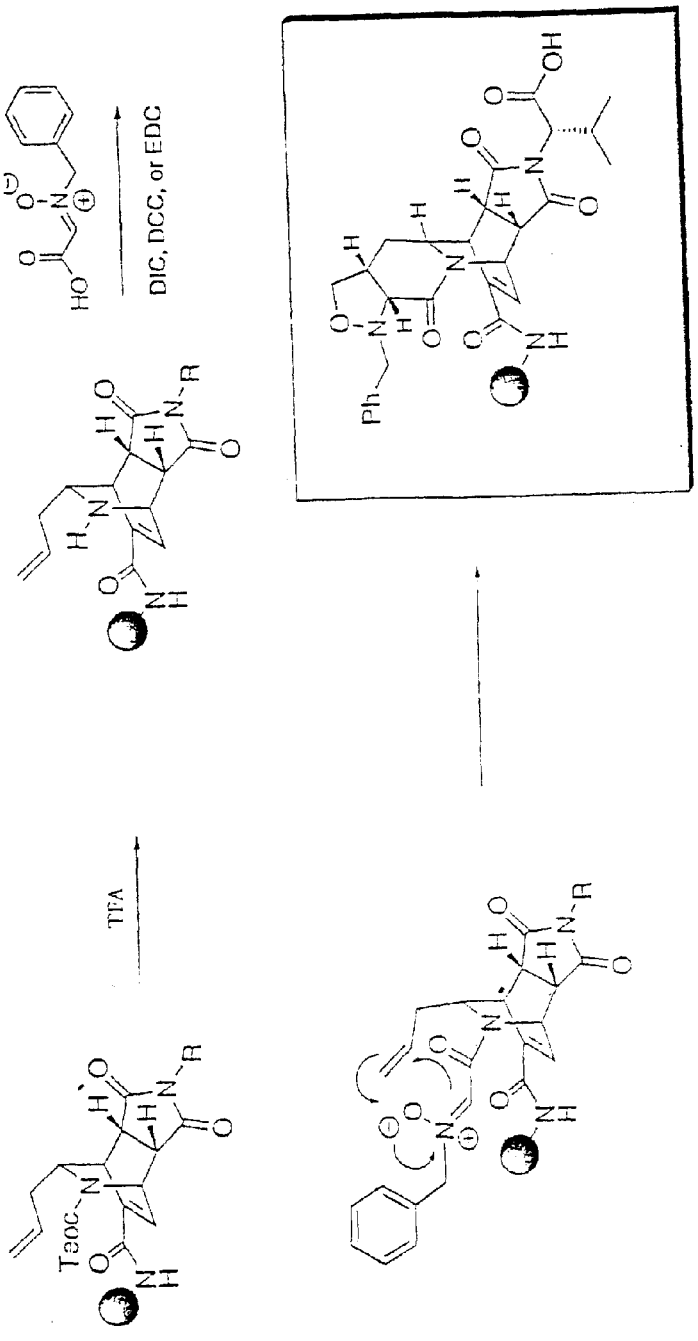
FIG. 24 depicts the synthesis of polycyclic alkaloid scaffold structures.

In yet another particularly preferred embodiment, the tandem acylation and [(3+2] cyclization employed in the shikimic acid based combinatorial library discussed above can also be utilized to generate a polycyclic alkaloid from the deprotected isoquinuclidine scaffold as shown in FIG. 24 and Compounds 9a and 9b below.

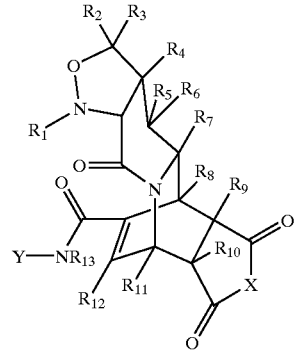

Compound 9a

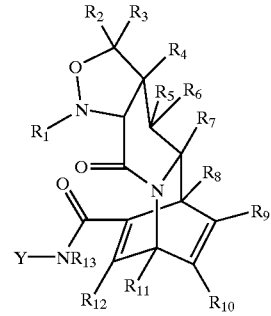

Compound 9b

Referring to Compounds 9a and 9b above, $R_1$–$R_{13}$ each independently includes, but is not limited to hydrogen, any linear or branched alkyl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, any functionality incorporating phosphorus, and substituted or unsubstituted heterocycle wherein said substituted heterocycle is preferably substituted with 1–5 substituents selected from the group consisting of lower alkyl, halo, hydroxy, amino, thio, lower alkoxy, lower alkylthio, lower alkylamino, nitro, phenoxy, and benzyloxy; X includes, but is not limited to, NR, wherein R includes but is not limited to any substituted or unsubstituted alkyl or aryl moiety, CH$_2$, O or S; and Y includes, but is not limited to, hydrogen, a solid support unit, a polymer or biomolecule. Furthermore, each of the above functionalities may be unsubstituted or substituted with appropriate chemical moieties. In particularly preferred embodiments, $R_1$ is a benzyl, and $R_2$–$R_{13}$ are each hydrogen, X is NR, wherein R includes but is not limited to any substituted or unsubstituted alkyl or aryl moiety, and Y is a solid support unit.

One of ordinary skill in the art will appreciate that the particular functional groups available at any site in the isonicotinamide-based template structures must be compatible with the particular reaction chemistry being utilized in the synthesis of the scaffold structures. Additionally, the compounds described herein contain one or more centers of asymmetry and may thus give rise to enantiomers, diastereomers and other stereoisomeric forms. The present invention is meant to include all such possible stereoisomers as well as their racemic and optically pure forms. Optically active (R) and (S) isomers may be prepared using chiral synthesis, chiral reagents or resolved using conventional techniques. When the compounds disclosed herein contain olefinic double bonds, it is intended to include both E and Z geometric isomers. Furthermore, the templates and scaffolds, and the functional groups contained therein and the reagents utilized, presented above are not intended to be exclusive; rather all equivalents thereof are intended to be within the scope of the presently claimed invention.

Reactions at Latent Functionality in the Inventive Scaffolds

Once the inventive scaffolds have been synthesized as discussed above, diversification reactions may be employed at each of the different latent functionality sites present in the scaffold. One of ordinary skill in the art will appreciate that the reactivity of a particular functionality must be considered when selecting a reagent for diversification.

Figure 25:
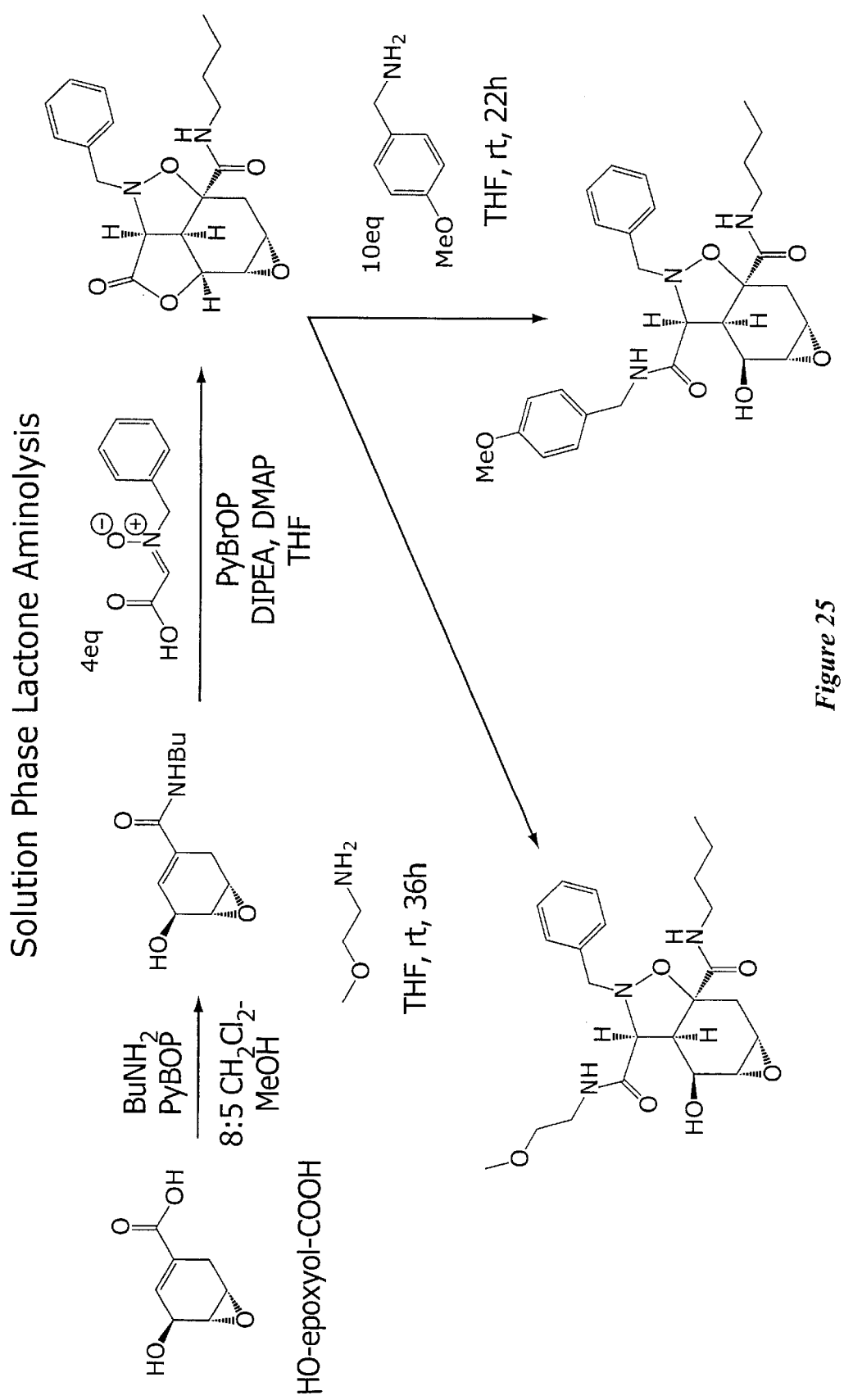
FIG. 25 depicts solution phase lactone aminolysis.
Figure 27:
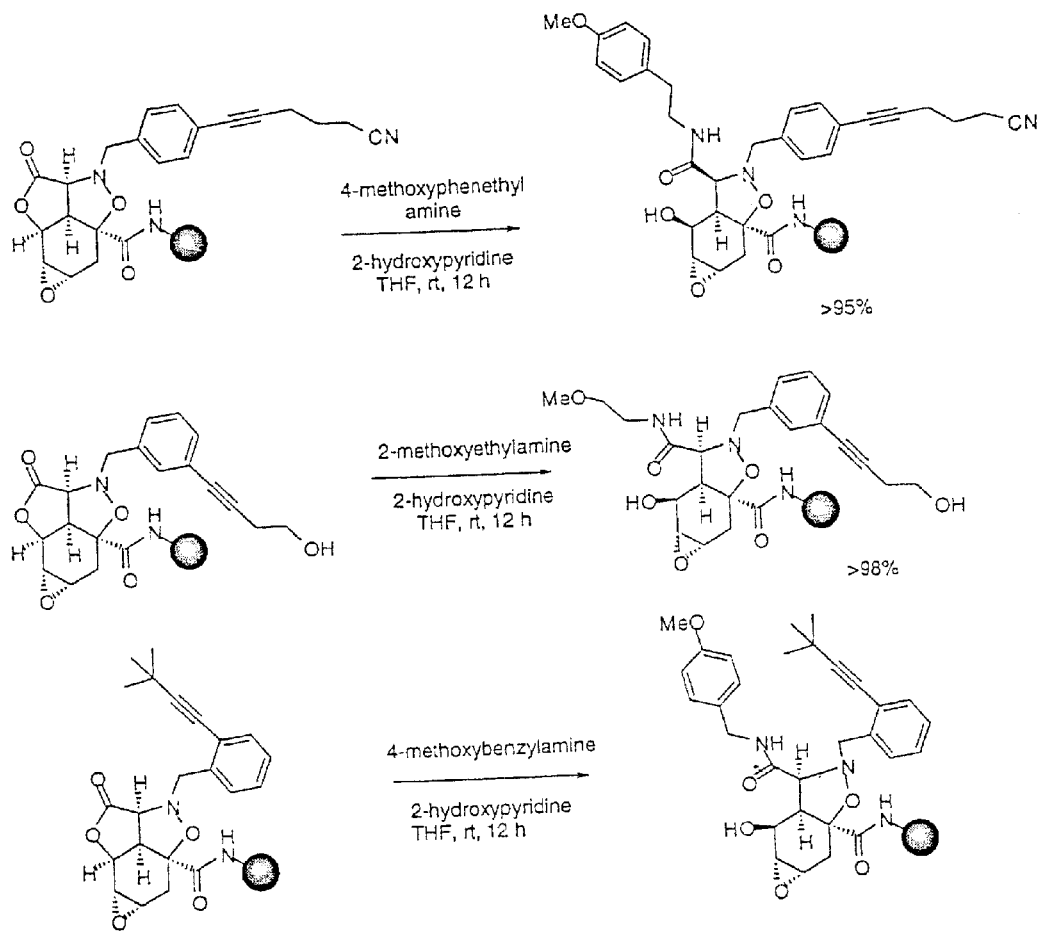
FIG. 27 depicts 2-hydroxypyridine-catalyzed butyrolactone aminolysis.
Figure 28:
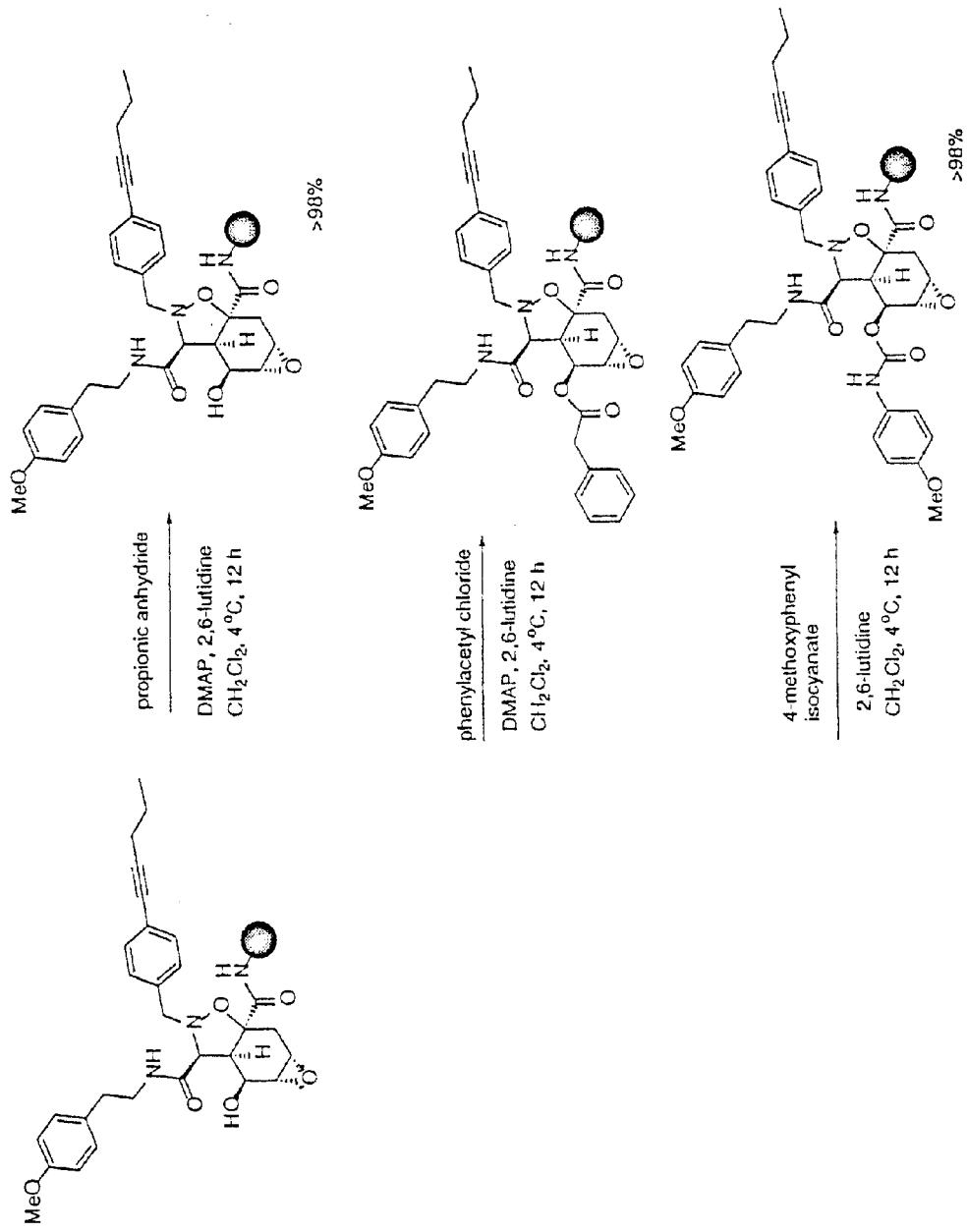
FIG. 28 depicts acylation of the unmasked hydroxyamide.
Figure 29:
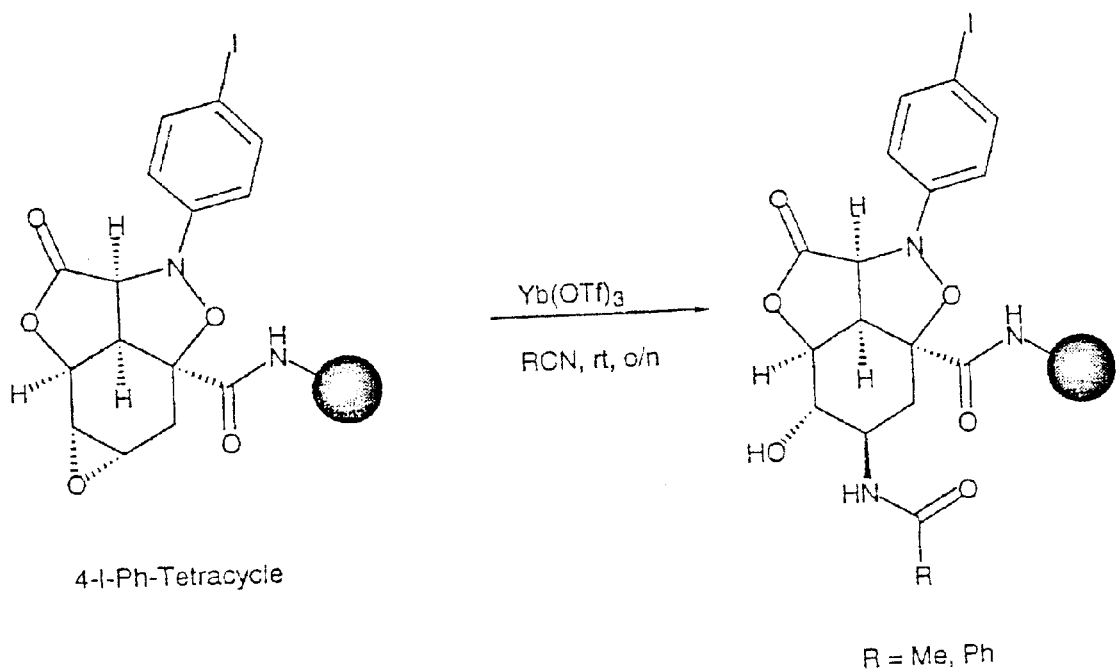
FIG. 29 depicts epoxide ring opening reactions.
Figure 30:
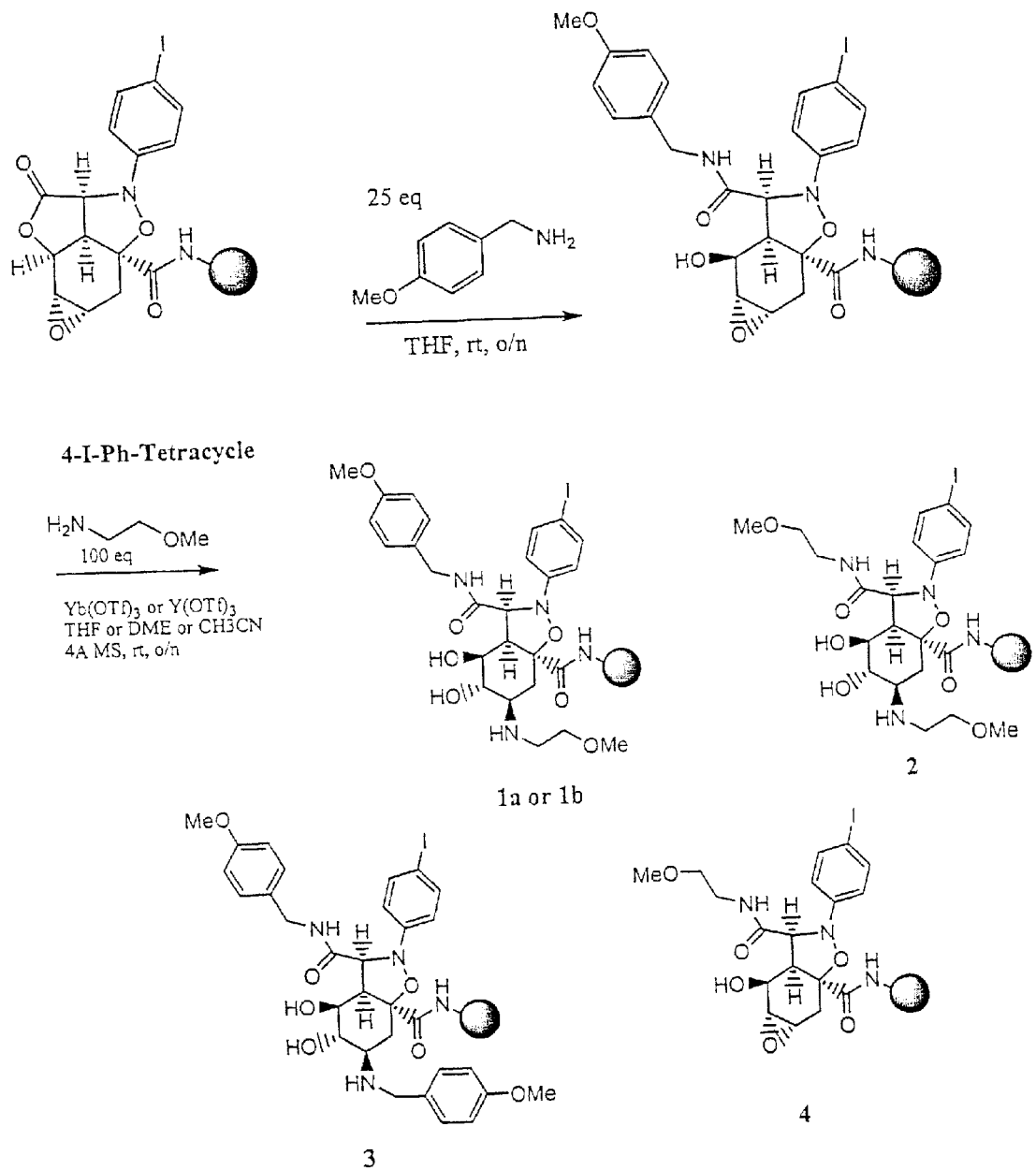
FIG. 30 depicts additional epoxide ring opening reactions.
Figure 32:
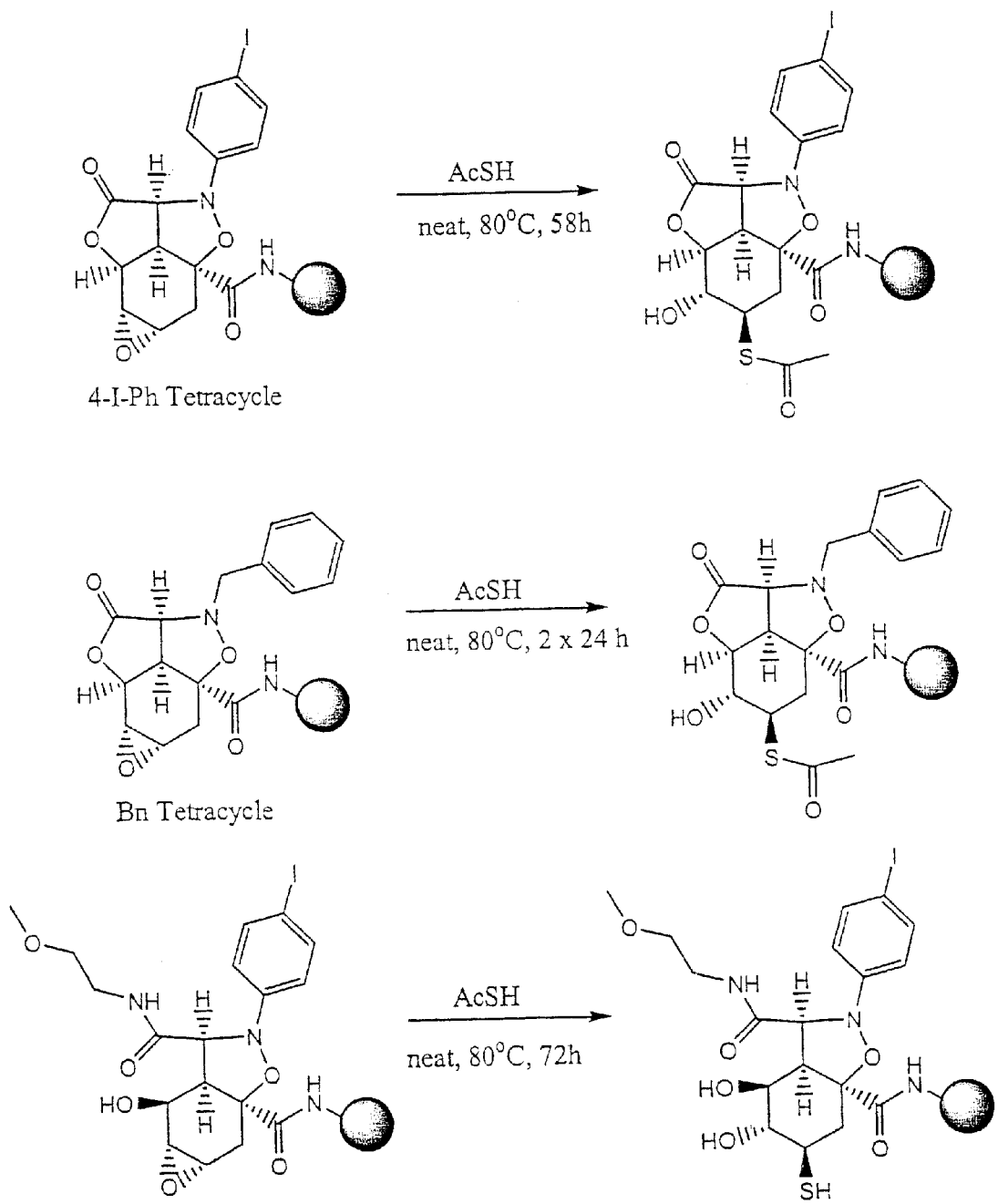
FIG. 32 depicts epoxide thiolysis.
Figure 33:
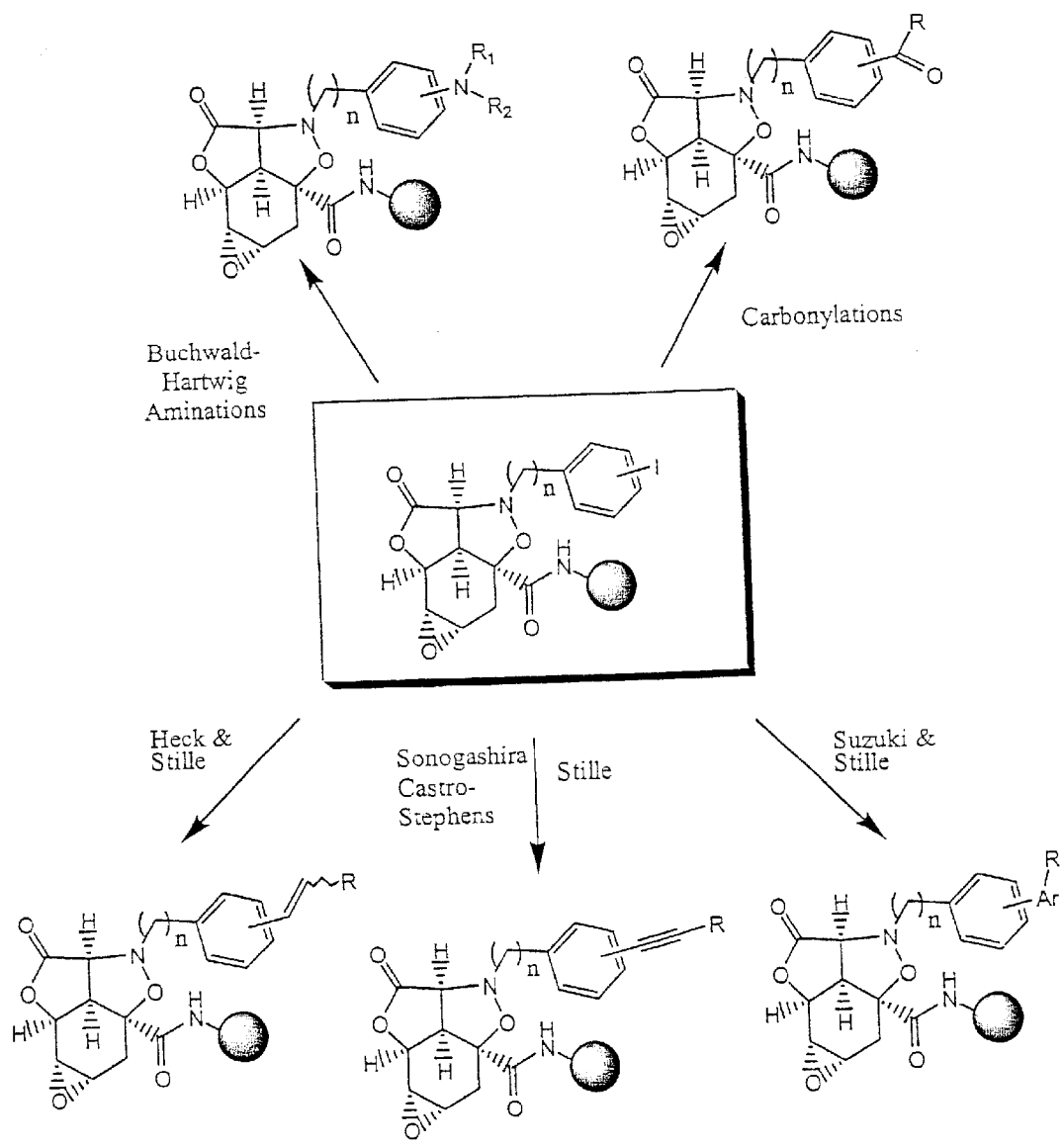
FIG. 33 depicts solid phase palladium chemistry.
Figure 34:
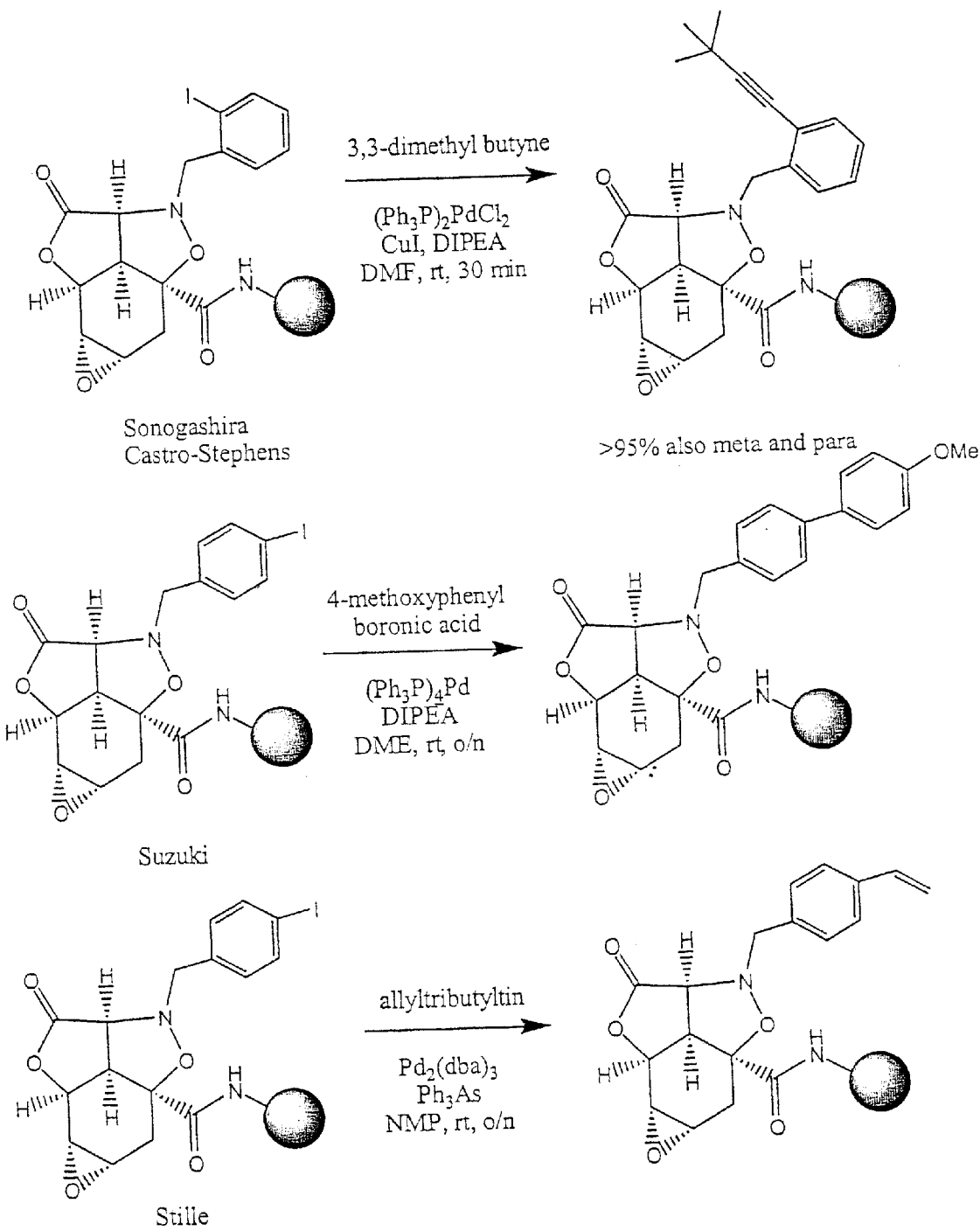
FIG. 34 depicts examples of palladium cross-coupling reactions at the aryl iodide.
Figure 35:
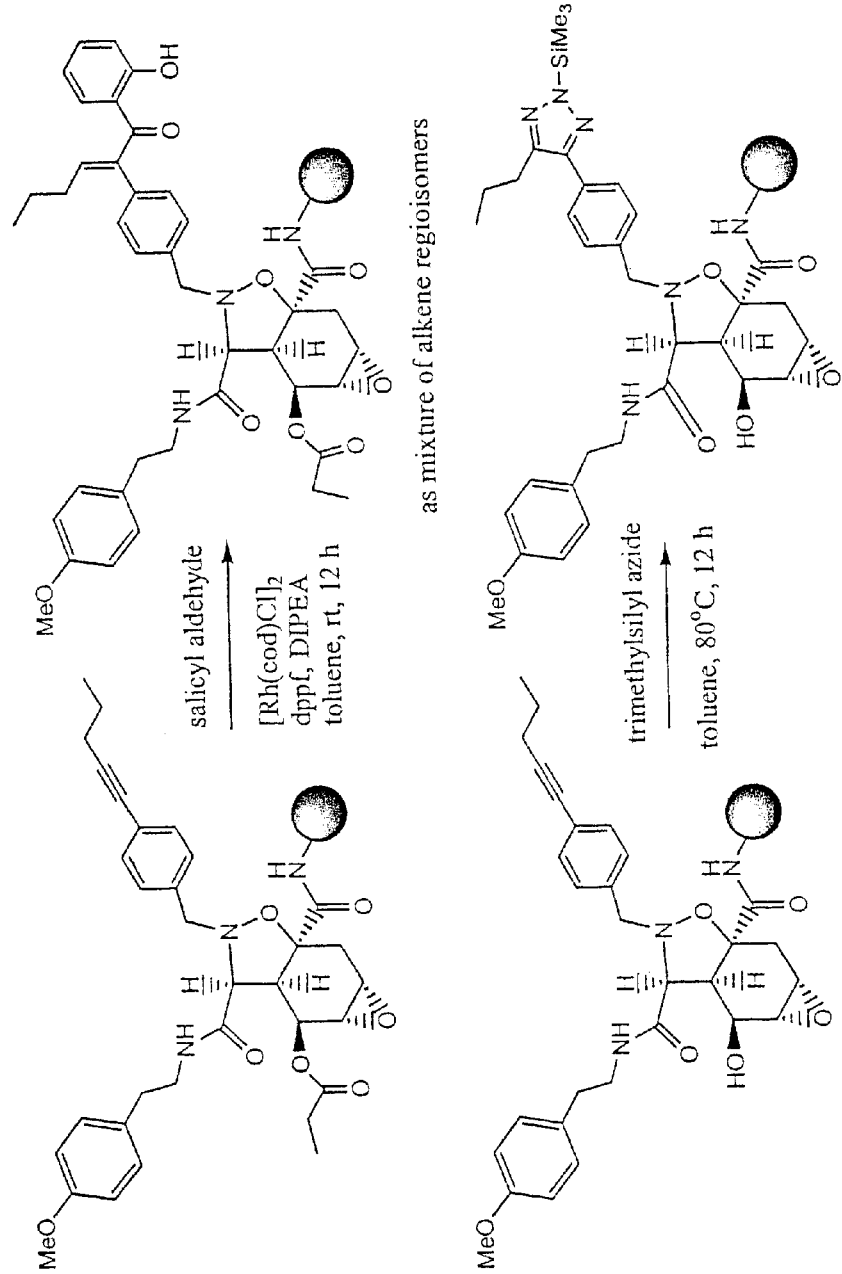
FIG. 35 depicts rhodium-catalyzed hydroacylation and azide cycloaddition at the aryl alkyne.
Figure 36:
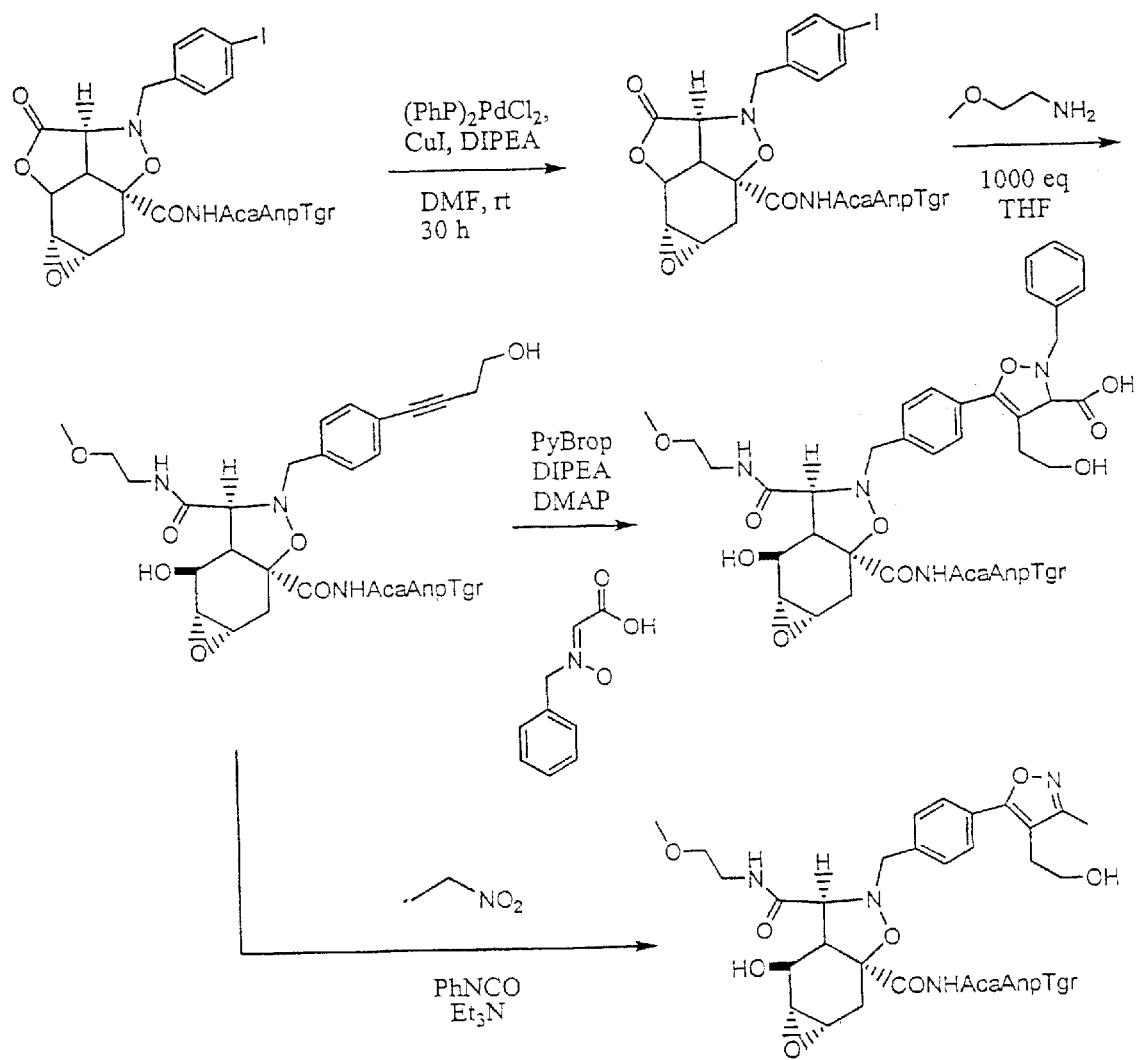
FIG. 36 depicts nitrone and nitrile oxide, alkyne cycloadditions.

In one particularly preferred embodiment, diversification reactions are employed on the shikimic acid based tetracyclic scaffold. Examples of specific reactions to which some or all of the shikimic acid based tetracyclic systems can be subjected in solution or on the solid support include i) addition of nucleophiles (primary and secondary amines) to the γ-lactone function as shown in FIGS. 25, 26 and 27; ii) functionalization of the free hydroxyl with electrophiles (for example, isocyanates, anhydrides, or acid chlorides as depicted in FIG. 28); iii) opening of the epoxide with nucleophiles, such as amines, under ytterbium catalysis as shown in FIGS. 29 and 30, or thiols or hydroxyls as shown in FIGS. 31 and 32); iv) cleavage of the N—O bond of tetrahydroisoxazole to release a 1,3 amino alcohol that can be functionalized with various electrophiles such as acid chlorides, sulfonyl chlorides, or isocyanates; and v) functionalization at the iodide in the aromatic ring. For example, functionalization of the iodide in the aromatic ring can be effected by conversion to such structures as amines, amides, aromatic rings, alkenes, alkynes, and heterocycles using palladium-catalyzed chemistry, as shown in FIG. 33 which depicts various diversification reactions that can be employed on an iodoaromatic ring, such as Buchwald-Hartwig aminations, Heck and Stille couplings, Sonogashira/Castro-Stephens couplings, Suzuki and Stille couplings, and carbonylations. More specifically, FIG. 34 depicts palladium cross-coupling reactions at the aryl iodide using the Sonogashira-Castro-Stephens, Suzuki and Stille reactions. Furthermore, resulting aryl alkynes can undergo rhodium-catalyzed hydroacylation and azide cycloaddition as shown in FIG. 35, and nitrone and nitrile oxide cycloaddition as shown in FIG. 36.

Figure 39:
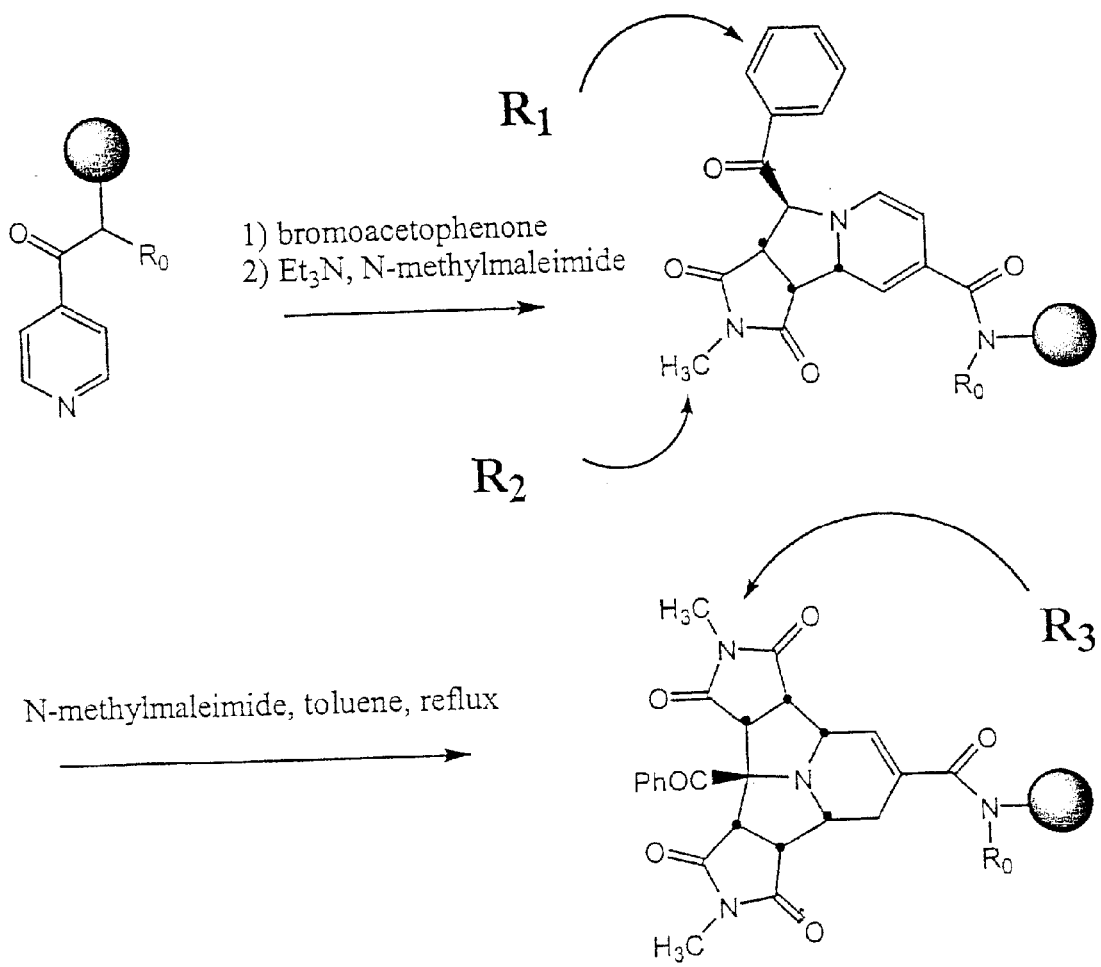
FIG. 39 depicts representative diversity sites for the cup-like pentacyclic scaffold.

In another particularly preferred embodiment, the isoquinuclidine core as shown in FIG. 37, can be diversified by reaction at potential diversity dites such as the amine, the bridge carbon and the amide functionality. For example, the amide may be functionalized using a Mitsunobu reaction to generate alcohols such as straight chain, branched, and cyclic alcohols. In particularly preferred embodiments, the alcohol should not have an unprotected site that could be acylated, such as an amine, or thiol. The bridge amine can be subjected to reaction to yield chloroformates, by reacting alcohols with phosgene, and anything that can acylate or alkylate an amine, such as alkyl bromides, mesylates, and aldehydes to name a few. The bridge carbon may also be functionalized to yield an allyl and any allyl derivative of allyltributyltin, thiazole or indole, but is not limited to these functionalities. Furthermore, the carboximide may be functionalized by reaction with reagents including, but limited to, amines, amino acids, and alcohols. FIG. 38 also depicts the use of amino acids to generate more diversity. Additionally, FIG. 39 depicts the potential diversity sites for the cup-like pentacyclic scaffold structure.

One of ordinary skill in the art will realize that the above examples are representative of the reactions that can be used to diversify the templates, scaffolds, compounds, and libraries of compounds of the presently claimed invention and are not intended to be exclusive. Rather, all equivalents thereof are intended to be within the scope of the presently claimed invention. A skilled artisan will be able to readily identify those reagents capable of reacting to create further diversity at selected sites in the inventive scaffold structures to generate compounds and libraries of compounds reminiscent of natural products.

Combinatorial Methods for the Synthesis of Complex Natural Product-Like Libraries According to the method of the present invention, the synthesis of libraries from the above-described scaffold structures can be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", Chemical and Engineering News, Feb. 24, 1997, p. 43; Thompson, L. A., Ellman, J. A., *Chem. Rev.* 1996, 96, 555.) One of ordinary skill in the art will realize that the choice of method will depend upon the specific number of compounds to be synthesized, the specific reaction chemistry, and the availability of specific instrumentation, such as robotic instrumentation for the preparation and analysis of the inventive libraries. In particularly preferred embodiments, the reactions to be performed on the inventive scaffolds to generate the libraries are selected for their ability to proceed in high yield, and in a stereoselective fashion, if applicable.

In one embodiment of the present invention, the inventive libraries are generated using a solution phase technique. Traditional advantages of solution phase techniques for the synthesis of combinatorial libraries include the availability of a much wider range of organic reactions, and the relative ease with which products can be characterized. Notable disadvantages of solution phase techniques includes the inability to easily synthesize libraries of compounds containing very large numbers, such as one million or more library members, because one reaction vessel must be provided for each library member, and the inability to use excess reagents without time-consuming purification steps, such as chromatography. Recently, however, advances have been made in solution phase synthesis techniques such as the use of a "covalent scavenger" which selectively removes from solution via covalent bond formation. The "covalent scavenger" is essentially a solid phase bound nucleophile or electrophile that reacts with these excess reagents. (Kaldor, Eli Lilly, Frechet et al., *Tetrahedron Lett.*, 21, 617 (1980)). In a preferred embodiment, for the generation of a solution phase combinatorial library, a parallel synthesis technique is utilized, in which all of the products are assembled separately in their own reaction vessels. In a particularly preferred parallel synthesis procedure, a microtitre plate containing n rows and m columns of tiny wells which are capable of holding a few milliliters of the solvent in which the reaction will occur, is utilized. It is possible to then use n variants of reactant A, such as a carboxylic acid, and m variants of reactant B, such as an amide to obtain n x m variants, in n×m wells. One of ordinary skill in the art will realize that this particular procedure is most useful when smaller libraries are desired, and the specific wells can provide a ready means to identify the library members in a particular well.

In another more particularly preferred embodiment of the present invention, a solid phase synthesis technique is utilized, in which the desired scaffold structures are attached to the solid phase directly or though a linking unit, as discussed above. Advantages of solid phase techniques include the ability to more easily conduct multi-step reactions and the ability to drive reactions to completion because excess reagents can be utilized and the unreacted reagent washed away. Perhaps one of the most significant advantages of solid phase synthesis is the ability to use a technique called "split and pool", in addition to the parallel synthesis technique, develped by Furka. (Furka et al., *Abstr.* 14*th Int. Congr. Biochem.*, Prague, Czechoslovakia, 1988, 5, 47; Furka et al., *Int. J. Pept. Protein Res.* 1991, 37, 487; Sebestyen et al., *Bioorg. Med. Chem. Lett.*, 1993, 3, 413.) In this technique, a mixture of related compounds can be made in the same reaction vessel, thus substantially reducing the number of containers required for the synthesis of very large libraries, such as those containing as many as or more than one million library members. As an example, the solid support scaffolds can be divided into n vessels, where n represents the number species of reagent A to be reacted with the scaffold structures. After reaction, the contents from n vessels are combined and then split into m vessels, where m represents the number of species of reagent B to be reacted with the scaffold structures. This procedure is repeated until the desired number of reagents is reacted with the scaffold structures to yield the inventive library.

The use of solid phase techniques in the present invention may also include the use of a specific encoding technique. Specific encoding techniques have been reviewed by Czarnik. (Czarnik, A. W., *Current Opinion in Chemical Biology*, 1997, 1, 60.) As used in the present invention, an encoding technique involves the use of a particular "identifying agent" attached to the solid support, which enables the determination of the structure of a specific library member without reference to its spatial coordinates. One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. It is most preferred, however for large combinatorial libraries, to use an alternative encoding technique to record the specific reaction history.

Examples of particularly preferred alternative encoding techniques that can be utilized in the present invention include, but are not limited to, spatial encoding techniques, graphical encoding techniques, including the "tea bag" method, chemical encoding methods, and spectrophotometric encoding methods. Spatial encoding refers to recording a reaction's history based on its location. Graphical encoding techniques involve the coding of each synthesis platform to permit the generation of a relational database. Examples of preferred spectrophotometic encoding methods include the use of mass spectroscopy, fluorescence emission, and nuclear magnetic resonance spectroscopy. In a most preferred embodiment, chemical encoding methods are utilized, which uses the structure of the reaction product to code for its identity. Decoding using this method can be performed on the solid phase or off of the solid phase. One of ordinary skill in the art will realize that the particular encoding method to be used in the present invention must be selected based upon the number of library members desired, and the reaction chemistry employed.

Figure 40:
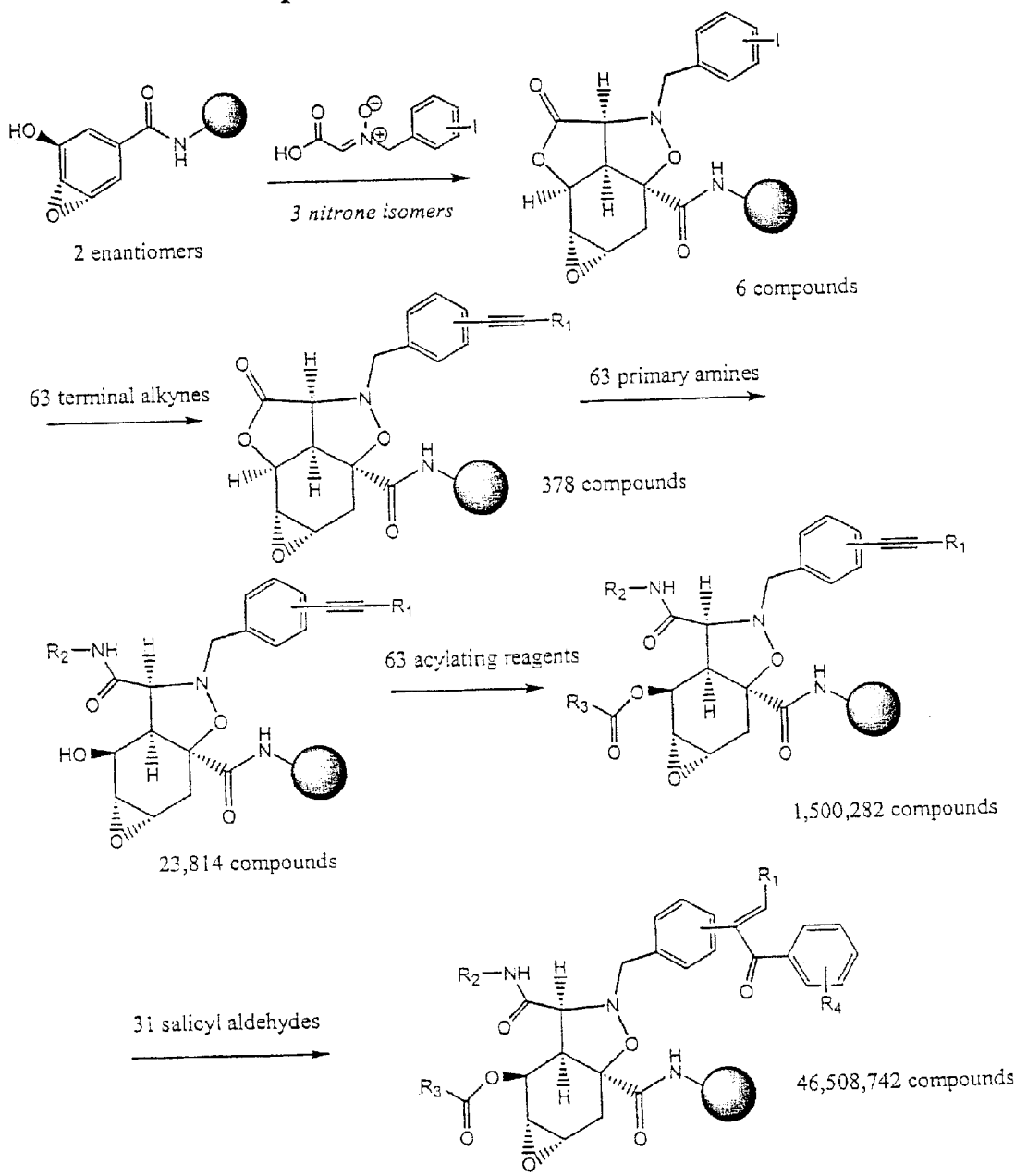
FIG. 40 depicts a synthetic plan for the geneation of 46.5 million complex molecules.

In an exemplary embodiment of the method of the present invention, more than 2,000,000 members of a shikimic acid based library can be generated. The preferred method of the invention begins with the attachment of one or more spacers to the linking reagent, preferably a photolinker. Subsequently, the resin can be pooled, divided into two portions, and one enantiomer of epoxycyclohexenol carboxylic acid coupled to each pool. After pooling and division into three portions, iodobenzyl nitrone acids can be coupled resulting in a total of 18 tetracyclic scaffolds. The stereoselective synthesis of the library of complex compounds reminiscent of natural products can be completed by reaction with 30 terminal alkynes, 62 primary amines, and finally 62 carboxylic acids, employing a split and pool technique at each step. Each of the reagents utilized are preferably selected for their ability to generate diversity and for their ability to react in high yield. As one of ordinary skill in the art will realize, the use also of a skip codon, or "blank", at each step yields further diversity. Furthermore, in particulary preferred embodiments, after each reaction step, the beads are "tagged" to encode the particular reaction choice employed. Preferred alkynes for use in the presently claimed invention include, but are not limited to acetaldehyde ethyl propargyl acetal, tert-butyl 1-methyl-2-propynyl ether, 4-(tert-butyl)phenylacetylene, tert-butyldimethylsilyl acetylene, 2-(3-butynloxy)tetrahydro-2H-pyran, 1-chloro-4-ethynylbenzene, 1,4-decadiyne (50% in hexane), 1,5-decadiyne, 3-dibutylamino-1-propyne, m-diethynylbenzene, 3,3-dimethyl-1-butyne, 1-dimethylamino-2-propyne, 1-dodecyne, ethyl ethynyl ether (50% in hexanes), ethynyl p-tolyl sulfone, 1-ethynyl-4-fluorobenzene, 1-ethynylcyclohexene, ethynylestradiol 3-methyl ether, 2-ethynylpyridine, 4-ethynyltoluene, 1,5-hexadiyne (50% in hexane), 1-hexyne, 5-hexynenitrile, methyl propargyl ether, 2-methyl-1-buten-3-yne, methyl-N-propargylbenzylamine, 1,8-nonadiyne, 1-pentyne, 4-phenyl-1-butyne, 3-phenyl-1-propyne, phenylacetylene, propargyl ether, propargyn-1H-benzotriazole, N-(propargyloxy)phthalimide, N-propargylphthalimide, propargyltriphenylphosphonium bromide, proiolaldehyde diethyl acetal, tetrahydro-2-(2-propynyloxy)-2H-pyran, triethylsilylacetylene, tripropargylamine, 2-(3-burynloxy)tetrahydro-2H-pyran, 3,5-dimethyl-1-hexyn-3-ol, 1,1-diphenyl-2-propyn-1-ol, 1-ethynyl-1-cyclohexanol, 1-ethynyl-4-fluorobenzene, 9-ethynyl-9-fluorenol, 1-ethynylcyclopentanol, 1-heptyne, 3-methyl-1-pentyn-3-ol, 2-phenyl-3-butyn-2-ol, and propiolaldehyde diethyl acetal. Preferred primary amines include, but are not limited to, allylamine, 2-amino-1-propene-1,1,3-tricarbonitrile, 3-amino-1H-isoindole hydrochloride, 3-amino-5-methylisoxazole, aminoacetaldehyde diethyl acetal, aminoacetaldehyde dimethyl acetal, aminoacetonitrile bisulfate, 4-(2-aminoethyl)benzenesulfonamide, 4-(2-aminoethyl)morpholine, 2-(2-aminomethyl)pyridine, 1-(2-aminoethyl)pyrrolidine, 2-aminoindan hydroxchloride, (R)-(−)-1-aminoindan, (S)-(+)-1-aminoindan, 2-(aminomethyl)-15-crown-5, 4-(aminomethyl)benzenesulfonamide hydrochloride, (aminomethyl)cyclopropane, 2-pyrenemethylamine hydrochloride, 3-(aminomethyl) pyridine, 4-(aminomethyl)pyridine, 3-aminopropionitrile furnarate, 1-(3-aminopropyl)-2-pyrrolidinone, 1-(3-aminopropyl)imidazole, 3-aminopropyltrimethoxysilane, (R)-(+)-3-aminoqauinuclidine dihydrochloride, (S)-(−)-3- aminoquinuclidine dihydrochloride, ammonia (0.5 M in dioxane), benzylamine, S-benzylcysteamine hydrochloride, (R)-(+)-bornylamine, butylamine, cyclobutylamine, cyclohexanemethylamine, cyclohexylamine, cyclopentylamine, cyclopropylamine, (R)-(+)-cycloserine, 3-(diethoxymethylsilyl)propylamine, 3,4-dimethoxyphenethylamine, 4-(dimethylamino)benzylamine dihydrochloride, 3-dimethylaminopropylamine, N,N-dimethylethylenediamine, ethylamine (2.0 M in THF), 1-ethylpropylamine, 2-fluoroethylamine hydrochloride, 4-fluorophenethylamine, furfurylamine, geranylamine, 3-fluorobenzylamine, (1R,2R,3R,5S)-(−)-isopinocampheylamine, (1S,2S,3S,5R)-(+)-isopinocampheylamine, isopropylamine, 2-methoxybenzylamine, 4-methoxybenzylamine, 2-methoxyethylamine, 2-methoxyphenethylamine, 3-methoxyphenethylamine, 4-methoxyphenethylamine, 3-methoxypropylamine, methylamine (2.0M in THF), (−)-cis-myrtanylamine, 1-napthylenemethylamine, 3-nitrobenzylamine hydrochloride, 4-nitrophenethylamine hydrochloride, octylamine, phenethylamine, trans-2phenylcyclopropylamine hydrochloride, 2-phenylglycinonitrile hydrochloride, piperonylamine, propargyl amine, (R)-(−)-tetrahydrofurfurylamine, (S)-(+)-tetrahydrofurfurylamine, N,N,2,2-tetramethyl-1,3-propanediamine, 2-thiophenethylamine, 2,2,2-trifluoroethylamine, tryptamine, veratrylamine, 2-(2-aminoethyl)pyridine, 3-(aminomethyl)pyridine, (R)-(−)-sec-butylamine, (S)-(+)-sec-butylamine, (R)-(−)-1-cyclohexylethylamine, (S)-(+)-1-cyclohexylethylamine, isoamylamine, (R)-(+)-a-methylbenzylamine, (S)-(−)-1-(1-napthyl)ethylamine, 4-(trifluoromethyoxy)benzylamine, and 3-(trifluoromethyl)benzylamine. Preferred carboxylic acids include, but are not limited to, acetic acid, 4-acetoxybenzoic acid, acetylsalicyclic acid, acrylic acid, m-anisic acid, o-anisic acid, p-anisic acid, benzoic acid, 2-butynoic acid, (3-carboxypropyl)trimethylammonium chloride, 3-chloropropionic acid, crotonic acid, cyanoacetic acid, 3-cyanobenzoic acid, 4-cyanobenzoic acid, cyclohexanecarboxylic acid, cyclopentanecarboxylic acid, cyclopentylacetic acid, cyclopropanecarboxylic acid, 3,4-dihydro-2,2-dimethyl-4-oxy-2H-pyran-6-carboxylic acid, 1,4-dihydro-2-methylbenzoic acid, 3-dimethylaminobenzoic acid, 4-dimethylaminobenzoic acid, N,N-dimethylglycine, ferroceneacetic acid, formic acid, trans-3-furanacrylic acid, 2-furoic acid, 3-furoic acid, furylacrylic acid, 2,4-hexadienoic acid (Sorbic acid), isobutyric acid, isonicotinic acid, isovaleric acid, levulinic acid, linolenic acid, (+)-menthoxyacetic acid, (−)-menthoxyacetic acid, methacrylic acid, methoxyacetic acid, (R)-(−)-a-methoxyphenylacetic acid, (S)-(+)-a-methoxyphenylacetic acid, 2-methoxyphenylacetic acid, 3-methoxyphenylacetic acid, 4-methoxyphenylacetic acid, 1-methyl(1S,2R)-(+)-cis-1,2,3,6-tetrahydrophthalate, mono-methyl glutarate, mono-methyl phthalate, mono-methyl terephthalate, [1R-(1-a,2b,3a)]-(+)-3-methyl-2-(nitromethyl)-5-oxocyclopentaneacetic acid, 4-(3-methyl-5-oxo-2-pyrazolin-1-yl)benzoic acid, 6-methylchromone-2-carboxylic acid, 3,4-(methylenedioxy) phenylacetic acid, 1-methylindole-2-carboxylic acid, nicotinic acid, 5-nitro-2-furoic acid, 4-nitrobenzoic acid, 4-nitrophenylacetic acid, 3-nitropropionic acid, 2-norbornaneacetic acid, orotic acid monohydrate, (S)-(+)-2-oxo-4-phenyl-3-oxazolidineacetic acid, anti-3-oxotricyclo[2.2.1.0(2,6)]heptane-7-carboxylic acid, phenylacetic acid, phenylpropiolic acid, phthalylsulfathiazole, picolinic acid, propionic acid, 2-pyrazinecarboxylic acid, 2-pyridylacetic acid hydrochloride, 3-pyridylacetic acid hydrochloride, 4-pyridylacetic acid hydrochloride, (2-pyrimidylthio)acetic acid, pyruvic acid, tetrahydro-2-furoic acid, tetrahydro-3-furoic acid, thioctic acid, 2-thiopheneacetic acid, 3-thiopheneacetic acid, 2-thiophenecarboxylic acid, 3-thiophenecarboxylic acid, 2-thiopheneglyoxylic acid, (α,α,α-trifluoro-p-tolyl)acetic acid, vinylacetic acid, acetoxyacetic acid, 2-benzofurancarboxylic acid, cinnoline-4-carboxylic acid, 3,5-diido-4-pyridone-1-acetic acid, 3,3-dimethylacrylic acid, ferrocenecarboxylic acid, 5-methoxy-1-indanone-3-acetic acid, 1-methyl-2-pyrrolecarboxylic acid, 3-oxo-1-indancarboxylic acid, trans-3-(3-pyridyl) acrylic acid, 3-(2-thienyl)acrylic acid, α,α,α-trifluoro-m-toluic acid, α,α,α-trifluoro-o-toluic acid, and α,α,α-trifluoro-p-toluic acid. Additionally, FIG. 40 depicts a plan for the synthesis of over 46.5 million complex molecules.

In another exemplary embodiment, the present invention provides a method for synthesizing over 30,000,000 members of an isoquinuclidine library as depicted in FIG. 41. First, 63 derivatized isonicotinamide templates are provided and reacted with allyltributyltin and TeocCl to yield a racemic mixture, thus providing 126 compounds. Subsequent reaction with maleic anhydride, 63 amino acids, and 63 amines, yields 500,094 compounds. Further reaction with 3 nitrone isomers, and 20 arylboronic acids yields over 30,000,000 complex compounds reminiscent of natural products.

Subsequent characterization of the library members can be performed using standard analytical techniques, such as mass spectrometry, Nuclear Magnetic Resonance Spectroscopy, and gas chromatrography. One of ordinary skill in the art will realize that the selection of a particular analytical technique will depend upon whether the inventive library members are in the solution phase or on the solid phase. As but one example, FIGS. 42 through 45 more particularly depict the synthesis and analysis of a test library of compounds; these examples are not intended to limit the scope of the present invention, however.

Uses

The methods, compounds and libraries of the present invention can be utilized in various disciplines. For example, one aspect of the present invention concerns a method for identifying natural product-like small molecules from the inventive libraries of compounds, which modulate the biological activity of a biological target, such as a protein, nucleic acid, lipid or combination thereof. In one preferred embodiment, the compounds of the present invention are utilized in chemical genetics assays to alter, i.e. inhibit or initiate, the action of such biological molecules. Alternatively or additionally, the compounds may be used in in vitro assays, or any other system that allows detection of a chemical or biological function.

In a particularly preferred embodiment of the invention, one or more inventive compounds is contacted with a biological target having a detectable biochemical activity. Such biological targets include, for example, enzymes, receptors, subunits involved in the formation of multimeric complexes. Such multimeric complex subunits may be characterized by catalytic capabilities (such as, for example, an ability to catalyze substrate conversion), or may alternatively be primarily active in binding to one or more other molecule. The biological target can be provided in the form of a purified or semi-purified composition, a cell lysate, a whole cell or tissue, or even a whole organism. The level of biochemical activity is detected in the presence of the compound, and a statistically significant change in the biochemical activity, relative to the level of biochemical activity in the absence of the compound, identifies the compound as a modulator, e.g. inhibitor or potentiator of the biological activity of the target protein. In some cases, particularly where assays are done on whole cells or organisms, the effect of the chemical compound may be to alter the amount, in addition to or instead of the activity, of the particular biological target. "Modulators", therefore, are chemical compounds that alter the level or activity of a particular target molecule.

In one particularly preferred embodiment of the present invention, multiple compounds are assayed simultaneously in a high-throughput format, preferably allowing simultaneous analysis of at least 500,000 compounds, preferably at least 1,000,000 compounds, and most preferably at least or more than 2,000,000 compounds. One such format, referred to herein as "nanodroplet format" is described in U.S. patent application Ser. No. 08/951,930, entitled "Droplet Assay System", which is incorporated herein by reference. In brief, the format involves ordered or stochastic arrays of small volume (preferably about 50–200 nL, most preferably about 100 nL) droplets into which chemical compounds to be assayed are distributed. Those of ordinary skill in the art will readily appreciate that this nanodroplet format can be employed for any of a large variety of assays. Any assay whose result may be observed in the context of a discrete liquid droplet is appropriate for use with the present invention. Preferred read-out assays for use in accordance with the present invention analyze chemical or biological activities of test compounds. Read-out assays can be designed to test in vitro or in vivo activities. Example 1 describes the preferred droplet assay procedure, and Examples 2 and 3 describe particularly preferred assays for analysis of the inventive chemical compounds.

As discussed above, once a specific desired effect on a biological target has been associated with a particular compound of the inventive library, the compounds of the present invention may be utilized as a therapeutic agent for a particular medical condition. A therapeutic agent for use in the present invention may include any pharmacologically active substances that produce a local or systemic effect in animals, preferably mammals, or humans. The term thus means any substance intended for use in the diagnosis, cure, mitigation, treatment or prevention of disease or in the enhancement of desirable physical or mental development and conditions in an animal or human. The therapeutic agent may be administered orally, topically or via injection by itself, or additionally may be provided as a pharmaceutical composition comprising the therapeutic agent and a biologically acceptable carrier. The inventive compositions can be, but are not limited to an aqueous solutions, emulsions,. creams, ointments, suspensions, gels, and liposomal suspensions. Particularly preferred biologically acceptable carriers include but are not limited to water, saline, Ringer's solution, dextrose solution and solutions of ethanol, glucose, sucrose, dextran, mannose, mannitol, sorbitol, polyethylene glycol (PEG), phosphate, acetate, gelatin, collagen, Carbopol, and vegetable oils. It is also possible to include suitable preservatives, stabilizers, antioxidants, antimicrobials, and buffering agents, for example including but not limited to BHA, BHT, citric acid, ascorbic acid, and tetracycline. The therapeutic agents of the presently claimed invention may also be incorporated or encapsulated in a suitable polymer matrix or membrane, thus providing a sustained-release delivery device suitable for implantation near the site to be treated locally.

As one of ordinary skill in the art will realize, the amount of the therapeutic agent required to treat any particular disorder will of course vary depending upon the nature and severity of the disorder, the age and condition of the subject, and other factors readily determined by one or ordinary skill in the art.

In alternative embodiments, the compounds and libraries of the present invention may also be used for the development of cosmetics, food additives, pesticides, and lubricants to name a few. Furthermore, the compounds and libraries of the present invention may also be used for the development of novel catalysts and materials. For example, the inventive compounds may be useful as ligands for transition metal catalysts and the inventive libraries may be useful for the rapid identification of novel ligands. These compounds and libraries of compounds may also function by acting in concert with a particular transition metal catalyst to effect a particular desired chemical reaction. Additionally, the inventive compounds and libraries of compounds are also useful in the area of materials science. Because of the reactive moieties present in these compounds, molecules such as lipids and other polymeric materials may be attached and thus generate potentially important biomaterials.

One of ordinary skill in the art will realize that the present invention is not intended to be limited to the abovementioned uses, but rather may be employed in many contexts and disciplines.

Furthermore, the specific examples presented below for the biological assays, and also the specific examples presented in the examples (for the more detailed experimentals for the synthesis of compounds and libraries of compounds, the characterization of said compounds and libraries of compounds, and the testing of the biological activity of said compounds and libraries of compounds) are intended to more particularly describe the present invention, but are not intended to limit the scope of the presently claimed invention.

EXAMPLES

Example 1

Nanodroplet Assay

Figure 46:
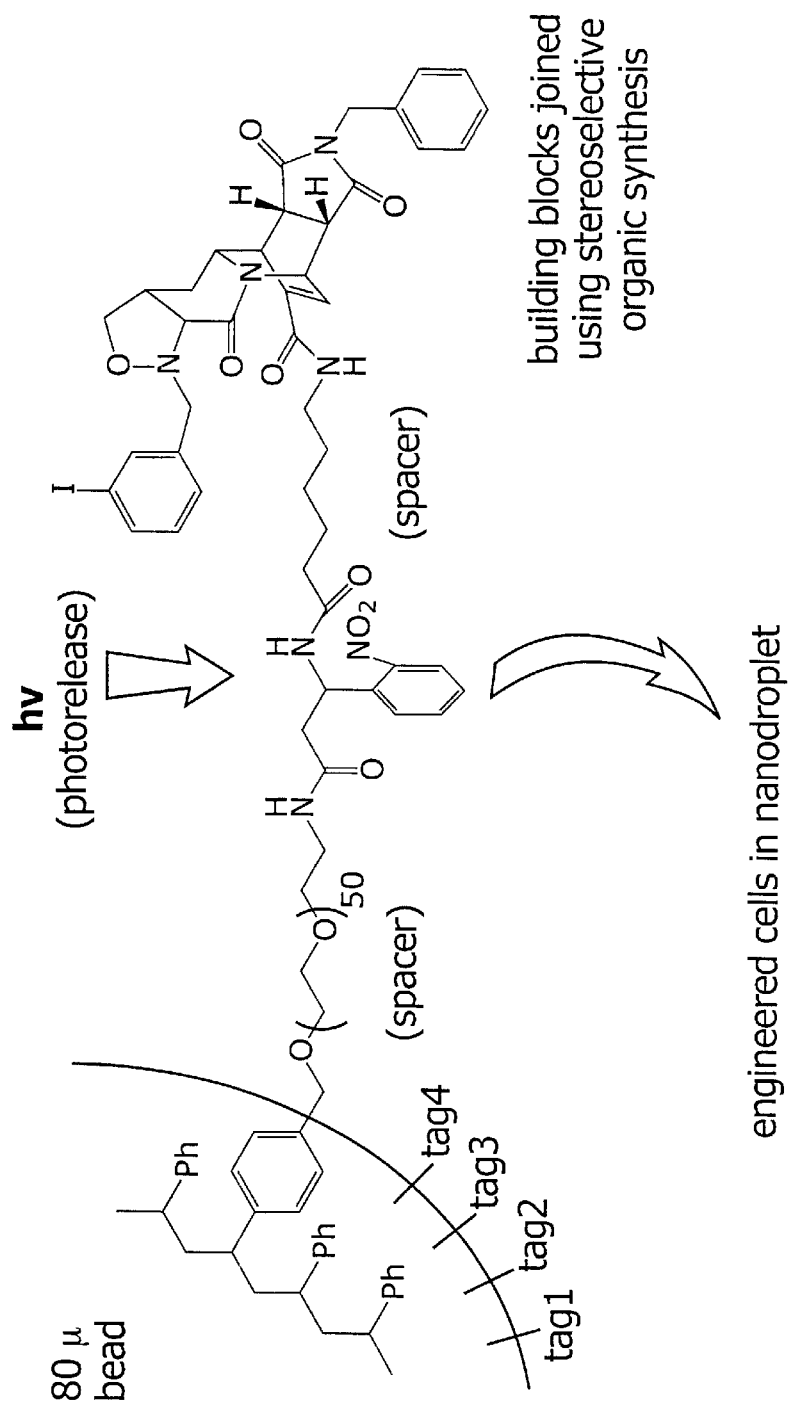
FIG. 46 depicts the use of photorelease of the inventive compounds into nanodroplets.

The ability of the preferred procedure utilized for the library synthesis to controllably release compounds from the individual $90\mu$ diameter beads into nanodroplet containing engineered wells enables the use of these miniaturized cell-based assays to detect specific characteristics of library members. In a particularly preferred embodiment of the invention, the compounds in an inventive encoded combinatorial library are attached to beads through a photocleavable linker. Each bead is labeled with a tag that identifies the bound compound. Additionally, the concentration of the test compound released in the droplet can be controlled by controlling the time of exposure to UV radiation. The amount of compound released in any particular experiment, of course, will depend on the efficiency of bead loading and the extent of bead functionalization. FIG. 46 depicts the photorelease of an inventive compound.

In particular, the present invention specifically contemplates the screening of the inventive compounds, especially libraries of these compounds in assays designed to detect their protein-binding properties (e.g., small molecule inactivation of protein targets or small molecule activation of protein targets).

Example 2

Assay to Detect Activation of Protein Targets

Figure 47:
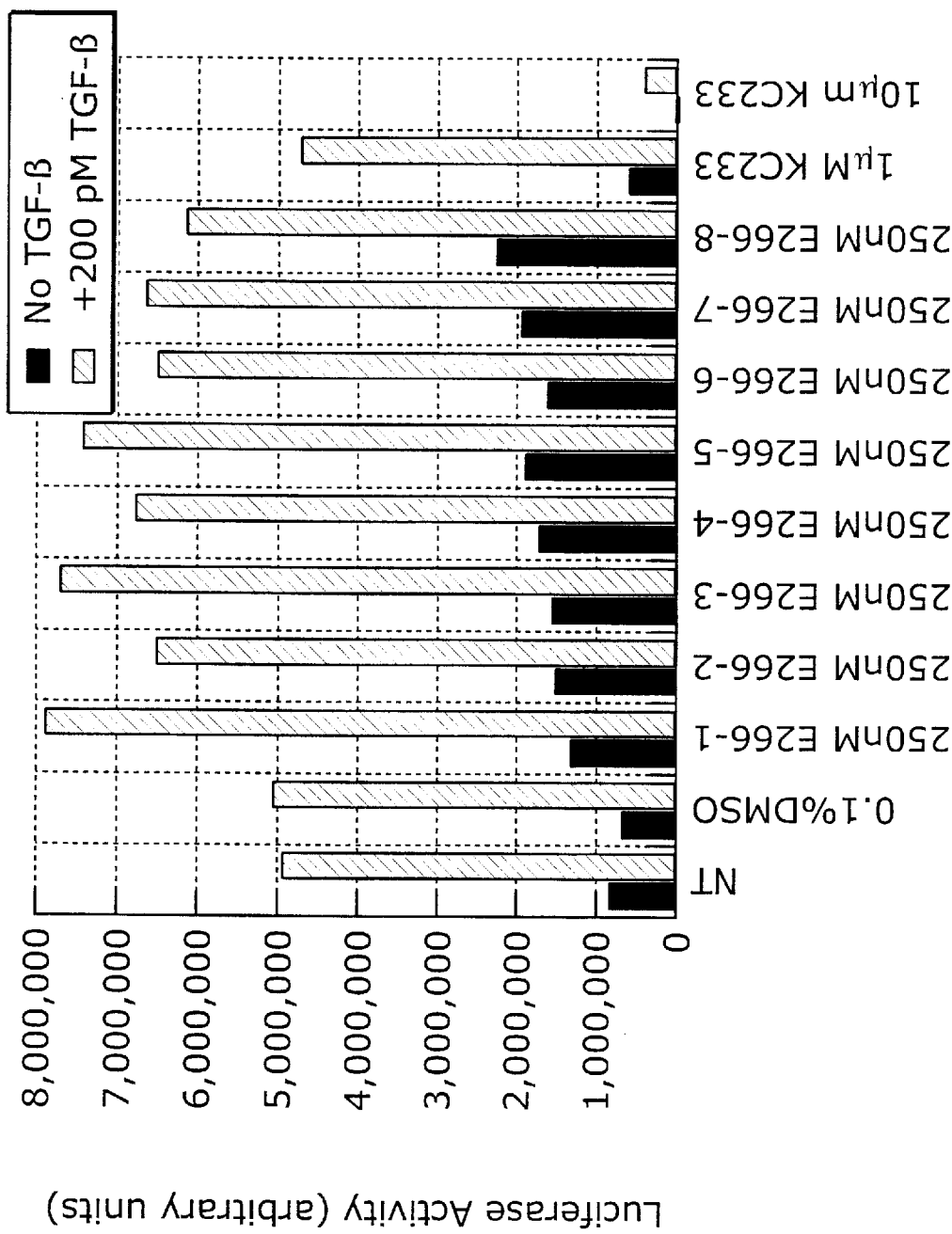
FIG. 47 depicts the ability of the shikimic acid test library to activate the 3TP promoter.

The inventive compounds and libraries of compounds synthesized by the inventive method are tested for activation of a luciferase reporter gene with pathway specific promoters such as a TGF-β responsive promoter/enhancer. The luciferase gene is a particularly preferred reporter gene because the determination of the expressed luciferase enzyme is rapid, easy to perform and detection is extremely sensitive. Furthermore, luciferase is a monomeric protein that does not require any post-translational processing and can thus be measured as a genetic reporter immediately upon translation. As shown in FIG. 47, 8 different pools, each containing 64 different isolated compounds selected from the shikimic acid test library as described in Example 4, were tested for the ability to induce luciferase activity and all were found to activate the reporter gene to various extents. Interestingly, KC233, an isolated compound selected from the inventive isoquinuclidine library, does not activate the reporter gene and furthermore also prohibits TGF-β from activating the reporter gene. FIG. 48 depicts this in greater detail.

These results suggest that the core structure of the shikimic acid library is useful for the activation of a signaling pathway that results in activation of the 3TP promoter, and that KC233, a member of the isoquinuclidine library is effective in preventing TGF-β-induced activation of the 3TP promoter/enhancer. One of ordinary skill in the art will realize that other reporter genes can be utilized to test the ability of the inventive compounds and libraries of compounds to promote different cellular responses. Exemplary reporter genes include, but are not limited to secreted alkaline phosphatase (seap), β-lactamase, chloramphenicol transferase (cat), and green fluorescent protein.

Example 3

Cell Proliferation Studies

Figure 49:
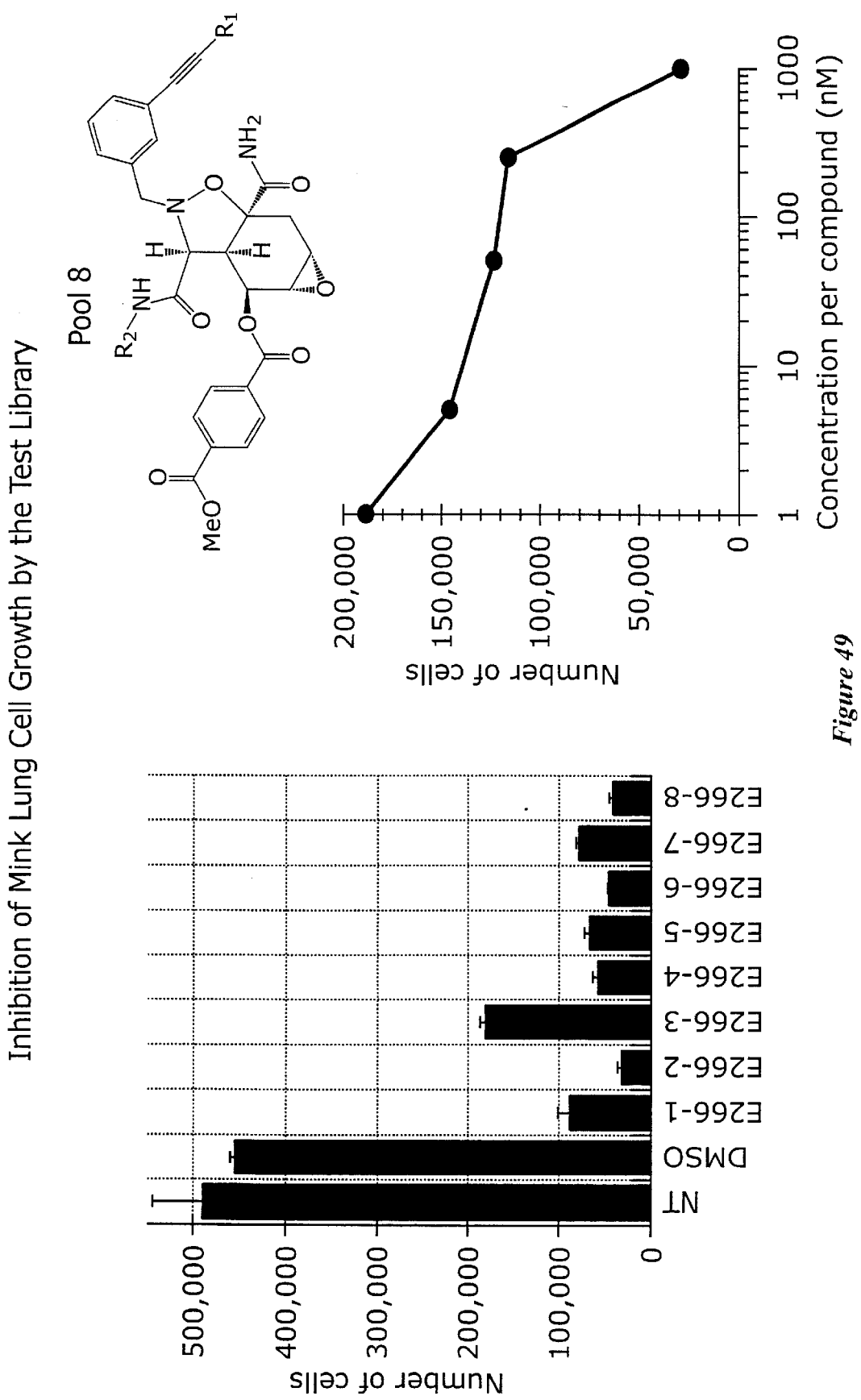
FIG. 49 depicts the inhibition of mink lung cell growth by the test library.
Figure 50:
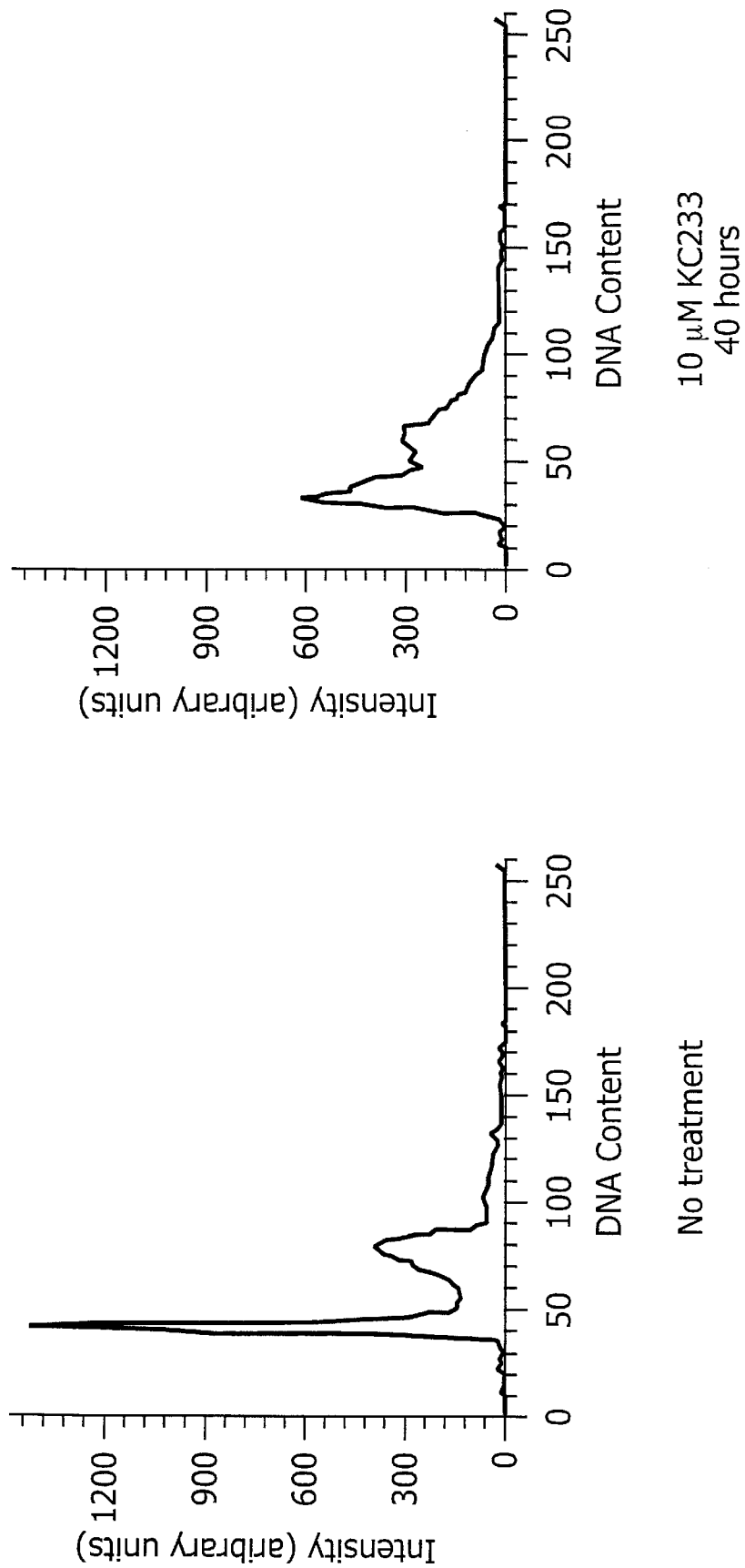
FIG. 50 depicts the ability of KC233 to arrest mink lung cells in the S-phase of the cell cycle.

In another illustrative embodiment, the inventive compounds and libraries of compounds were tested for their ability to inhibit cell proliferation in mink lung cells. FIG. 49 depicts the ability of each of the specific pools of 64 compounds (1 μM per compound) selected from the shikimic acid test library to inhibit cell proliferation. These results suggest that the inventive compounds and libraries of compounds are useful as inhibitors of cell proliferation, and thus may also be useful as potential therapeutics for cancer or other conditions such as autoimmune diseases in which the inhibition of cell proliferation, specifically tumor cell proliferation or hematopoietic cell growth is important. Furthermore, FIG. 50 depicts the ability of KC233, a member of the inventive isoquinuclidine library (KC233 shown in FIG. 48), to arrest mink lung cells in the S-phase of the cell cycle. After treatment of mink lung cells with 10 μM KC233 for 40 hours, the DNA content corresponding to the G1, G2 and M phases decreases, and the corresponding DNA content associated with the S phase increases. Thus, these results suggest that KC233 is useful as a therapeutic for arresting lung cell cancers. Additionally, the ability of KC233 to act as a general cell cycle arresting agent suggests its ability to function analogously to other cell-cycle arresting drugs. For example, hydroxyurea, the currently cytotoxic agent of choice for treatment of chronic myelocytic leukemia, also arrests cells in the S-phase. Another example of a cell-cycle arresting drug in which the cell cycle is arrested in mitosis (M-phase) is the well-known anticancer drug paclitaxel (Taxol), currently approved for ovarian cancer and head and neck cancer. One of ordinary skill in the art will realize that these represent only a few examples of cell-cycle arresting drugs, and that the inventive compounds and libraries of compounds may function as analogues of other cell-cycle arresting drugs.

Example 3

Testing the Inventive Libraries for the Ability to Act as a Ligand for the Receptor of Human Growth Hormone Another interesting application for the complex radially arrayed combinatorial libraries of the presently claimed invention is as a ligand for the receptor for human growth hormone, which induces homodimerization of the receptor and initiates the intracellular growth hormone signalling pathway, as depicted in FIG. 3. The "hot spot", which is a small patch of residues identified as being responsible for the majority of the binding energy between hGH and its receptor is an excellent target for the library.

Materials and Methods

Cell Culture: MvlLu mink lung epithelial cells were obtained from the American Type Culture Collection (catalog # CCL64). Clone 6f is a stably transfected derivative of MvlLu cells containing the p3TPLux reporter plasmid as well as the construct $MF_{pK}3TI[D]$ (see Stockwell B R and Schreiber S L *Current Biology* (1998), 8: 761–770). MvlLu and 6f cells were cultured in DMEM with 10% FEBS, 100 units/mL penicillin G sodium, 100 μg/mL streptomycin sulfate and 100 μM each of the amino acids Ala, Asp, Glu, Gly, Asn and Pro.

Luciferase Assay: $2.0 \times 10^5$ 6f cells were seeded in each 35 mm well of a six well dish in 10% FBS. After 20 hours, the cells were washed once and incubated in DMEM containing 0.2% FBS and the non-essential amino acids (NEAA) and the reagent of interest (e.g., library pool, KC233, or TGF-β) for 25 to 30 hours. Cells were incubated on ice for 15 minutes, washed three times with HBSS and lysed in extraction buffer (25 mM glycylglycine, pH 7.8, 15 mM MgSO4, 4 mM egta, 1% Triton X, 1 mM DTT, 1 mM PMSF) by shaking gently at 4 C for 30 minutes. The lysates were centrifuged for 5 minutes at 10,000 g at 4° C. and stored on ice. 100 μL of lysate was added to 150 μL of assay mixture (25 mM glycylglycine pH 7.8, 15 mM $MgSO_4$, 4 mM egta, 15 mM $K_2HPO_4$, pH 7.8, 1 mM DTT, 4 mM ATP) and 150 μL of luciferin buffer (25 mM glycylglycine pH 7.8, 15 mM $MgSO_4$, 4 mM egta, 10 mM DTT, 167 μM D-luciferin). This mixture was placed in a 500 μL microfuge tube inside a glass scintillation vial, and luminescence was detected by counting in single photon mode (SPM) on a Beckman LS 6500 liquid scintillation counter for 15 seconds. The error bars reported represent plus or minus one standard deviation. All experiments were performed multiple times in triplicate.

Growth Inhibition Assay: MvlLu cells were seeded in 6 well clusters (20,000 cells per well) and allowed to attach overnight in a 10% serum. Media was changed to 1% FBS with or without the test compound. After four days the cells were washed, trypsinized and counted. The cell number reported represents live cells, since dead cells detach and are washed away by this protocol.

Example 4

Synthesis of a Shikimic Acid-based Library of Compounds

I) General Methods:

Materials: Reagents were obtained from Aldrich Chemical Co. (Milwaukee, Wis.), GFS Chemicals (Powell, Ohio), Advanced Chemtech (Louisville, Ky.), Novabiochem (San Diego, Calif.), or Eastman Chemicals (Rochester, N.Y.) and used without further purification. Solvents were obtained from Mallinckrodt or E. Merck. Wash solvents were used as received. Reaction solvents were distilled under nitrogen as follows: Tetrahydrofuran (THF) from sodium/benzophenone ketyl; methylene chloride (CH$_2$Cl$_2$), ethylacetate (EtOAc), and diisopropylethylamine (DIPEA) from calcium hydride; methanol (MeOH) from magnesium methoxide. Anhydrous dimethylformnamide (DMF) and 1-methyl-2-pyrrolidinone (NMP) were obtained from Aldrich in SureSeal™ bottles. Water (H$_2$O) was double distilled. Tentagel S NH$_2$ was obtained from Rapp Polymer (Germany). Solution phase reactions were performed in oven-or flame-dried glassware under positive N$_2$ pressure.

Solid Phase Reactions: Small-scale solid phase reactions (5–10 mg resin) were performed in 500 µL polypropylene Eppendorf tubes (VWR 20170-310) with mixing provided by a Vortex Genie-2 vortexer (VWR 58815-178, setting V2–V3) fitted with a 60 microtube insert. Medium-scale solid phase reactions (20–500 mg resin) were performed in 2 mL fritted polypropylene Bio-Spin chromatography columns (Bio-Rad 732-6008) or 10 mL fritted polypropylene PD-10 columns (Pharmacia Biotech 17-0435-01) with 360° rotation on a Barustead-Thermolyne Labquake™ Shaker (VWR 56264-306). Large scale solid phase reactions (>500 mg resin) were performed in silanized 50 or 100 mL fritted glass tubes equipped for vacuum filtration and N$_2$ bubbling. The tubes were silanized by treatment with 20% dichlorodimethylsilane/CH$_2$Cl$_2$ for 15 minutes, MeOH for 15 min, followed by oven heating at 120° C. for at least 2 h.

After small-scale reactions, resin samples were transferred to 2 mL BioSpin™ columns via vacuum canula. Resin samples in polypropylene columns were washed on a Vac-Man™ Laboratory Vacuum Manifold (Promega A7231) fitted with nylon 3-way stopcocks (Biorad 732-8107). Resin samples in glass tubes were washed in the tubes with alternating periods of N$_2$ bubbling and vacuum draining. The following standard wash procedure was used: 3×THF, 3×DMF (Method A) or NMP (Method B), 3×iPrOH, 3×DMF/NMP, 3×CH$_2$Cl$_2$, 3×DMF/NMP, 3×CH$_3$CN, 3×THF, 3×CH$_2$Cl$_2$.

Resin samples were then transferred via spatula to 500 µL Ependorf tubes and suspended in Ar-degassed HPLC grade CH$_3$CN. The tubes were parefilmed and fixed with rubber bands to a 2"×3" piece of cardboard which had been wrapped with aluminum foil. The tubes were then placed on a vortexer (setting S1–S2) under a UVP High Intensity Longwave UV Lamp (Fisher 11-984-79) at a distance of 3 inches (~21.7 mW/cm$^2$). Photocleavage products were recovered by filtration and evaportation or by sampling of the supernatant where appropriate.

Purification and Analysis. Flash chromatography was performed on E. Merck 60 230–400 mesh silica gel. TLC was performed on 0.25 mm E. Merck silica gel 60 F$_{254}$ plates and visualized by UV (254 nm) and cerium ammonium molybdate (CAM). HPLC was performed on a Nest Group (Southborough, Mass.) Hypersil C18 100 Å 3µ 4.6 mm×6 cm column using a flow rate of 3 mL/min and a 4 min gradient of 0–99.9% CH$_3$CN in H$_2$O/0.1% TFA, constant 0.1% MeOH with diode array UV detection. Melting point determinations were performed on a Laboratory Devices (Cambridge, Mass.) Mel-temp apparatus and are uncorrected (benzoic acid, lit. 122–123° C., found 119.0–121.5° C.). Optical rotations were measured on a Perkin-Elmer 241 Polarimeter. IR spectra were recorded on a Nicolet 5PC FT-IR Spectrometer with peaks reported in cm$^{-1}$. NMR spectra were recorded on Varian Inova 600 and Bruker DMX500, AM500, and AM400 instruments. Chemical shifts are expressed in ppm relative to TMS (0.00 ppm) or residual solvent signals (CDCl$_3$ 7.26 ppm/77.0 ppm; CD$_3$CN 1.93 ppm/1.3 ppm, CD$_3$OD 3.30 ppm/49.0 ppm). Peak assignments were made based on extensive homonuclear decoupling and/or two-dimensional DQF-COSY, TOCSY, and NOESY experiments. Mass spectra were obtained on JEOL AX-505H or SX-102A mass spectrometers by electron impact ionization (EI), chemical ionization (CI) with ammonia (NH$_3$), or fast atom bombardment ionization (FAB) with glycerol or 3-nitrobenzyl alcohol/sodium iodide (NBA/NaI) matrices. Time-of-flight electrospray ionization (TOF-ESI) data were obtained on a Micromass LCT mass spectrometer. Tandem high pressure liquid chromatography-mass spectrometry (LC-MS) data were obtained on a Micromass Platform II mass spectrometer in atmospheric pressure chemical ionization (AP-CI) mode attached to a Hewlett-Packard Series 1050 HPLC system. LC-MS chromatography was performed on a Hewlett-Packard ODS Hypersil 5µ, 2.1 mm×10 cm column using a flow rate of 0.4 mL/min and a 5 min gradient of 30–90% CH$_3$CN in H$_2$O, constant 0.1% formic acid with detection at 214 nm.

Characterization Data: Atom numbers shown in structures below refer only to NMR peak assignments and not to CAS or trivial nomenclature. Compound numbers followed by R represent molecules still attached to the solid support.

II) Epoxycyclohexenol Carboxylic Acid Synthesis (2):

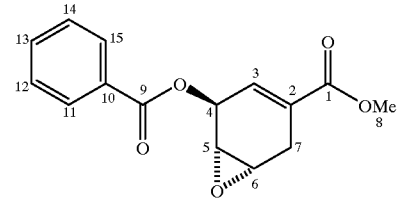

(1S,5S,6S)-5-Benzoyloxy-7-oxabicyclo[4.1.0]hept-3-ene-3-carboxylic acid, methyl ester (Benzoyl epoxycyclohexenol, methyl ester). (1S,5R,6S)-5-Hydroxy-7-oxabicyclo[4.1.0]hept-3-ene-3-carboxylic acid, methyl ester (4.75 g, 27.9 mmol, 1.0 eq) made from shikimic acid 1, essentially as previously described (McGowan, D. A.; Berchtold, G. A. *J. Org. Chem.* 1981, 46, 2381–2383) was dissolved in 125 mL THF. Triphenylphosphine (13.18 g, 50.3 mmol, 1.8 equiv) and benzoic acid (6.14 g, 50.3 mmol, 1.8 equiv) were added and the solution was cooled to 0° C. in an ice bath. Diethylazodicarboxylate (7.9 mL, 50.3 mmol, 1.8 equiv) was added via syringe and the reaction was allowed to warm slowly to rt. After stirring overnight, the THF was evaporated and the crude mixture was taken up in 150 mL Et$_2$O and filtered twice to remove the triphenylphosphine oxide and bis(carboethoxy)hydrazine byproducts. The solvent was evaporated and the crude mixture was taken up in 100 mL Et$_2$O and again filtered twice. The crude product (17.8 g) was purified by silica gel flash chromatography (17:3 hexanes/EtOAc) to yield the pure benzoyl ester 6 as a clear, colorless oil (6.77 g, 88%). TLC: R$_f$ 0.35 (3:1 hexanes/EtOAc). IR (film): 1718, 1669, 1246. $^1$H-NMR (400 MHz, CDCl$_3$): δ 8.06 (dd, 2H, J=6.3,3.3, C11-H, C15-H), 7.69 (t, 2H, J=7.7, C12-H, C14-H), 7.59 (tt, 1H, J=7.4, 1.4, C13-H), 6.86 (ddd, 1H, J=7.7, 2.9, 1.7, C3-H), 5.92 (app dt, 1H, J=4.6, 2.0, 0.9, C4-H), 3.77 (s, 3H, C8-H$_3$), 3.51 (dd, 1H, J=3.7, 2.8, C5-H), 3.41 (ddd, 1H, J=4.5, 2.7, 1.7, C6-H), 3.05 (ddd, 1H, J=20.0, 2.7, 1.3, C7-H$_a$), 2.76 (ddd, 1H, J=20.0, 4.8, 2.7, C7-H$_b$). $^{13}$C-NMR (100 MHz, CDCl$_3$): δ 166.2, 165.3, 133.2, 129.7, 129.5, 129.4, 128.8, 128.2, 64.9, 51.8, 50.4, 50.1, 24.1. I-MS (NH$_3$) m/z (rel int): 292

([M+NH$_4$]$^+$, 100), 275 ([M+H]$^+$, 58). HRMS (NH$_3$) m/z calcd for C$_{15}$H$_{18}$NO$_5$ 292.1185; found 292.1179.

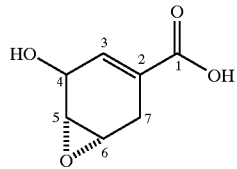

(+)-(1S,5S,6S)-5-Hydroxy-7-oxabicyclo[4.1.0]hept-3-ene-3-carboxylic acid ((+)-Epoxycyclohexenol carboxylic acid, (+)-2). The benzoyl epoxycyclohexenol methyl ester above (1.05 g, 3.84 mmol, 1.0 equiv) was dissolved in 40 mL THF and 10 mL H$_2$O and cooled to 0° C. in an ice bath. Lithium hydroxide monohydrate (483 mg, 11.52 mmol, 3.0 equiv) was dissolved in 10 mL H$_2$O and added dropwise via addition funnel to the stirring reaction mixture. When the reaction was complete by TLC, the solution was acidified at 0° C. to pH 5 with Amberlite IR-120(plus) resin, filtered, and evaporated to yield the crude product as an off-white solid. NMR analysis indicated approximately 25% Payne rearrangement. Purification on silica gel (25:75:1 hexanes/EtOAc/AcOH, dry loaded from THF) afforded epoxycyclohexenol carboxylic acid (+)-7 as a white solid (352 mg, 59%). TLC: R$_f$ 0.24 (25:75:1 hexanes/EtOAc/AcOH); R$_f$ 0.49 (85:15:1 CH$_2$Cl$_2$/MeOH/AcOH). mp: 115.5–116.5° C. [α]$_D^{23}$=+57.6 (c 1.0, MeOH). IR (KBr pellet): 3700–2800, 1713, 1661, 1248. $^1$H-NMR (500 MHz, CD$_3$CN): δ 6.67 (m, 1H, C3-H), 4.46 (m, 1H, C4-H), 3.36 (m, 1H, C6-H), 3.14 (m, 1H, C5-H), 2.76 (app dq, 1H, J=19.8, 1.4, C7-H$_\alpha$), 2.57 (app dq, 1H, J=19.8, 2.4, C7-H$_\beta$). $^1$H-NMR (400 MHz, CD$_3$OD): δ 6.73 (m, 1H, C3-H), 4.47 (m, 1H, C4-H), 3.41 (m, 1H, C6-H), 3.19 (m, 1H, C5-H), 2.81 (app dq, 1H, J=19.8, 1.3, C7-H$_\alpha$), 2.60 (app dq, 1H, J=19.8, 2.5, C7-H). $^{13}$C-NMR (125 MHz, CD$_3$CN): δ 168.6 (C1), 135.9 (C3), 127.0 (C2), 63.4 (C4), 53.6 (C6), 51.3 (C6), 25.1 (C7). $^{13}$C-NMR (125 MHz, CD$_3$OD): δ 170.0 (C1), 135.4 (C3), 127.8 (C2), 63.7 (C4), 54.1 (C5), 51.9 (C6), 25.4 (C7). CI-MS (NH$_3$) m/z (rel int): 174 ([M+NH$_4$]$^+$, 66). HRMS (NH$_3$) m/z calcd for C$_7$H$_{12}$NO$_4$ 174.0766; found 174.0762.

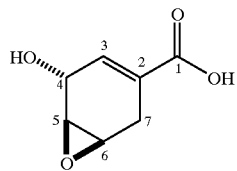

(−)-(1R,5R,6R)-5-Hydroxy-7-oxabicyclo[4.1.0]hept-3-ene-3-carboxylic acid ((−)-Epoxycyclohexenol carboxylic acid, (−)-2). The methyl ester of epoxycyclohexenol carboxylic acid (−)-2 was prepared essentially as previously described (Wood et al. *J. Am. Chem. Soc.* 1990, 112, 8907) and recovered as a 1.6:1 mixture with the Payne rearranged isomer in 51% combined yield. This mixture (1.21 g, 7.15 mmol, 1.0 equiv) was dissolved in 14 mL 1:1 THF/H$_2$O and cooled to 0° C. in an ice bath. Lithium hydroxide (330 mg, 7.87 mmol, 1.1 equiv) in 3.3 mL H$_2$O was added dropwise over 10 min. The reaction was stirred at 0° C. until the starting material was consumed (approx 2 h, TLC: 25:75:1 hexanes/EtOAc/AcOH). The solution was acidified at 0° C. to pH 5 with Amberlyte IR-120(plus) resin, filtered, and evaporated to yield the crude product as a clear oil. Purification on silica gel (0–5% MeOH in CH$_2$Cl$_2$ gradient) afforded epoxycyclohexenol carboxylic acid (−)-7 as a white solid (477 mg, 43% based on mixture). TLC and $^1$H-NMR identical to (+)-7 above. [α]$_D^{23}$=−50.6 (c 1.0, MeOH). CI-MS (NH$_3$) m/z (rel int): 174 ([M+NH$_4$]$^+$, 75). HRMS (NH$_3$) m/z calcd for C$_7$H$_{12}$NO$_4$ 174.0766; found 174.0770.

III. Nitrone Carboxylic Acid Synthesis (6d–7b-d):

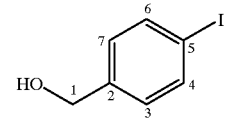

4-Iodobenzyl alcohol. (Acheson, R. M.; Lee. G. C. M. *J. Chem. Soc. Perkin Trans. I* 1987, 2321–2332.) To a stirred suspension of sodium borohydride (5.68 g, 150 mmol, 2.0 equiv) in 50 mL dioxane at 0° C. was added dropwise a solution of 4-iodobenzoyl chloride (19.99 g, 75 mmol, 1.0 equiv) in 50 mL dioxane over 25 min. The resulting mixture was heated to 100° C. for 90 min under a reflux condenser then cooled to 0° C. 50 mL H$_2$O was added cautiously under a flowing stream of nitrogen. [CAUTION: Evolves gas!] The mixture was extracted 3×125 mL CH$_2$Cl$_2$ and the combined organic extracts were washed with 2×H$_2$O, 2×0.1N HCl, 2×1N NaOH, H$_2$O, and brine, dried (MgSO$_4$), filtered, and evaporated to yield 16.9 g of crude 4-iodobenzyl alcohol as a white solid, determined by NMR to contain 78% desired product with the remainder residual starting material and 4-iodobenzoic acid. The crude product was used without further purification. mp: 61.0–66.5° C. TLC R$_f$: 0.27 (3:1 hexanes/EtOAc). IR (film): 3306, 1005, 791. $^1$H-NMR (400 MHz, CDCl$_3$): δ 7.69 (d, 2H, J=8.3, C4-H, C6-H), 7.12 (d, 2H, J=8.5, C3-H, C7-H), 4.66 (br d, 2H, J=:4.1, C1-H$_2$), 1.67 (br t, 1H, C1-OH). $^{13}$C-NMR (125 MHz, CDCl$_3$): δ 140.4, 137.6, 128.8, 93.0, 64.6. EI-MS m/z (rel int): 234 (M$^+$, 100).

General Procedure for Synthesis of Iodobenzaldehydes. (Acheson, R. M.; Lee, G. C. M. *J. Chem. Soc. Perkin Trans. I* 1987, 2321–2332.) To a stirred suspension of pyridinium dichromate (1.5 equiv) in CH$_2$Cl$_2$ was added the appropriate iodobenzyl alcohol (1.0 equiv) at rt. The mixture was stirred vigorously for 20–40 h until the reaction was complete by TLC. Et$_2$O was added and the mixture was filtered through a column of 2" celite over 2" silica gel. Elution of the product with additional Et$_2$O and evaporation of solvents yielded the crude iodobenzaldehyde which was approximately 95% pure by $^1$H-NMR and used without further purification.

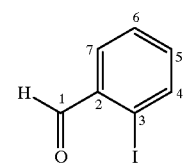

2-Iodobenzaldehyde. Commercially available 2-iodobenzyl alcohol (10.0 g, 42.7 mmol) was dissolved in 200 mL CH$_2$Cl$_2$. Upon completion, the reaction was diluted with 250 mL Et$_2$O. The product was recovered as a brown liquid (10.3 g, 104%). TLC: R$_f$ 0.57 (3:1 hexanes/EtOAc). IR (neat): 3061, 2853, 2745, 1696, 1580, 1561. $^1$H-NMR (400 MHz, CDCl$_3$): δ 10.07 (s, 1H, C1-H), 7.95 (dd, 1H, J=7.9, 1.0, C4-H), 7.88 (dd, 1H, J=7.7, 1.8, C7-H), 7.47 (td, 1H, J=7.5 0.8, C6-H), 7.29 (td, 1H, J=7.6, 1.8, C5-H). $^{13}$C-NMR (100 MHz, CDCl$_3$): δ 195.1, 140.2, 135.1, 134.7, 129.9, 128.4, 100.5. EI-MS m/z (rel int): 232 (M⁺, 100), 231 ([M−H]⁺, 40), 203 ([M−CHO]⁺, 15), 105 ([M−I]⁺, 3).

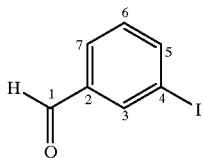

3-Iodobenzaldehyde. Commercially available 3-iodobenzyl alcohol (5.32 mL, 41.9 mmol) was dissolved in 200 mL CH$_2$Cl$_2$. Upon completion, the reaction was diluted with 250 mL Et$_2$O. The product was recovered as off-white crystals (8.1 g, 83.4%) mp: 48.0–55.0° C. TLC: R$_f$ 0.54 (3:1 hexanes/EtOAc). IR (neat): 3058, 2824, 2728, 1698, 1586, 1566. $^1$H-NMR (400 MHz, CDCl$_3$): δ 9.93 (s, 1H, C1-H), 8.22 (t, 1H, J=1.6, C3-H), 7.96 (dt, 1H, J=7.7, 1.4, C5-H), 7.85 (dt, 1H, J=7.7, 1.3, C7-H), 7.29 (t, 1H, J=7.7, C6-H). $^{13}$C-NMR (125 MHz, CDCl$_3$): δ 190.6, 143.1, 138.4, 138.0, 130.7, 128.8, 94.6. EI-MS m/z (rel int): 232 (M⁺, 100), 231 ([M−H]⁺, 25), 203 ([M−CHO]⁺, 14), 104 ([M−HI]⁺, 38).

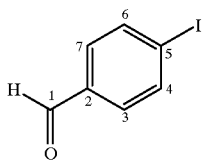

4-Iodobenzaldehyde. 4-Iodobenzyl alcohol prepared above (16.9 g, 72.2 mmol) was dissolved in 350 mL CH$_2$Cl$_2$. Upon completion, the reaction was diluted with 250 mL Et$_2$O. The product was recovered as a white solid (13.7 g, 81.8%) mp: 71.0–73.5° C. TLC: R$_f$ 0.50 (3:1 hexanes/EtOAc). IR (film): 2820, 2726, 1690, 1584, 1564, 804. $^1$H-NMR (400 MHz, CDCl$_3$): δ 9.93 (s, 1H, C1-H), 7.92 (d, 2H, J=8.5, C4-H, C6-H), 7.59 (d, 2H, J=8.1, C3-H, C7-H). $^{13}$C-NMR (100 MHz, CDCl$_3$): δ 191.4, 138.4, 135.6, 130.8, 102.8. EI-MS m/z (rel int): 232 (M⁺, 100), 203 ([M−CHO]⁺, 24).

General Procedure for Synthesis of N-(Iodobenzyl) hydroxylamines. (Borch, R. F.; Bernstein, M. D.; Durst, H. D. *J. Am. Chem. Soc.* 1971, 93, 2897–2904.) To a stirred solution of the appropriate iodobenzaldehyde (1.0 equiv) in a mixture of MeOH and THF was added a trace of Methyl Orange at rt. Hydroxylamine hydrochloride (1.25 equiv) was dissolved in H$_2$O and added to the iodobenzaldehyde solution. The pH was raised to 9 with 6N KOH and additional THF, MeOH, and/or H$_2$O were added to form a homogeneous solution. Solid sodium cyanoborohydride (1.0 equiv) was added and 2N HCl in aq MeOH was added via addition funnel until the solution was ruby red. [CAUTION: Evolves gas!] Additional acid was added as necessary to maintain the color during the reaction. After the reaction was complete by NMR (15–20 h), the bulk of the MeOH and THF were evaporated. The remaining aq solution was adjusted to pH 12 with 6N KOH and extracted with 4×CH$_2$Cl$_2$. The combined organic extracts were washed with H$_2$O and brine, dried (MgS04), filtered, and evaporated to yield the crude N-(iodobenzyl)hydroxylamine which was determined by NMR to contain 90–94% of the desired product with the remainder N,N-bis(iodobenzyl)hydroxylamine. The crude product was used without further purification.

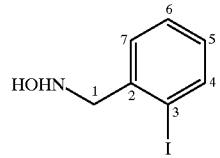

N-(2-Iodobenzyl)hydroxylamine. 2-Iodobenzaldehyde prepared above (10.3 g, 44.4 mmol) was dissolved in 50 mL MeOH and 10 mL THF. After addition of H$_2$NOH.HCl (10 mL H$_2$O) and 6N KOH, an additional 50 mL THF, 30 mL H$_2$O, and 30 mL MeOH were added. The product was recovered as a cloudy orange oil (9.46 g, 85.6%, 90% desired product). IR (film): 3256, 3057, 2872, 1564, 1466, 1435, 1013, 748. $^1$H-NMR (400 MHz, CDCl$_3$): δ 7.92 (dd, 1H, J=7.8, 1.2, C4-H), 7.58 (dd, 1H, J=7.4, 1.8, C7-H), 7.34 (td, 1H, J=7.4, 1.2, C6-H), 7.00 (td, 1H, J=7.6, 1.8, C5-H), 5.5 (br s, 1H, C1-NHOH), 5.0 (br s, 1H, C1-NHOH), 4.13 (s, 2H, C1-H$_2$). $^{13}$C-NMR (100 MHz, CDCl$_3$): δ 139.5, 139.1, 131.0, 129.4, 128.3, 100.1, 62.0. EI-MS m/z (rel int): 249 (M⁺, 36), 217 ([M−NHOH]⁺, 100), 122 ([M−I], 30). CI-MS (NH3) m/z (rel int): 284 ([M+2NH$_3$+H]⁺, 30), 267 ([M+NH$_4$]⁺, 100), 250 ([M+H]⁺, 27).

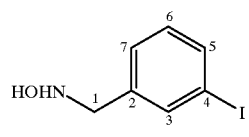

N-(3-Iodobenzyl)hydroxylamine. 3-Iodobenzaldehyde prepared above (8.1 g, 34.9 mmol) was dissolved in 50 mL MeOH and 20 mL THF. After addition of H$_2$NOH.HCl (10 mL H$_2$O) and 6N KOH, an additional 20 mL H$_2$O, 10 mL THF, and 10 mL MeOH were added. The product was recovered as a white solid (7.96 g, 91.6%, 92% desired product). mp: 63.0–70.0° C. IR (film): 3256, 3056, 2857, 1591, 1564, 1470, 1420, 1063, 995, 777. $^1$H-NMR (400 MHz, CDCl$_3$): δ 7.73 (t, 1H, J=1.6, C6-H), 7.63 (dt, 1H, J=7.9, 1.3, C5-H), 7.31 (d, 1H, J=7.6, C7-H), 7.09 (t, 1H, J=7.8, C6-H), 5.5 (br s, 1H, C1-NHOH), 5.1 (br s, 1H, C1-NHOH), 3.98 (s, 2H, C1-H$_2$). $^{13}$C-NMR (100 MHz, CDCl$_3$): δ 139.9,137.9, 136.6, 130.2, 128.2, 94.4, 57.4. EI-MS m/z (rel int): 249 (M⁺, 65), 217 ([M−NHOH]⁺, 100). CI-MS (NH$_3$) m/z (rel int): 284 ([M+2NH$_3$+H]⁺, 28), 267 ([M+NH$_4$]⁺, 100), 250 ([M+H]⁺, 45).

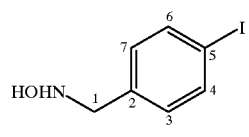

N(4-Iodobenzyl)hydroxylamine. 4-Iodobenzaldehyde prepared above (13.7 g, 59.0 mmol) was dissolved in 80 mL MeOH and 60 mL THF. After addition of H$_2$NOH.HCl (10 mL H$_2$O) and 6N KOH, an additional 30 mL H$_2$O was added. The product was recovered as a white solid (11.8 g, 80.3%, 94% desired product). mp: 89.0–95.0° C. IR (film): 3245, 3173, 2916, 2847, 1483, 1007, 787. $^1$H-NMR (400 MHz, CDCl$_3$): δ 7.66 (d, 2H, J=8.3, C4-H, C6-H), 7.06 (d, 2H, J=8.3, C3-H, C7-H), 5.4–4.7 (br s, 2H, C1-NHOH), 3.90 (s, 2H, C1-H$_2$). $^{13}$C-NMR (100 MHz, CDCl$_3$): 137.6, 137.4, 131.0, 93.2, 57.4. EI-MS m/z (rel int): 249 (M⁺, 29), 217 ([M−NHOH]⁺, 100). CI-MS (NH$_3$) m/z (rel int): 267 ([M+

NH$_4$]$^+$, 40), 250 ([M+H]$^+$, 100), 234 ([M−NHOH+NH$_3$]$^+$, 52), 217 ([M−NHOH]$^+$, 63).

General Procedure for Synthesis of [[(Iodophenyl) methyl]oxidoimino]acetic acids (Iodobenzyl Nitrone Acids) (Keirs, D.; Overton, K. *Heterocycles* 1989, 28, 841). The appropriate N-(iodobenzyl)hydroxylamine (see Supporting Information, 1.0 equiv) and glyoxylic acid monohydrate (1.05 equiv) were dissolved in CH$_2$Cl$_2$ and stirred at rt until the reaction was complete by NMR (24 h). The reaction mixture was washed with 2×H$_2$O and 1×brine, dried (MgSO$_4$), filtered, and evaporated to yield the crude nitrone. The crude product was slurried in THF, then Et$_2$O was added with vigorous stirring. After trituration overnight, the pure nitrone carboxylic acid 11 was recovered by vacuum filtration in 47–67% yield.

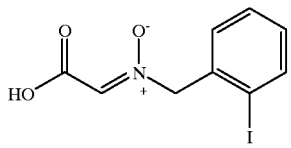

[[(2-Iodophenyl)methyl]oxidoimino]acetic acid (2-Iodobenzyl nitrone acid, 7b). N-(2-Iodobenzyl) hydroxylamine (9.46 g, 38.0 mmol) was reacted in 250 mL CH$_2$Cl$_2$. The crude product was recovered as a slightly yellow solid (10.9 g) and slurried in 10 mL THF then 250 mL Et$_2$O. The pure product was recovered as white flakes (6.22 g, 54%). mp: 82° C. (dec). IR (film): 1715, 1470, 1414. $^1$H-NMR (400 MHz, CDCl$_3$): δ 7.96 (dd, 1H, J=8.0, 1.0), 7.51 (dd, 1H, J=7.6, 2.0), 7.48 (td, 1H, J=7.4, 1.1), 7.44 (br s, 1H), 7.22 (s, 1H), 7.19 (ddd, 1H, J=7.9, 7.2, 2.0), 5.21 (s, 2H). $^{13}$C-NMR (125 MHz, CDCl$_3$): 160.6, 140.5, 132.4, 132.3, 132.1, 130.5, 129.4, 101.0, 74.2. CI-MS (NH3) m/z (rel int): 340 ([M+2NH$_3$+H]$^+$, 7), 323 ([M+NH$_4$]$^+$, 100), 306 ([M+H]$^+$, 10).

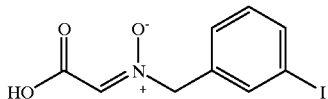

[[(3-Iodophenyl)methyl]oxidoimino]acetic acid (3-Iodobenzyl nitrone acid, 7c). N-(3-Iodobenzyl) hydroxylamine (7.96 g, 32.0 mmol) was reacted in 250 mL CH$_2$Cl$_2$. After dilution with 250 mL CH$_2$Cl$_2$ and washing, the crude product was recovered as a slightly yellow solid (9.1 g) and slurried in 10 mL THF then 350 mL Et$_2$O. The pure product was recovered as white flakes (6.58 g, 68%). mp: 109.0–109.5° C. (dec). IR (film): 1715, 1470, 1412. $^1$H-NMR (400 MHz, CDCl$_3$): δ 7.84 (dt, 1H, J=8.0, 1.3), 7.80 (t, 1H, J=1.7), 7.63 (br s, 1H), 7.42 (dt, 1H, J=7.7), 7.29 (s, 1H), 7.23 (t, 1H, J=7.8), 5.00 (s, 2H). $^{13}$C-NMR (125 MHz, CDCl$_3$): 160.5, 139.4, 138.6, 131.8, 131.0, 130.0, 128.9, 94.9, 69.8. CI-MS (NH$_3$) m/z (rel int): 340 ([M+2NH$_3$+H]$^+$, 14), 323 ([M+NH$_4$]$^+$, 100), 306 ([M+H]$^+$, 4).

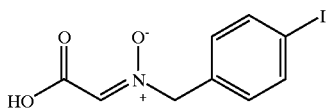

[[(4-Iodophenyl)methyl]oxidoimino]acetic acid (4-Iodobenzyl nitrone acid, 7d). N-(4-Iodobenzyl) hydroxylamine (11.8 g, 47.4 mmol) was reacted in 300 mL CH$_2$Cl$_2$. The crude product was recovered as a white powder (10.2 g) and slurried in 15 mL THF then 300 mL Et$_2$O. The pure product was recovered as a white powder (6.89 g, 48%). mp: 124.0° C. (dec, peach), 156–173° C. (dec, brown oil). IR (film): 1711, 1466, 1447, 1424, 1402. $^1$H-NMR (400 MHz, CDCl$_3$): δ 7.82 (d, 2H, J=8.4), 7.27 (s, 1H), 7.17 (d, 2H, J=8.3), 4.99 (s, 2H). $^{13}$C-NMR (100 MHz, CDCl$_3$): 160.5, 138.7, 131.4, 129.8, 129.2, 96.8, 70.2. EI-MS m/z (rel int): 305 (M$^+$, 2), 261 ([M−CO$_2$]$^+$, 6), 217 ([M−HOOC—CH—NO]$^+$, 100). FAB-MS (NBA/NaI) m/z (rel int): 328 ([M+Na]$^+$, 42), 306 ([M+H]$^+$, 25).

IV. Demonstration Compound Synthesis (10a–f, 11a–f, 12a–f, 13a–f)

To demonstrate the suitability of the reaction sequence for library synthesis, we carried six different iodobenzyl tetracycle substrates through the entire synthesis. The final products (FIG. 45) were recovered in 80–90% purity following six steps on solid-phase with no purification. All 26 precursors, intermediates, and products were fully characterized by 1H NMR, MS, HRMS, TLC and HPLC. All NMR peaks were unambiguously assigned by a combination of extensive homonuclear decoupling experiments and/or two-dimensional DQF-COSY, TOCSY, and NOESY experiments.

Methods. For demonstration compound photocleavage reactions, 50 mg of resin was divided between two 500 μL Eppendorf tubes, suspended in 450 μL CH$_3$CN each, and photolyzed for 2 h. Trace impurities resulting only from the photocleavage reaction were identified by photolysis of underivatized 3-amino-3-o-nitrophenylpropionic acid (Anp)-loaded resin (see below) and discounted in purity calculations.

H$_2$N-Anp-TentaGel Resin. TentaGel S NH? (10.0 g, 0.29 meq/g, 2.9 mmol, 1.0 equiv) was placed in a 100 mL fritted glass tube and swollen in distd THF with N$_2$ bubbling for 2 min. The vessel was drained and the resin was swollen in distd CH$_2$Cl$_2$ for another 2 min. The vessel was drained and Fmoc-Anp-OH (1.881 g, 4.35 mmol, 1.5 equiv), HATU (1.654 g, 4.35 mmol, 1.5 equiv), NMP (50 mL), and DIPEA (1.52 mL, 8.70 mmol, 3.0 equiv) were added in sequence. The reaction was allowed. to proceed for 5 h. The resin was washed with 4×NMP and 4×CH$_2$Cl$_2$ to yield Fmoc-Anp-TentaGel which was negative to Kaiser ninhydrin test. The Fmoc group was removed by 2×15 min treatments with 50 mL of freshly prepared 20% piperidine in DMF. The resin was washed as above to yield H$_2$N-Anp-TentaGel resin (10.6 g, 100% by mass) which turned brown after heating for 2 min under Kaiser conditions.

Identification of Photolysis Byproducts. 50 mg of underivatized H$_2$N-Anp-Tentagel resin was photolyzed and analyzed by TLC, HPLC, $^1$H-NMR and FAB-MS as follows: TLC (trace amounts, detectable by UV only): R$_f$ 0.55 (9:1 CH$_2$Cl$_2$/MeOH); R$_f$ 0.71, 0.82 (1:1 CH$_2$Cl$_2$/THF); R$_f$ 0.47, 0.71 (4:1 CH$_2$Cl$_2$/THF); R$_f$ 0.18, 0.63 (1:1 CH$_2$Cl$_2$/EtOAc). HPLC (trace amounts): t$_R$=2.073 min, λ$_{max}$=217, 244, 303 nm; t$_R$=2.462 min, λ$_{max}$=242, 301 nm; t$_R$=2.980 min, λ$_{max}$=243 nm; t$_R$=3.141 min, λ$_{max}$=239 nm. $^1$H-NMR (500 MHz, CD$_3$CN, trace amounts except for PEG): δ 7.70 (dd, J=5.6, 3.3), 7.60 (obs md, J=5.9, 2.5), 7.57 (td, J=7.8, 1.3), 7.52 (d, J=7.4), 7.09 (td, J=7.5, 0.8), 6.95 (d, J=7.9), 4.44 (br s), 4.30 (q, J=7.1), 4.22 (m), 3.55 (s, PEG), 2.85–2.50 (br), 1.31 (t, J=7.1), 1.26 (br s). FAB-MS (glycerol) m/z (rel int): 503 ([M+H]$^+$, 2). FAB-MS (NBA/NaI) m/z (rel int): 569 ([M+Na]$^+$, 100), 547 ([M+H]$^+$, 13), 553 ([M+Na]$^+$, 58), 531 ([M+H]$^+$, 25). Dibutylphthalate was occasionally detected by HPLC and LC-MS (HPLC: t$_R$=3.30 min; LC-MS: t$_R$=5.0 min, [M+H]$^+$=279). HPLC analysis also showed varying amounts of a secondary peak which trailed each product by 0.3–0.4 min and was highly UV active at 254 and 280 nm. This impurity could not be identified by LC-MS but might result form product cleavage at polyethyleneglycol rather than at the Anp linker. Adventitious oxidation of polyethyleneglycol to labile peroxides or esters has been discussed in the literature (Rapp Polymere Home Page. http://www.rapp-polymere.com (accessed June 1999).

H$_2$N-Aca-Anp-TentaGel Resin. H$_2$N-Anp-TentaGel resin (3.18 g, 0.27 meq/g, 0.873 mmol, 1.0 equiv) was placed in a 50 mL fritted glass tube and swollen in distd CH$_2$Cl$_2$ for 2 min. The vessel was drained and N-Fmoc-co-Aminocaproic acid (Fmoc-Aca-OH, 925.6 mg, 2.619 mmol, 3.0 equiv), PyBOP (1.363 g, 2.619 mmol, 3.0 equiv), 30 mL NMP, and DIPEA (0.760 mL, 4.365 mmol, 5.0 equiv) were added in sequence. After 1 h, the resin was washed as above to yield Fmoc-Aca-Anp-TentaGel resin which was negative to Kaiser test. Fmoc deprotection as above yielded H$_2$N-Aca-Anp-TentaGel resin (3.24 g, 99% by mass) which was positive to Kaiser test.

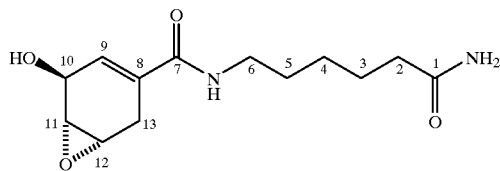

(1S,5S,6S)-N-(6-amino-6-oxohexyl)-5-hydroxy-7-oxabicyclo[4.1.0]hept-3-ene-3-carboxamide (Epoxycyclohexenol ω-amino caproic carboxamide, 3). H$_2$N-Aca-Anp-Tentagel resin (1.63 g, 0.27 meq/g, 0.434 mmol, 1.0 eq) was placed in a 50 mL fritted glass tube. Epoxycyclohexenol carboxylic acid (+)-2 (74.5 mg, 0.477 mmol, 1.1 eq), PyBOP (248.2 mg, 0.477 mmol, 1.1 eq), anhydrous NMP (20 mL), and DIPEA (227 μL, 1.301 mmol, 3.0 eq) were added in sequence. After 2 h, the resin was washed as above to yield Epoxycyclohexenol-Aca-Anp-Tentagel resin 3R (1.6425 g, 97.2% by mass) which was negative to Kaiser test. Photolysis of the resin yielded the crude epoxycyclohexenol carboxamide, 3, as a yellow oil. TLC: R$_f$ 0.09 (9:1 CH$_2$Cl$_2$/MeOH); R$_f$ 0.03 (1:1 CH$_2$Cl$_2$/THF). HPLC: t$_R$=1.717 min, λ$_{max}$=203, 211 nm. $^1$H-NMR (500 MHz, CD$_3$CN): δ 6.60 (br s, 1H, C7-NH), 6.20 (m, 1H, C9-H), 6.04 (br s, 1H, C1-NH$_a$), 5.51 (br s, 1H, C1-NH$_b$), 4.41 (m, 1H, C10-H), 3.35 (m, 1H, C11-H), 3.17 (q, 2H, J=6.8, C6-H$_2$), 3.14 (m, 1H, C12-H), 2.72 (app ddd, 1H, J=19.8, 2.7, 1.3, C13-H$_a$), 2.58 (app dq, 1H, J=19.6, 2.4, C13-H$_b$), 2.11 (t, 2H, J=7.5, C2-H$_2$), 1.54 (quint, 2H, J=7.6, C5-H$_2$), 1.47 (quint, 2H, J=7.3, C3-H$_2$), 1.29 (m, 2H, C4-H$_2$). FAB-MS (NBA/NaI) m/z (rel int): 291 ([M+Na]$^+$, 100), 269 ([M+H]$^+$, 22). HRMS (NBA/NaI) m/z calcd for C$_{13}$H$_{20}$N$_2$O$_4$Na 291.1321; found 291.1320.

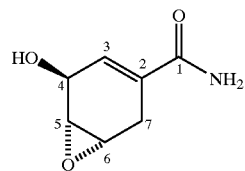

(1S,5S,6S)-5-Hydroxy-7-oxabicyclo[4.1.0]hept-3-ene-3-carboxamide (Epoxycyclohexenol carboxamide, 3'). Epoxycyclohexenol-Anp-Tentagel resin 3R' was synthesized essentially as above from H$_2$N-Anp-Tentagel resin (99% yield by mass). Photolysis of the resin yielded the crude epoxycyclohexenol carboxamide 3' as a yellow oil. TLC: R$_f$ 0.18 (9:1 CH$_2$Cl$_2$/MeOH); R$_f$ 0.11 (1:1 CH$_2$Cl$_2$/THF). HPLC: t$_R$=0.306 min, λ$_{max}$=215 nm. $^1$H-NMR (400 MHz, CD$_3$CN): δ 6.28 (m, 1H, C3-H), 4.42 (m, 1H, C4-H), 3.35 (m, 1H, C5-H), 3.13 (m, 1H, C6-H), 2.73 (ddq, 1H, J=4.0, 1.3, C7-H$_a$), 2.59 (app dq, 1H, J=7.3, 2.5, C7-H$_b$). CI-MS (NH3) m/z (rel int): 173 ([M+NH$^4$]$^+$, 90), 156 ([M+H]$^+$, 33). HRMS (NH$_3$) m/z for C$_7$H$_{13}$N$_2$O$_3$ 173.0926; found 173.0929.

General Procedure for Tandem Acylation-1,3-Dipolar Cycloaddition Reaction. In a PD-10 column were placed the appropriate epoxycyclohexenol resin, 3R (533 mg, 0.26 meq/g, 133.9 μmol, 1.0 equiv), PyBroP (127.6 mg, 273.8 μmol, 2.0 equiv), and the appropriate iodobenzyl nitrone acid, 7 (83.5 mg, 273.8 μmol, 2.0 equiv). CH$_2$Cl$_2$ (5.3 mL) was added and the tube was flushed with Ar, capped, vortexed briefly, and immediately cooled to 0° C. in an ice bath. DIPEA (95.4 μL, 547.5 μmol, 4.0 equiv) was added and the tube was vortexed briefly and returned to 0° C. DMAP (18.4 mg, 150.6 μmol, 1.1 equiv) was added as 97.4 μL of a CH$_2$Cl$_2$ stock solution and the tube was vortexed briefly and returned to 0° C. for 10 min. The tube was then wrapped with parafilm, wrapped in foil, and transferred to a Labquake in a 4° C. cold cabinet. After mixing overnight, the resin was washed (Method B) and exposed to the coupling conditions twice more to yield the iodobenzyl tetracycle resin, 10R. Photolysis of the resin yielded the crude iodobenzyl tetracycle, 10, as a yellow oil.

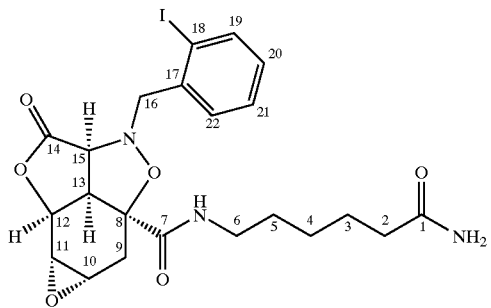

[2aS-(2aα,4aα,5aβ,6aβ,6bα,6cα)]-N-(6-Amino-6-oxohexyl)hexahydro-3-[(2-iodophenyl)methyl]-2-oxo-2H-furo[4,3,2-cd]oxireno[f][1,2]benzisoxazole-4a(3H)-carboxamide (2-Iodobenzyl tetracycle ω-aminocaproic carboxamide, 10a). TLC: R$_f$ 0.42 (9:1 CH$_2$Cl$_2$/MeOH); R$_f$ 0.14 (1:1 CH$_2$Cl$_2$/THF). HPLC: t$_R$=2.894 min, λ$_{max}$=202, 229 nm. $^1$H-NMR (400 MHz, CD$_3$CN): δ 7.89 (dd, 1H, J=7.9, 1.2, C19-H), 7.48 (dd, 1H, J=8.3, 2.3, C22-H), 7.40 (td, 1H, J=7.5, 1.2, C21-H), 7.05 (td, 1H, J=7.6, 1.8, C20-H), 6.11 (br s, 1H, C7-NH), 6.02 (br s, 1H, C1-NH$_a$), 5.50 (br s, 1H, C1-NH$_b$), 5.11 (dd, 1H, J=7.2, 2.7, C 12-H), 4.39 (d, 1H, J=8.2, C15-H), 4.33 (d, 1H, J=14.7, C16-H$_a$), 4.07 (d, 1H, J=14.6, C16-H$_b$), 3.86 (t, 1H, J=7.7, C13-H), 3.50 (dd, 1H, J=3.6, 2.7, C11-H), 3.29 (dd, 1H, J=6.3, 2.5, C10-H), 3.02 (m, 1H, C6-H$_a$), 2.85 (m, 1H, C6-H$_b$), 2.31 (dd, 1H, J=16.6, 1.9, C9-H$_a$), 2.21 (dd, 1H, J=16.8, 2.7, C9-H$_b$), 2.07 (t, 2H, J=7.5, C2-H$_2$), 1.46 (m, 2H, C3-H$_2$), 1.26 (m, 2H, C5-H$_2$), 1.14 (m, 2H, C4-H$_2$). FAB-MS (glycerol) m/z (rel int): 556 ([M+H]$^+$, 33). HRMS (glycerol) m/z calcd for C$_{22}$H$_{27}$IN$_3$O$_6$ 556.0945; found 556.0957.

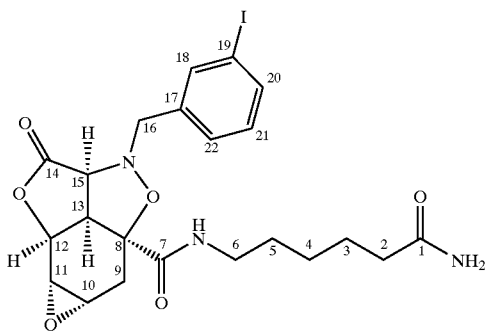

[2aS-(2aα,4aα,5aβ,6aβ,6bα,6cα)]-N-(6-Amino-6-oxohexyl)hexahydro-3-[(3-iodophenyl)methyl]-2-oxo-2H-furo[4,3,2-cd]oxireno[f][1,2]benzisoxazole-4a(3H)-carboxamide (3-Iodobenzyl tetracycle ω-aminocaproic carboxamide, 10b). TLC: $R_f$ 0.38 (9:1 $CH_2Cl_2$/MeOH); $R_f$ 0.15 (1:1 $CH_2Cl_2$/THF). HPLC: $t_R$=2.962 min, $\lambda_{max}$=207, 229 nm. $^1$H-NMR (400 MHz, $CD_3CN$): δ 7.75 (app d, 1H, J=1.4, C18-H), 7.67 (dd, 1H J=7.9, 1.2, C20-H), 7.37 (dd, 1H, J=7.7, 1.0, C22-H), 7.14 (t, 1H, J=7.8, C21-H), 6.25 (br s, 1H, C7-NH), 6.02 (br s, 1H, C1-$NH_a$), 5.50 (br s, 1H, C1-$NH_b$), 5.09 (dd, 1H, J=7.3, 2.6, C12-H), 4.34 (d, 1H, J=8.2, C15-H), 4.24 (d, 1H, J=14.2, C16-$H_a$), 3.94 (d, 1H, J=14.2, C16-$H_b$), 3.84 (t, 1H, J=7.7, C13-H), 3.49 (dd, 1H, J=3.6, 2.7, C11-H), 3.28 (dd, 1H, J=6.0, 2.6, C10-H), 3.07 (m, 1H, C6-$H_a$), 2.96 (m, 1H, C6-$H_b$), 2.28 (dd, 1H, J=16.8, 1.9, C9-$H_a$), 2.21 (dd, 1H, J=16.8, 2.8, C9-$H_b$), 2.08 (t, 2H, J=7.5, C2-H2), 1.50 (m, 2H, C3-H2), 1.26 (m, 2H, C5-H2), 2H, C4-H2). FAB-MS (glycerol) m/z (rel int): 556 ([M+H]+, 100). HRMS (glycerol) m/z calcd for $C_{22}H_{27}IN_3O_6$ 556.0945; found 556.0953.

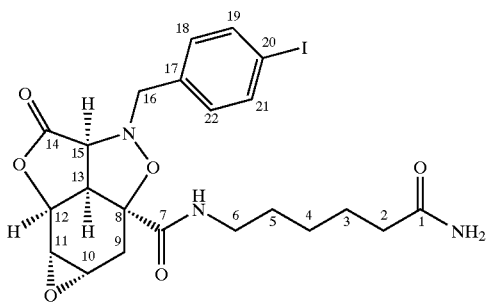

[2aS-(2aα,4aα,5aβ,6aβ,6bα,6cα)]-N-(6-Amino-6-oxohexyl)hexahydro-3-[(4-iodophenyl)methyl]-2-oxo-2H-furo[4,3,2-cd]oxireno[f][1,2]benzisoxazole-4a(3H)-carboxamide (4-Iodobenzyl tetracycle ω-aminocaproic carboxamide, 10c). TLC: $R_f$ 0.32 (9:1 $CH_2Cl_2$/MeOH); $R_f$ 0.15 (1:1 THF/$CH_2Cl_2$). HPLC: $t_R$=2.974 min, $\lambda_{max}$=204, 234 nm. $^1$H-NMR (400 MHz, $CD_3CN$): δ 7.71 (d, 2H, J=8.3, C19-H, C21-H), 7.15 (d, 2H, J=8.3, C18-H, C22-H), 6.21 (br s, 1H, C7-NH), 6.02 (br s, 1H, C1-$NH_a$), 5.51 (br s, 1H, C1-$NH_b$), 5.08 (dd, 1H, J=7.2, 2.6, C12-H), 4.32 (d, 1H, J=8.2, C15-H), 4.22 (d, 1H, J=14.1, C11-H), 3.27 (d, 1H, J=14.1, C16-$H_b$), 3.83 (t, 1H, J=7.7, C13-H), 3.49 (dd, 11H, J=3.6, 2.7, C11-H), 3.27 (dd, 11H, J=6.2, 2.4, C10-H), 3.03 (m, 1H, C6-$H_a$), 2.92 (m, 1H, C6-$H_b$), 2.28 (m, 1H, C9-$H_a$), 2.20 (m, 11H, C9-$H_b$), 2.09 (t, 2H, J=7.7, C2-$H_2$), 1.5 (m, 2H, C3-$H_2$), 1.3–1.1 (m, 4H, C5-$H_2$, C4-$H_2$). FAB-MS (glycerol) m/z (rel int): 556 ([M+H]+, 100). HRMS (glycerol) m/z calcd for $C_{22}H_{27}IN_3O_6$ 556.0945; found 556.0947.

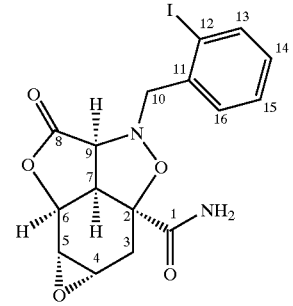

[2aS-(2aα,4aα,5aβ,6aβ,6bα,6cα)]-Hexahydro-3-[(2-iodophenyl)methyl]-2-oxo-2H-furo[4,3,2-cd]oxireno[f][1,2benzisoxazole-4a(3H)-carboxamide (2-Iodobenzyl tetracycle carboxamide, 10d). TLC: $R_f$ 0.38 (4:1 $CH_2Cl_2$/THF); $R_f$ 0.27 (1:1 $CH_2Cl_2$/EtOAc). HPLC: $t_R$=2.573 min, $\lambda_{max}$= 202, 230 nm. $^1$H-NMR (400 MHz, $CD_3CN$): δ 7.87 (dd, 1H, J=7.9, 1.2, C13-H), 7.52 (dd, 1H, J=7.8, 1.7, C16-H), 7.38 (td, 1H, J=7.5, 1.2, C15-H), 7.04 (td, 1H, J=7.5, 1.8, C14-H), 6.06 (br s, 1H, C1-$NH_a$), 5.51 (br s, 1H, C1-$NH_b$), 5.12 (dd, 1H, J=7.2, 2.7, C6-H), 4.38 (d, 1H, J=8.2, C9-H), 4.35 (d, 1H, J=14.6, C10-$H_a$), 4.09 (d, 1H, J=14.6, C10-$H_b$), 3.87 (t, 1H, J=7.5, C7-H), 3.51 (dd, 1H, J=3.6, 2.7, C5-H), 3.30 (dd, 1H, J=6.2, 2.4, C4-H), 2.34 (dd, 1H, J=16.8, 1.7, C3-$H_a$), 2.25 (dd, 1H, J=16.8, 2.7, C3-$H_b$). FAB-MS (glycerol) m/z (rel int): 443 ([M+H]+, 42). HRMS (glycerol) m/z calcd for $C_{16}H_{16}IN_2O_5$ 443.0104; found 443.0110.

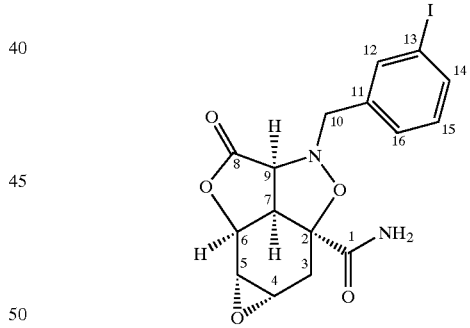

[2aS-(2aα,4aα,5aβ,6aβ,6bα,6cα)]-Hexahydro-3-[(3-iodophenyl)methyl]-2-oxo-2H-furo[4,3,2-cd]oxireno[f][1,2]benzisoxazole-4a(3H)-carboxamide (3-Iodobenzyl tetracycle carboxamide, 10e). TLC: $R_f$ 0.38 (4:1 $CH_2Cl_2$/THF); $R_f$ 0.30 (1:1 $CH_2Cl_2$/EtOAc). HPLC: $t_R$=2.893 min, $\lambda_{max}$= 203, 229 nm. $^1$H-NMR (400 MHz, $CD_3CN$): δ 7.77 (app d, 1H, J=1.6, C12-H), 7.65 (dd, 1H, J=7.8, 1.4, C14-H), 7.37 (dd, 1H, J=7.7, 1.0, C16-H), 7.12 (t, 1H, J=7.8, C15-H), 6.09 (br s, 1H, C1-$NH_a$), 5.70 (br s, 1H, C1-$NH_b$), 5.09 (dd, 1H, J=7.2, 2.6, C6-H), 4.32 (d, 1H, J=8.2, C9-H), 4.26 (d, 1H, J=14.2, C10-$H_a$), 3.95 (d, J=14.2, C10-$H_b$), 3.86 (t, 1H, J=7.5, C7-H), 3.49 (dd, 1H, J=3.6, 2.7, C5-H), 3.28 (dd, 1H, J=6.2, 2.3, C4-H), 2.34 (dd, 1H, J=16.8, 1.7, C3-$H_a$), 2.25 (dd, 1H, J=16.8, 2.7, C3-$H_b$). FAB-MS (glycerol) m/z (rel int): 443 ([M+H]⁺, 38). HRMS (glycerol) m/z calcd for $C_{16}H_{16}IN_2O_5$ 443.0104; found 443.0105.

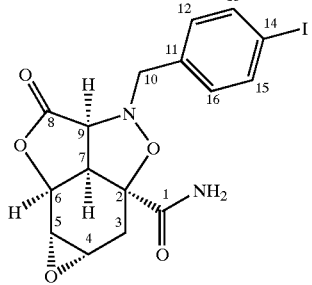

[2aS-(2aα,4aα,5aβ,6aβ,6bα,6cα)]-Hexahydro-3-[(4-iodophenyl)methyl]-2-oxo-2H-furo[4,3,2-cd]oxireno[f][1,2]benzisoxazole-4a(3H)-carboxamide (4-Iodobenzyl tetracycle carboxamide, 10e). TLC: $R_f$ 0.38 (4:1 $CH_2Cl_2$/THF); $R_f$ 0.27 (1:1 $CH_2Cl_2$/EtOAc). HPLC: $t_R$=2.898 min, $\lambda_{max}$= 202, 234 nm. ¹H-NMR (400 MHz $CD_3CN$): δ 7.69 (d, 2H, J=8.3, C13-H, C15-H), 7.17 (d, 2H, J=8.3, C12-H, C16-H), 6.06 (br s, 1H, C1-NH$_a$), 5.65 (br s, 1H, C1-NH$_b$), 5.09 (dd, 1H, J=7.3, 2.6, C6-H), 4.32 (d, 1H, J=8.2, C9-H), 4.24 (d, 1H, J=14.1, C10-H$_a$), 3.95 (d, 1H, J=14.1, C10-H$_b$), 3.85 (t, 1H, J=7.5, C7-H), 3.49 (dd, 1H, J=3.6, 2.7, C5-H), 3.28 (dd, 1H, J=6.22.4, C4-H), 2.34 (dd, 1H, J=16.8, 1.7, C3-H$_a$), 2.23 (dd, 1H, J=16.8, 2.7, C3-H$_b$). FAB-MS (glycerol) m/z (rel int): 443 ([M+H]⁺, 28). HRMS (glycerol) m/z calcd for $C_{16}H_{16}IN_2O_5$ 443.0104; found 443.0102.

General Procedure for Sonogashira/Castro-Stephens Alkyne Coupling Reaction. To 50 mg (10.5 μmol) of the appropriate iodobenzyl tetracycle resin, 10R, in a 2 mL Bio-Spin® column was added copper(I)iodide (4.4 mg, 23.1 μmol, 2.2 equiv) and bis(triphenylphosphine)palladium(II) chloride (8.1 mg, 11.55 μmol, 1.1 equiv). DMF (500 μL) was added and the tube was flushed with Ar, capped, and shaken to dissolve the reagents. DIPEA (54.9 μL, 315 μmol, 30 equiv) and the appropriate alkyne (20 equiv) were added and the tube was capped, shaken, wrapped with parafilm, and wrapped in foil. After mixing at rt (para: 15 min, meta: 30 min, ortho: 45 min), the resin was washed (Method A) and dried under vacuum. Photolysis of the resin, 11R, yielded the crude alkynylbenzyl tetracycle, 11, as a yellow oil.

General Procedure for Sonogashira/Castro-Stephens Alkyne Coupling Reaction with Bis(Terminal Alkynes). The same procedure was used as above except (Ph₃P)₂PdCl₂ was replaced with tetrakis(triphenylphosphine)palladium(0) (prepared as previously described) (Coulson, D. L. *Inorg. Synth.* 1972, 13, 121) and 70 equiv of DIPEA and 50 equiv of alkyne were used.

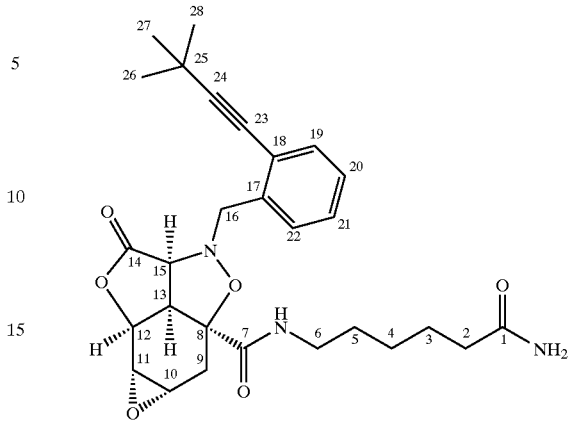

[2aS-(2aα,4aα,5aβ,6aβ,6bα,6cα)]-N-(6-Amino-6-oxohexyl)-3-[[2-(3,3-dimethyl-1-butynyl)phenyl]methyl]hexahydro-2-oxo-2H-furo[4,3,2-cd]oxireno[f][1,2]benzisoxazole-4a(3H)-carboxamide (o-(3,3-Dimethyl-1-butynyl)benzyl tetracycle ω-aminocaproic carboxamide, 11a). TLC: $R_f$ 0.43 (9:1 $CH_2Cl_2$/MeOH); $R_f$ 0.20 (1:1 $CH_2Cl_2$/THF). HPLC: $t_R$=3.257 min, $\lambda_{max}$=209, 247 nm. ¹H-NMR (500 MHz, $CD_3CN$): δ 7.44 (d, 1H, J=7.5, C19-H), 7.35 (dd, 1H, J=7.7, 1.2, C22-H), 7.32 (td, 1H, J=7.7, 1.4, C20-H), 7.26 (td, 1H, J=7.4, 1.3, C21-H), 6.14 (br s, 1H, C7-NH), 6.00 (br s, 1H, C1-NH$_a$), 5.50 (br s, 1H, C1-NH$_b$), 5.10 (dd, 1H, J=7.2, 2.6, C12-H), 4.37 (d, 1H, J=8.2, C15-H), 4.35 (d, 1H, J=16.6, C16-H$_a$). 4.18 (d, 1H, J=14.4, C16-H$_b$), 3.85 (t, 1H, J=7.6, C13-H), 3.50 (t, 1H, J=3.2, C11-H), 3.28 (dd, 1H, J=6.0, 2.6, C10-H), 3.01 (m, 1H, C6-H$_a$), 2.88 (m, 1H, C6-H$_b$), 2.31 (d, 1H, J=16.8, C9-H$_a$), 2.19 (dd, 1H, J=16.7, 2.8, C9-H$_b$), 2.06 (t, 2H, J=7.5, C2-H$_2$), 1.46 (m, 2H, C3-H$_2$), 1.31 (obs m, 2H, C5-H$_2$), 1.30 (s, 9H, C26-H$_3$, C27-H$_3$, C28-H$_3$), 1.13 (m, 2H, C4-H$_2$). FAB-MS (glycerol) m/z (rel int): 510 ([M+H]⁺, 100). HRMS (glycerol) m/z calcd for $C_{28}H_{36}N_3O_6$ 510.2604; found 510.2612.

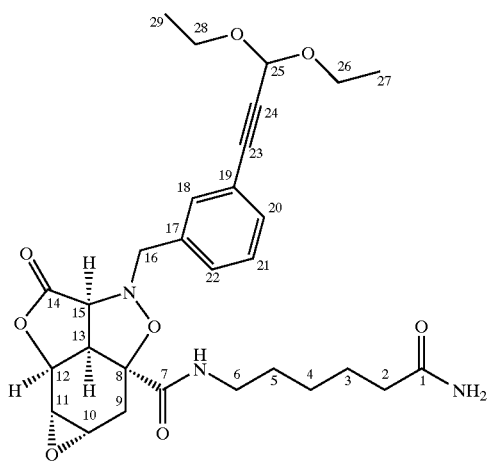

[2aS-(2aα,4aα,5aβ,6aβ,6bα,6cα)]-N-(6-Amino-6-oxohexyl)-3-[[3-(3,3-dimethxy-1-propynyl)phenyl]methyl]hexahydro-2-oxo-2H-furo[4,3,2-cd]oxireno[f][1,2]benzisoxazole-4a(3H)-carboxamide (m-(3,3-Diethoxy-1-propynyl)benzyl tetracycle ω-aminocaproic carboxamide, 11b). TLC: R$_f$ 0.39 (9:1 CH$_2$Cl$_2$/MeOH); R$_f$ 0.17 (1:1 CH$_2$Cl$_2$/THF). HPLC: t$_R$ =3.105 min, λ$_{max}$=206, 243, 246 nm. $^1$H-NMR (500 MHz, CD$_3$CN): δ 7.51 (s, 1H, C18-H), 7.43–7.34 (m, 3H, C20-H, C21-H, C22-H), 6.22 (br s, 1H, C7-NH), 6.00 (br s, 1H, C1-NH$_a$), 5.46 (br s, 1H, C1-NH$_b$), 5.45 (s, 1H, C25-H), 5.09 (dd, 1H, J=7.3, 2.5, C12-H), 4.34 (d, 1H, J=8.1, C15-H), 4.28 (d, 1H, J=14.1, C16-H$_a$), 3.98 (d, 1H, J=14.2, C16-H$_b$), 3.85 (t, 1H, J=7.7, C13-H), 3.74 (m, 2H, C26-H$_a$, C28-H$_a$), 3.60 (m, 2H, C26-H$_b$, C28-H$_b$), 3.50 (app t, 1H, J=3.5, 2.8, C11-H), 3.28 (app q, 1H, J=5.8, 2.7, C10-H), 3.06 (m, 1H, J=13.2, 6.4, C6-H$_a$), 2.94 (m, 1H, J=13.2, 5.6, C6-H$_b$), 2.28 (dd, 1H, J=16.9, 1.4, C9-H$_a$), 2.21 (dd, 1H, J=16.8, 2.8, C9-H$_b$), 2.09 (t, 2H, J=7.4, C2-H$_2$), 1.49 (quint, 2H, J=7.5, C3-H$_2$), 1.24 (obs m, 2H, C5-H$_2$), 1.20 (t, 6H, J=7.1, C27-H$_3$, C29-H$_3$), 1.16 (obs m, 2H, C4-H$_2$). FAB-MS (gylcerol) m/z (rel int): 510 ([M–OEt]$^+$, 100), 556 ([M+H]$^+$, 7). FAB-MS (NBA/NaI) m/z (rel int): 578 ([M+Na]$^+$, 100), 510 ([M–OFt]$^+$, 11). HRMS (NBA/NaI) m/z calcd for C$_{29}$H$_{37}$N$_3$O$_8$Na 578.2478; found 578.2475.

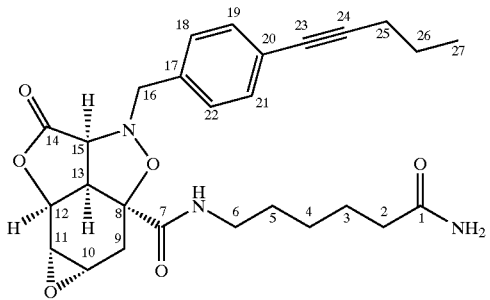

[2aS-(2aα,4aα,5aβ,6aβ,6bα,6cα)]-N-(6-Amino-6-oxohexyl)hexahydro-2-oxo-3-[[4-(1-pentynyl)phenyl]methyl]-2H-furo[4,3,2-cd]oxireno[f][1,2]benzisoxazole-4a(3H)-carboxamide (p-(1-Pentynyl)benzyl tetracycle ω-aminocaproic carboxamide, 11c). TLC: R$_f$ 0.31 (9:1 CH$_2$Cl$_2$/MeOH); R$_f$ 0.18 (1:1 CH$_2$Cl$_2$/THF). HPLC: t$_R$=3.255 min, λ$_{max}$=203, 248, 251 nm. $^1$H-NMR (500 MHz, CD3CN): δ 7.35 (d, 2H, J=8.3, C19-H, C21-H), 7.30 (d, 2H, J=8.1, C18-H, C22-H), 6.21 (br s, 1H, C7-NH), 6.01 (br s, 1H, C1-NH$_a$), 5.50 (br s, 1H, C1-NH$_b$), 5.08 (dd, 1H, J=7.2, 2.6, C12-H), 4.32 (d, 1H, J=8.1, C15-H), 4.26 (d, 1H, J=14.1, C16-H$_a$), 3.98 (d, 1H, J=14.1, C16-H$_b$), 3.83 (t, 1H, J=7.7, C13-H), 3.49 (app t, 1H, J=3.2, C11-H), 3.28 (app dd, 1H, J=5.9, 2.7, C10-H), 3.02 (m, 1H, C6-H$_a$), 2.91 (m, 1H, C6-H$_b$), 2.37 (t, 2H, J=7.0, C25-H$_2$), 2.27 (br d, 1H, J=16.8, C9-H$_a$), 2.20 (dd, 1H, J=16.8, 2.9, C9-H$_b$), 2.08 (t, 2H, J=7.7, C2-H$_2$), 1.59 (sxt, 2H, J=7.2, C26-H$_2$), 1.49 (quint, 2H, J=7.4, C3-H$_2$), 1.22 (m, 2H, C5-H$_2$), 1.17 (m, 2H, C4-H$_2$), 1.02 (t, 3 H, J=7.3, C27-H3). FAB-MS (glycerol) m/z rel int): 496 ([M+H]$^+$, 100). FAB-MS (NBA/NaI) m/z (rel int): 518 ([M+Na]$^{30}$, 100), 496 ([M+H]$^+$, 13). HRMS (glycerol) m/z calcd for C$_{27}$H$_{34}$N$_3$O$_6$ 496.2448; found 496.2463.

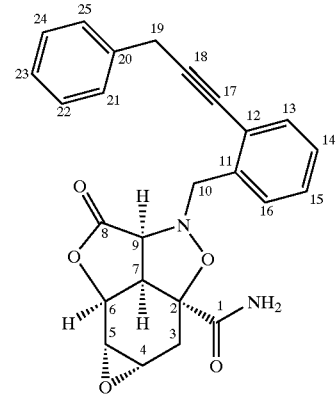

[2aS-(2aα,4aα,5aβ,6aβ,6bα,6cα)]-Hexahydro-3-[[2-(3-phenyl-1-propynyl)phenyl]methyl]-2-oxo-2H-furo[4,3,2-cd]oxireno[f][1,2]benzisoxazole-4a(3H)-carboxamide (o-(3-Phenyl-1-propynyl)benzyl Tetracycle Carboxamide, 11d). TLC: R$_f$ 0.44 (4:1 CH$_2$Cl$_2$/THF); R$_f$ 0.30 (1:1 CH$_2$Cl$_2$/EtOAc). HPLC: t$_R$=3.114 min, λ$_{max}$=(203), 208, 246 nm. $^1$H-NMR (500 MHz, CD$_3$CN): δ 7.50 (d, 1H, J=7.4, C13-H), 7.44 (d, 1H, J=7.4, C16-H), 7.43 (obs d, 2H, C21-H, C25-H), 7.36 (t, 2H, J=7.7, C22-H, C24-H), 7.33 (td, 1H, J=7.5, 1.4, C14-H), 7.28 (td, 1H, J=7.5, 1.3, C15-H), 7.26 (t, 1H, J=7.2, C23-H), 6.04 (br s, 1H, C1-NH$_a$), 5.58 (br s, 1H, C1-NH$_b$), 5.05 (dd, 1H, J=7.1, 2.7, C6-H), 4.41 (d, 1H, J=14.0, C10-H$_a$), 4.24 (d, 1H, J=13.9, C10-H$_b$), 4.24 (d. 1H, J=8.2, C9-H), 3.88 (s, 2H, C19-H$_2$), 3.79 (t, 1H, J=7.6, C7-H), 3.49 (t, 1H, J=3.3, C5-H), 3.28 (app dd, 1H, J=6.2, 2.5, C4-H), 2.39 (d, 1H, J=16.5, C3-H$_a$), 2.20 (dd, 1H, J=16.7, 2.6, C3-H$_b$). FAB-MS (glycerol) m/z (rel int): 431 ([M+H]$^+$, 33). FAB-MS (NBA/NaI) m/z (rel int): 453 ([M+Na]$^+$, 40), 431 ([M+H]$^+$, 5). HRMS (NBA/NaI) m/z calcd for C$_{25}$H$_{22}$N$_2$O$_5$Na 453.1426; found 453.1432.

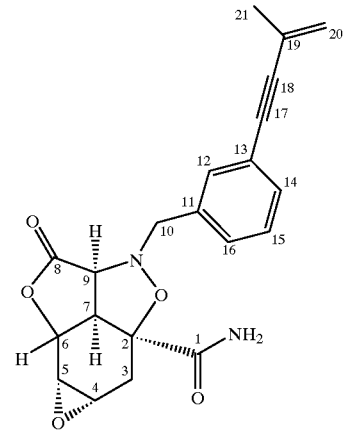

[2aS-(2aα,4aα,5aβ,6aβ,6bα,6cα)]-Hexahydro-3-[[3-(3-methyl-3-buten-1-ynyl)phenyl]methyl]-2-oxo-2H-furo[4,3,2-cd]oxireno[f][1,2]benzisoxazole-4a(3H)-carboxamide (m-(3-Methyl-3-buten-1-ynyl)benzyl tetracycle carboxamide, lie). TLC: R$_f$ 0.41 (4:1 CH$_2$Cl$_2$/THF); R$_f$ 0.33 (1:1 CH$_2$Cl$_2$/EtOAc). HPLC: t$_R$=3.182 min, λ$_{max}$=(203), 212, 270, (282) nm. $^1$H-NMR (500 MHz, CD$_3$CN): δ 7.57 (s, 1H, C12-H), 7.37 (m, 2H, C14-H, C16-H), 7.33 (t, 1H, J=7.4, C15-H), 6.09 (br s, 1H, C1-NH$_a$), 5.64 (br s, 1H, C1-NH$_b$), 5.38 (app q, 1H, J=1.0, C20-H$_Z$), 5.36 (app q, 1H, J=1.7, C20-H$_E$), 5.09 (dd, 1H, J=7.2, 2.6, C6-H), 4.32 (d, 1H, J=8.2, C9-H), 4.29 (d, 1H, J=13.9, C10-H$_a$), 4.00 (d, 1H, J=13.9, C10-H$_b$), 3.86 (t, 1H, J=7.7, C7-H), 3.50 (t, 1H, J=3.2, C5-H), 3.29 (dt, 1H, J=3.7, 2.5, C4-H), 2.36 (dd, 1H, J=16.9, 1.6, C3-H$_a$), 2.26 (dd, 1H, J=16.8, 2.7, C3-H$_b$), 1.97 (dd, 3H, J=2.5, 1.4, C21-H$_3$). FAB-MS (glycerol) m/z (rel int): 381 ([M+H]$^+$, 100). FAB-MS (NBA/NaI) m/z (rel int): 403 ([M+Na]$^+$, 27). HRMS (glycerol) m/z calcd for C$_{21}$H$_{21}$N$_2$O$_5$ 381.1450; found 381.1442.

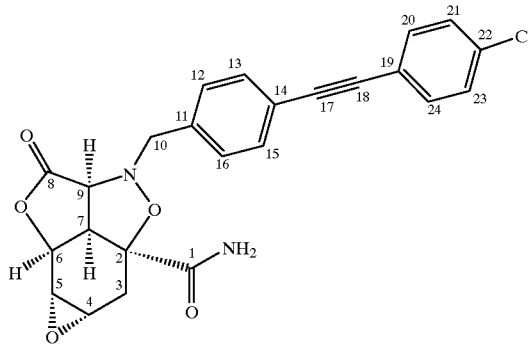

[2aS-(2aα,4aα,5aβ,6aβ,6bα,6cα)]-3-[[4-(4-Chlorophenyl)ethynyl]phenyl]methyl]hexahydro-2-oxo-2H-furo[4,3,2-cd]oxireno[f][1,2]benzisoxazole-4a(3H)-carboxamide (p-(4-Chlorophenylethynyl)benzyl tetracycle carboxamide, 11f). TLC: R$_f$ 0.40 (4:1 CH$_2$Cl$_2$/THF); R$_f$ 0.30 (1:1 CH$_2$Cl$_2$/EtAc). HPLC: t$_R$=3.618 min, λ$_{max}$=202, (222), (276), 289, 303 nm. $^1$H-NMR (400 MHz, CD$_3$CN): δ 7.51 (app d, 4H, J=8.4, C13-H, C15-H, C20-H, C24-H), 7.41 (obs d, 2H, J=8.7, C12-H, C16-H), 7.41 (obs d, 2H, J=8.2, C21-H, C23- H), 6.06 (br s, 1H, C1-NH$_a$), 5.66 (br s, 1H, C1-NH$_b$), 5.10 (dd, 1H, J=7.2, 2.7, C6-H), 4.35 (d, 1H, J=8.2, C9-H), 4.32 (d, 1H, J=14.2, C10-H$_a$), 4.03 (d, 1H, J=14.2, C10-H$_b$), 3.87 (t, 1H, J=7.7, C7-H), 3.50 (dd, 1H, J=3.5, 2.9, C5-H), 3.29 (dt, 1H, J=3.8, 2.5, C4-H), 2.35 (dd, 1H, J=16.8, 1.5, C3-H$_a$), 2.25 (dd, 1H, J=16.8, 2.8, C3-H$_b$). FAB-MS (glycerol) m/z (rel int): 451 ([M+H]$^+$, 46). HRMS (glycerol) m/z calcd for C$_{24}$H$_{20}$ClN$_2$O$_5$ 451.1061; found 451.1060.

General Procedure for Lactone Aminolysis. To 50 mg (10.5 μmol) of the appropriate alkynylbenzyl tetracycle resin, 11R, in a 2 mL Bio-Spin® column was added 2-hydroxypyridine (5.0 mg, 52.5 μmol, 5 equiv). THF (500 μL) was added and the tube was flushed briefly with Ar, capped, and shaken until the 2-hydroxypyridine was dissolved. The appropriate amine (25 equiv) was added and the tube was immediately capped, shaken, wrapped with parafilm, and wrapped in foil. After mixing 12–16 h at rt, the resin was washed (Method A) and dried under vacuum. Photolysis of the resin, 12R yielded the crude alkynylbenzyl γ-hydroxyamido tricycle, 12, as a yellow oil.

General Procedure for Lactone Aminolysis with α-Branched Amines. The same procedure was used as above except 10 equiv 2-hydroxypyridine and 50 equiv amine were used.

General Procedure for Lactone Aminolysis with Amine Hydrochlorides. To 50 mg (10.5 μmol) of the appropriate alkynylbenzyl tetracycle resin, 11R, in a 2 mL Bio-Spin® column was added 2-hydroxypyridine (5.0 mg, 52.5 μmol, 5 equiv) and the amine hydrochloride (25 equiv). CH$_2$Cl$_2$ (300 μL) and DMF (200 μL) were added and the tube was flushed briefly with N$_2$. DIPEA (91.5 mL, 525 μmol, 50 equiv) was added and the tube was immediately capped, shaken, wrapped with parafilm, and wrapped in foil. After mixing 12–16 h at rt, the resin was washed (Method A+3×20% DIPEA/CH$_2$Cl$_2$) and dried under vacuum. Photolysis of the resin, 12R, yielded the crude alkynylbenzyl γ-hydroxyamido tricycle, 12, as a yellow oil.

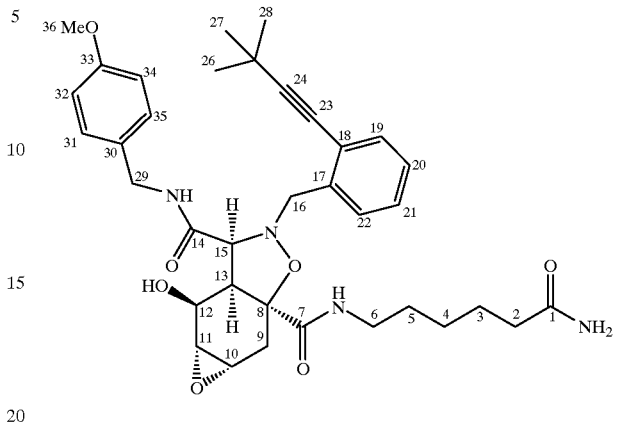

[3S-(3aα,3aβ,4aα,4aβ,5aα,6aβ)]-N$^{6a}$-(6-Amino-6-oxohexyl)-2-[[2-(3,3-dimethyl-1-butynyl)phenyl]methyl]hexahydro-4-hydroxy-N$^3$-[(4-methoxyphenyl)methyl]oxireno[f]-1,2-benzisoxazole-3,6a(2H)-dicarboxamide (o-(3,3-Dimethyl-1-butynyl)benzyl 4-methoxybenzylamido hydroxy tricycle ω-aminocaproic carboxamide, 12a). TLC: R$_f$ 0.43 (9:1 CH$_2$Cl$_2$/MeOH); R$_f$ 0.20 (1:1 CH$_2$Cl$_2$/THF). HPLC: t$_R$=3.385 min, λ$_{max}$=202, 230, 245, (275) nm. $^1$H-NMR (500 MHz, CD$_3$CN): δ 8.09 (br t, 1H J=5.8, C14-NH), 7.58 (d, 1H J=7.5, C19-H), 7.33 (dd, 1H, J=7.4, 1.1, C22-H), 7.31 (td, 1H, J=7.3, 1.3, C20-H), 7.25 (td, 1H, J=7.4, 1.3, C21-H), 7.11 (d, 2H, J=8.7, C31-H, C35-H), 6.82 (d, 2H J=8.6, C32-H, C34-H), 6.67 (br t, 1H, J=5.7, C7-NH), 5.99 (br s, 1H, C1-NH$_a$), 5.46 (br s, 1H, C1-NH$_b$), 5.38 (d, 1H, J=10.8, C12-OH), 4.26 (dd, 1H, J=14.6,6.5, C29-H$_a$), 4.25 (d, 1H, J=13.1, C16-H$_a$), 4.18 (dd, 1H, J=14.6, 6.1, C29-H$_b$), 4.08 (d, 1H, J=13.1, C16-H$_b$), 3.97 (d, 1H, J=8.8, C15-H), 3.84 (dd, 1H, J=9.0, 5.3, C13-H), 3.74 (s, 3H, C36-H$_3$), 3.73 (obs m, 1H, C12-H), 3.11 (m, 2H, C6-H$_2$), 2.97 (dd, 1H, J=4.2, 3.3, C11-H), 2.83 (td, 1H J=5.4,4.4, C10-H), 2.17 (obs m, 1H, C9-H$_a$), 2.06 (t, 2H, J=7.4, C2-H$_2$), 1.62 (dd, 1h J=16.4, 3.2, C9-H$_b$), 1.48 (m, 2H, C3-H$_2$), 1.38 (m, 2H, C5-H$_2$), 1.22 (m, 2H, C4-H$_2$), 1.30 (s, 9H, C26-H$_3$, C27-H$_3$, C28-H$_3$). FAB-MS (glycerol) m/z (rel int): 647 ([M+H]$^+$, 100). HRMS (glycerol) m/z calcd for C$_{36}$H$_{47}$N$_4$O$_7$ 647.3445; found 647.3463.

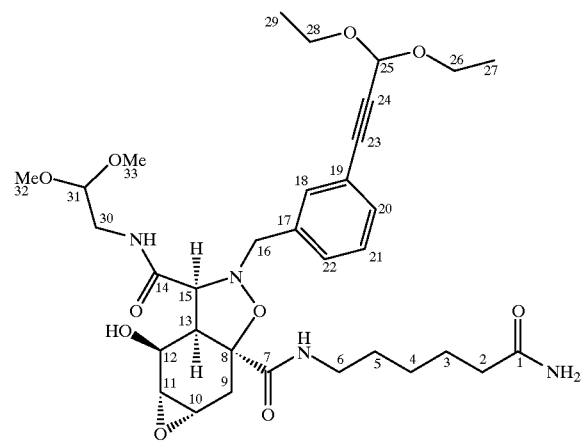

[3S-(3aα,3aβ,4aα,4aβ,5aα,6aβ)]-N$^{6a}$-(6-Amino-6-oxohexyl)-2-[[3-(3,3-dimethyl-1-propynyl)phenyl]methyl]-

N³-(2,2-dimethoxyethyl)hexahydro-4-hydroxyoxireno[f]-1,2-benzisoxazole-3,6a(2H)-dicarboxamide (m-(3,3-Diethoxy-1-propynyl)benzyl 2,2-dimethoxyethylamido hydroxy tricycle ω-aminocaproic carboxamide, 12b). TLC: $R_f$ 0.33 (9:1 CH$_2$Cl$_2$/MeOH); $R_f$ 0.09 (1:1 CH$_2$Cl$_2$/THF). HPLC: $t_R$=2.995 min, $\lambda_{max}$=204, 243, 246 nm. ¹H-NMR (500 MHz. CD$_3$CN): δ 7.78 (br t, 1 H, J=5.5, C 14-NH), 7.51 (s, 1H, C18-H), 7.40 (m, 2H, C20-H, C22-H), 7.35 (t, 1H, J=7.5, C21-H), 6.68 (br t, 1H, J=5.7, C7-NH), 6.07 (br s, 1H, C1-NH$_a$), 5.61 (br s, 1H, C1-NH$_b$), 5.46 (s, 1H, C25-H), 4.87 (d, 1H, J=8.4, C12-OH), 4.38 (t, 1H, J=5.0, C31-H), 4.12 (d, 1H, J=13.9, C16-H$_a$), 4.01 (ddd, 1H, J=8.4, 4.6, 3.7, C12-H), 3.89 (d, 1H, J=13.9, C16-H$_b$), 3.86 (d, 1H, J=8.0, C15-H), 3.74 (dq, 2H, J=9.5, 7.1, C26-H$_a$, C28-H$_a$), 3.60 (dq, 2H, J=9.4, 7.1, C26-H$_b$, C28-H$_b$), 3.53 (obs dd, 1H, J=8.2, 4.9, C13-H), 3.37 (m, 1H, C30-H$_a$), 3.32 (s, 3H, C32-H$_3$), 3.32 (s, 3H, C33-H$_3$), 3.22 (obs m, 1H, C30-H$_b$), 3.19 (obs m, 3H, C6-H$_2$, C11-H), 3.14 (obs m, 1H, C10-H), 2.24 (dd, 1H, J=16.3, 3.4, C9-H$_a$), 2.12 (obs t, 2H, J=7.3, C2-H$_2$), 1.93 (obs m, 1H, C9-H$_b$), 1.53 (m, 2H, C3-H$_2$), 1.45 (m, 2H, C5-H$_2$), 1.27 (m, 2H, C4-H$_2$), 1.20 (t, 6H, J=7.1, C27-H$_3$, C29-H$_3$). FAB-MS (glycerol) m/z (rel int): 661 ([M+H]⁺, 55), 615 ([M−OEt]⁺, 18). HRMS (glycerol) m/z calcd for C$_{33}$H$_{49}$N$_4$O$_{10}$ 661.3449; found 661.3464.

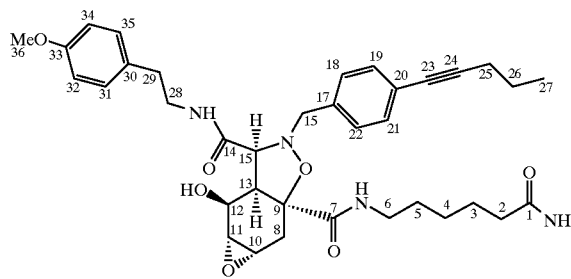

[3S-(3aα,3aβ,4aα,4aβ,5aα,6aβ)]-N⁶ᵃ-(6-Amino-6-oxohexyl)hexahydro-4-hydroxy-N³-[2-(4-methoxyphenyl)ethyl-2-[f][4-(1-pentynyl)phenyl]methyl]oxireno[f]-1,2-benzisoxazole-3,6a(2H)-dicarboxamide (p-(1-Pentynyl)benzyl 4-methoxyphenethylamido hydroxy tricycle ω-aminocaproic carboxamide, 12c). TLC: $R_f$ 0.23 (9:1 CH$_2$Cl$_2$/MeOH); $R_f$ 0.09 (1:1 CH$_2$Cl$_2$/THF). HPLC: $t_R$=3.428 min, $\lambda_{max}$=201, 232, 251, (279) nm. ¹H NMR (500 MHz, CD$_3$CN): δ 7.60 (br t, 1H, C14-NH), 7.32 (d, 2H, J=8.1, C19-H, C21-H), 7.23 (d, 2H, J=8.1, C18-H, C22-H), 7.11 (d, 2H, J=8.6, C31-H, C35-H), 6.82 (d, 2H, J=8.7, C32-H, C34-H), 6.63 (br t, 1H, J=6.0, C7-NH), 6.05 (br s, 1H, C1-NH$_a$), 5.52 (br s, 1H, C1-NH$_b$), 5.05 (br s, 1H, C1-NH$_b$), 5.05 (d, 1H, J=8.8, C12-OH), 4.06 (d, 1H, J=13.9, C16-H$_b$), 3.79 (m, 3H, C12-H, C15-H, C16-H$_a$), 3.73 (s, 3H, C36-H$_3$), 3.52 (obs m, 1H, C13-H), 3.42 (sxt, 1H, J=6.3, C28-H$_a$), 3.36 (sxt, 1H, J=6.2, C28-H$_b$), 3.12 (t, 2H, J=6.6, C6-H$_2$), 3.02 (app dd, 1H, J=7.0, 4.0, C10-H), 2.68 (td, 2H, J=6.9, 2.7, C29-H$_2$), 2.37 (t, 2H, J=7.0, C25-H$_2$), 2.16 (obs d, 1H, C9-H$_a$), 2.09 (, 2H, J=7.4, C2-H$_2$), 1.82 (dd, 1H, J=16.2, 2.9, C9-H$_b$), 1.59 (sxt, 2H, J=7.3, C26-H$_2$), 1.51 (m, 2H, C5-H$_2$), 1.41 (m, 2H, C3-H$_2$), 1.25 (m, 2H, C4-H$_2$), 1.02 (t, 3H, J=7.4, C27-H$_3$). FAB-MS (glycerol) m/z (rel int): 647 ([M+H]⁺, 85). FAB-MS (NBA/NaI) m/z (rel int): 669 ([M+Na]⁺, 100), 647 ([M+H]⁺, 60). HRMS (NBA/NaI) m/z calcd for C$_{24}$H$_{27}$N$_3$O$_5$Na 669.3264; found 669.3252.

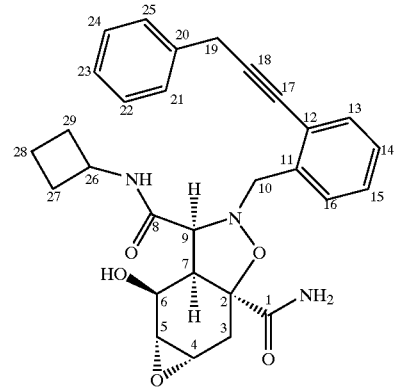

[3S-(3aα,3aβ,4aα,4aβ,5aα,6aβ)]-(N³-cyclobutyl)hexahydro-4-hydroxy-2-[[2-(3-phenyl-1-propynyl)phenyl]methyl]-oxireno[f]-1,2-benzisoxazole-3,6a(2H)-dicarboxamide (o-(3-Phenyl-1-propynyl)benzyl cyclobutylamido hydroxy tricycle carboxamide, 12d). TLC: $R_f$ 0.14 (4:1 CH$_2$Cl$_2$/THF); $R_f$ 0.06 (1:1 CH$_2$Cl$_2$/EtOAc). HPLC: $t_R$=3.141 min, $\lambda_{max}$=(203), 209, 247 mm. ¹H-NMR (500 MHz, CD$_3$CN): δ 7.56 (br s, 1H, C9-NH), 7.50 (dd, 1H, J=7.3, 1.4, C13-H), 7.48 (obs d, 2H, C21-H, C25-H), 7.43 (dd, 1H, J=7.5, 1.3, C16-H), 7.38 (t, 2H, J=7.7, C22-H, C24-H), 7.32 (td, 1H, J=7.5, 1.5, C 14-H), 7.27 (td, 3H, J=7.5, 1.4, C15-H, C23-H), 6.54 (br s, 1H, C1-NH$_a$), 5.89 (br s, 1H, C1-NH$_b$), 5.11 (d, 1H, J=9.7, C6-OH), 4.43 (d, 1H, J=12.8, C10-H$_a$), 4.11 (obs sxt, 1H, J=8.1, C26-H), 4.11 (d, 1H, J=12.8, C10-H$_b$), 3.91 (s, 2H, C19-H$_2$), 3.90 (obs m, 1H, C6-H), 3.86 (d, 1H, J=8.4, C9-H), 3.62 (app ddd, 1H, J=8.4, 5.4, 1.4, C7-H), 3.12 (td, 1H, J=4.0, 2.7, C4-H), 3.09 (dd, 1H, J=4.0, 3.1, C5-H), 2.26 (dd, 1H, J=16.4, 3.7, C³-H$_a$), 2.10 (obs m, 1H, C27-H$_a$), 2.05 (obs m, 1H, C29-H$_a$), 1.99 (dt, 1H, J=16.4, 2.1, C3-H$_b$), 1.75 (app sxt, 2H, J=10.2, C27-H$_b$, C29-H$_b$), 1.60 (m, 2H, C28-H$_2$). FAB-MS (glycerol) m/z (rel int): 502 ([M+H]⁺, 62). FAB-MS (NBA/NaI) m/z (rel int): 524 ([M+Na]⁺, 70), 502 ([M−H]⁺, 13). HRMS (glycerol) m/z calcd for C$_{29}$H$_{32}$N$_3$O$_5$ 502.2342; found 502.2336.

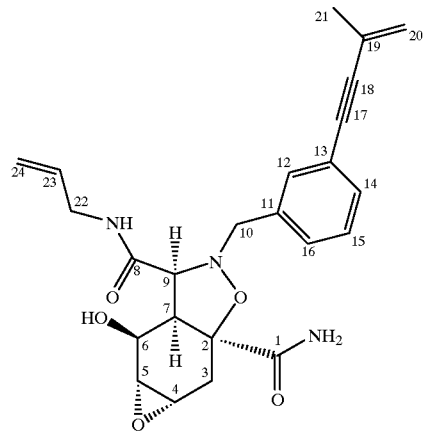

[3S-(3aα,3aβ,4aα,4aβ,5aα,6aβ)]-Hexahydro-4-hydroxy-2-[[3-(3-methyl-3-buten-1-ynyl)phenyl]methyl]-N³-(2-propenyl)oxireno[f]-1,2-benzisoxazole-3,6a(2H)-dicarboxamide (m-(3-Methyl-3-buten-1-ynyl)benzyl allylamido hydroxy tricycle carboxamide, 12e). TLC: $R_f$ 0.12 (4:1 CH$_2$Cl$_2$/THF); $R_f$ 0.07 (1:1 CH$_2$Cl$_2$/EtOAc). HPLC: $t_R$=3 034 min, $\lambda_{max}$=213, 270, (283) nm. $^1$H-NMR (400 MHz, CD$_3$CN): δ 7.64 (br t, 1H, C8-NH), 7.51 (s, 1H, C12-H), 7.38 (dt, 1H, J=7.0, 1.7, C14-H), 7.35 (dd, 1H, J=5.7, 1.7, C16-H), 7.32 (t, 1H, J=7.5, C15-H), 6.42 (s, 1H, C1-NH$_a$), 5.93 (s, 1H, C1-NH$_b$), 5.79 (ddt, 1H, J=17.2, 10.5, 5.3, C23-H), 5.37 (obs m, 1H, C20-H$_Z$), 5.36 (obs m, 1H, C20-H$_E$), 5.11 (dq, 1H, J=17.4, 1.6, C24-H$_Z$), 5.06 (dq, 1H, J=10.3, 1.5, C24-H$_E$), 5.02 (d, 1H, J=9.4, C6-OH), 4.17 (d, 1H, J=13.7, C10-H$_a$), 3.93 (obs m, 1H, C6-H), 3.92 (obs d, 1H, J=8.1, C9-H), 3.91 (obs d, 1H, J=13.9, C10-H$_b$), 3.78 (tt, 2H, J=5.8, 1.4, C22-H$_2$), 3.64 (dd, 1H, J=8.3, 5.1, C7-H), 3.14 (obs m, 1H, C5-H), 3.13 (obs m, 1H, C4-H), 2.26 (dd, 1H, J=16.3, 3.4, C3-H$_a$), 1.97 (t, 3H, J=1.3, C21-H$_3$), 1.91 (obs dd, 1H, J=1.9, C3-H$_b$). FAB-MS (glycerol) m/z (rel int): 438 ([M+H]$^+$, 60). FAB-MS (NBA/NaI) m/z (rel int): 438 ([M+H]$^+$, 78), 460 ([M+Na]$^+$, 43). HRMS (NBA/NaI) m/z calcd for C$_{24}$H$_{27}$N$_3$O$_5$Na 460.1848; found 460.1853.

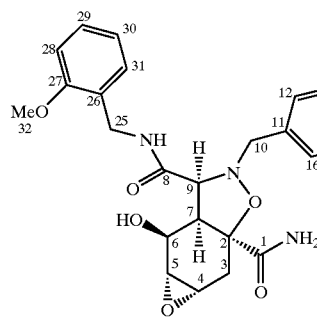

[3S-(3aα,3aβ,4aα,4aβ,5aα,6aβ)]-2-[[4-[2-(4-Chlorophenyl)-1-ethynyl]phenyl]methyl]hexahydro-4-hydroxy-N³-[(2-methoxyphenyl)methyl]oxireno[f]-1,2-benzisoxazole-3,6a(2H)-dicarboxamide (p-(4-Chlorophenylethynyl)benzyl 2-methoxybenzylamido hydroxy tricycle carboxamide, 12f). TLC: $R_f$ 0.13 (4:1 CH$_2$Cl$_2$/THF); $R_f$ 0.06 (1:1 CH$_2$Cl$_2$/EtOAc). HPLC: $t_R$=3.778 min, $\lambda_{max}$=201, 222, (276), 289, 303 nm. $^1$H-NMR (500 MHz, CD$_3$CN): δ 7.97 (br t, 1H, C8-NH), 7.52 (d, 1H, J=8.5, C20-H, C24-H), 7.49 (d, 1H, J=8.1, C13-H, C15-H), 7.42 (obs d, 1H, J=8.1, C21-H, C23-H), 7.42 (obs d, 1H, J=8.1, C12-H, C16-H), 7.27 (td, 1H, J=7.9, 1.4, C29-H), 7.13 (dd, 1H, J=7.3, C31-H), 6.97 (d, 1H, J=8.1, C28-H), 6.89 (td, 1H, J=7.4, C30-H), 6.37 (br s, 1H, C1-NH$_a$), 5.88 (br s, 1H, C1-NH$_b$), 5.13 (d, 1H, J=10.0, C6-OH), 4.37 (dd, 1H, J=15.0, 6.2, C25-H$_a$), 4.33 (dd, 1H, J=14.8, 6.1, C25-H$_b$), 4.21 (d, 1H, J=13.8, C10-H$_a$), 3.95 (d, 1H, J=8.6, C9-H), 3.93 (d, 1H, J=13.9, C10-H$_b$), 3.85 (s, 3H, C32-H), 3.83 (obs m, 1H, C6-H), 3.67 (dd, 1H, J=8.4, 5.5, C7-H), 3.01 (t, 1H, J=3.7, C5-H), 2.78 (m, 1H, C4-H), 2.15 (dd, 1H, J=16.4, 4.1, C3-H$_a$), 1.82 (dd, J=16.4, 2.6, C3-H$_b$). FAB-MS (glycerol) m/z (rel int): 588/590 ([M+H]$^+$, 52/28). FAB-MS (NBA/NaI) m/z (rel int): 610/612 ([M+Na]$^+$, 22/10). HRMS (glycerol) m/z calcd for C$_{32}$H$_{31}$ClN$_3$O$_6$ 588.1901; found 588.1896.

General Procedure for Alcohol Esterification. To 50 mg (10.5 μmol) of the appropriate alkynylbenzyl γ-hydroxyamido tricycle resin, 12R, in a 2 mL Bio-Spin® column was added 200 μL CH$_2$Cl$_2$. The tube was flushed with Ar and cooled to 0° C. in an ice bath. The appropriate carboxylic acid (50 equiv) was dissolved or suspended in 400 μL CH$_2$Cl$_2$ in an oven-dried 2 mL Wheaton vial and activated with DIPC (41.1 μl, 262.5 μmol, 25 equiv). After stirring at rt for 2 min, DIPEA (91.5 μL, 525 μL, 50 equiv) was added and stirring continued for another 3 min. The activated acid solution was then added to the resin via pipette with manual agitation followed by DMAP (6.4 mg, 52.5 μmol, 5 equiv) in 50 μL CH$_2$Cl$_2$. After standing 15 min at 0° C., the tube was warmed to rt, wrapped with parafilm, wrapped in foil, and mixed at rt for 12–16 h. After washing (Method A+3×20% DIPEA/CH$_2$Cl$_2$), photolysis of the resin, 13R, yielded the crude alkynylbenzyl amido acyl tricycle, 13, as a yellow oil.

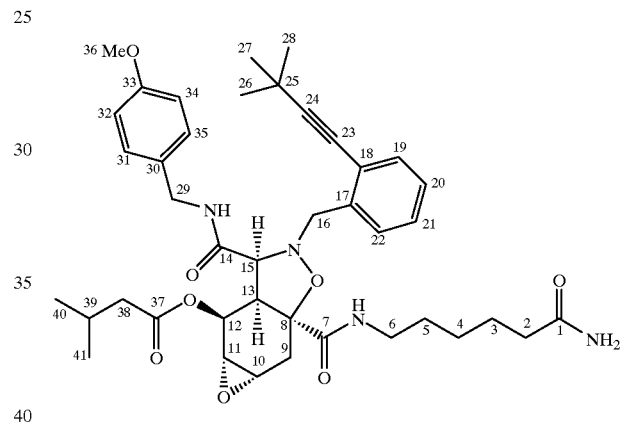

[3S-(3aα,3aβ,4aα,4aβ,5aα,6aβ)]-3-Methylbutanoic acid, 6a-[[(6-amino-6-oxohexyl)amino]carbonyl]-2-[[2-(3,3-dimethyl-1-butynyl)phenyl]methyl]-3-[[[(4-methoxyphenyl)methyl]aminoicarbonyl]octahydrooxireno[f]-1,2-benzisoxazol-4-yl ester (o-(3,3-Dimethyl-1-butynyl)benzyl 4-methoxybenzylamido isovaleryl tricycle ω-aminocaproic carboxamide, 13a). TLC: $R_f$ 0.49 (9:1 CH$_2$Cl$_2$/MeOH); $R_f$ 0.29 (1:1 CH$_2$Cl$_2$/THF). HPLC: $t_R$=3.742 min, $\lambda_{max}$=(203), (215), 232, 247, (275) nm. $^1$H-NMR (500 MHz, CD$_3$CN): δ 7.46 (d, 1H, J=8.0, C19-H), 7.27 (obs dd, 1H, J=7.6, 1.2, C22-H), 7.25 (obs td, 1H, J=7.5, 1.6, C20-H), 7.20 (td, 1H, J=7.4, 1.2, C21-H), 7.18 (obs br t, 1H, C14-NH), 6.88 (d, 2H, J=8.5, C31-H, C35-H), 6.83 (br t, 1H, C7-NH), 6.77 (d, 2H, J=8.7, C32-H, C34-H), 5.97 (br s, 1H, C1-H$_a$), 5.45 (br s, 1H, C1-NH$_b$), 5.31 (t, 1H, J=4.1, C12-H), 4.38 (d, 1H, J=13.1, C16-H$_a$), 4.05 (d, 1H, J=13.2, C16-H$_b$), 3.99 (dd, 1H, J=14.6, 6.3, C29-H$_a$), 3.91 (dd, 1H, J=14.6, 5.9, C29-H$_b$), 3.87 (d, 1H, J=8.9, C15-H), 3.77 (dd, 1H, J=8.8, 4.1, C13-H), 3.74 (s, 3H, C36-H$_3$), 3.40 (t, 1H, J=4.2, C 1-H), 3.18 (q, 2H, J=6.7, C6-H$_2$), 3.15 (obs m, 1H, C10-H), 2.29 (app s, 2H, C9-H$_2$), 2.09 (obs m, 5H, C2-H$_2$, C38-H$_2$, C39-H), 1.52 (obs m, 2H, C3-H$_2$), 1.47 (obs m, 2H, C3-C5-H$_2$), 1.31 (s, 9H, C26-H$_3$, C27-H$_3$, C28-H$_3$), 1.27 (obs m, 2H, C4-H$_2$), 0.89 (t, 6H, J=5.9, C40-H$_3$, C41-H$_3$). FAB-MS (glycerol) m/z (rel int): 731 ([M+H]$^+$, 13). FAB-MS (NBA/NaI) m/z (rel int): 753 ([M+Na]$^+$, 100), 731 ([M+H]$^+$, 22). HRMS (NBA/NaI) m/z calcd for C$_{41}$H$_{54}$N$_4$O$_8$Na 753.3839; found 753.3842.

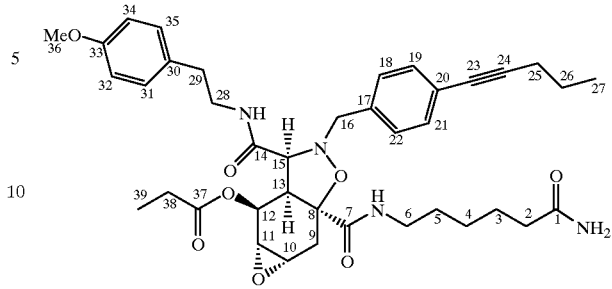

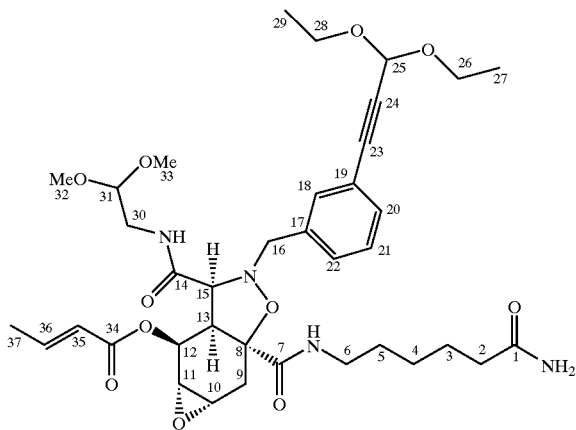

[3S-(3aα,3aβ,4aα,4aβ,5aα,6aβ)]-2-Butenoic acid, 6a-[[(6-amino-6-oxohexyl)amino]carbonyl]-2-[[3-(3,3-diethoxy-1-propynyl)phenyl]methyl]-3-[[(2,2-dimethoxyethyl)amino]carbonyl]octahydrooxireno[f]-1,2-benzisoxazol-4-yl ester (m-(3,3-Diethoxy-1-propynyl) benzyl 2,2-dimethoxyethylamido crotonyl tricycle ω-aminocaproic carboxamide, 13b). TLC: R$_f$ 0.40 (9:1 CH$_2$Cl$_2$/MeOH); R$_f$ 0.16 (1:1 CH$_2$Cl$_2$/THF). HPLC: t$_R$=3.285 min, λ$_{max}$=207, 241, 246 nm. $^1$H-NMR (500 MHz, CD$_3$CN): δ 7.53 (s, 1H, C18-H), 7.40 (m, 3H, C20-H, C21-H, C22-H), 7.09 (obs br t, 1H, C14-NH), 7.05 (dq, 1H, J=15.4, 6.9, C36-H), 6.78 (br t, 1H, J=6.5, C7-NH), 6.04 (s, 1H, C1-NH$_a$), 5.83 (dq, 1H, J=15.4, 1.7, C35-H), 5.55 (s, 1H, C1-NH$_b$), 5.46 (s, 1H, C25-H), 5.34 (t, 1H, J=4.0, C12-H), 4.25 (dd, 1H, J=5.8, 4.5, C31-H), 4.04 (d, 1H, J=14.3, C16-H$_a$), 3.89 (d, 1H, J=14.3, C16-H$_b$), 3.74 (obs m, 2H, C26-H$_a$, C28-H$_a$), 3.73 (obs m, 1H, C15-H), 3.64 (dd, 1H, J=8.0, 4.0, C13-H), 3.60 (app dq, 2H, J=9.5, 7.1, C26-H$_b$, C28-H$_b$), 3.43 (dd, 1H, J=7.8, 4.5, C30-H$_a$), 3.40 (obs m, 1H, C11-H), 3.29 (s, 3H, C32-H$_3$), 3.27 (s, 3H, C33-H$_3$), 3.24 (m, 2H, C6-H$_2$), 3.15 (m, 1H, C10-H), 2.86 (ddd, 1H, J=13.7, 5.8, 3.8, C30-H$_b$), 2.27 (app d, 2H, J=2.4, C9-H$_2$), 2.12 (m, 2H, C2-H$_2$), 1.89 (dd, 3H, J=6.9, 1.7, C37-H$_3$), 1.57 (m, 2H, C3-H$_2$), 1.53 (m, 2H, C5-H$_2$), 1.31 (m, 2H, C4-H$_2$), 1.20 (t, 6H, J=7.1, C27-H$_3$, C29-H$_3$). FAB-MS (glycerol) m/z (rel int): 729 ([M+H]$^+$, 13). FAB-MS (NBA/NaI) m/z (rel int): 751 ([M+Na]$^+$, 100), 729 ([M+H]$^+$, 6). HRMS (NBA/NaI) m/z calcd for C$_{37}$H$_{52}$N$_4$O$_{11}$Na 751.3530; found 751.3536.

[3S-(3aα,3aβ,4aα,4aβ,5aα,6aβ)]-Propanoic acid, 6a-[[(6-amino-6-oxohexyl)amino]carbonyl]-3-[[[2-(4-methoxyphenyl)ethyl]amino]carbonyl]octahydro-2-[[4-(1-pentynyl)phenyl]methyl]oxireno[f]-1,2-benzisoxazol-4-yl ester (p-(1-Pentynyl)benzyl 4-methoxyphenethylamido propionyl tricycle ω-aminocaproic carboxamide, 13c). TLC: R$_f$ 0.33 (9:1 CH$_2$Cl$_2$/MeOH); R$_f$ 0.23 (1:1 CH$_2$Cl$_2$/THF). HPLC: t$_R$=3.602 min, λ$_{max}$=202, 231, 252, (280) nm. $^1$H-NMR (500 MHz, CD$_3$CN): δ 7.33 (d, 2H, J=8.1, C19-H, C21-H), 7.20 (d, 2H, J=8.1, C18-H, C22-H), 7.04 (d, 2H, J=8.4, C31-H, C35-H), 6.90 (br t, 1H, J=5.5, C14-NH), 6.74 (d, 2H, J=8.7, C32-H, C34-H), 6.72 (br t, 1H, J=5.5, C7-NH), 6.03 (br s, 1H, C1-NH$_a$), 5.55 (br s, 1H, C1-NH$_b$), 5.25 (t, 1H, J=4.0, C12-H), 3.98 (d, 1H, J=14.2, C16-H$_a$), 3.74 (d, 1H, J=14.4, C16-H$_b$), 3.67 (s, 3H, C36-H$_3$), 3.63 (d, 1H, J=8.4, C15-H), 3.60 (dd, 1H, J=8.4, 4.1, C13-H), 3.50 (obs m, 1H, C28-H$_a$), 3.32 (app t, 1H, J=4.2, C11-H), 3.20 (obs m, 1H, C6-H$_a$), 3.16 (obs m, 1H, C6-H$_b$), 3.14 (obs m, 1H, C10-H), 3.02 (m, 1H, C28-H$_b$), 2.64–2.50 (m, 2H, C29-H$_2$), 2.38 (t, 2H, J=7.0, C25-H$_2$), 2.28–2.16 (m, 4H, C9-H$_2$, C38-H$_2$), 2.10 (t, 2H, J=7.3, C2-H$_2$), 1.59 (sxt, 2H, J=7.2, C26-H$_2$), 1.53 (quint, 2H, J=7.7, C3-H$_2$), 1.47 (m, 2H, C5-H$_2$), 1.27 (m, 2H, C4-H$_2$), 1.03 (t, 3H, J=7.5, C39-H$_3$), 1.02 (t, 3H, J=7.3, C27-H$_3$). FAB-MS (glycerol) m/z (rel int): 703 ([M+H]$^+$, 18). FAB-MS (NBA/NaI) m/z (rel int): 725 ([M+Na]$^+$, 100), 703 ([M+H]$^+$, 17). HRMS (NBA/NaI) m/z calcd for C$_{39}$H$_{50}$N$_4$O$_8$Na 725.3526 found 725.3527.

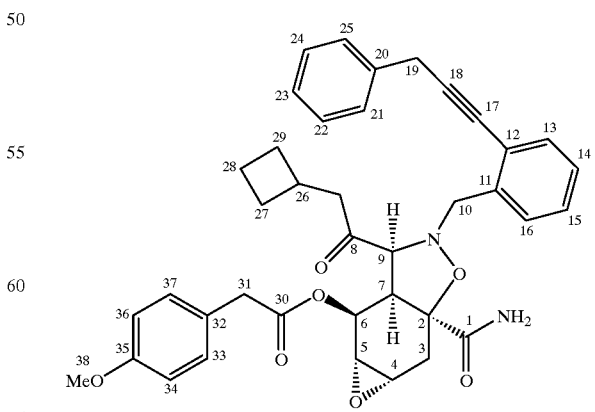

[3S-(3aα,3aβ,4aα,4aβ,5aα,6aβ)]-4-Methoxyphenylacetic acid, 6a-(aminocarbonyl)-2-[f][2-(3-phenyl-1-propynyl)phenyl]methyl]octahydro-3-[(cyclobutylamino)carbonyl]oxireno[f]-1,2-benzisoxazol-4-yl ester (o-(3-Phenyl-1-propynyl)benzyl cyclobutylamido 4-methoxyphenylacetyl tricycle carboxamide, 13d). TLC: $R_f$ 0.25 (4:1 $CH_2Cl_2$/THF); $R_f$ 0.10 (1:1 $CH_2Cl_2$/EtOAc). HPLC: $t_R$=3.532 min, $\lambda_{max}$=202, (209), 235, (250), (274) nm. $^1$H-NMR(500 MHz,$CD_3CN$): δ 7.49 (d, 3H, J=7.4, C13-H, C21-H, C25-H), 7.46 (d, 1H, J=7.7, C16-H), 7.36 (t, 2H, J=7.7, C22-H, C24-H), 7.33 (td, 1H, J=7.5, 1.6, C14-H), 7.29 (td, 1H, J=7.6, 1.4, C15-H), 7.25 (t, 1H, J=7.5, C23-H), 7.17 (d, 2H, J=8.7, C33-H, C37-H), 6.87 (d, 1H, J=8.7, C8-NH), 6.84 (d, 2H, J=8.7, C34-H, C36-H), 6.64 (br s, 1H, C1-NH$_a$), 5.91 (br s, 1H, C1-NH$_b$), 5.31 (t, 1H, J=3.9, C6-H), 4.61 (d, 1H, J=12.3, C10-H$_a$), 4.17 (d, 1H, J=12.3, C10-H$_b$), 3.92 (app d, 2H, J=2.7, C19-H$_2$), 3.81 (d, 1H, J=8.6, C9-H), 3.80 (obs m, 1H, C26-H), 3.75 (s, 3H, C38-H$_3$), 3.69 (dd, 1H J=8.5, 3.8, C7-H), 3.48 (d, 1H, J=15.5, C31-H$_a$), 3.37 (d, 1H, J=15.5, C31-H$_b$), 3.31 (t, 1H, J=4.1, C5-H), 3.10 (ddd, 1H, J=4.2, 3.0, 1.9, C4-H), 2.40 (dd, 1H, J=16.2, 3.0, C3-H$_a$), 2.34 (dd, 1H, J=16.1, 1,8, C3-H$_b$), 1.94 (obs m, 1H, C27-H$_a$), 1.84 (obs m, 1H, C29-H$_a$), 1.63 (quint, 1H, J=9.8, C27-H$_b$), 1.50 (m, 2H, C28-H$_2$), 1.33 (quint, 1H, J=9.9, C29-H$_b$). FAB-MS (glycerol) m/z (rel int): 650 ([M+H]$^+$, 65). FAB-MS (NBA/NaI) m/z (rel int): 672 ([M+Na]$^+$, 35), 524 ([M+H]$^+$, 9). HRMS (glycerol) m/z calcd for $C_{38}H_{40}N_3O_7$ 650.2866; found 650.2836.

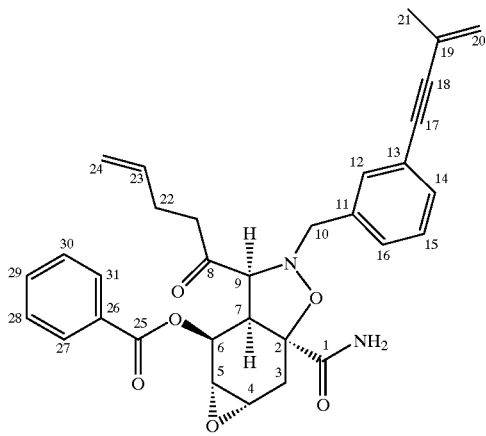

[3S-(3aα,3aβ,4aα,4aβ,5aα,6aβ)]-Benzoic acid, 6a-(aminocarbonyl)-2-[[3-(3-methylbut-3-en-1-ynyl)phenyl]methyl]octahydro-3-[[(2-propenyl)amino]carbonyl]oxireno[f]-1,2-benzisoxazol-4-yl ester (m-(3-Methyl-3-buten-1-ynyl)benzyl allylamido benzoyl tricycle carboxamide, 13e). TLC: $R_f$ 0.22 (4:1 $CH_2Cl_2$/THF); $R_f$ 0.13 (1:1 $CH_2Cl_2$/EtOAc). HPLC: $t_R$=3.601 min, $\lambda_{max}$=201, 220, (236), 270, (282) nm. $^1$H-NMR (500 MHz, $CD_3CN$): δ 8.15 (dd, 2H, J=8.2, 1.2, C27-H, C31-H), 7.64 (tt, 1H, J=7.4, 1.5, C29-H), 7.56 (s, 1H, C12-H), 7.55 (obs t, 2H, J=7.6, C28-H, C30-H), 7.37 (m, 3H, C14-H, C15-H, C16-H), 6.71 (br t, 1H, C8-NH), 6.53 (br s, 1H, C1-NH$_a$), 5.99 (br s, 1H, C1-NH$_b$), 5.63 (t, 1H, J=3.9, C6-H), 5.40 (m, 2H, C20-H$_2$), 5.22 (ddt, 1H, J=16.8, 10.3, 6.1, C23-H), 4.70 (app dq, 1H, J=10.2, 1.3, C24-H$_E$), 4.64 (app dq, 1H, J=17.1, 1.5, C24-H$_Z$), 4.26 (d, 1H, J=14.1, C10-H$_a$), 3.96 (d, 1H, J=14.1, C10-H$_b$), 3.86 (d, 1H, J=8.0, C9-H), 3.77 (dd, 1H, J=8.0, 3.6, C7-H), 3.54 (obs m, 1H, C5-H). 3.53 (obs m, 1H, C22-H$_a$), 3.17 (app quint, 1H, J=2.1, C4-H), 3.01 (dddt, 1H, J=15.2, 6.2, 4.9, C22-H$_b$), 2.44 (dd, 1H, J=16.6, 2.5, C3-H$_a$), 2.40 (dd, 1H, J=16.5, 1.8, C3-H$_b$), 1.99 (app t, 3H, J=1.2, C21-H$_3$). FAB-MS m/z (rel int): 542 ([M+H]$^+$, 100). FAB-MS (NBA/NaI) m/z (rel int): 564 ([M+Na]$^+$, 100), 542 ([M+H]$^+$, 18). HRMS (NBA/NaI) m/z calcd for $C_{31}H_{31}N_3O_6Na$ 564.2111; found 564.2100.

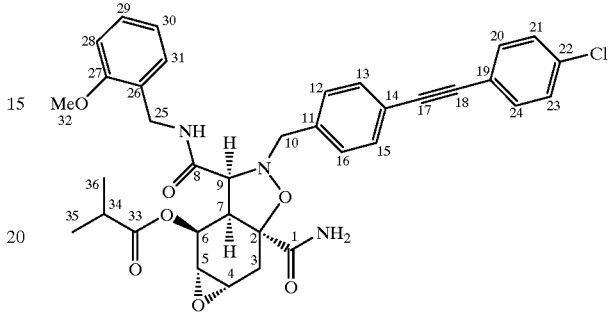

[3S-(3aα,3aβ,4aα,4aβ,5aα,6aβ)]-2-Methylpropanoic acid, 6a-(aminocarbonyl)-2-[[4-[2-(4-chlorophenyl)-1-ethynyl]phenyl]methyl]-3-[[[(2-methoxyphenyl)methyl]amino]carbonyl]octahydrooxireno[f]-1,2-benzisoxazol-4-yl ester p-(4-Chlorophenylethynyl)benzyl 2-methoxybenzylamido isobutyryl tricycle carboxamide, 13f). TLC: $R_f$ 0.19 (4:1 $CH_2Cl_2$/THF); $R_f$ 0.12 (1:1 $CH_2Cl_2$/EtOAc). HPLC: $t_R$=4.072 min, $\lambda_{max}$=202, 222, (270), 291, 304 nm. $^1$H-NMR (500 MHz, $CD_3CN$): δ 7.52 (d, 2H, J=8.5, C20-H, C24-H), 7.45 (d, 2H, J=8.1, C13-H, C15-H), 7.42 (d, 2H, J=8.5, C21-H, C23-H), 7.39 (obs m, 1H, C8-NH), 7.35 (d, 2H, J=8.1, C12-H, C16-H), 7.25 (td, 1H, J=7.8, 1.7, C29-H), 7.02 (dd, 1H, J=7.4, 1.3, C31-H), 6.94 (d, 1H, J=8.2, C28-H), 6.87 (t, 1H, J=7.5, C30-H), 6.48 (br s, 1H, C1-NH$_a$), 5.92 (br s, 1H, C1-NH$_b$), 5.36 (t, 1H, J=4.0, C6-H), 4.39 (dd, 1H, J=14.6, 7.3, C25-H$_a$), 4.18 (d, 1H, J=14.1, C10-H$_a$), 4.06 (dd, 1H, J=14.7, 4.8, C25-H$_b$), 3.87 (d, 1H, J=14.2, C10-H$_b$), 3.78 (obs d, 1H, J=8.6, C9-H), 3.76 (s, 3H, C32-H$_3$), 3.67 (dd, 1H, J=8.4, 3.9, C7-H), 3.37 (t, 1H, J=4.2, C5-H), 3.15 (dt, 1H, J=4.1, 2.6, C4-H), 2.40 (sept, 1H, J=7.0, C34-H), 2.35 (dd, 1H, J=16.4, 2.9, C3-H$_a$), 2.29 (dd, 1H, J=16.2, 2.0, C3-H$_b$), 1.13 (d, 3H, J=7.1, C35-H$_3$), 1.09 (d, 3H, J=7.0, C36-H$_3$). FAB-MS (glycerol) m/z (rel int): 658/660 ([M+H]$^+$, 6/3). FAB-MS (NBA/NaI) m/z (rel int): 680/682 ([M+Na]$^+$, 20/10), 658/660 ([M+H]$^+$, 12/6). HRMS (NBA/NaI) m/z calcd for $C_{36}H_{36}ClN_3O_7Na$ 680.2139; found 680.2147.

Figure 43:
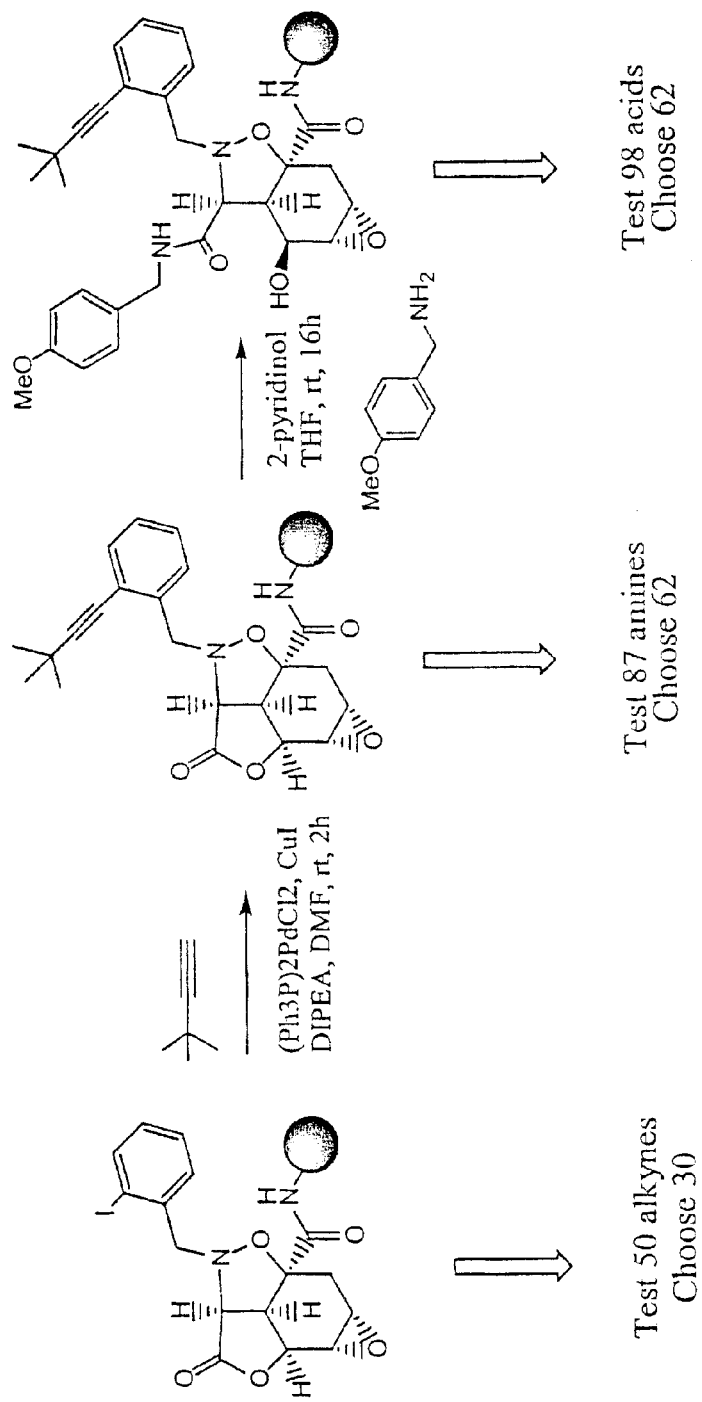
FIG. 43 depicts monomer screening.
Figure 44A:
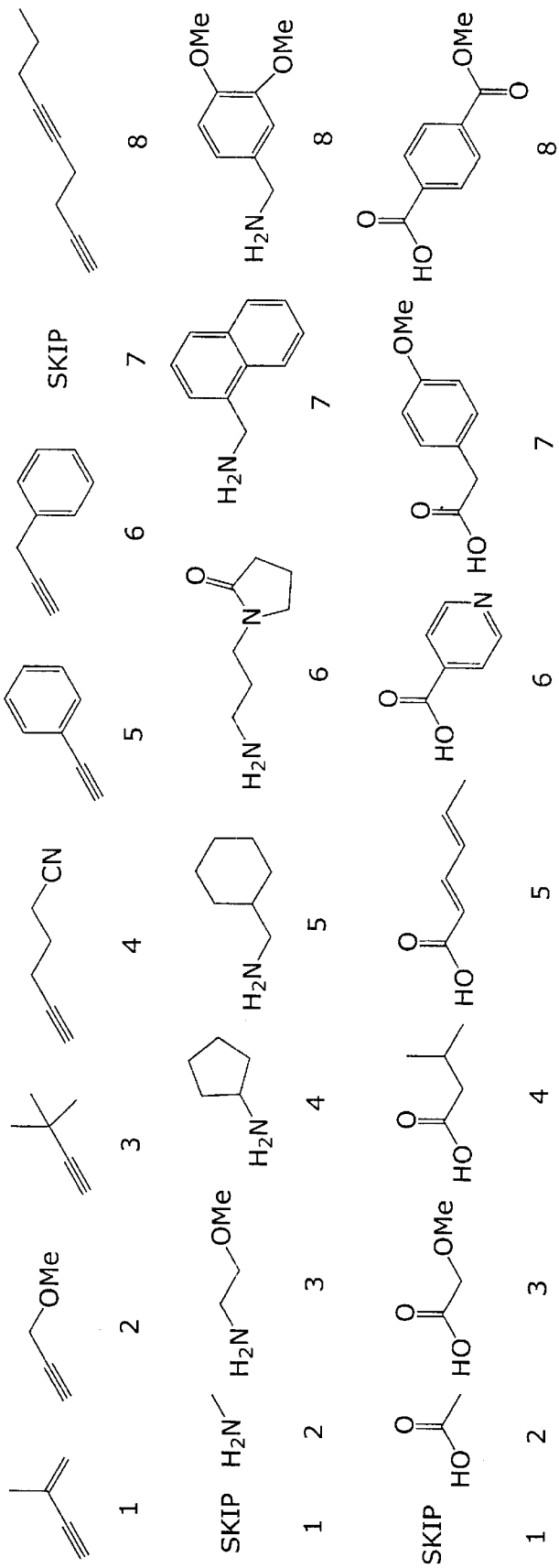
FIGS. 44A and 44B depict library quality control for a small test library.
Figure 44B:
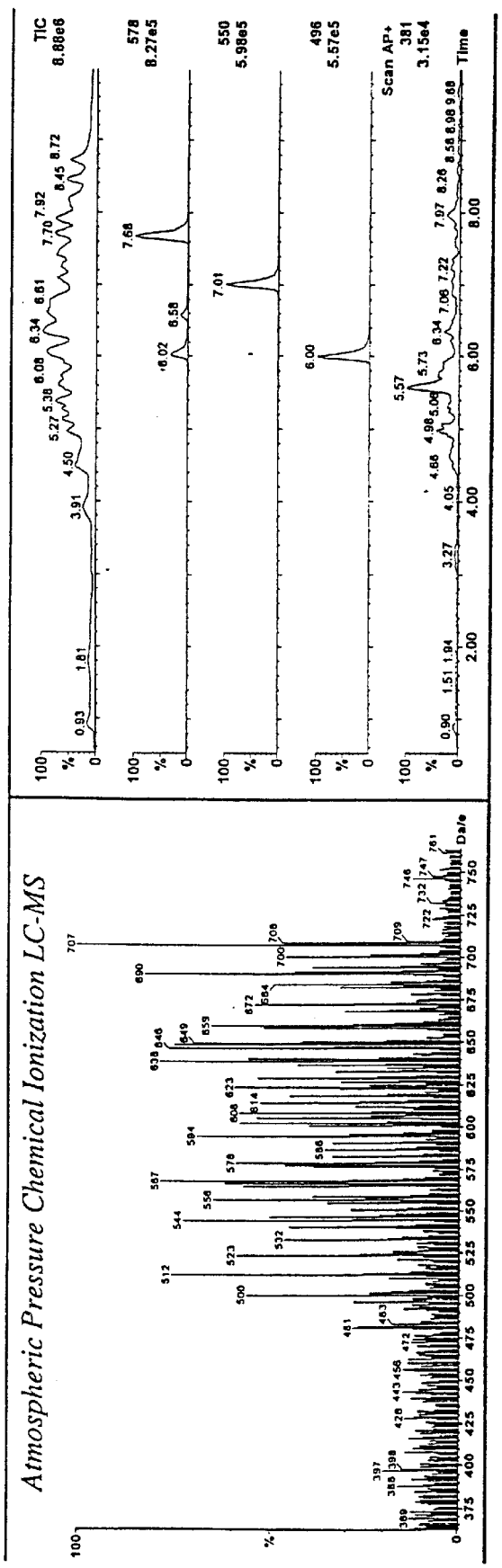
Figure 45:
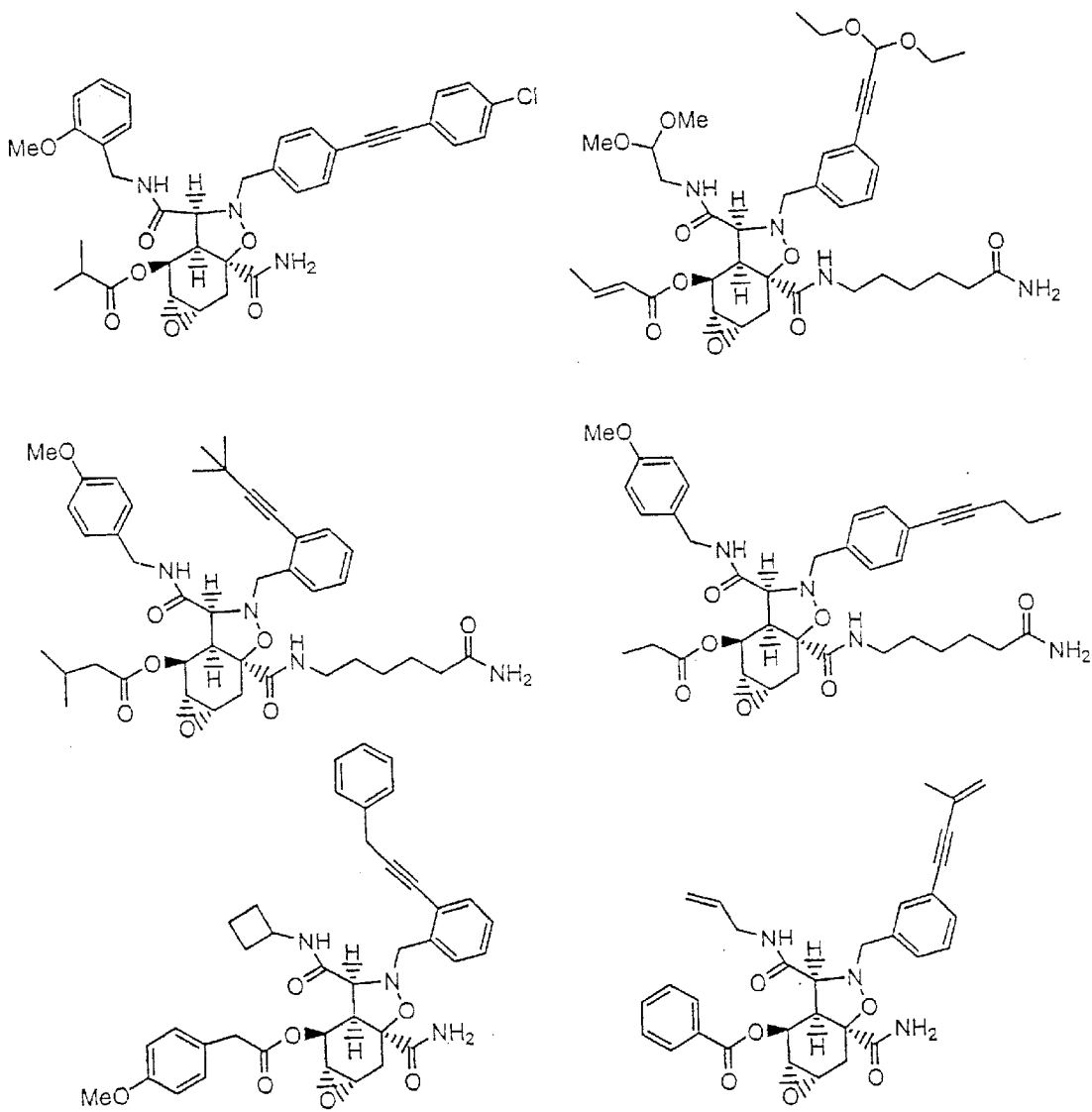
FIG. 45 depicts demonstration compounds.
Figure 51A:
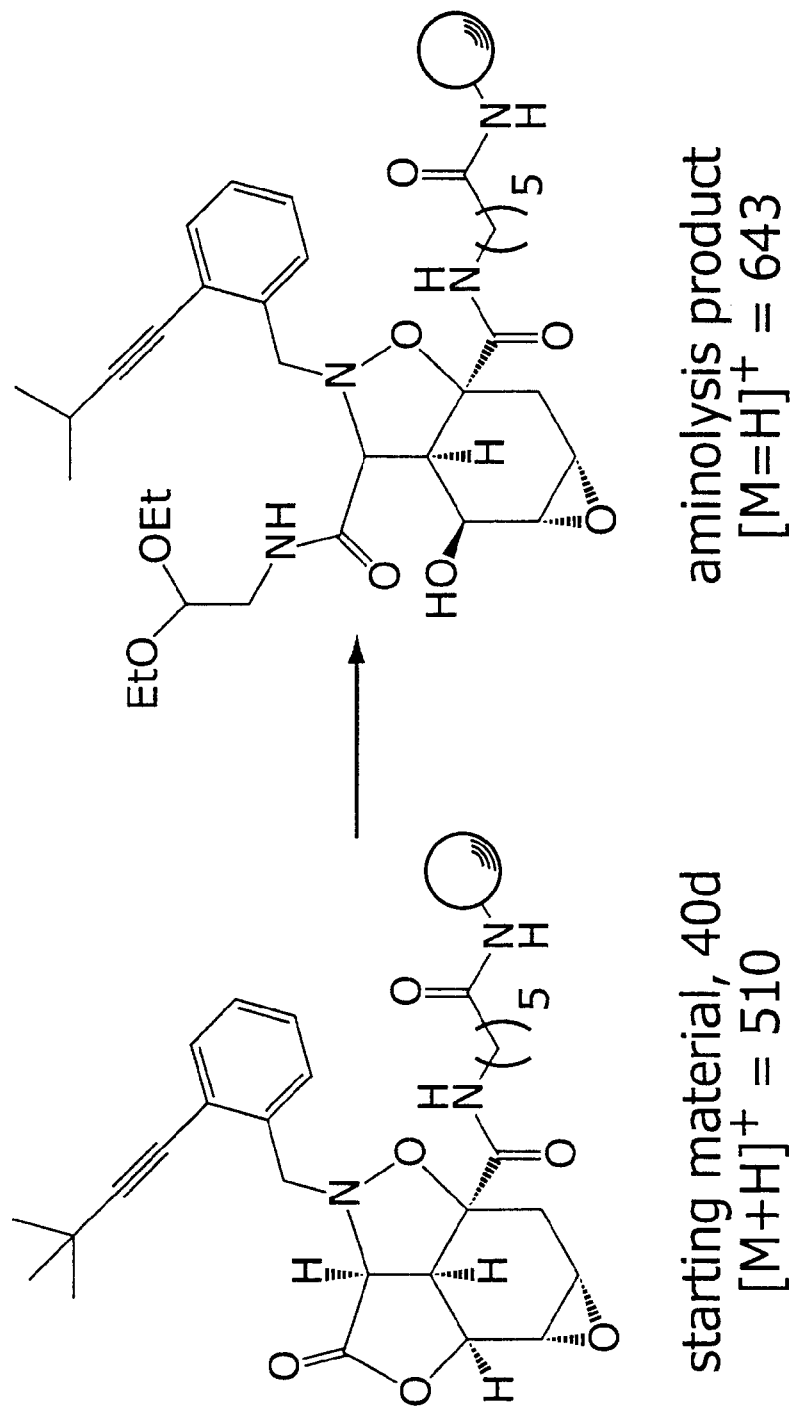
FIGS. 51A and 51B depict representative LC-MS data for building block testing: UV trace (214 nm), TIC trace, product mass trace, starting material mass trace, averaged mass spectrum for product peak (5.52 min), and corresponding structures. While the starting material is difficult to detect in the UV and TIC traces, a minor amount is clearly detected in the single mass trace. Note the slight (0.09 min) delay between UV detector retention time and mass detector retention times.
Figure 51B:
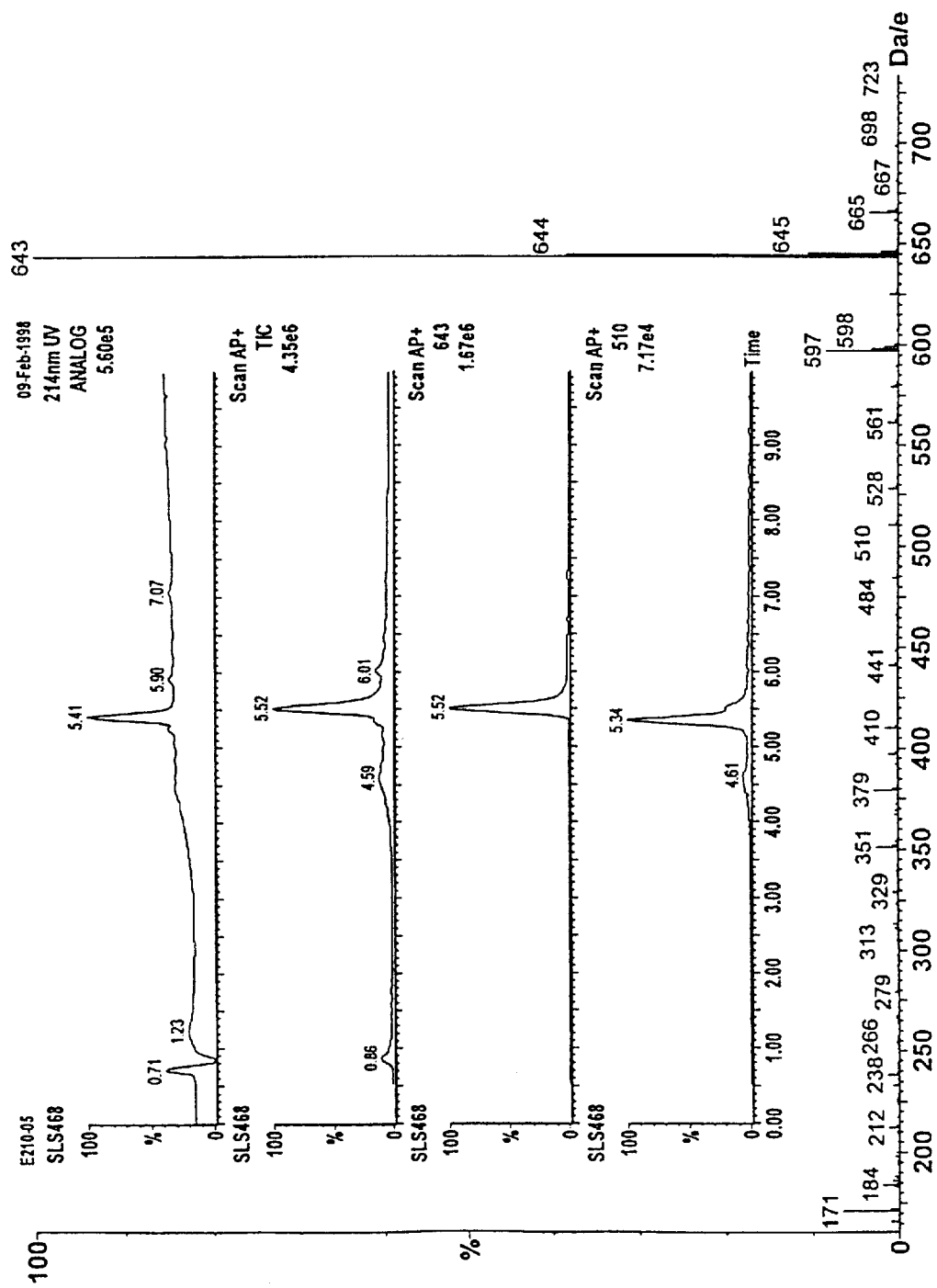
Figure 52A:
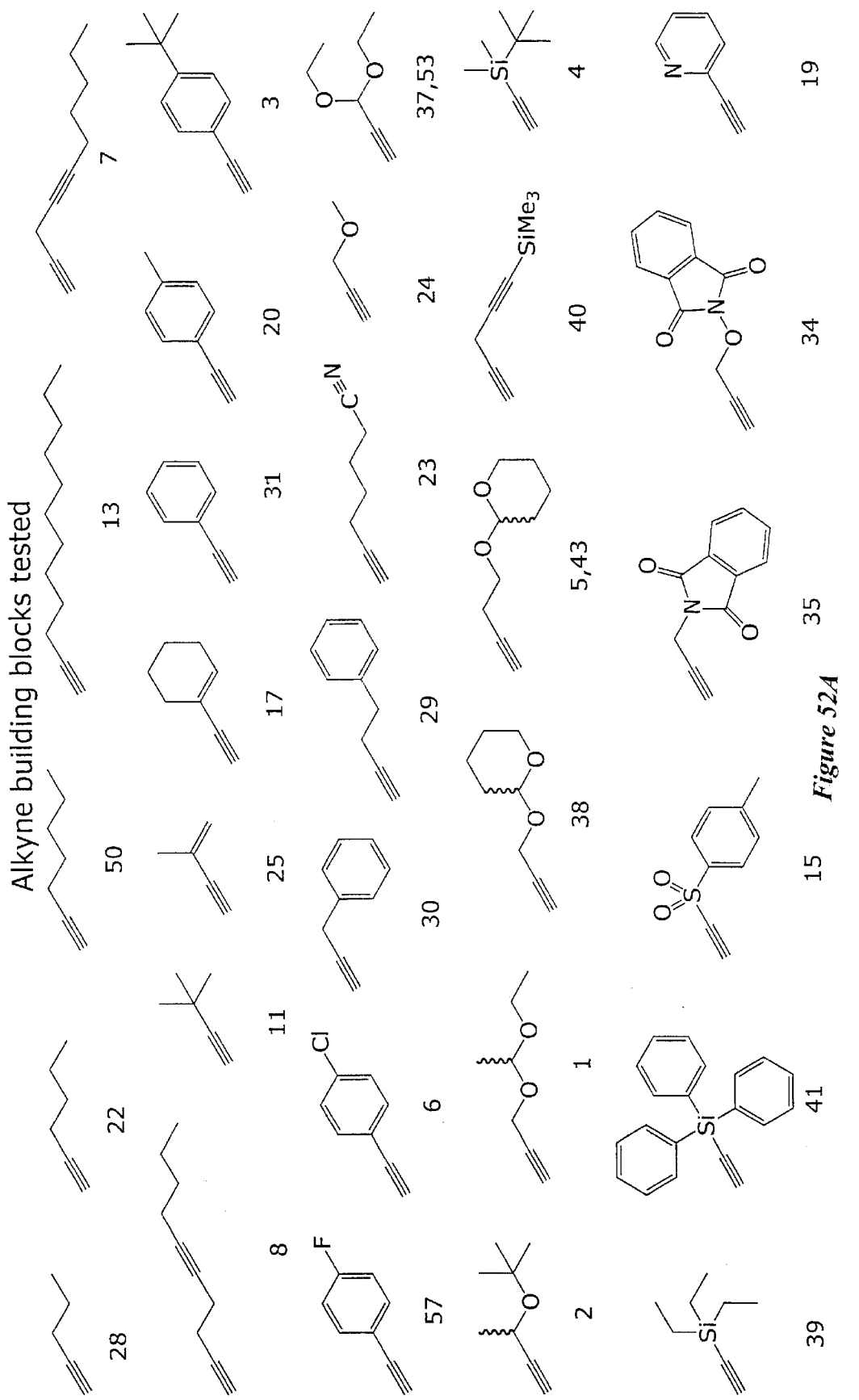
FIGS. 52A and 52B depict exemplary alkyne building blocks.
Figure 52B:
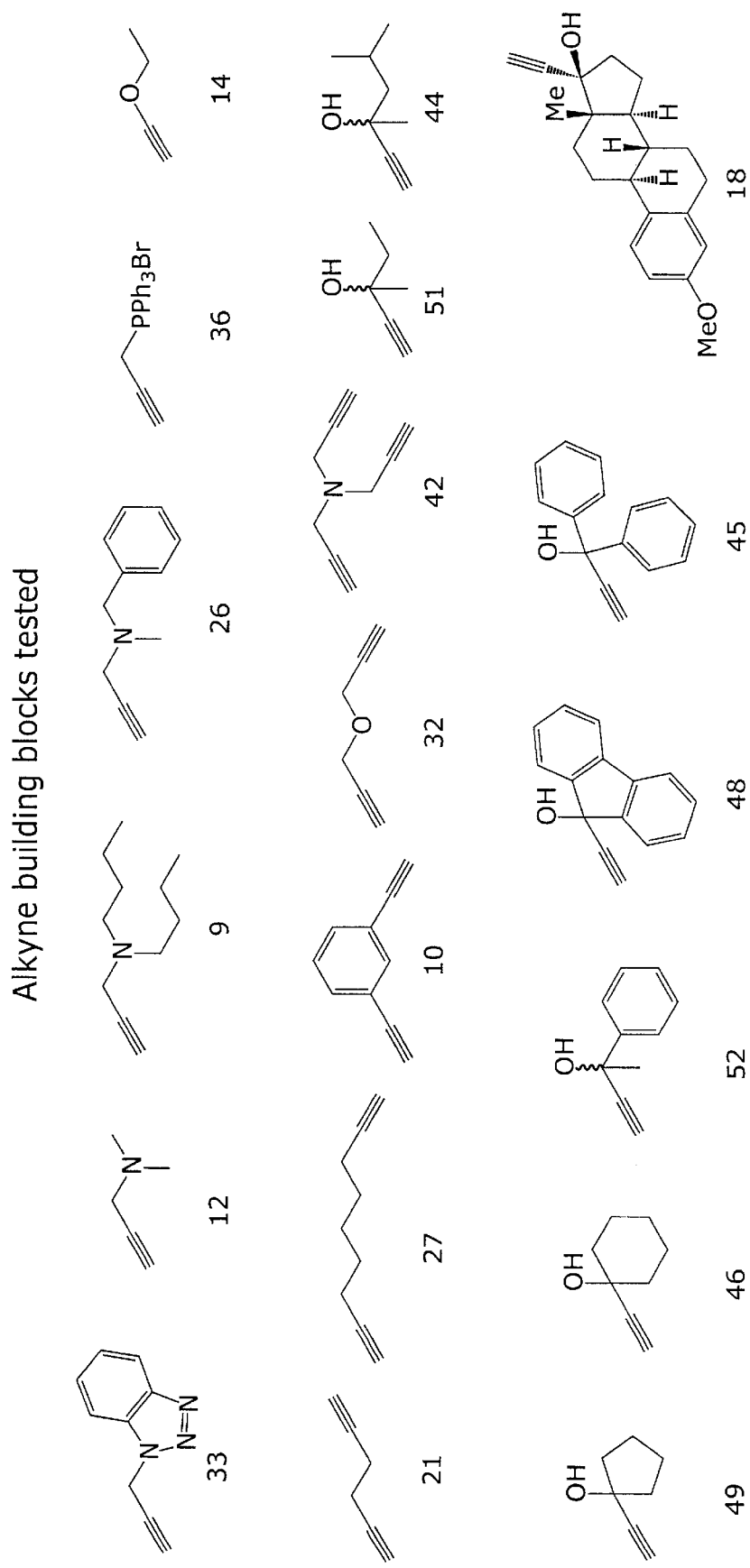
Figure 53A:
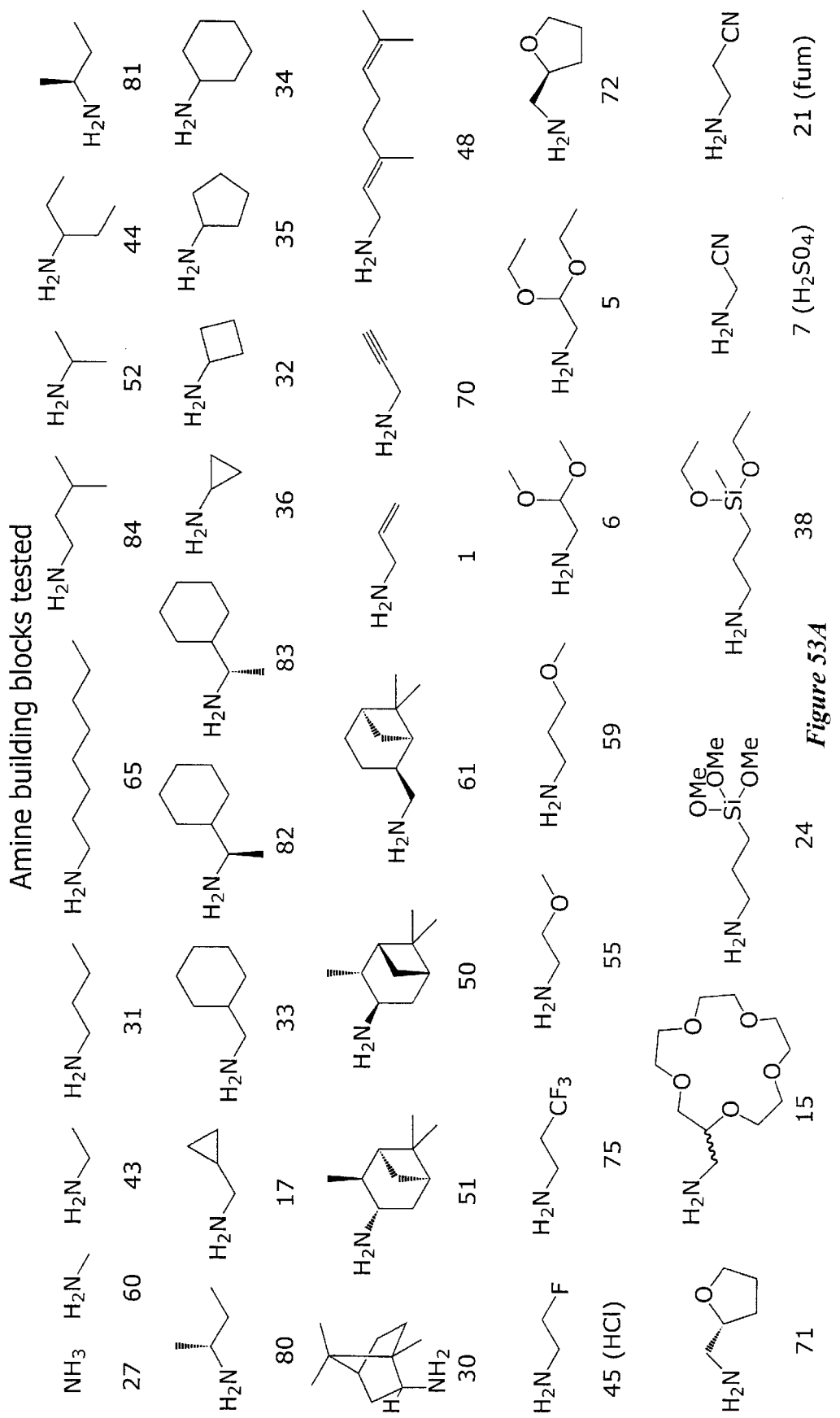
FIGS. 53A, 53B and 53C depict exemplary amine building blocks.
Figure 53B:
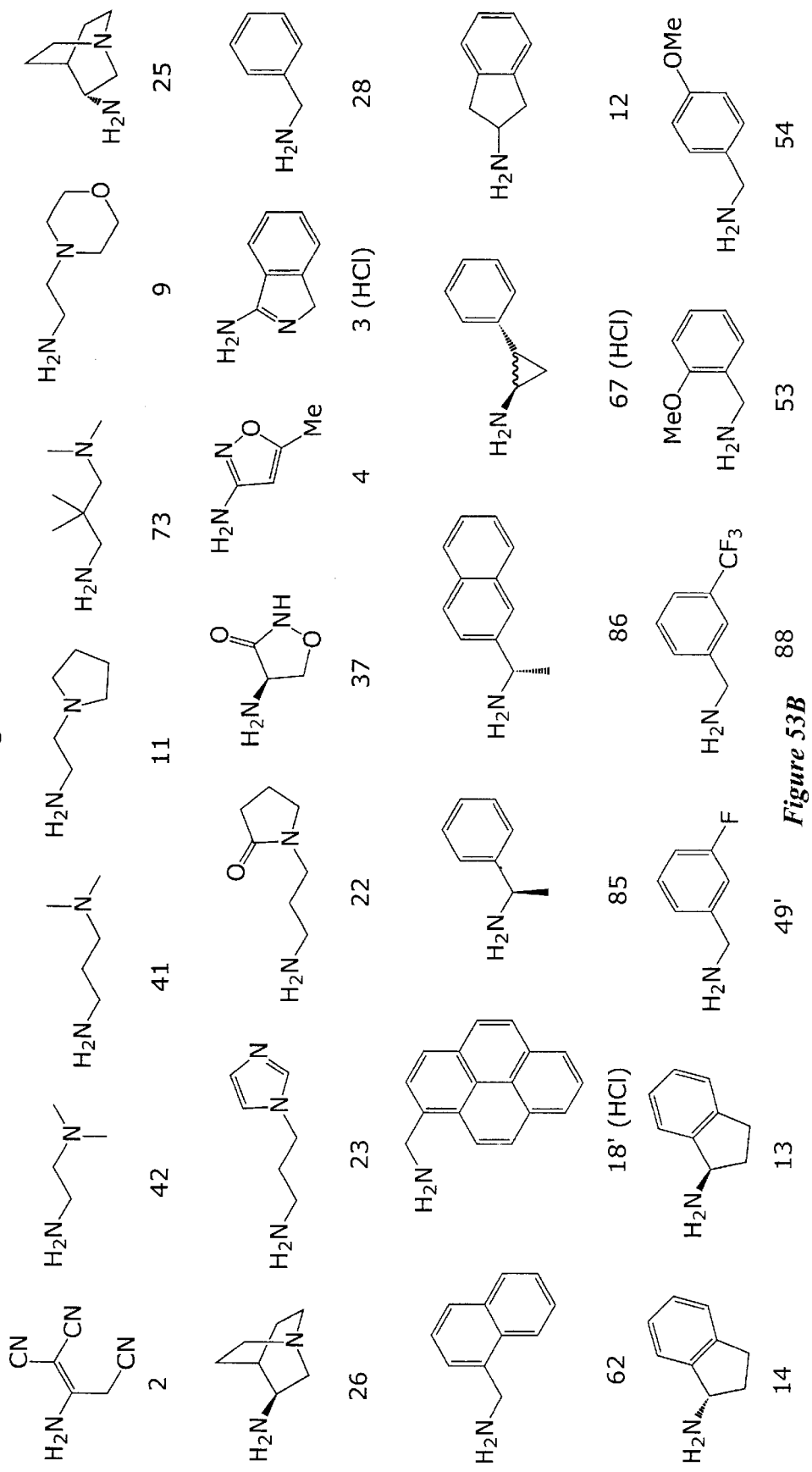
Figure 53C:
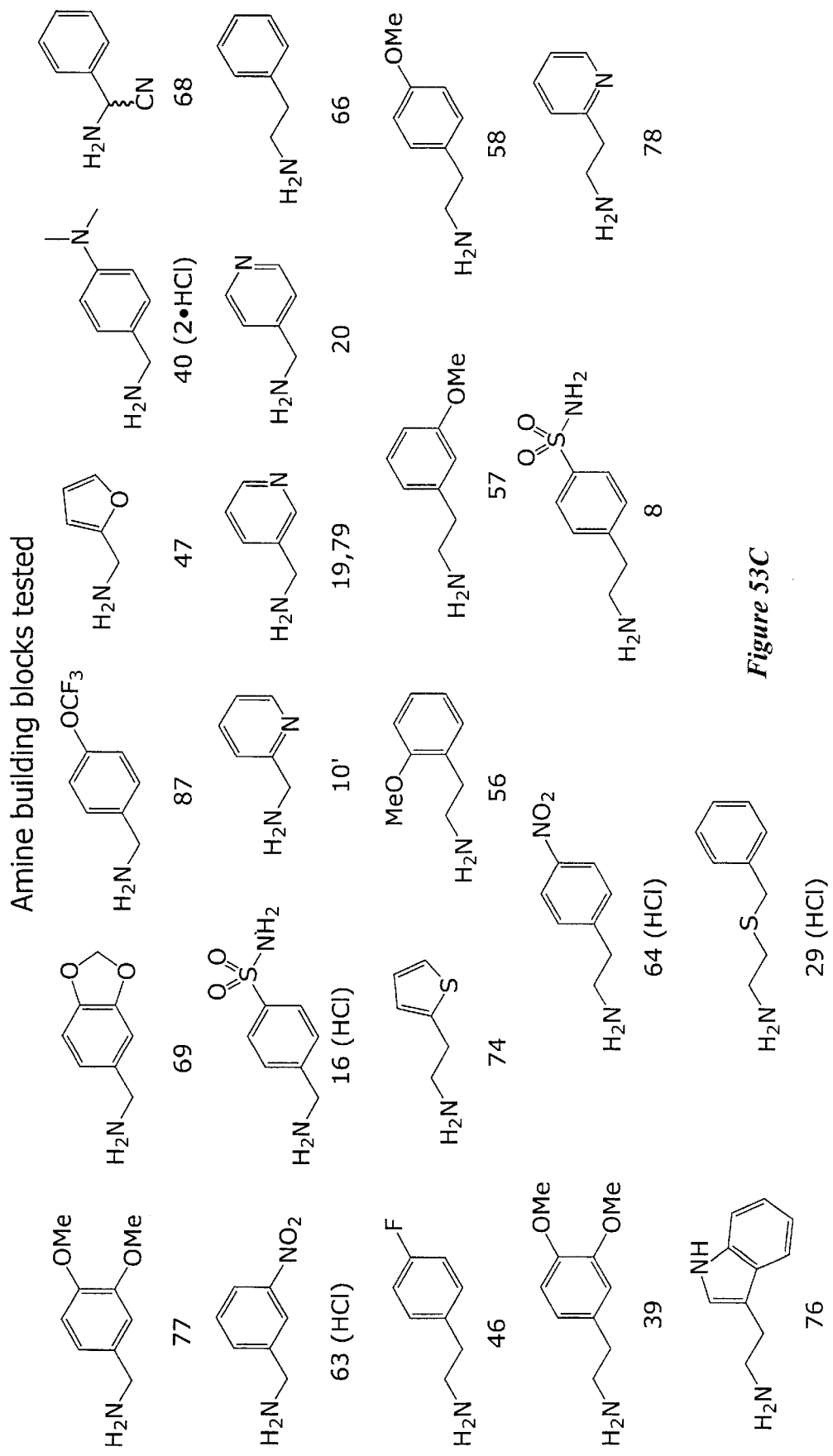
Figure 54A:
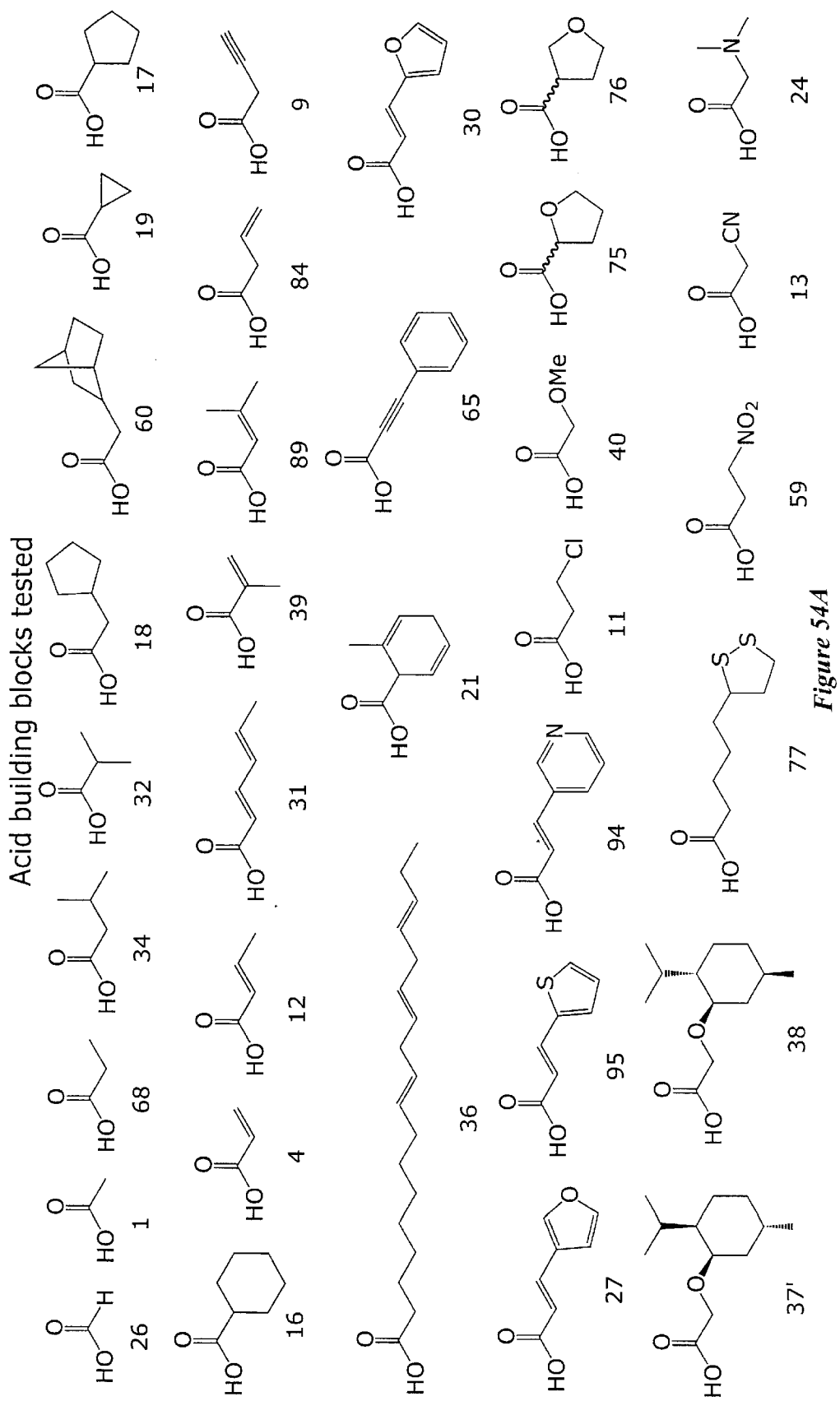
FIGS. 54A, 54B, 54C and 54D depict exemplary acid building blocks.
Figure 54B:
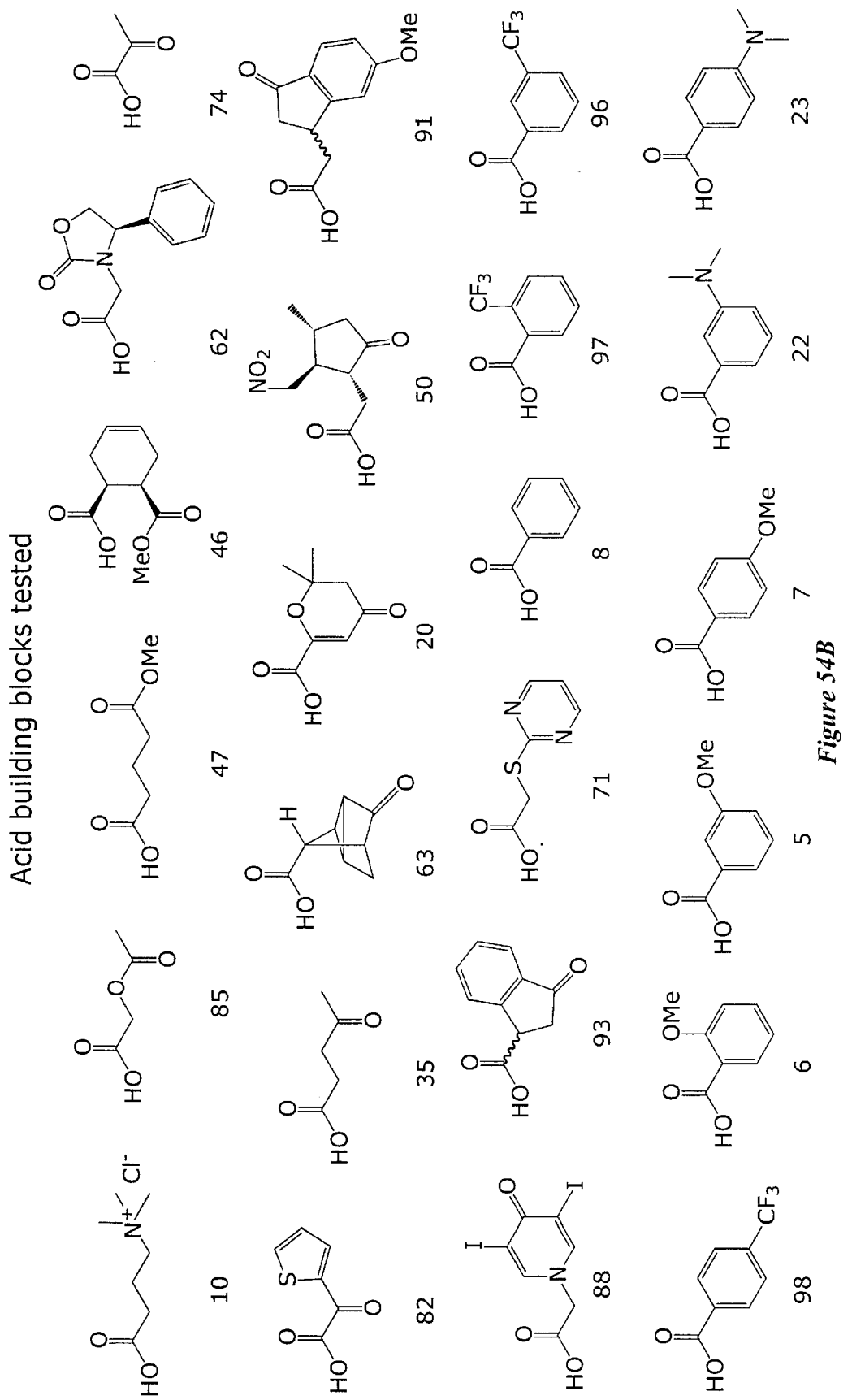
Figure 54C:
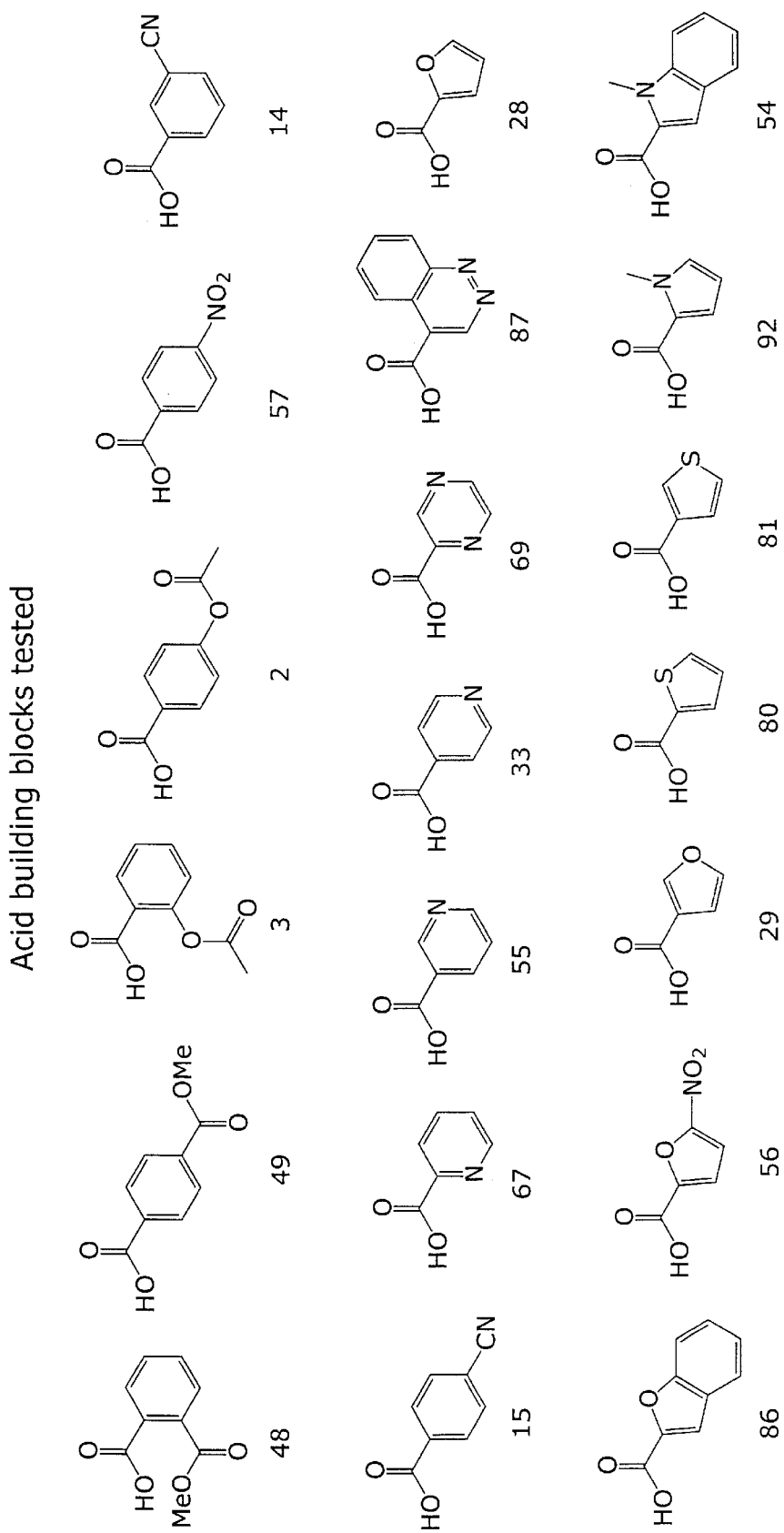
Figure 54D:
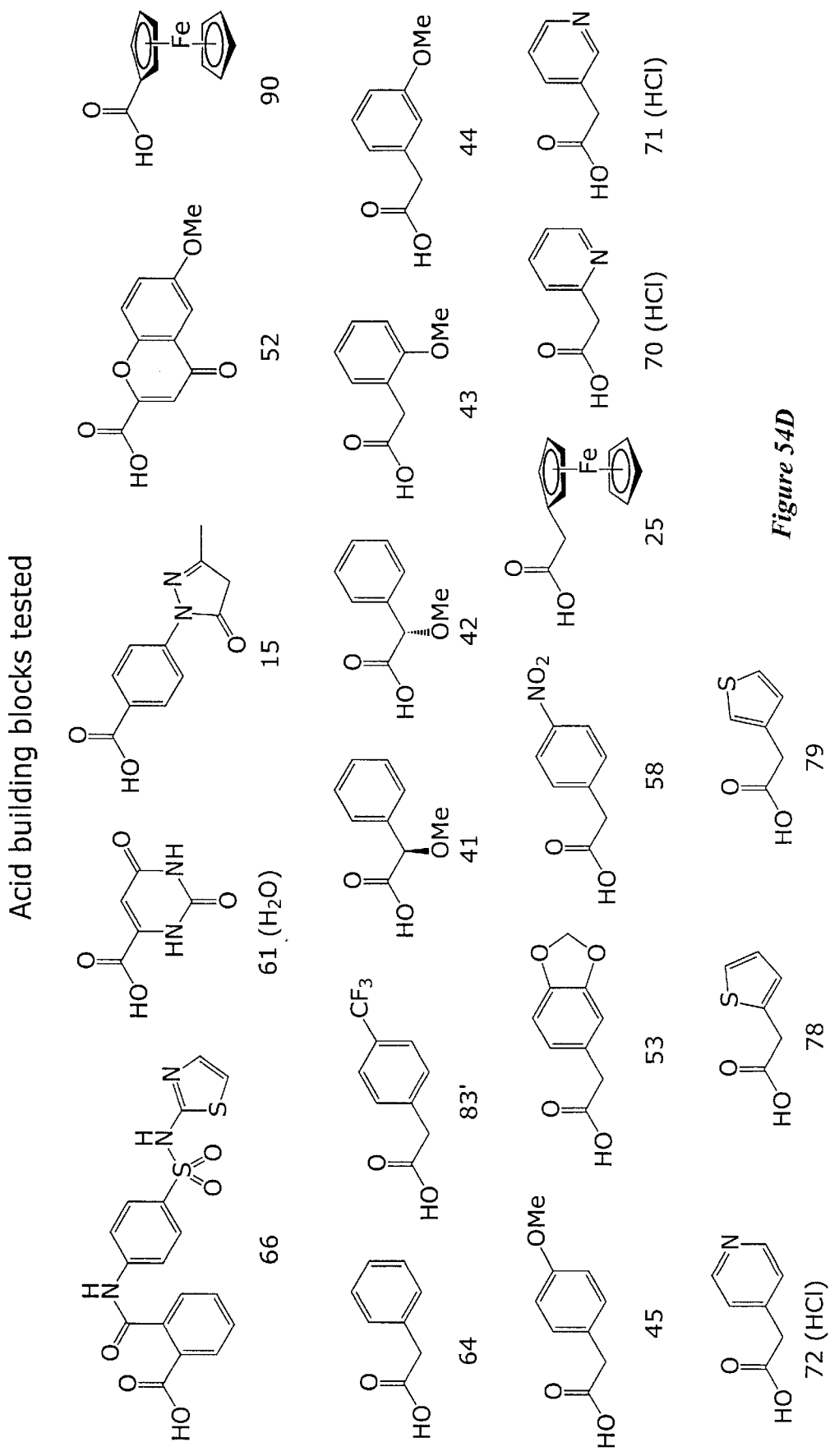

V. Building Block Testing:

To ensure that all of the building blocks included in the library synthesis were viable coupling partners, a total of 235 building blocks (FIGS. 52–54) were tested in their respective couplings by reaction with a single common substrate at each step (FIG. 43). The photocleavage products from each reaction were analyzed by HPLC and LC-MS (FIG. 51, Tables A-C). Certain acid-sensitive products were analyzed by TLC and FAB-MS. Building blocks reacting with generally greater than or equal to 90% conversion and purity were selected for inclusion in library synthesis.

Methods. All solids were measured to within 10%. All liquids were dispensed via Gilson automatic pipettemen with polypropylene tips. Reactions were performed using the small-scale solid phase reaction procedures described above. Resin samples were photolyzed in sets of 11 for 1 h. After photolysis, the samples were centrifuged briefly and 10 μL of the supernatant was submitted for HPLC analysis. An additional 5 μL was diluted to 50 μL with $CH_3CN$ and submitted for LC-MS analysis (10 μL injection). Where necessary, additional samples were removed for TLC and FAB-MS analysis.

Alkyne Testing. 2-Iodobenzyl tetracycle ω-aminocaproic-Anp-TentaGel resin 10aR (10 mg, 0.24 meq/g, 2.39 μmol, 1.0 equiv), copper(I)iodide (1.0 mg, 5.26 μmol, 2.2 equiv), and bis(triphenylphosphine)palladium(II)chloride (1.84 mg, 2.63 μmol, 1.1 equiv) or tetrakis(triphenylphosphine) palladium(0) for polyynes (3.04 mg, 2.63 μmol, 1.1 equiv) were combined and 100 μL DMF was added, followed by DIPEA (12.5 μL, 71.76 μmol, 30 equiv for monoynes; 29.17 μL, 167.43 μmol, 70 equiv for diynes; or 43.75 μL, 251.1 μmol, 105 equiv for triynes). The tube was vortexed vigorously, centrifuged briefly, then the appropriate alkyne (47.84 μmol, 20 equiv for monoynes; 119.6 μmol, 50 equiv for diynes; or 179.4 μmol, 75 equiv for triynes) was added as a neat liquid or solid. The tube was again vortexed vigorously, centrifuged briefly, wrapped with parafilm, and finally vortexed gently for 1 h. After washing, the resin was photolyzed in 125 μL $CH_3CN$.

Amine Testing. o-(3,3-Dimethyl-1-butynyl)benzyl tetracycle ω-aminocaproic-Anp-TentaGel resin 11aR (5 mg, 0.24 meq/g, 1.21 μmol, 1.0 equiv) and solid amines where appropriate (30.23 μmol, 25 equiv for non-α-branched amines; 60.49 μmol, 50 equiv for α-branched amines) were combined, then 2-hydroxypyridine (0.575 mg, 6.05 μmol, 5 equiv for non-α-branched amines; 1.150 mg, 12.09 μmol, 10 equiv for α-branched amines) was added as a 50 μL stock solution in THF (free amines) or 2:1 $CH_2Cl_2$/DMF (amine hydrochlorides). Neat liquid amines (30.23 μmol, 25 equiv for non-α-branched amines; 60.49 μmol, 50 equiv for α-branched amines) were added where appropriate. DIPEA was added as necessary to neutralize amine hydrochlorides (10.53 μL, 60.46 μmol, 50 equiv for non-α-branched monohydrochlorides; 21.06 μL, 120.92 μmol, 100 equiv for non-c-branched dihydrochlorides and α-branched monohydrochlorides; 42.12 μL, 241.84 μmol, 200 equiv for α-branched dihydrochlorides). The tubes were wrapped with teflon tape and parafilm and vortexed gently for 13 h. After washing, the resin was photolyzed in 60 μL $CH_3CN$.

Acid Testing. In 2 mL oven-dried Wheaton vials fitted with teflon septum caps and stir bars were placed the appropriate carboxylic acids (292.6 μmol, 250 equiv) and 182.62 μL $CH_2Cl_2$. DIPC (22.90 μL, 146.3 μmol, 125 equiv) was added to each vial and the mixtures stirred for 2 min. DIPEA (50.95 μL, 292.6 μmol, 250 equiv; 101.9 μL, 585.2 μmol, 500 equiv for amino acid hydrochlorides) was added to each vial and the mixtures stirred for another 5 min. Approximately ⅕th of each preactivation mixture (60 μL normally; 70 μL for hydrochlorides; 25 equiv activated acid) was added to o-(3,3-dimethyl-1-butynyl)benzyl 4-methoxybenzylamido hydroxy tricycle ω-aminocaproic-Anp-TentaGel resin 12aR (5 mg, 0.23 meq/g, 1.17 μmol, 1.0 equiv). DMAP (0.715 mg, 5.85 μmol, 5 equiv) was added to each tube as a 10 μL stock solution in $CH_2Cl_2$ and the tubes were wrapped with teflon tape and parafilm then vortexed gently for 14 h. The resin was exposed to the standard wash procedure with an additional 20% DIPEA in $CH_2Cl_2$ wash inserted between the $CH_2Cl_2$ and DMF wash steps. Finally, the resin was photolyzed in 60 μL $CH_3CN$.

Results. For each 50 mL LC-MS sample, a 10 mL injection was chromatographed and mass analyzed according to the procedure in II. General Methods. For each sample, a UV trace (214 nm) and Total Ion Count (TIC) trace were collected. The data were then scanned for starting material and product masses and the results displayed as single mass traces. Finally an averaged mass spectrum of the product peak was calculated.

Complete HPLC (52 pages) and LCMS data (235 pages) are available upon request. A representative example is shown (FIG. 51) and the remaining results are summarized in tabular format (Tables A–C).

TABLE A

Alkyne building blocks tested.

| Test # | Vendor | Catalog # | Chemical Name | mono terminal alkynes / bis terminal alkynes (italicized) mg or uL alkyne | MW | d | 47.84 umol alkyne (20 eq) / 119.60 umol alkyne (50 eq) ✓ = ≥90% conversion & purity HPLC | Mass | LCMS | TLC |
|---|---|---|---|---|---|---|---|---|---|---|
| ±1 | Aldrich | 33,482-0 | Acetaldehyde ethyl propargyl acetal | 6.83 | 128.17 | 0.898 | 50% | 555 | 60% | |
| ±2 | Aldrich | 38,425-9 | Butyl 1-methyl-2-propynyl ether, tert- | 7.59 | 126.20 | 0.795 | ✓ | 553 | ✓ | |
| 3 | GPS | 115730 | Butyl)phenylacetylene, 4-(tert- | 8.50 | 158.00 | 0.889 | 80% | 585 | ✓ | |
| 4 | Aldrich | 39,926-4 | Butyldimethylsilyl)acetylene, (tert- | 8.94 | 140.30 | 0.751 | 50% | 567 | 50% | |
| ±5 | Aldrich | 30,586-3 | Butynloxy)tetrahydro-2H-pyran, 2-(3- | 7.50 | 154.21 | 0.984 | NR | 581 | NR | 50%c |
| 6 | Aldrich | 20,647-4 | Chloro-4-ethynylbenzene, 1- | 6.53 | 136.58 | 1.000 | ✓ | 564 | ✓ | |
| 7 | GPS | 126504 | Decadiyne (50% in hexane), 1,4- | 12.84 | 134.22 | 0.500 | 20% | 561 | 20% | |
| 8 | GPS | 126706 | Decadiyne, 1,5- | 6.42 | 134.22 | 1.000 | ✓ | 561 | ✓ | |
| 9 | GPS | 129103 | Dibutylamino-1-propyne, 3- | 6.61 | 111.19 | 0.804 | NR | 538 | NR | |
| 10 | GPS | 130100 | Diethynylbenzene, m- | 15.09 | 126.15 | 1.000 | 60% | 553 | 80% | |
| 11 | Aldrich | 24,439-2 | Dimethyl-1-butyne, 3,3- | 5.89 | 82.15 | 0.667 | ✓ | 509 | ✓ | |
| 12 | Aldrich | 14,306-5 | Dimethylamino-2-propyne, 1- | 5.15 | 83.13 | 0.772 | 50% | 510 | 10% | 80%c |
| 13 | Aldrich | 24,440-6 | Dodecyne, 1- | 10.23 | 166.31 | 0.778 | 80% | 593 | 90% | |
| 14 | Aldrich | 27,136-5 | Ethyl ethynyl ether (50% in hexanes) | 6.71 | 70.09 | 0.500 | NR | 497 | NR | |

TABLE A-continued

Alkyne building blocks tested.

mono terminal alkynes  
bis terminal alkynes (italicized)

47.84 umol alkyne (20 eq)  
119.60 umol alkyne (50 eq)

Test mg or uL    ✓ = ≥90% conversion & purity

| Test # | Vendor | Catalog # | Chemical Name | alkyne | MW | d | HPLC | Mass | LCMS | TLC |
|---|---|---|---|---|---|---|---|---|---|---|
| 15 | Aldrich | 41,986-9 | Ethynyl p-tolyl sulfone | 8.62 | 180.23 | 1.000 | NR | 607 | NR | |
| 16 | Aldrich | 40,433-0 | Ethynyl-4-fluorobenzene, 1- | 5.48 | 120.13 | 1.048 | n.d. | 547 | n.d. | |
| 17 | Aldrich | 31,657-1 | Ethynylcyclohexene, 1- | 5.62 | 106.17 | 0.903 | ✓ | 533 | ✓ | |
| 18 | Aldrich | 85,587-1 | Ethynylestradiol 3-methyl ether | 14.85 | 310.44 | 1.000 | ✓ | 737 | ✓ | |
| 19 | GPS | 143907 | Ethynylpyridine, 2- | 5.25 | 103.12 | 0.940 | NR | 530 | 50% | 70%c |
| 20 | Aldrich | 20,650-4 | Ethynyltoluene, 4- | 6.07 | 116.16 | 0.916 | ✓ | 543 | ✓ | |
| 21 | *Aldrich* | 40,729-1 | *Hexadiyne (50% in hexane), 1,5-* | 18.68 | 78.11 | 0.500 | 30% | 505 | 40% | |
| 22 | Aldrich | 24,442-2 | Hexyne, 1- | 5.50 | 82.15 | 0.715 | ✓ | 509 | ✓ | |
| 23 | Aldrich | 27,134-9 | Hexynenitrile, 5- | 5.01 | 93.13 | 0.889 | ✓ | 520 | ✓ | |
| 24 | Aldrich | 17,719-9 | Methyl propargyl ether | 4.04 | 70.09 | 0.830 | 70% | 497 | 80% | |
| 25 | Aldrich | M3,280-1 | Methyl-1-buten-3-yne, 2- | 4.55 | 66.10 | 0.695 | ✓ | 493 | ✓ | |
| 26 | Aldrich | M7,425-3 | Methyl-N-propargylbenzylamine, N- | 8.07 | 159.23 | 0.944 | ✓ | 586 | ✓ | 90%c |
| 27 | *Aldrich* | 16,130-6 | *Nonadiyne, 1,8-* | 17.99 | 120.20 | 0.799 | nuked | 547 | nuked | baseline |
| 28 | Aldrich | 25,656-0 | Pentyne, 1- | 4.72 | 68.12 | 0.691 | ✓ | 495 | ✓ | |
| 29 | GPS | 184701 | Phenyl-1-butyne, 4- | 6.73 | 130.19 | 0.926 | ✓ | 557 | ✓ | |
| 30 | Aldrich | 37,684-1 | Phenyl-1-propyne, 3- | 5.95 | 116.16 | 0.934 | ✓ | 543 | ✓ | |
| 31 | Aldrich | 11,770-6 | Phenylacetylene | 5.25 | 102.14 | 0.930 | ✓ | 529 | ✓ | |
| 32 | *Aldrich* | 41,696-7 | *Propargyl ether* | 12.31 | 94.11 | 0.914 | NR | 521 | 30% | |
| 33 | Aldrich | 44,694-7 | Propargyl-1H-benzotriazole, 1- | 7.52 | 157.18 | 1.000 | 30% | 584 | 10% | |
| 34 | Aldrich | P5,133-8 | Propargyloxy)phthalimide, N-( | 9.62 | 201.18 | 1.000 | NR | 628 | 10% | |
| 35 | GPS | 187530 | Propargylphthalimide, N- | 8.86 | 185.18 | 1.000 | 40% | 612 | 30% | |
| 36 | Aldrich | 22,648-3 | Propargyltriphenylphosponium bromide | 18.24 | 381.26 | 1.000 | NR | 808 | NR | |
| 37 | Aldrich | 30,360-7 | Proplolaldehyde diethyl acetal | 6.86 | 128.17 | 0.804 | NR | 555 | NR | |
| ±38 | Aldrich | 30,081-0 | Tetrahydro-2-(2propynyloxy)-2H-pyran | 6.73 | 140.18 | 0.997 | 40% | 567 | 40% | |
| 39 | Aldrich | 34,697-7 | Triethylsilyl)acetylene, ( | 8.57 | 140.30 | 0.783 | 70% | 567 | 80% | |
| 40 | GPS | 193080 | Trimethylsilyl-1,4-pentadiyne, 1- | 6.52 | 136.27 | 1.000 | NR | 563 | 20% | |
| 41 | Aldrich | 36,005-8 | Triphenylsilyl)acetylene, ( | 13.61 | 284.44 | 1.000 | 40% | 711 | 40% | |
| 42 | *Aldirch* | T8,496-4 | *Tripropargylamine* | 25.39 | 131.18 | 0.927 | NR | 558 | 30% | |
| 43 | Aldrich | 30,586-3 | Butynloxy)tetrahydro-2H-pyran, 2-(3- | 7.50 | 154.21 | 0.984 | ✓ | 581 | ✓ | |
| 44 | GPS | 133502 | Dimethyl-1-hexyn-3-ol, 3,5- | 6.04 | 126.20 | 1.000 | ✓ | 553 | ✓ | |
| 45 | GPS | 136101 | Diphenyl-2-propyn-1-ol, 1,1- | 9.96 | 208.26 | 1.000 | ✓ | 635 | ✓ | |
| 46 | Aldrich | E5,140-6 | Ethynyl-1-cyclohexanol, 1- | 6.14 | 124.18 | 0.967 | ✓/NR? | 551 | 80%p | |
| 47 | Aldrich | 40,433-0 | Ethynyl-4-fluorobenzene, 1- | 5.48 | 120.13 | 1.048 | ✓ | 547 | ✓ | |
| 48 | GPS | 143705 | Ethynyl-9-fluorenol, 9- | 9.87 | 206.25 | 1.000 | ✓ | 633 | ✓ | |
| 49 | Aldrich | 13,086-9 | Ethynylcyclopentanol, 1- | 5.48 | 110.16 | 0.962 | ✓/NR? | 537 | 80%p | |
| 50 | Aldrich | 24,441-4 | Heptyne, 1- | 6.28 | 96.17 | 0.733 | 70%c | 523 | 60%c | |
| 51 | Aldrich | 13,756-1 | Methyl-1-pentyn-3-ol, 3- | 5.42 | 98.15 | 0.866 | 80%p | 525 | 80%p | |
| 52 | GPS | 184903 | Phenyl-3-butyn-2-ol, 2- | 6.99 | 146.19 | 1.000 | ✓ | 573 | ✓ | |
| 53 | Aldrich | 30,360-7 | Propiolaldehyde diethyl acetal | 6.86 | 128.17 | 0.894 | 40%c | 555 | 40%c | |

TABLE B

Amine building blocks tested.

beta-branched or greater (mult = 1)
alpha-branched (mult = 2)
2-hydroxypyridine (2-pyr) stock solutions 30.23 umol amine (25 eq)
60.49 umol amine (50 eq)
1.0 6.05 umol (5 eq) in THF
1.x 6.05 umol (5 eq) in 3:2 CH2Cl2/DMF
2.0 12.09 umol (10 eq) in THF
2.x 12.09 umol (10 eq) in 3:2 CH2Cl2/DMF ✓ = ≥90% conversion and purity

| Test # | Aldrich Catalog # | Chemical Name | 2-pyr | mg or uL amine | uL DIPEA | MW | d | mult | salt | acid | HPLC | Mass | LCMS | TLC | FAB rel int SM/Pdt |
|---|---|---|---|---|---|---|---|---|---|---|---|---|---|---|
| 1 | 24,107-5 | Allylamine | 1.0 | 2.27 | | 57.10 | 0.761 | 1 | | | ✓ | 566 | ✓ | NR | |
| 2 | 10,741-7 | Amino-1-propene-1,1,3-tricarbonitrile, 2- | 2.0 | 7.99 | | 132.13 | 1.000 | 2 | | | NR? | 541 | NR | 30%? | 5/100 |
| 3 | 41,592-8 | Amino-1H-isoindole hydrochloride, 3- | 2.1 | 10.20 | 21.06 | 168.63 | 1.000 | 2 | 1 | | NR? | 642 | NR | NR | |
| 4 | 23,227-0 | Amino-5-methylisoxazole, 3- | 2.0 | 5.93 | | 98.10 | 1.000 | 2 | | | ✓ | 607 | ✓ | | |
| 5 | A3,720-0 | Aminoacetaldehyde diethyl acetal | 1.0 | 4.40 | | 133.19 | 0.916 | 1 | | | ✓ | 642 | ✓ | | |
| 6 | 12,196-7 | Aminoacetaldehyde dimethyl acetal | 1.0 | 3.29 | | 105.14 | 0.965 | 1 | | | ✓ | 614 | ✓ | | |
| 7 | 13,052-4 | Aminoacetonitrile bisulfate | 1.1 | 2.80 | 10.53 | 92.53 | 1.000 | 1 | 1 | | NR? | 565 | NR | NR? | 5/100 |
| 8 | 27,524-7 | Aminoethyl)benzenesulfonamide, 4-(2- | 1.0 | 6.05 | | 200.26 | 1.000 | 1 | | | ✓ | 709 | 70% | 70% | 100/11 |
| 9 | A5,500-4 | Aminoethyl)morpholine, 4-(2- | 1.0 | 3.97 | | 130.19 | 0.992 | 1 | | | ✓ | 639 | NR | 90% | 100/2 |
| 10" | A6,540-9 | Aminoethyl)pyridine, 2-(2- | 1.0 | 3.08 | | 108.14 | 1.062 | 1 | | | ✓ | 617 | NR | 70% | 100/— |
| 11 | A5,535-5 | Aminoethyl)pyrrolidine, 1-(2- | 1.0 | 3.83 | | 114.19 | 0.901 | 1 | | | 50% | 623 | NR | 40% | |
| 12 | A5,952-2 | Aminoindan hydrochloride, 2- | 2.1 | 10.26 | 21.06 | 169.66 | 1.000 | 2 | 1 | | ✓ | 643 | 20% | | |
| 13 | 44,534-7 | Aminoindan, (R)-(–)-1- | 2.0 | 7.76 | | 133.19 | 1.038 | 2 | | | ✓ | 642 | 80% | | |
| 14 | 44,535-5 | Aminoindan, (S)-(+)-1- | 2.0 | 7.76 | | 133.19 | 1.038 | 2 | | | ✓ | 642 | 70% | | |
| ±15 | 38,841-6 | Aminomethyl)-15-crown-5, 2-( | 1.0 | 6.65 | | 249.31 | 1.134 | 1 | | | ✓ | 758 | | 40% | |
| 16 | A6,180-2 | Aminomethyl)benzenesulfonamide hydrochloride, 4-( | 1.1 | 6.73 | 10.53 | 222.69 | 1.000 | 1 | 1 | | 40% | 695 | 40% | | |
| 17 | 35,952-1 | Aminomethyl)cyclopropane, ( | 1.0 | 2.62 | | 71.12 | 0.820 | 1 | | | ✓ | 580 | ✓ | | |
| 18" | 40,163-3 | Pyrenemethylamine hydrochloride, 2- | 1.1 | 8.09 | 10.53 | 267.76 | 1.000 | 1 | 1 | | NR? | 740 | ✓ | ? | |
| 19 | A6,540-9 | Aminomethyl)pyridine, 3-( | 1.0 | 3.08 | | 108.14 | 1.062 | 1 | | | ✓ | 617 | NR | NR | |
| 20 | A6,560-3 | Aminomethyl)pyridine, 4-( | 1.0 | 3.07 | | 108.14 | 1.065 | 1 | | | ✓ | 617 | nuked | 80% | |
| 21 | A7,642-7 | Aminopropionitrile fumarate, 3- | 1.1 | 3.87 | 10.53 | 128.13 | 1.000 | 1 | 1 | | NR? | 579 | NR | | |
| 22 | 13,656-5 | Aminopropyl)-2-pyrrolidinone, 1-(3- | 1.0 | 4.24 | | 142.20 | 1.014 | 1 | | | ✓ | 651 | ✓ | | |
| 23 | 27,226-4 | Aminopropyl)imidazole, 1-(3- | 1.0 | 3.61 | | 125.18 | 1.049 | 1 | | | ✓ | 634 | 60% | ✓? | 100/0 |
| 24 | 28,177-8 | Aminopropyltrimethoxysilane, 3- | 1.0 | 5.28 | | 179.29 | 1.027 | 1 | | | ✓ | 688 | 20% | ✓? | 100/2 |
| 25 | 41,571-5 | Aminoquinuclidine dihydrochloride, (R)-(+)-3- | 2.2 | 12.04 | 42.12 | 199.14 | 1.000 | 2 | 2 | | ✓ | 636 | NR | NR | |
| 26 | 41,572-3 | Aminoquinuclidine dihydrochloride, (S)-(–)-3- | 2.2 | 12.04 | 42.12 | 199.14 | 1.000 | 2 | 2 | | ✓ | 636 | NR | NR | |
| 27 | 40,766-6 | Ammonia (0.5M in dioxane) | 1.0 | 60.46 | | 2000 | 1.000 | 1 | | | NR? | 526 | NR | NR | |
| 28 | 18,570-1 | Benzylamine | 1.0 | 3.30 | | 107.16 | 0.981 | 1 | | | ✓? | 616 | ✓ | | |
| 29 | 40,817-4 | Benzylcysteamine hydrochloride, S- | 1.1 | 6.16 | 10.53 | 203.74 | 1.000 | 1 | 1 | | NR? | 677 | 50% | | |
| 30 | 35,993-9 | Bornylamine, (R)-(+)- | 2.0 | 9.27 | | 153.27 | 1.000 | 2 | | | 60% | 662 | 70% | | |
| 31 | 23,991-7 | Butylamine | 1.0 | 2.99 | | 73.14 | 0.740 | 1 | | | ✓ | 582 | ✓ | | |
| 32 | 25,518-5 | Cyclobutylamine | 1.0 | 5.16 | | 71.12 | 0.833 | 2 | | | ✓ | 580 | ✓ | | |
| 33 | 10,184-2 | Cyclohexanemethylamine | 2.0 | 3.93 | | 113.20 | 0.870 | 1 | | | ✓ | 622 | ✓ | | |
| 34 | 24,064-8 | Cyclohexylamine | 2.0 | 6.92 | | 99.18 | 0.867 | 2 | | | ✓ | 608 | ✓ | | |
| 35 | C11,500-2 | Cyclopentylamine | 2.0 | 5.97 | | 85.15 | 0.863 | 2 | | | ✓ | 594 | ✓ | | |
| 36 | 12,550-4 | Cyclopropylamine | 2.0 | 4.19 | | 57.10 | 0.824 | 2 | | | 90% | 566 | 70% | 70% | |
| 37 | 85,857-9 | Cycloserine, (R)-(+)- | 2.0 | 6.17 | | 102.09 | 1.000 | 2 | | | NR? | 611 | NR | NR | |
| 38 | 37,189-0 | Diethoxymethylsilyl)propylamine, 3-( | 1.0 | 6.31 | | 191.35 | 0.916 | 1 | | | ✓ | 700 | 80% | ✓ | 100/0 |

TABLE B-continued

Amine building blocks tested.

beta-branched or greater (mult = 1)
alpha-branched (mult = 2)
2-hydroxypyridine (2-pyr) stock solutions 30.23 umol amine (25 eq)
60.49 umol amine (50 eq)
1.0 6.05 umol (5 eq) in THF
1.x 6.05 umol (5 eq) in 3:2 CH2Cl2/DMF
2.0 12.09 umol (10 eq) in THF
2.x 12.09 umol (10 eq) in 3:2 CH2Cl2/DMF

| Test # | Aldrich Catalog # | Chemical Name | 2-pyr | mg or uL amine | uL DIPEA | MW | d | mult | acid salt | HPLC | Mass | LCMS | TLC | FAB rel int SM/Pdt |
|---|---|---|---|---|---|---|---|---|---|---|---|---|---|---|
| 39 | D13,620-4 | Dimethoxyphenethylamine, 3,4- | 1.0 | 5.10 | | 181.24 | 1.074 | 1 | | ✓ | 690 | ✓ | NR | —/100 |
| 40 | 28,563-3 | Dimethylamino)benzyamine dihydrochloride, 4-( | 1.2 | 6.75 | 21.06 | 223.15 | 1.000 | 1 | 2 | NR? | 659 | NR | 50% | 100/2 |
| 41 | 24,005-2 | Dimethylaminopropylamine, 3- | 1.0 | 3.80 | | 102.18 | 0.812 | 1 | | 50% | 611 | NR | 50% | 0/27 |
| 42 | D15,780-5 | Dimethylethylenediamine, N,N- | 1.0 | 3.22 | | 88.15 | 0.828 | 2 | | NR | 597 | NR | | |
| 43 | 39,507-2 | Ethylamine (2.0M in THF) | 1.0 | 15.12 | | 500.00 | 1.000 | 1 | | ✓ | 554 | ✓ | | |
| 44 | 19,019-5 | Ethylpropylamine, 1- | 2.0 | 7.05 | | 87.17 | 0.748 | 1 | | ✓ | 596 | 80% | | |
| 45 | 42,905-8 | Fluoroethylamine hydrochloride, 2- | 1.1 | 3.01 | 10.53 | 99.54 | 1.000 | 1 | 1 | 80% | 573 | 50% | 70% | |
| 46 | 36,182-8 | Fluorophenethylamine, 4- | 1.0 | 3.97 | | 139.17 | 1.061 | 1 | | ✓ | 648 | ✓ | | |
| 47 | F2,000-9 | Furlurylamine | 1.0 | 2.67 | | 97.12 | 1.099 | 1 | | 30% | 606 | 30% | 10% | |
| 48 | 41,264-3 | Geranylamine | 1.0 | 5.59 | | 153.27 | 0.829 | 1 | | ✓ | 662 | ✓ | | |
| 49' | 12,689-6 | Fluorobenzylamine, 3- | 1.0 | 3.45 | | 125.15 | 1.097 | 1 | | ✓ | 634 | ✓ | | |
| 50 | 39,165-4 | Isopinocampheylamine, (1R,2R,3R,5S)-(−)- | 2.0 | 10.19 | | 153.27 | 0.909 | 2 | | ✓ | 662 | ✓ | | |
| 51 | 39,166-2 | Isopinocampheylamine, (1S,2S,3S,5R)-(+)- | 2.0 | 10.19 | | 153.27 | 0.909 | 2 | | ✓ | 662 | ✓ | | |
| 52 | 10,906-1 | Isopropylamine | 2.0 | 5.15 | | 59.11 | 0.694 | 2 | | ✓ | 568 | ✓ | | |
| 53 | 15,988-3 | Methoxybenzylamine, 2- | 1.0 | 3.95 | | 137.18 | 1.051 | 1 | | ✓? | 646 | ✓ | | |
| 54 | M1,110-3 | Methoxybenzylamine, 4- | 1.0 | 3.95 | | 137.18 | 1.050 | 1 | | ✓ | 646 | ✓ | | |
| 55 | 24,106-7 | Methoxyethylamine, 2- | 1.0 | 2.63 | | 75.11 | 0.864 | 1 | | ✓ | 584 | ✓ | | |
| 56 | 37,359-1 | Methoxyphenethylamine, 2- | 1.0 | 4.43 | | 151.21 | 1.033 | 1 | | ✓ | 660 | ✓ | | |
| 57 | 27,022-9 | Methoxyphenethylamine, 3- | 1.0 | 4.43 | | 151.21 | 1.038 | 1 | | ✓ | 660 | ✓ | | |
| 58 | 18,730-5 | Methoxyphenethylamine, 4- | 1.0 | 4.43 | | 151.21 | 1.033 | 1 | | ✓ | 660 | ✓ | | |
| 59 | M2,500-7 | Methoxypropylamine, 3- | 1.0 | 3.08 | | 89.14 | 0.874 | 1 | | ✓ | 598 | ✓ | | |
| 60 | 39,505-6 | Methylamine (2.0M in THF) | 1.0 | 15.12 | | 500.00 | 1.000 | 1 | | ✓ | 540 | ✓ | | |
| 61 | 18,080-7 | Myrtanylamine, (−)-cis- | 1.0 | 5.06 | | 153.27 | 0.915 | 1 | | ✓ | 662 | ✓ | | |
| 62 | 12,703-5 | Naphtylenemethylamine, 1- | 1.0 | 4.43 | | 157.22 | 1.073 | 1 | | ✓ | 666 | 70% | 60% | |
| 63 | 19,166-3 | Nitrobenzylamine hydrochloride, 3- | 1.1 | 5.70 | 10.53 | 188.62 | 1.000 | 1 | 1 | 60% | 662 | 50% | 10% | |
| 64 | 18,480-2 | Nitrophenethylamine hydrochloride, 4- | 1.1 | 6.13 | 10.53 | 202.64 | 1.000 | 1 | 1 | NR? | 676 | 10% | | |
| 65 | O-580-2 | Octylamine | 1.0 | 5.00 | | 129.25 | 0.782 | 1 | | ✓ | 638 | ✓ | | |
| 66 | 40,726-7 | Phenethylamine | 1.0 | 3.80 | | 121.18 | 0.965 | 1 | | ✓ | 630 | 80% | | |
| ±67 | P2,237-0 | Phenylcyclopropylamine hydrochloride, trans-2- | 2.1 | 10.26 | 21.06 | 169.66 | 1.000 | 2 | 1 | 40% | 642 | 40% | NR? | 100/68 |
| ±68 | P2,555-8 | Phenylglycinonitrile hydrochloride, 2- | 2.1 | 10.20 | 21.06 | 168.63 | 1.000 | 2 | 1 | NR | 641 | 10% | NR? | 10/96 |
| 69 | P4,950-3 | Piperonylamine | 1.0 | 3.76 | | 151.17 | 1.214 | 1 | | ✓ | 660 | ✓ | | |
| 70 | P5,090-0 | Propargyl amine | 1.0 | 2.07 | | 55.08 | 0.803 | 1 | | 80% | 564 | 80% | | |
| 71 | 41,293-7 | Tetrahydrolurfurylamine, (R)-(−)- | 1.0 | 3.12 | | 101.15 | 0.980 | 1 | | ✓ | 610 | 80% | | |
| 72 | 41,294-5 | Tetrahydrofurfurylamine, (S)-(+) | 1.0 | 3.12 | | 101.15 | 0.980 | 1 | | ✓ | 610 | ✓ | | |
| 73 | 22,741-2 | Tetramethyl-1,3-propanediamine, N,N,2,2- | 1.0 | 4.81 | | 130.24 | 0.818 | 1 | | 70% | 639 | 10% | 70% | 100/— |
| 74 | 42,327-0 | Thiopheneethylamine, 2- | 1.0 | 3.54 | | 127.21 | 1.087 | 1 | | ✓ | 636 | ✓ | | |
| 75 | 26,904-2 | Trifluoroethylamine, 2,2,2- | 1.0 | 2.41 | | 99.06 | 1.245 | 1 | | NR? | 608 | 10% | NR | 5/100 |
| 76 | 19,374-7 | Tryptamine | 1.0 | 4.84 | | 160.22 | 1.000 | 1 | | 70% | 669 | 80% | | |
| 77 | V130-9 | Veratrylamine | 1.0 | 4.56 | | 167.21 | 1.109 | 1 | | NR? | 676 | 80% | | |

TABLE B-continued

Amine building blocks tested.

beta-branched or greater (mult = 1)
alpha-branched (mult = 2)
2-hydroxypyridine (2-pyr) stock solutions 30.23 umol amine (25 eq)
60.49 umol amine (50 eq)
1.0 6.05 umol (5 eq) in THF
1.x 6.05 umol (5 eq) in 3:2 CH2Cl2/DMF
2.0 12.09 umol (10 eq) in THF
2.x 12.09 umol (10 eq) in 3:2 CH2Cl2/DMF

| | | | | | mg or uL | uL | | | | | acid | | | ✓ = ≥90% conversion and purity | | | FAB rel int |
| Test # | Aldrich Catalog # | Chemical Name | 2-pyr | amine | DIPEA | MW | d | mult | salt | HPLC | Mass | LCMS | TLC | SM/Pdt |
|---|---|---|---|---|---|---|---|---|---|---|---|---|---|---|
| 78 | A5,530-6 | Aminoethyl)pyridine, 2-(2- | 1.0 | 3.62 | | 122.17 | 1.021 | 1 | | ✓ | 509 | nuked | | |
| 79 | A6,540-9 | Aminomethyl)pyridine, 3-( | 1.0 | 3.08 | | 108.14 | 1.062 | 1 | | ✓ | 631 | 80%c | | |
| 80 | 29,664-3 | Butylamine, (R)-(−)-sec- | 2.0 | 6.05 | | 73.14 | 0.731 | 2 | | ✓ | 617 | 80%p | | |
| 81 | 29,665-1 | Butylamine, (S)-(+)-sec- | 2.0 | 6.05 | | 73.14 | 0.731 | 2 | | ✓ | 582 | 80%p | | |
| 82 | 33,650-5 | Cyclohexylethylamine, (R)-(−)-1- | 2.0 | 8.99 | | 127.33 | 0.856 | 2 | | ✓ | 582 | 80%p | | |
| 83 | 33,651-3 | Cyclohexylethylamine, (S)-(+)-1- | 2.0 | 8.99 | | 127.33 | 0.856 | 2 | | ✓ | 636 | ✓ | | |
| 84 | 12,681-0 | Isoamylamine | 1.0 | 3.51 | | 87.17 | 0.751 | 1 | | ✓ | 636 | ✓ | | |
| | | | | | | | | | | | 596 | | | |
| | | | | | | | | | | | 509 | | | |
| 85 | 42,193-6 | Methylbenzylamine, (R)-(+)-a- | 2.0 | 7.79 | | 121.18 | 0.940 | 2 | | ✓ | 630 | ✓ | | |
| 86 | 27,745-0 | Napthyl)ethylamine, (S)-(−)-1-(1- | 2.0 | 9.77 | | 171.25 | 1.060 | 2 | | 80%c | 680 | 80%c | | |
| 87 | 34,098-7 | Trifluoromethoxy)benzylamine, 4-( | 1.0 | 4.62 | | 191.15 | 1.252 | 1 | | ✓ | 700 | ✓ | | |
| 88 | 26,349-4 | Trifluoromethyl)benzylamine, 3-( | 1.0 | 4.33 | | 175.16 | 1.222 | 1 | | ✓ | 684 | ✓ | | |

TABLE C

Acid building blocks tested.
carboxylic acids 58.52 umol (50 eq)
amino acid hydrochlorides (italics) neutralized with an additional 50 eq DIPEA

| Test # | Aldrich Catalog # | Chemical Name | mg or uL acid | MW | d | HPLC | Mass | LCMS | Comment |
|---|---|---|---|---|---|---|---|---|---|
| | | | | | | ✓ = ≧90% conversion and purity | | | |
| 1 | 33,882-6 | Acetic acid | 15.92 | 57.06 | 1.049 | ✓ | 688 | ✓ | |
| 2 | 24,851-7 | Acetoxybenzoic acid, 4- | 52.71 | 180.16 | 1.000 | NR/✓? | 808 | 20% p | 80% OAc |
| 3 | 23,936-1 | Acetylsalicylic acid | 52.71 | 180.16 | 1.000 | ✓ | 808 | 20% p | 80% OAc |
| 4 | 14,723-0 | Acrylic acid | 20.06 | 72.06 | 1.051 | 50% p | 700 | 50% p | |
| 5 | 11,771-4 | Anisic acid, m- | 44.52 | 152.15 | 1.000 | ✓ | 780 | 80% p | |
| 6 | 16,997-8 | Anisic acid, o- | 44.52 | 152.15 | 1.000 | 60% c | 780 | 60% c | |
| 7 | 11,739-0 | Anisic acid, p- | 44.52 | 152.15 | 1.000 | 70% p | 780 | 20% p | 30% c |
| 8 | 24,238-1 | Benzoic acid | 35.73 | 122.12 | 1.000 | ✓ | 750 | 80% p | |
| 9 | 30,366-6 | Butynoic acid, 2- | 24.60 | 84.07 | 1.000 | 70% p | 712 | 40% c | |
| 10 | 40,324-5 | Carboxypropyl)trimethylammonium chloride, (3- | 53.15 | 181.66 | 1.000 | NR? | 774 | NR | |
| 11 | 13,269-1 | Chloropropionic acid, 3- | 31.75 | 108.52 | 1.000 | 20% p | 737 | 10% p | |
| 12 | 23,956-9 | Crotonic acid | 25.19 | 86.09 | 1.000 | ✓ | 714 | 70% p | |
| 13 | C8,850-5 | Cyanoacetic acid | 24.89 | 85.06 | 1.000 | ✓ | 713 | 10% c | |
| 14 | 15,716-3 | Cyanobenzoic acid, 3- | 43.05 | 147.13 | 1.000 | ✓ | 775 | 80% p | |
| 15 | C8,980-3 | Cyanobenzoic acid, 4- | 43.05 | 147.13 | 1.000 | ✓ | 775 | 80% p | |
| 16 | 10,183-4 | Cyclohexanecarboxylic acid | 36.30 | 128.17 | 1.033 | ✓ | 756 | ✓ | |
| 17 | C11,200-3 | Cyclopentanecarboxylic acid | 31.72 | 114.14 | 1.053 | ✓ | 742 | ✓ | |
| 18 | 12,549-0 | Cyclopentylacetic acid | 36.70 | 128.17 | 1.022 | ✓ | 756 | ✓ | |
| 19 | C11,660-2 | Cyclopropanecarboxylic acid | 23.15 | 86.09 | 1.088 | ✓ | 714 | 80% p | |
| 20 | 19,572-3 | Dihydro-2,2-dimethyl-4-oxo-2H-pyran-6-carboxylic acid, 3,4- | 49.79 | 170.16 | 1.000 | 60% p | 798 | 60% p | 3 isomers |
| 21 | 30,035-7 | Dihydro-2-methylbenzoic acid, 1,4- | 40.43 | 138.17 | 1.000 | ✓ | 766 | 80% p | |
| 22 | 24,640-9 | Dimethylaminobenzoic acid, 3- | 48.33 | 165.19 | 1.000 | 40% c? | 793 | 10% c | |
| 23 | D13,945-9 | Dimethylaminobenzoic acid, 4- | 48.33 | 165.19 | 1.000 | NR | 793 | NR | |
| 24 | 29,223-0 | Dimethylglycine, N,N- | 30.17 | 103.12 | 1.000 | NR? | 731 | 10% c | |
| 25 | 33,504-5 | Ferroceneacetic acid | 71.42 | 244.08 | 1.000 | 70% c | 872 | 70% c | |
| 26 | 25,136-4 | Formic acid | 11.04 | 46.03 | 1.220 | NR/✓? | 674 | NR | |
| 27 | 33,638-6 | Furanacrylic acid, trans-3- | 40.41 | 138.12 | 1.000 | ✓ | 766 | ✓ | |
| 28 | F2,050-5 | Furoic acid, 2- | 32.79 | 112.08 | 1.000 | ✓ | 740 | ✓ | |
| 29 | 16,339-2 | Furoic acid, 3- | 32.79 | 112.08 | 1.000 | ✓ | 740 | ✓ | |
| 30 | F2,080-7 | Furylacrylic acid | 40.41 | 138.12 | 1.000 | 40% p | 766 | 10% p | 798? |
| 31 | 24,010-9 | Hexadienoic acid, 2,4- (Sorbic acid) | 32.81 | 112.13 | 1.000 | ✓ | 740 | ✓ | |
| 32 | 24,016-8 | Isobutyric acid | 27.14 | 88.11 | 0.950 | ✓ | 716 | ✓ | |
| 33 | I-1,750-8 | Isonicotinic acid | 36.02 | 123.11 | 1.000 | ✓ | 751 | ✓ | |
| 34 | 12,954-2 | Isovaleric acid | 31.89 | 102.13 | 0.937 | ✓ | 730 | ✓ | |
| 35 | 1,200-9 | Levulinic acid | 29.96 | 116.12 | 1.134 | 80% p | 744 | 80% p | |
| 36 | 85,601-0 | Linolenic acid | 89.14 | 278.44 | 0.914 | ✓ | 906 | 938? | FAB: 906 ✓ |
| 37* | 44,869-7 | Menthoxyacetic acid, (+)- | 61.48 | 214.31 | 1.020 | ✓ | 842 | ✓ | |
| 38 | M300-0 | Menthoxyacetic acid, (−)- | 61.48 | 214.31 | 1.020 | ✓ | 842 | ✓ | |
| 39 | 39,537-4 | Methacrylic acid | 24.82 | 86.09 | 1.015 | 70% p | 714 | 70% p | |
| 40 | 19,455-7 | Methoxyacetic acid | 22.45 | 90.08 | 1.174 | ✓ | 718 | ✓ | |
| 41 | 24,896-7 | Methoxyphenylacetic acid, (R)-(−)-a- | 48.62 | 166.18 | 1.000 | 70% p | 794 | 60% p | 40% diast |
| 42 | 24,898-3 | Methoxyphenylacetic acid, (S)-(+)-a- | 48.62 | 166.18 | 1.000 | 60% p | 794 | 60% p | 40% diast |
| 43 | 18,065-3 | Methoxyphenylacetic acid, 2- | 48.62 | 166.18 | 1.000 | ✓ | 794 | ✓ | |
| 44 | M1,900-7 | Methoxyphenylacetic acid, 3- | 48.62 | 166.18 | 1.000 | 80% c | 794 | 80% c | |
| 45 | M1,920-1 | Methoxyphenylacetic acid, 4- | 48.62 | 166.18 | 1.000 | ✓ | 794 | ✓ | |
| 46 | 36,728-1 | Methyl (1S, 2R)-(+)-cis,1,2,3,6-tetrahydrophthalate, 1- | 53.89 | 184.19 | 1.000 | ✓ | 812 | ✓ | |
| 47 | M4,735-3 | Methyl glutarate, mono- | 37.54 | 146.14 | 1.139 | ✓ | 774 | ✓ | |
| 48 | 31,764-0 | Methyl phthalate, mono- | 52.71 | 180.16 | 1.000 | ✓ | 808 | ✓ | |
| 49 | 32,838-3 | Methyl terephthalate, mono- | 52.71 | 180.16 | 1.000 | ✓ | 808 | ✓ | |
| 50 | 29,295-8 | Methyl-2-(nitromethyl)-5-oxocyclopentaneacetic acid, [1R-(1-a,2b,3a)]-(+)-3- | 62.97 | 215.21 | 1.000 | NR | 843 | NR | |
| 51 | 19,755-6 | Methyl-5-oxo-2-pyrazolin-1-yl)benzoic acid, 4-(3- | 63.85 | 218.21 | 1.000 | NR? | 846 | NR | |
| 52 | 41,749-1 | Methylchromone-2-carboxylic acid, 6- | 59.75 | 204.19 | 1.000 | 10% p | 832 | 30% p | |
| 53 | 32,967-3 | Methylenedioxy)phenylacetic acid, 3,4-( | 52.71 | 180.16 | 1.000 | 80% c | 808 | ✓ | |
| 54 | 13,415-5 | Methylindole-2-carboxylic acid, 1- | 51.26 | 175.19 | 1.000 | ✓ | 803 | ✓ | |
| 55 | N785-0 | Nicolinic acid | 36.02 | 123.11 | 1.000 | ✓ | 751 | ✓ | |
| 56 | 15,571-3 | Nitro-2-furoic acid, 5- | 45.96 | 157.10 | 1.000 | 50% p | 785 | 10% p | 80% 754? |
| 57 | N1,179-5 | Nitrobenzoic acid, 4- | 48.90 | 167.12 | 1.000 | 60% p | 795 | 60% p | 809? |
| 58 | N2,020-4 | Nitrophenylacetic acid, 4- | 53.00 | 181.15 | 1.000 | NR/✓? | 809 | NR | |
| 59 | N2,290-8 | Nitropropionic acid, 3- | 34.84 | 119.08 | 1.000 | NR | 747 | NR | |
| 60 | 12,726-4 | Norbornaneacetic acid, 3- | 42.37 | 154.21 | 1.065 | ✓ | 782 | ✓ | |
| 61 | O-840-2 | Orotic acid monohydrate | 50.94 | 174.11 | 1.000 | NR/✓? | 784 | NR | |
| 62 | 39,134-4 | Oxo-4-phenyl-3-oxazolidineacetic acid, (S)-(+)-2- | 64.73 | 221.21 | 1.000 | ✓ | 849 | ✓ | |
| 63 | 32,285-7 | Oxotricyclo[2,2,1,0(2,6)]heptane-7-carboxylic acid, anti-3- | 44.52 | 152.15 | 1.000 | ✓ | 780 | ✓ | |
| 64 | P1,662-1 | Phenylacetic acid | 36.85 | 136.15 | 1.081 | 80% c | 764 | 90% c | |
| 65 | P3,120-5 | Phenylpropiolic acid | 42.76 | 146.15 | 1.000 | 60% c | 774 | 10% c | |
| 66 | 21,183-4 | Phthalylsulfathiazole | 118.05 | 403.44 | 1.000 | NR | 1031 | NR | |
| 67 | P4,280-0 | Picolinic acid | 36.02 | 123.11 | 1.000 | ✓ | 751 | ✓ | |
| 68 | 40,290-7 | Propionic acid | 21.83 | 74.08 | 0.993 | ✓ | 702 | ✓ | |
| 69 | P5,610-0 | Pyrazinecarboxylic acid, 2- | 36.31 | 124.10 | 1.000 | ✓ | 752 | ✓ | |
| 70 | P6,560-6 | Pyridylacetic acid hydrochloride, 2- | 50.80 | 173.60 | 1.000 | NR | 766 | NR | |

TABLE C-continued

Acid building blocks tested.
carboxylic acids 58.52 umol (50 eq)
amino acid hydrochlorides (italics) neutralized with an additional 50 eq DIPEA

| Test # | Aldrich Catalog # | Chemical Name | mg or uL acid | MW | d | HPLC | Mass | LCMS | Comment |
|---|---|---|---|---|---|---|---|---|---|
| 71 | P6,580-0 | Pyridylacetic acid hydrochloride, 3- | 50.80 | 173.60 | 1.000 | NR✓ | 766 | NR | |
| 72 | P6,585-1 | Pyridylacetic acid hydrochloride, 4- | 50.80 | 173.60 | 1.000 | NR✓ | 766 | NR | |
| 73 | 27,553-0 | Pyrimidylthio)acetic acid, (2- | 49.80 | 170.19 | 1.000 | NR/✓? | 798 | NR | |
| 74 | 10,736-0 | Pyruvic acid | 20.34 | 88.06 | 1.267 | NR/✓? | 716 | NR | |
| ±75 | 34,151-7 | Tetrahydro-2-furoic acid | 28.10 | 116.12 | 1.209 | 60% p | 744 | 60/40 | 2 diast |
| ±76 | 33,995-4 | Tetrahydro-3-furoic acid | 27.99 | 116.12 | 1.214 | ✓ | 744 | ✓ | 2 diast |
| 77 | T2,860-6 | Thioctic acid | 60.37 | 206.33 | 1.000 | nuked | 834 | 0% p | 60% 866? |
| 78 | 19,594-4 | Thiopheneacetic acid, 2- | 41.60 | 142.18 | 1.000 | NR? | 770 | NR | |
| 79 | 22,063-9 | Thiopheneacetic acid, 3- | 41.60 | 142.18 | 1.000 | 50% c | 770 | 50% c | |
| 80 | T3,260-3 | Thiophenecarboxylic acid, 2- | 37.50 | 128.15 | 1.000 | ✓ | 756 | ✓ | |
| 81 | 24,776-6 | Thiophenecarboxylic acid, 3- | 37.50 | 128.15 | 1.000 | ✓ | 756 | ✓ | |
| 82 | 22,227-5 | Thiopheneglyoxylic acid, 2- | 45.69 | 156.16 | 1.000 | NR | 784 | NR | |
| 83* | 23,302-1 | Trifluoro-p-tolyl)acetic acid, (a,a,a- | 59.73 | 204.15 | 1.000 | NR | 832 | 20% c | |
| 84 | 13,471-6 | Vinylacetic acid | 24.87 | 86.09 | 1.013 | ✓ | 714 | ✓ | |
| Questionable starting material quality for 85–98 | | | | | | | | | |
| 85 | 30,234-1 | Acetoxyacetic acid | 34.55 | 118.09 | 1.000 | 70% p | 746 | 40% p | |
| 86 | 30,727-0 | Benzofuroncarboxylic acid, 2- | 47.44 | 162.14 | 1.000 | 30% p | 790 | 60% p | OK |
| 87 | C8,215-9 | Cinnoline-4-carboxylic acid | 50.96 | 174.16 | 1.000 | 30% p | 802 | 60% p | OK |
| 88 | D12,380-3 | Diiodo-4-pyridone-1-acetic acid, 3,5- | 118.48 | 404.93 | 1.000 | 10% p | 1033 | NR | |
| 89 | D13,860-6 | Dimethylacrylic acid, 3,3- | 29.30 | 100.12 | 1.000 | 10% p | 728 | 50% c | |
| 90 | 10,688-7 | Ferrocenecarboxylic acid | 67.31 | 230.05 | 1.000 | 20% p | 858 | NR | |
| 91 | 22,528-2 | Methoxy-1-indanone-3-acetic acid, 5- | 64.44 | 220.23 | 1.000 | 30% p | 848 | 50% p | OK |
| 92 | 15,314-t | Methyl-2-pyrrolecarboxylic acid, 1- | 36.61 | 125.13 | 1.000 | 20% p | 753 | NR | |
| 93 | 41,077-2 | Oxo-1-indancarboxylic acid, 3- | 51.55 | 176.17 | 1.000 | 40% c | 804 | NR | |
| 94 | P6,620-3 | Pyridyl)acrylic acid, trans-3-(3- | 43.64 | 149.15 | 1.000 | ✓/NR? | 777 | 80% p | OK |
| 95 | 13,058-3 | Thienyl)acrylic acid, 3-(2- | 45.12 | 154.19 | 1.000 | 40% p | 782 | 60% p | OK |
| 96 | 18,034-4 | Trifluoro-m-toluic acid, a,a,a- | 55.63 | 190.12 | 1.000 | 40% p | 818 | 70% p | OK |
| 97 | 19,688-6 | Trifluoro-o-toluic acid, a,a,a- | 55.63 | 190.12 | 1.000 | 40% p | 818 | 60% p | OK |
| 98 | 19,689-4 | Trifluoro-p-toluic acid, a,a,a- | 55.63 | 190.12 | 1.000 | 40% p | 818 | 60% p | OK |

✓ = ≧90% conversion and purity

VI. Test Library Synthesis:

The building block testing experiments above indicated which coupling partners were able to undergo the desired coupling reactions. However, there remained the potential for interaction between building blocks reacting at different sites. For instance, coupling of a certain alkyne at the aryl iodide position might preclude introduction of a specific type of amine into the γ-butyrolactone. To address these issues, we generated a small test library by split-pool synthesis (FIG. 42).

Seven alkynes and seven amines representing a range of sizes and functional groups were selected along with the aryl iodide and γ-butyrolactone skip codons such that all 64 possible products would have unique masses (FIG. 55, FIG. 56). Seven acids along with the free alcohol resin were photolyzed and analyzed for the expected masses by LC-MS. Because all eight final pools contained the same eight γ-butyrolactone compounds corresponding to the aminolysis skip codon, a total of 456 compounds were generated.

Figure 57A:
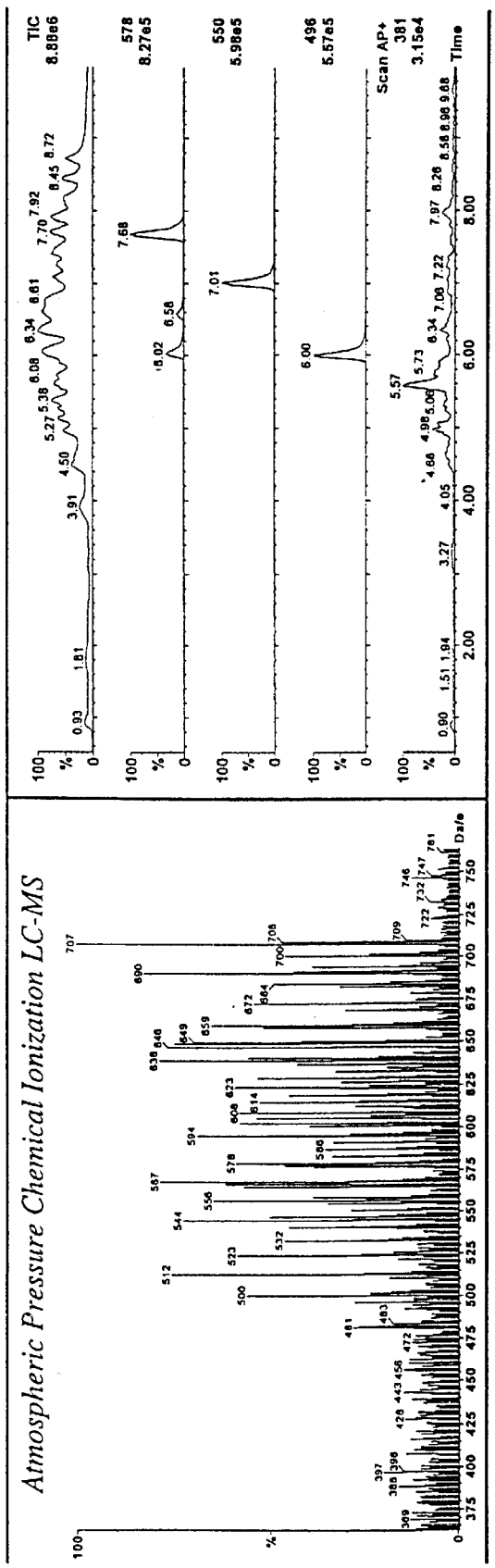

Of the 456 expected masses all 456 (100%) were detected by LC-MS at some level. 418 (92%) were detected at greater than or equal to 10% of the average intensity for the pool. 400 (88%) were detected at greater than or equal to 20% of the average intensity for the pool (FIG. 57, Tables E–G). All of the weak signals resulted from two building blocks at the amine position 1 and 6. The closed γ-butyrolactone resulting from the amine skip codon (1) might have been hydrolyzed to some extent during the subsequent acid coupling reactions, resulting in weaker signals. 1-(3-Aminopropyl)-2-pyrrolidinone (6) is known to cyclize to DBN with loss of H2O. Treatment with strong bases has been found to decompose these compounds and/or the photolinker (data not shown).

These results verify that synthesis of these compounds can be carried out in a split-pool fashion. Furthermore, no evidence for interaction between different building block positions was found. However, this experiment indicates that the 1-(3-aminopropyl)-2-pyrrolidinone amine building block 6, should not be included in the large library synthesis. Also, amine skip codon compounds with closed γ-butyrolactones should be excluded from the final acid coupling step.

Methods. All solids were measured to within 10%. All liquids were dispensed via Gilson automatic pipettemen with polypropylene tips. Reactions were performed in tared 2 mL BioSpin®g columns. Resin was distributed to each column as 1 mL of an 8 mL isopicnic slurry in DMSO/CH$_2$Cl$_2$ with a P1000 pipetteman fitted with a P1000 polypropylene tip trimmed by approximately 2 mm. The resin was washed with distd THF and distd CH$_2$Cl$_2$, dried, and weighed. This method of resin distribution proved consistent to within ±5% (data not shown). After reaction according to the medium-scale solid phase procedures in General Methods, the resin portions were washed using the standard wash procedure (Method A) and a sample was photolyzed for 2 h followed by HPLC and LC-MS analysis of the supernatant. The remaining resins were pooled in a PD-10 column via vacuum cannula transfer from the reaction vessels and mixed thoroughly by repeated washing with $CH_2Cl_2$.

Alkyne Coupling. To 7 aliquots of m-Iodobenzyl Tetracycle-Anp-Tentagel resin 10eR (31.25 mg 0.25 meq/g, 7.68 µmol, 1.0 eq) were added CuI (3.2 mg, 16.90 µmol, 2.2 eq) and $(PPh_3)_2PdCl_2$ (5.9 mg, 8.45 µmol, 1.1 eq). 300 µL DMF was added, the tubes flushed with Ar and vortexed briefly. DIPEA (40.15 µL, 230.5 mmol, 30 eq) was added to each tube followed by the appropriate alkyne (153.65 µmol, 20 eq). The tubes were parafilmed and mixed for 2 h. After washing, approximately 1 mg of resin was removed from each tube and photolyzed in 30 µL $CH_3CN$. 10 mL was submitted for HPLC analysis and an additional 4 µL was diluted to 30 mL and submitted for LC-MS analysis (10 µL injection). The remaining resin was pooled to yield a mixture of 8-m-Alkynylbenzyl Tetracycle-Anp-Tentagel resins, 11gR.

Amine Coupling. To 7 aliquots of resins 11gR (30 mg, 0.25 meq/g avg 7.43 µmol avg, 1.0 eq) was added 2-hydroxypyridine (3.53 mg, 37.14 µmol, 5 eq) as a 300 µL stock solution in THF. An additional 5 eq of 2-hydroxypyridine was added as a solid to Pool #4 (α-branched amine). The tubes were flushed with Ar, and the appropriate amine (185.7 µmol, 25 eq; 371.4 µmol, 50 eq for Pool #4) was added to each. The tubes were wrapped with teflon tape and parafilm and mixed for 15 h. After washing, approx. 2 mg of resin was removed from each tube and photolyzed in 40 µL $CH_3CN$. 10 µL was submitted for HPLC analysis and an additional 10 µL was submitted without dilution for LC-MS analysis. The remaining resin was pooled to yield a mixture of 64-m-Alkynylbenzyl Hydroxyamido Tricycle-Anp-Tentagel resins, 12gR.

Acid Coupling. In 2 mL oven-dried Wheaton vials fitted with septum caps and stir bars were placed the appropriate carboxylic acids (326.5 µmol, 50 eq) and 300 µmol $CH_2Cl_2$. DIPC (25.60 µL, 163.25 µL, 25 eq) was added to each vial and the mixtures stirred for 2 min. DIPEA (56.9 µL, 326.5 µmol, 50 eq) was added to each vial and the mixtures stirred for another 5 min. 7 aliquots of resins 12gR (27 mg, 0.24 meq/g avg, 6.53 µmol avg., 1.0 eq) were each swollen with 100 µL $CH_2Cl_2$, flushed with Ar, and cooled to 0° C. in an ice bath. The appropriate preactivation mixture was then added to each tube followed by DMAP (3.99 mg, 32.65 µmol, 5 eq) as a 50 µL stock solution in $CH_2Cl_2$. Each tube was vortexed briefly and allowed to stand at 0° C. for 15 min. 20% DIPEA/$CH_2Cl_2$ wash was added between the $CH_2Cl_2$ and DMF steps of the standard wash procedure. After drying, 12 mg of each m-Alkynylbenzyl Amido Ester Tricycle-Anp-Tentagel resin 13R(1-8) was weighed out and photolyzed in 120 µL $CH_3CN$. The supernatant from each tube was filtered through a new BioSpin column into a new Eppendorf tube and the photolysis tubes and resin rinsed with an additional 50 µL $CH_3CN$. The 8 samples were concentrated for 15' on a Savant AES 1000 SpeedVac at Low Drying Rate, redissolved in 11 µL $CH_3CN$, and transferred to an HPLC autosampler vial. Each tube was rinsed with an additional 11 µL $CH_3CN$ transferred to the same vials. 10 µL of each sample was submitted for HPLC analysis and an additional 10 µL was submitted for LC-MS analysis.

Results. For each LC-MS sample, a 10 µL injection was chromatographed and mass analyzed according to the procedure in II. General Methods. For each sample, a UV trace (214 mm) and Total Ion Count (TIC) trace were collected. An averaged mass spectrum for the entire chromatogram was also calculated. The data were then scanned for each of the expected masses in the pool and the results displayed as single mass traces.

Complete HPLC (14 pages) and LC-MS data (168 pages) are available upon request. A respresentative example is shown (FIG. 57) and the remaining results are summarized in tabular format (Tables E–G).

TABLE E

Alkyne building blocks used in test library synthesis.
mono terminal alkyne 153.65 umol alkyne (20 eq)

| BB# | Test # | Chemical Name | mg or uL alkyne | MW | d | Vendor | Catalog # | HPLC | Mass | LCMS Int | Rel Int |
|---|---|---|---|---|---|---|---|---|---|---|---|
| 1 | 25 | Methyl-1-buten-3-yne, 2- | 14.61 | 66.10 | 0.695 | Aldrich | M3,280-1 | ✓ | 380 | 0.0047 | 0.12 |
| 2 | 24 | Methyl propargyl ether | 12.98 | 70.09 | 0.830 | Aldrich | 17,719-9 | 80% c | 384 | 0.0020 | 0.05 |
| 3 | 11 | Dimethyl-1-butyne, 3,3- | 18.92 | 82.15 | 0.667 | Aldrich | 24,439-2 | ✓ | 396 | 0.0433 | 1.12 |
| 4 | 23 | Hexynenitrile, 5- | 16.10 | 93.13 | 0.889 | Aldrich | 27,134-9 | ✓ | 407 | 0.0092 | 0.24 |
| 5 | 31 | Phenylacetylene | 16.88 | 102.14 | 0.930 | Aldrich | 11,770-6 | ✓ | 416 | 0.0271 | 0.70 |
| 6 | 30 | Phenyl-1-propyne, 3- | 19.11 | 116.16 | 0.934 | Aldrich | 37,684-1 | ✓ | 430 | 0.0297 | 0.77 |
| 7 | — | SKIP CODON | — | 128.00 | 1.000 | — | — | ✓ | 442 | 0.1160 | 2.99 |
| 8 | 8 | Decadiyne, 1,5- | 20.62 | 134.22 | 1.000 | GPS | 126706 | ✓ | 448 | 0.0788 | 2.03 |
| | | | AVERAGE | 99.00 | | | | | 413 | 0.0388 | |

TABLE F

Amine building blocks used in test library synthesis.
beta-branched or greater (mult = 1) 185.70 umol amine (25 eq)
alpha-branched (mult = 2) 371.40 umol amine (50 eq)
2-hydroxypyridine (2-pyr) 1.0 37.14
stock solutions 2.0 74.28

| BB# | Test # | Chemical Name | 2 pyr | mg or ul amine | MW | d | mult | Aldrich Catalog # | Mass | LCMS Int | Rel Int |
|---|---|---|---|---|---|---|---|---|---|---|---|
| 1 | — | SKIP CODON | — | — | 0.00 | — | — | — | 380 | 0.032 | 0.57 |
|   |    |             |   |   |      |   |   |   | 384 | 0.016 | 0.28 |
|   |    |             |   |   |      |   |   |   | 396 | 0.114 | 2.07 |
|   |    |             |   |   |      |   |   |   | 407 | 0.056 | 1.02 |
|   |    |             |   |   |      |   |   |   | 416 | 0.052 | 0.94 |
|   |    |             |   |   |      |   |   |   | 430 | 0.055 | 1.01 |
|   |    |             |   |   |      |   |   |   | 442 | 0.046 | 0.83 |
|   |    |             |   |   |      |   |   |   | 448 | 0.074 | 1.34 |
|   |    |             |   |   |      |   |   | AVERAGE | 413 | 0.055 |  |
| 2 | 60 | Methylamine (2.0M in THF) | 1.0 | 92.85 | 500.00 | 1.000 | 1 | 39,505-6 | 411 | 0.056 | 0.39 |
|   |    |             |   |   |      |   |   |   | 415 | 0.080 | 0.55 |
|   |    |             |   |   |      |   |   |   | 427 | 0.209 | 1.45 |
|   |    |             |   |   |      |   |   |   | 438 | 0.103 | 0.72 |
|   |    |             |   |   |      |   |   |   | 447 | 0.140 | 0.97 |
|   |    |             |   |   |      |   |   |   | 461 | 0.182 | 1.26 |
|   |    |             |   |   |      |   |   |   | 473 | 0.057 | 0.39 |
|   |    |             |   |   |      |   |   |   | 479 | 0.328 | 2.28 |
|   |    |             |   |   |      |   |   | AVERAGE | 444 | 0.144 |  |
| 3 | 55 | Methoxyethylamine, 2- | 1.0 | 16.14 | 75.11 | 0.864 | 1 | 24,106-7 | 455 | 0.109 | 0.48 |
|   |    |             |   |   |      |   |   |   | 459 | 0.142 | 0.62 |
|   |    |             |   |   |      |   |   |   | 471 | 0.410 | 1.79 |
|   |    |             |   |   |      |   |   |   | 482 | 0.162 | 0.71 |
|   |    |             |   |   |      |   |   |   | 491 | 0.266 | 1.16 |
|   |    |             |   |   |      |   |   |   | 505 | 0.270 | 1.18 |
|   |    |             |   |   |      |   |   |   | 517 | 0.088 | 0.38 |
|   |    |             |   |   |      |   |   |   | 523 | 0.385 | 1.68 |
|   |    |             |   |   |      |   |   | AVERAGE | 488 | 0.229 |  |
| 4 | 35 | Cyclopentylamine | 2.0 | 36.65 | 85.15 | 0.863 | 2 | C11,500-2 | 465 | 0.080 | 0.50 |
|   |    |             |   |   |      |   |   |   | 469 | 0.116 | 0.73 |
|   |    |             |   |   |      |   |   |   | 481 | 0.319 | 1.99 |
|   |    |             |   |   |      |   |   |   | 492 | 0.179 | 1.12 |
|   |    |             |   |   |      |   |   |   | 501 | 0.173 | 1.08 |
|   |    |             |   |   |      |   |   |   | 515 | 0.108 | 0.68 |
|   |    |             |   |   |      |   |   |   | 527 | 0.109 | 0.68 |
|   |    |             |   |   |      |   |   |   | 533 | 0.194 | 1.21 |
|   |    |             |   |   |      |   |   | AVERAGE | 498 | 0.160 |  |
| 5 | 33 | Cyclohexanemethylamine | 1.0 | 24.16 | 113.20 | 0.870 | 1 | 10,184-2 | 493 | 0.389 | 0.76 |
|   |    |             |   |   |      |   |   |   | 497 | 0.455 | 0.89 |
|   |    |             |   |   |      |   |   |   | 509 | 0.819 | 1.59 |
|   |    |             |   |   |      |   |   |   | 520 | 0.401 | 0.78 |
|   |    |             |   |   |      |   |   |   | 529 | 0.553 | 1.08 |
|   |    |             |   |   |      |   |   |   | 543 | 0.614 | 1.19 |
|   |    |             |   |   |      |   |   |   | 555 | 0.303 | 0.59 |
|   |    |             |   |   |      |   |   |   | 561 | 0.578 | 1.12 |
|   |    |             |   |   |      |   |   | AVERAGE | 526 | 0.514 |  |
| 6 | 22 | Aminopropyl)-2-pyrrolidinone, 1-(3- | 1.0 | 26.04 | 142.20 | 1.014 | 1 | 13,656-5 | 522 | 0.009 | 0.64 |
|   |    |             |   |   |      |   |   |   | 526 | 0.013 | 0.91 |
|   |    |             |   |   |      |   |   |   | 538 | 0.022 | 1.57 |
|   |    |             |   |   |      |   |   |   | 549 | 0.012 | 0.84 |
|   |    |             |   |   |      |   |   |   | 558 | 0.010 | 0.71 |
|   |    |             |   |   |      |   |   |   | 572 | 0.010 | 0.71 |
|   |    |             |   |   |      |   |   |   | 584 | 0.005 | 0.35 |
|   |    |             |   |   |      |   |   |   | 590 | 0.029 | 2.10 |
|   |    |             |   |   |      |   |   | AVERAGE | 555 | 0.014 |  |
| 7 | 62 | Napthylenemethylamine, 1- | 1.0 | 27.21 | 157.22 | 1.073 | 1 | 12,703-5 | 537 | 0.144 | 0.45 |
|   |    |             |   |   |      |   |   |   | 541 | 0.324 | 1.02 |
|   |    |             |   |   |      |   |   |   | 553 | 0.524 | 1.65 |
|   |    |             |   |   |      |   |   |   | 564 | 0.369 | 1.16 |
|   |    |             |   |   |      |   |   |   | 573 | 0.247 | 0.78 |
|   |    |             |   |   |      |   |   |   | 587 | 0.279 | 0.88 |
|   |    |             |   |   |      |   |   |   | 599 | 0.287 | 0.91 |
|   |    |             |   |   |      |   |   |   | 605 | 0.365 | 1.15 |
|   |    |             |   |   |      |   |   | AVERAGE | 570 | 0.317 |  |
| 8 | 77 | Veratrylamine | 1.0 | 28.00 | 167.21 | 1.109 | 1 | V130-9 | 547 | 0.168 | 0.66 |
|   |    |             |   |   |      |   |   |   | 551 | 0.136 | 0.53 |
|   |    |             |   |   |      |   |   |   | 563 | 0.532 | 2.08 |
|   |    |             |   |   |      |   |   |   | 574 | 0.227 | 0.89 |
|   |    |             |   |   |      |   |   |   | 583 | 0.229 | 0.89 |

TABLE F-continued

Amine building blocks used in test library synthesis.
beta-branched or greater (mult = 1) 185.70 umol amine (25 eq)
alpha-branched (mult = 2) 371.40 umol amine (50 eq)
2-hydroxypyridine (2-pyr) 1.0 37.14
stock solutions 2.0 74.28

| BB# | Test # | Chemical Name | 2 pyr | mg or ul amine | MW | d | mult | Aldrich Catalog # | Mass | LCMS Int | Rel Int |
|---|---|---|---|---|---|---|---|---|---|---|---|
| | | | | | | | | | 597 | 0.266 | 1.04 |
| | | | | | | | | | 609 | 0.184 | 0.72 |
| | | | | | | | | | 615 | 0.303 | 1.18 |
| | | | | | | | | AVERAGE | 580 | 0.256 | |
| | | | | AVERAGE | 155.01 | | | | | | |

TABLE G

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| 1 | — | SKIP CODON | — | — | — | | | | | | | |
| (1, 1, 1) | | 442.0 + −18.0 + 18.0 + −128.0 + 66.0 + 0.0 + 0.0 = | | | | 380 | 5.62 | 0.054 | 0.21 | | | |
| (1, 1, 2) | | 442.0 + −18.0 + 18.0 + −128.0 + 66.0 + 0.0 + 31.0 = | | | | 411 | 4.24 | 0.109 | 0.43 | | | |
| (1, 1, 3) | | 442.0 + −18.0 + 18.0 + −128.0 + 66.0 + 0.0 + 75.0 = | | | | 455 | 4.58 | 0.266 | 1.06 | | | |
| (1, 1, 4) | | 442.0 + −18.0 + 18.0 + −128.0 + 66.0 + 0.0 + 85.0 = | | | | 465 | 5.60 | 0.191 | 0.76 | | | |
| (1, 1, 5) | | 442.0 + −18.0 + 18.0 + −128.0 + 66.0 + 0.0 + 113.0 = | | | | 493 | 6.45 | 0.270 | 1.07 | | | |
| (1, 1, 6) | | 442.0 + −18.0 + 18.0 + −128.0 + 66.0 + 0.0 + 142.0 = | | | | 522 | 5.49 | 0.067 | 0.26 | | | |
| (1, 1, 7) | | 442.0 + −18.0 + 18.0 + −128.0 + 66.0 + 0.0 + 157.0 = | | | | 537 | 6.40 | 0.270 | 1.07 | | | |
| (1, 1, 8) | | 442.0 + −18.0 + 18.0 + −128.0 + 66.0 + 0.0 + 167.0 = | | | | 547 | 5.33 | 0.182 | 0.72 | | | |
| (1, 2, 1) | | 442.0 + −18.0 + 18.0 + −128.0 + 70.0 + 0.0 + 0.0 = | | | | 384 | 3.97 | 0.031 | 0.12 | | 1 | |
| (1, 2, 2) | | 442.0 + −18.0 + 18.0 + −128.0 + 70.0 + 0.0 + 31.0 = | | | | 415 | 1.62 | 0.122 | 0.48 | | | |
| (1, 2, 3) | | 442.0 + −18.0 + 18.0 + −128.0 + 70.0 + 0.0 + 75.0 = | | | | 459 | 1.92 | 0.262 | 1.04 | | | |
| (1, 2, 4) | | 442.0 + −18.0 + 18.0 + −128.0 + 70.0 + 0.0 + 85.0 = | | | | 469 | 4.10 | 0.241 | 0.96 | | | |
| (1, 2, 5) | | 442.0 + −18.0 + 18.0 + −128.0 + 70.0 + 0.0 + 113.0 = | | | | 497 | 5.36 | 0.414 | 1.64 | | | |
| (1, 2, 6) | | 442.0 + −18.0 + 18.0 + −128.0 + 70.0 + 0.0 + 142.0 = | | | | 526 | 1.44 | 0.018 | 0.07 | 1 | 1 | |
| (1, 2, 7) | | 442.0 + −18.0 + 18.0 + −128.0 + 70.0 + 0.0 + 157.0 = | | | | 541 | 5.44 | 0.344 | 1.37 | | | |
| (1, 2, 8) | | 442.0 + −18.0 + 18.0 + −128.0 + 70.0 + 0.0 + 167.0 = | | | | 551 | 3.86 | 0.219 | 0.87 | | | |
| (1, 3, 1) | | 442.0 + −18.0 + 18.0 + −128.0 + 82.0 + 0.0 + 0.0 = | | | | 396 | 6.05 | 0.121 | 0.48 | | | |
| (1, 3, 2) | | 442.0 + −18.0 + 18.0 + −128.0 + 82.0 + 0.0 + 31.0 = | | | | 427 | 4.90 | 0.307 | 1.22 | | | |
| (1, 3, 3) | | 442.0 + −18.0 + 18.0 + −128.0 + 82.0 + 0.0 + 75.0 = | | | | 471 | 5.17 | 0.647 | 2.57 | | | |
| (1, 3, 4) | | 442.0 + −18.0 + 18.0 + −128.0 + 82.0 + 0.0 + 85.0 = | | | | 481 | 6.10 | 0.422 | 1.67 | | | |
| (1, 3, 5) | | 442.0 + −18.0 + 18.0 + −128.0 + 82.0 + 0.0 + 113.0 = | | | | 509 | 6.99 | 0.565 | 2.24 | | | |
| (1, 3, 6) | | 442.0 + −18.0 + 18.0 + −128.0 + 82.0 + 0.0 + 142.0 = | | | | 538 | 4.56 | 0.050 | 0.20 | | | |
| (1, 3, 7) | | 442.0 + −18.0 + 18.0 + −128.0 + 82.0 + 0.0 + 157.0 = | | | | 553 | 6.88 | 0.410 | 1.63 | | | |
| (1, 3, 8) | | 442.0 + −18.0 + 18.0 + −128.0 + 82.0 + 0.0 + 167.0 = | | | | 563 | 5.78 | 0.438 | 1.74 | | | |
| (1, 4, 1) | | 442.0 + −18.0 + 18.0 + −128.0 + 93.0 + 0.0 + 0.0 = | | | | 407 | 4.50 | 0.146 | 0.58 | | | |
| (1, 4, 2) | | 442.0 + −18.0 + 18.0 + −128.0 + 93.0 + 0.0 + 31.0 = | | | | 438 | 2.02 | 0.190 | 0.75 | | | |
| (1, 4, 3) | | 442.0 + −18.0 + 18.0 + −128.0 + 93.0 + 0.0 + 75.0 = | | | | 482 | 2.50 | 0.253 | 1.00 | | | |
| (1, 4, 4) | | 442.0 + −18.0 + 18.0 + −128.0 + 93.0 + 0.0 + 85.0 = | | | | 492 | 4.53 | 0.283 | 1.12 | | | |
| (1, 4, 5) | | 442.0 + −18.0 + 18.0 + −128.0 + 93.0 + 0.0 + 113.0 = | | | | 520 | 5.49 | 0.532 | 2.11 | | | |
| (1, 4, 6) | | 442.0 + −18.0 + 18.0 + −128.0 + 93.0 + 0.0 + 142.0 = | | | | 549 | 1.76 | 0.010 | 0.04 | 1 | 1 | |
| (1, 4, 7) | | 442.0 + −18.0 + 18.0 + −128.0 + 93.0 + 0.0 + 157.0 = | | | | 564 | 5.57 | 0.377 | 1.50 | | | |
| (1, 4, 8) | | 442.0 + −18.0 + 18.0 + −128.0 + 93.0 + 0.0 + 167.0 = | | | | 574 | 4.37 | 0.291 | 1.15 | | | |
| (1, 5, 1) | | 442.0 + −18.0 + 18.0 + −128.0 + 102.0 + 0.0 + 0.0 = | | | | 416 | 5.97 | 0.086 | 0.34 | | | |
| (1, 5, 2) | | 442.0 + −18.0 + 18.0 + −128.0 + 102.0 + 0.0 + 31.0 = | | | | 447 | 4.93 | 0.201 | 0.80 | | | |
| (1, 5, 3) | | 442.0 + −18.0 + 18.0 + −128.0 + 102.0 + 0.0 + 75.0 = | | | | 491 | 5.14 | 0.483 | 1.92 | | | |
| (1, 5, 4) | | 442.0 + −18.0 + 18.0 + −128.0 + 102.0 + 0.0 + 85.0 = | | | | 501 | 6.00 | 0.303 | 1.20 | | | |
| (1, 5, 5) | | 442.0 + −18.0 + 18.0 + −128.0 + 102.0 + 0.0 + 113.0 = | | | | 529 | 6.77 | 0.385 | 1.53 | | | |
| (1, 5, 6) | | 442.0 + −18.0 + 18.0 + −128.0 + 102.0 + 0.0 + 142.0 = | | | | 558 | 4.61 | 0.020 | 0.08 | 1 | 1 | |
| (1, 5, 7) | | 442.0 + −18.0 + 18.0 + −128.0 + 102.0 + 0.0 + 157.0 = | | | | 573 | 6.69 | 0.315 | 1.25 | | | |
| (1, 5, 8) | | 442.0 + −18.0 + 18.0 + −128.0 + 102.0 + 0.0 + 167.0 = | | | | 583 | 5.70 | 0.291 | 1.15 | | | |
| (1, 6, 1) | | 442.0 + −18.0 + 18.0 + −128.0 + 116.0 + 0.0 + 0.0 = | | | | 430 | 6.05 | 0.081 | 0.32 | | | |
| (1, 6, 2) | | 442.0 + −18.0 + 18.0 + −128.0 + 116.0 + 0.0 + 31.0 = | | | | 461 | 5.06 | 0.242 | 0.96 | | | |
| (1, 6, 3) | | 442.0 + −18.0 + 18.0 + −128.0 + 116.0 + 0.0 + 75.0 = | | | | 505 | 5.28 | 0.516 | 2.05 | | | |
| (1, 6, 4) | | 442.0 + −18.0 + 18.0 + −128.0 + 116.0 + 0.0 + 85.0 = | | | | 515 | 6.05 | 0.279 | 1.11 | | | |
| (1, 6, 5) | | 442.0 + −18.0 + 18.0 + −128.0 + 116.0 + 0.0 + 113.0 = | | | | 543 | 6.85 | 0.324 | 1.29 | | | |
| (1, 6, 6) | | 442.0 + −18.0 + 18.0 + −128.0 + 116.0 + 0.0 + 142.0 = | | | | 572 | 4.96 | 0.009 | 0.04 | 1 | 1 | |
| (1, 6, 7) | | 442.0 + −18.0 + 18.0 + −128.0 + 116.0 + 0.0 + 157.0 = | | | | 587 | 6.72 | 0.311 | 1.23 | | | |
| (1, 6, 8) | | 442.0 + −18.0 + 18.0 + −128.0 + 116.0 + 0.0 + 167.0 = | | | | 597 | 5.78 | 0.266 | 1.06 | | | |
| (1, 7, 1) | | 442.0 + −18.0 + 18.0 + −128.0 + 128.0 + 0.0 + 0.0 = | | | | 442 | 4.64 | 0.114 | 0.45 | | | |
| (1, 7, 2) | | 442.0 + −18.0 + 18.0 + −128.0 + 128.0 + 0.0 + 31.0 = | | | | 473 | 1.97 | 0.093 | 0.37 | | | |

TABLE G-continued

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| (1, 7, 3) | | 442.0 + −18.0 + 18.0 + −128.0 + 128.0 + 0.0 + 75.0 = | | | | 517 | 2.56 | 0.291 | 1.15 | | | |
| (1, 7, 4) | | 442.0 + −18.0 + 18.0 + −128.0 + 128.0 + 0.0 + 85.0 = | | | | 527 | 4.77 | 0.234 | 0.93 | | | |
| (1, 7, 5) | | 442.0 + −18.0 + 18.0 + −128.0 + 128.0 + 0.0 + 113.0 = | | | | 555 | 5.84 | 0.365 | 1.45 | | | |
| (1, 7, 6) | | 442.0 + −18.0 + 18.0 + −128.0 + 128.0 + 0.0 + 142.0 = | | | | 584 | 5.70 | 0.120 | 0.48 | | | |
| (1, 7, 7) | | 442.0 + −18.0 + 18.0 + −128.0 + 128.0 + 0.0 + 157.0 = | | | | 599 | 5.84 | 0.307 | 1.22 | | | |
| (1, 7, 8) | | 442.0 + −18.0 + 18.0 + −128.0 + 128.0 + 0.0 + 167.0 = | | | | 609 | 4.45 | 0.236 | 0.94 | | | |
| (1, 8, 1) | | 442.0 + −18.0 + 18.0 + −128.0 + 134.0 + 0.0 + 0.0 = | | | | 448 | 6.80 | 0.095 | 0.38 | | | |
| (1, 8, 2) | | 442.0 + −18.0 + 18.0 + −128.0 + 134.0 + 0.0 + 31.0 = | | | | 479 | 5.92 | 0.311 | 1.23 | | | |
| (1, 8, 3) | | 442.0 + −18.0 + 18.0 + −128.0 + 134.0 + 0.0 + 75.0 = | | | | 523 | 6.10 | 0.483 | 1.92 | | | |
| (1, 8, 4) | | 442.0 + −18.0 + 18.0 + −128.0 + 134.0 + 0.0 + 85.0 = | | | | 533 | 6.90 | 0.254 | 1.01 | | | |
| (1, 8, 5) | | 442.0 + −18.0 + 18.0 + −128.0 + 134.0 + 0.0 + 113.0 = | | | | 561 | 7.68 | 0.377 | 1.50 | | | |
| (1, 8, 6) | | 442.0 + −18.0 + 18.0 + −128.0 + 134.0 + 0.0 + 142.0 = | | | | 590 | 5.62 | 0.028 | 0.11 | | 1 | |
| (1, 8, 7) | | 442.0 + −18.0 + 18.0 + −128.0 + 134.0 + 0.0 + 157.0 = | | | | 605 | 7.52 | 0.299 | 1.19 | | | |
| (1, 8, 8) | | 442.0 + −18.0 + 18.0 + −128.0 + 134.0 + 0.0 + 167.0 = | | | | 615 | 6.53 | 0.319 | 1.27 | | | |
| | | AVERAGE | | | | 509 | 5.2 | 0.252 | TOTAL | 4 | 6 | |
| 2 | 1 | Acetic acid | 17.76 | 57.06 | 1.049 | | | | | | | |
| (2, 1, 1) | | | | | | 380 | 5.57 | 0.029 | 0.05 | 1 | | |
| (2, 1, 2) | | 442.0 + −18.0 + 60.0 + −128.0 + 66.0 + 0.0 + 31.0 = | | | | 453 | 4.90 | 0.348 | 0.66 | | | |
| (2, 1, 3) | | 442.0 + −18.0 + 60.0 + −128.0 + 66.0 + 0.0 + 75.0 = | | | | 497 | 5.22 | 0.782 | 1.47 | | | |
| (2, 1, 4) | | 442.0 + −18.0 + 60.0 + −128.0 + 66.0 + 0.0 + 85.0 = | | | | 507 | 5.94 | 0.315 | 0.59 | | | |
| (2, 1, 5) | | 442.0 + −18.0 + 60.0 + −128.0 + 66.0 + 0.0 + 113.0 = | | | | 535 | 6.66 | 0.610 | 1.15 | | | |
| (2, 1, 6) | | 442.0 + −18.0 + 60.0 + −128.0 + 66.0 + 0.0 + 142.0 = | | | | 564 | 4.56 | 0.020 | 0.04 | 1 | 1 | |
| (2, 1, 7) | | 442.0 + −18.0 + 60.0 + −128.0 + 66.0 + 0.0 + 157.0 = | | | | 579 | 6.64 | 0.397 | 0.75 | | | |
| (2, 1, 8) | | 442.0 + −18.0 + 60.0 + −128.0 + 66.0 + 0.0 + 167.0 = | | | | 589 | 5.57 | 0.365 | 0.69 | | | |
| (2, 2, 1) | | | | | | 384 | 4.21 | 0.046 | 0.09 | 1 | 1 | |
| (2, 2, 2) | | 442.0 + −18.0 + 60.0 + −128.0 + 70.0 + 0.0 + 31.0 = | | | | 457 | 2.31 | 0.299 | 0.56 | | | |
| (2, 2, 3) | | 442.0 + −18.0 + 60.0 + −128.0 + 70.0 + 0.0 + 75.0 = | | | | 501 | 3.10 | 0.389 | 0.73 | | | |
| (2, 2, 4) | | 442.0 + −18.0 + 60.0 + −128.0 + 70.0 + 0.0 + 85.0 = | | | | 511 | 4.80 | 0.795 | 1.50 | | | |
| (2, 2, 5) | | 442.0 + −18.0 + 60.0 + −128.0 + 70.0 + 0.0 + 113.0 = | | | | 539 | 5.38 | 0.692 | 1.30 | | | |
| (2, 2, 6) | | 442.0 + −18.0 + 60.0 + −128.0 + 70.0 + 0.0 + 142.0 = | | | | 568 | 1.89 | 0.038 | 0.07 | 1 | 1 | |
| (2, 2, 7) | | 442.0 + −18.0 + 60.0 + −128.0 + 70.0 + 0.0 + 157.0 = | | | | 583 | 5.76 | 0.406 | 0.76 | | | |
| (2, 2, 8) | | 442.0 + −18.0 + 60.0 + −128.0 + 70.0 + 0.0 + 167.0 = | | | | 593 | 4.42 | 0.541 | 1.02 | | | |
| (2, 3, 1) | | | | | | 396 | 6.98 | 0.080 | 0.15 | | 1 | |
| (2, 3, 2) | | 442.0 + −18.0 + 60.0 + −128.0 + 82.0 + 0.0 + 31.0 = | | | | 469 | 5.38 | 1.100 | 2.07 | | | |
| (2, 3, 3) | | 442.0 + −18.0 + 60.0 + −128.0 + 82.0 + 0.0 + 75.0 = | | | | 513 | 5.70 | 0.831 | 1.56 | | | |
| (2, 3, 4) | | 442.0 + −18.0 + 60.0 + −128.0 + 82.0 + 0.0 + 85.0 = | | | | 523 | 6.42 | 1.050 | 1.98 | | | |
| (2, 3, 5) | | 442.0 + −18.0 + 60.0 + −128.0 + 82.0 + 0.0 + 113.0 = | | | | 551 | 7.17 | 1.230 | 2.32 | | | |
| (2, 3, 6) | | 442.0 + −18.0 + 60.0 + −128.0 + 82.0 + 0.0 + 142.0 = | | | | 560 | 5.09 | 0.900 | 1.69 | | | |
| (2, 3, 7) | | 442.0 + −18.0 + 60.0 + −128.0 + 82.0 + 0.0 + 157.0 = | | | | 595 | 7.06 | 1.100 | 2.07 | | | |
| (2, 3, 8) | | 442.0 + −18.0 + 60.0 + −128.0 + 82.0 + 0.0 + 167.0 = | | | | 605 | 5.97 | 0.688 | 1.30 | | | |
| (2, 4, 1) | | | | | | 407 | 4.50 | 0.116 | 0.22 | | | |
| (2, 4, 2) | | 442.0 + −18.0 + 60.0 + −128.0 + 93.0 + 0.0 + 31.0 = | | | | 480 | 3.09 | 0.340 | 0.64 | | | |
| (2, 4, 3) | | 442.0 + −18.0 + 60.0 + −128.0 + 93.0 + 0.0 + 75.0 = | | | | 524 | 3.97 | 0.594 | 1.12 | | | |
| (2, 4, 4) | | 442.0 + −18.0 + 60.0 + −128.0 + 93.0 + 0.0 + 85.0 = | | | | 534 | 5.01 | 0.807 | 1.52 | | | |
| (2, 4, 5) | | 442.0 + −18.0 + 60.0 + −128.0 + 93.0 + 0.0 + 113.0 = | | | | 562 | 5.73 | 0.725 | 1.37 | | | |
| (2, 4, 6) | | 442.0 + −18.0 + 60.0 + −128.0 + 93.0 + 0.0 + 142.0 = | | | | 591 | 2.50 | 0.020 | 0.04 | 1 | 1 | |
| (2, 4, 7) | | 442.0 + −18.0 + 60.0 + −128.0 + 93.0 + 0.0 + 157.0 = | | | | 606 | 5.81 | 0.692 | 1.30 | | | |
| (2, 4, 8) | | 442.0 + −18.0 + 60.0 + −128.0 + 93.0 + 0.0 + 167.0 = | | | | 616 | 4.72 | 0.643 | 1.21 | | | |
| (2, 5, 1) | | | | | | 416 | 6.02 | 0.048 | 0.09 | 1 | 1 | |
| (2, 5, 2) | | 442.0 + −18.0 + 60.0 + −128.0 + 102.0 + 0.0 + 31.0 = | | | | 489 | 5.38 | 0.590 | 1.11 | | | |
| (2, 5, 3) | | 442.0 + −18.0 + 60.0 + −128.0 + 102.0 + 0.0 + 75.0 = | | | | 533 | 5.62 | 0.815 | 1.53 | | | |
| (2, 5, 4) | | 442.0 + −18.0 + 60.0 + −128.0 + 102.0 + 0.0 + 85.0 = | | | | 543 | 6.29 | 0.557 | 1.05 | | | |
| (2, 5, 5) | | 442.0 + −18.0 + 60.0 + −128.0 + 102.0 + 0.0 + 113.0 = | | | | 571 | 6.96 | 0.582 | 1.10 | | | |
| (2, 5, 6) | | 442.0 + −18.0 + 60.0 + −128.0 + 102.0 + 0.0 + 142.0 = | | | | 600 | 5.04 | 0.042 | 0.08 | 1 | 1 | |
| (2, 5, 7) | | 442.0 + −18.0 + 60.0 + −128.0 + 102.0 + 0.0 + 157.0 = | | | | 615 | 6.90 | 0.639 | 1.20 | | | |
| (2, 5, 8) | | 442.0 + −18.0 + 60.0 + −128.0 + 102.0 + 0.0 + 167.0 = | | | | 625 | 5.92 | 0.557 | 1.05 | | | |
| (2, 6, 1) | | | | | | 430 | 6.05 | 0.078 | 0.15 | | 1 | |
| (2, 6, 2) | | 442.0 + −18.0 + 60.0 + −128.0 + 116.0 + 0.0 + 31.0 = | | | | 503 | 5.46 | 0.569 | 1.07 | | | |
| (2, 6, 3) | | 442.0 + −18.0 + 60.0 + −128.0 + 116.0 + 0.0 + 75.0 = | | | | 547 | 5.70 | 0.492 | 0.93 | | | |
| (2, 6, 4) | | 442.0 + −18.0 + 60.0 + −128.0 + 116.0 + 0.0 + 85.0 = | | | | 557 | 6.34 | 0.569 | 1.07 | | | |
| (2, 6, 5) | | 442.0 + −18.0 + 60.0 + −128.0 + 116.0 + 0.0 + 113.0 = | | | | 585 | 6.98 | 0.737 | 1.39 | | | |
| (2, 6, 6) | | 442.0 + −18.0 + 60.0 + −128.0 + 116.0 + 0.0 + 142.0 = | | | | 614 | 5.17 | 0.041 | 0.08 | 1 | 1 | |
| (2, 6, 7) | | 442.0 + −18.0 + 60.0 + −128.0 + 116.0 + 0.0 + 157.0 = | | | | 629 | 6.93 | 0.643 | 1.21 | | | |
| (2, 6, 8) | | 442.0 + −18.0 + 60.0 + −128.0 + 116.0 + 0.0 + 167.0 = | | | | 639 | 5.97 | 0.504 | 0.95 | | | |
| (2, 7, 1) | | | | | | 442 | 4.66 | 0.096 | 0.18 | | 1 | |
| (2, 7, 2) | | 442.0 + −18.0 + 60.0 + −128.0 + 128.0 + 0.0 + 31.0 = | | | | 515 | 3.25 | 0.208 | 0.39 | | | |
| (2, 7, 3) | | 442.0 + −18.0 + 60.0 + −128.0 + 128.0 + 0.0 + 75.0 = | | | | 559 | 4.21 | 0.688 | 1.30 | | | |
| (2, 7, 4) | | 442.0 + −18.0 + 60.0 + −128.0 + 128.0 + 0.0 + 85.0 = | | | | 569 | 5.30 | 0.606 | 1.14 | | | |
| (2, 7, 5) | | 442.0 + −18.0 + 60.0 + −128.0 + 128.0 + 0.0 + 113.0 = | | | | 597 | 6.13 | 0.795 | 1.50 | | | |
| (2, 7, 6) | | 442.0 + −18.0 + 60.0 + −128.0 + 128.0 + 0.0 + 142.0 = | | | | 626 | 5.92 | 0.251 | 0.47 | | | |
| (2, 7, 7) | | 442.0 + −18.0 + 60.0 + −128.0 + 128.0 + 0.0 + 157.0 = | | | | 641 | 6.16 | 0.766 | 1.44 | | | |

TABLE G-continued

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| (2, 7, 8) | | 442.0 + −18.0 + 60.0 + −128.0 + 128.0 + 0.0 + 167.0 = | | | | 651 | 4.85 | 0.418 | 0.79 | | | |
| (2, 8, 1) | | | | | | 448 | 6.82 | 0.108 | 0.20 | | | |
| (2, 8, 2) | | 442.0 + −18.0 + 60.0 + −128.0 + 134.0 + 0.0 + 31.0 = | | | | 521 | 6.26 | 0.938 | 1.77 | | | |
| (2, 8, 3) | | 442.0 + −18.0 + 60.0 + −128.0 + 134.0 + 0.0 + 75.0 = | | | | 565 | 6.50 | 1.080 | 2.03 | | | |
| (2, 8, 4) | | 442.0 + −18.0 + 60.0 + −128.0 + 134.0 + 0.0 + 85.0 = | | | | 575 | 7.17 | 0.493 | 0.93 | | | |
| (2, 8, 5) | | 442.0 + −18.0 + 60.0 + −128.0 + 134.0 + 0.0 + 113.0 = | | | | 603 | 7.81 | 1.060 | 2.00 | | | |
| (2, 8, 6) | | 442.0 + −18.0 + 60.0 + −128.0 + 134.0 + 0.0 + 142.0 = | | | | 632 | 5.97 | 0.046 | 0.09 | 1 | 1 | |
| (2, 8, 7) | | 442.0 + −18.0 + 60.0 + −128.0 + 134.0 + 0.0 + 157.0 = | | | | 647 | 7.68 | 1.230 | 2.32 | | | |
| (2, 8, 8) | | 442.0 + −18.0 + 60.0 + −128.0 + 134.0 + 0.0 + 167.0 = | | | | 657 | 6.69 | 0.766 | 1.44 | | | |
| | | AVERAGE | | | | 546 | 5.5 | 0.531 | TOTAL | 9 | 12 | |
| 3 | 40 | Methoxyacetic acid | 25.05 | 90.08 | 1.174 | | | | | | | |
| (3, 1, 1) | | | | | | 380 | 5.57 | 0.025 | 0.04 | 1 | 1 | |
| (3, 1, 2) | | 442.0 + −18.0 + 90.0 + −128.0 + 66.0 + 0.0 + 31.0 = | | | | 483 | 4.90 | 0.524 | 0.84 | | | |
| (3, 1, 3) | | 442.0 + −18.0 + 90.0 + −128.0 + 66.0 + 0.0 + 75.0 = | | | | 527 | 5.22 | 0.856 | 1.37 | | | |
| (3, 1, 4) | | 442.0 + −18.0 + 90.0 + −128.0 + 66.0 + 0.0 + 85.0 = | | | | 537 | 5.97 | 0.360 | 0.58 | | | |
| (3, 1, 5) | | 442.0 + −18.0 + 90.0 + −128.0 + 66.0 + 0.0 + 113.0 = | | | | 565 | 6.66 | 0.561 | 0.90 | | | |
| (3, 1, 6) | | 442.0 + −18.0 + 90.0 + −128.0 + 66.0 + 0.0 + 142.0 = | | | | 594 | 4.64 | 0.030 | 0.05 | 1 | 1 | |
| (3, 1, 7) | | 442.0 + −18.0 + 90.0 + −128.0 + 66.0 + 0.0 + 157.0 = | | | | 609 | 6.61 | 0.582 | 0.93 | | | |
| (3, 1, 8) | | 442.0 + −18.0 + 90.0 + −128.0 + 66.0 + 0.0 + 167.0 = | | | | 619 | 5.57 | 0.561 | 0.90 | | | |
| (3, 2, 1) | | | | | | 384 | 4.24 | 0.047 | 0.07 | 1 | 1 | |
| (3, 2, 2) | | 442.0 + −18.0 + 90.0 + −128.6 + 70.0 + 0.0 + 31.0 = | | | | 487 | 2.32 | 0.340 | 0.54 | | | |
| (3, 2, 3) | | 442.0 + −18.0 + 90.0 + −128.0 + 70.0 + 0.0 + 75.0 = | | | | 531 | 3.22 | 0.442 | 0.71 | | | |
| (3, 2, 4) | | 442.0 + −18.0 + 90.0 + −128.0 + 70.0 + 0.0 + 85.0 = | | | | 541 | 4.80 | 0.635 | 1.01 | | | |
| (3, 2, 5) | | 442.0 + −18.0 + 90.0 + −128.0 + 70.0 + 0.0 + 113.0 = | | | | 569 | 5.65 | 0.725 | 1.16 | | | |
| (3, 2, 6) | | 442.0 + −18.0 + 90.0 + −128.0 + 70.0 + 0.0 + 142.0 = | | | | 598 | 1.97 | 0.042 | 0.07 | 1 | 1 | |
| (3, 2, 7) | | 442.0 + −18.0 + 90.0 + −128.0 + 70.0 + 0.0 + 157.0 = | | | | 613 | 5.73 | 0.586 | 0.94 | | | |
| (3, 2, 8) | | 442.0 + −18.0 + 90.0 + −128.0 + 70.0 + 0.0 + 167.0 = | | | | 623 | 4.45 | 0.713 | 1.14 | | | |
| (3, 3, 1) | | | | | | 396 | 6.98 | 0.082 | 0.13 | | 1 | 3 |
| (3, 3, 2) | | 442.0 + −18.0 + 90.0 + −128.0 + 82.0 + 0.0 + 31.0 = | | | | 499 | 5.41 | 1.570 | 2.51 | | | |
| (3, 3, 3) | | 442.0 + −18.0 + 90.0 + −128.0 + 82.0 + 0.0 + 75.0 = | | | | 543 | 5.70 | 1.050 | 1.68 | | | |
| (3, 3, 4) | | 442.0 + −18.0 + 90.0 + −128.0 + 82.0 + 0.0 + 85.0 = | | | | 553 | 6.42 | 1.310 | 2.09 | | | |
| (3, 3, 5) | | 442.0 + −18.0 + 90.0 + −128.0 + 82.0 + 0.0 + 113.0 = | | | | 581 | 7.17 | 1.510 | 2.41 | | | |
| (3, 3, 6) | | 442.0 + −18.0 + 90.0 + −128.0 + 82.0 + 0.0 + 142.0 = | | | | 610 | 5.14 | 0.100 | 0.16 | | 1 | |
| (3, 3, 7) | | 442.0 + −18.0 + 90.0 + −128.0 + 82.0 + 0.0 + 157.0 = | | | | 625 | 7.06 | 1.440 | 2.30 | | | |
| (3, 3, 8) | | 442.0 + −18.0 + 90.0 + −128.0 + 82.0 + 0.0 + 167.0 = | | | | 635 | 6.00 | 1.080 | 1.73 | | | |
| (3, 4, 1) | | | | | | 407 | 4.53 | 0.115 | 0.18 | | 1 | |
| (3, 4, 2) | | 442.0 + −18.0 + g0.0 + −128.0 + 93.0 + 0.0 + 31.0 = | | | | 510 | 3.20 | 0.307 | 0.49 | | | |
| (3, 4, 3) | | 442.0 + −18.0 + 90.0 + −128.0 + 93.0 + 0.0 + 75.0 = | | | | 554 | 3.97 | 0.717 | 1.15 | | | |
| (3, 4, 4) | | 442.0 + −18.0 + 90.0 + −128.0 + 93.0 + 0.0 + 85.0 = | | | | 564 | 5.01 | 0.668 | 1.07 | | | |
| (3, 4, 5) | | 442.0 + −18.0 + 90.0 + −128.0 + 93.0 + 0.0 + 113.0 = | | | | 592 | 5.76 | 0.684 | 1.09 | | | |
| (3, 4, 6) | | 442.0 + −18.0 + 90.0 + −128.0 + 93.0 + 0.0 + 142.0 = | | | | 621 | 2.50 | 0.030 | 0.05 | 1 | 1 | |
| (3, 4, 7) | | 442.0 + −18.0 + 90.0 + −128.0 + 93.0 + 0.0 + 157.0 = | | | | 636 | 5.78 | 0.840 | 1.34 | | | |
| (3, 4, 8) | | 442.0 + −18.0 + 90.0 + −128.0 + 93.0 + 0.0 + 167.0 = | | | | 646 | 4.72 | 0.864 | 1.38 | | | |
| (3, 5, 1) | | | | | | 416 | 6.00 | 0.034 | 0.05 | 1 | 1 | |
| (3, 5, 2) | | 442.0 + −18.0 + 90.0 + −128.0 + 102.0 + 0.0 + 31.0 = | | | | 519 | 5.38 | 0.709 | 1.13 | | | |
| (3, 5, 3) | | 442.0 + −18.0 + 90.0 + −128.0 + 102.0 + 0.0 + 75.0 = | | | | 563 | 5.62 | 0.897 | 1.43 | | | |
| (3, 5, 4) | | 442.0 + −18.0 + 90.0 + −128.0 + 102.0 + 0.0 + 85.0 = | | | | 573 | 6.29 | 0.676 | 1.08 | | | |
| (3, 5, 5) | | 442.0 + −18.0 + 90.0 + −128.0 + 102.0 + 0.0 + 113.0 = | | | | 601 | 6.93 | 0.848 | 1.35 | | | |
| (3, 5, 6) | | 442.0 + −18.0 + 90.0 + −128.0 + 102.0 + 0.0 + 142.0 = | | | | 630 | 5.12 | 0.058 | 0.09 | 1 | 1 | |
| (3, 5, 7) | | 442.0 + −18.0 + 90.0 + −128.0 + 102.0 + 0.0 + 157.0 = | | | | 645 | 6.90 | 0.844 | 1.35 | | | |
| (3, 5, 8) | | 442.0 + −18.0 + 90.0 + −128.0 + 102.0 + 0.0 + 167.0 = | | | | 655 | 5.89 | 0.860 | 1.37 | | | |
| (3, 6, 1) | | | | | | 430 | 6.02 | 0.071 | 0.11 | | 1 | |
| (3, 6, 2) | | 442.0 + −18.0 + 90.0 + −128.0 + 116.0 + 0.0 + 31.0 = | | | | 533 | 5.49 | 0.725 | 1.16 | | | |
| (3, 6, 3) | | 442.0 + −18.0 + 90.0 + −128.0 + 116.0 + 0.0 + 75.0 = | | | | 577 | 5.70 | 0.602 | 0.96 | | | |
| (3, 6, 4) | | 442.0 + −18.0 + 90.0 + −128.0 + 116.0 + 0.0 + 85.0 = | | | | 587 | 6.32 | 0.705 | 1.13 | | | |
| (3, 6, 5) | | 442.0 + −18.0 + 90.0 + −128.0 + 116.0 + 0.0 + 113.0 = | | | | 615 | 6.98 | 0.913 | 1.46 | | | |
| (3, 6, 6) | | 442.0 + −18.0 + 90.0 + −128.0 + 116.0 + 0.0 + 142.0 = | | | | 644 | 5.20 | 0.054 | 0.09 | 1 | 1 | |
| (3, 6, 7) | | 442.0 + −18.0 + 90.0 + −128.0 + 116.0 + 0.0 + 157.0 = | | | | 659 | 6.93 | 0.754 | 1.20 | | | |
| (3, 6, 8) | | 442.0 + −18.0 + 90.0 + −128.0 + 116.0 + 0.0 + 167.0 = | | | | 669 | 5.97 | 0.578 | 0.92 | | | |
| (3, 7, 1) | | | | | | 442 | 4.64 | 0.092 | 0.15 | | 1 | |
| (3, 7, 2) | | 442.0 + −18.0 + 90.0 + −128.0 + 128.0 + 0.0 + 31.0 = | | | | 545 | 3.46 | 0.231 | 0.37 | | | |
| (3, 7, 3) | | 442.0 + −18.0 + 90.0 + −128.0 + 128.0 + 0.0 + 75.0 = | | | | 589 | 4.24 | 0.885 | 1.41 | | | |
| (3, 7, 4) | | 442.0 + −18.0 + 90.0 + −128.0 + 128.0 + 0.0 + 85.0 = | | | | 599 | 5.33 | 0.508 | 0.81 | | | |
| (3, 7, 5) | | 442.0 + −18.0 + 90.0 + −128.0 + 128.0 + 0.0 + 113.0 = | | | | 627 | 6.13 | 1.110 | 1.77 | | | |
| (3, 7, 6) | | 442.0 + −18.0 + 90.0 + −128.0 + 128.0 + 0.0 + 142.0 = | | | | 656 | 5.89 | 0.311 | 0.50 | | | |
| (3, 7, 7) | | 442.0 + −18.0 + 90.0 + −128.0 + 128.0 + 0.0 + 157.0 = | | | | 671 | 6.13 | 0.831 | 1.33 | | | |
| (3, 7, 8) | | 442.0 + −18.0 + 90.0 + −128.0 + 128.0 + 0.0 + 167.0 = | | | | 681 | 4.88 | 0.573 | 0.92 | | | |
| (3, 8, 1) | | | | | | 448 | 6.80 | 0.134 | 0.21 | | | |
| (3, 8, 2) | | 442.0 + −18.0 + 90.0 + −128.0 + 134.0 + 0.0 + 31.0 = | | | | 551 | 6.26 | 0.987 | 1.58 | | | |
| (3, 8, 3) | | 442.0 + −18.0 + 90.0 + −128.0 + 134.0 + 0.0 + 75.0 = | | | | 595 | 6.50 | 1.200 | 1.92 | | | |
| (3, 8, 4) | | 442.0 + −18.0 + 90.0 + −128.0 + 134.0 + 0.0 + 85.0 = | | | | 605 | 7.14 | 0.582 | 0.93 | | | |

TABLE G-continued

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| (3, 8, 5) | | 442.0 + −18.0 + 90.0 + −128.0 + 134.0 + 0.0 + 113.0 = | | | | 633 | 7.81 | 1.460 | 2.33 | | | |
| (3, 8, 6) | | 442.0 + −18.0 + 90.0 + −128.0 + 134.0 + 0.0 + 142.0 = | | | | 662 | 5.97 | 0.074 | 0.12 | | 1 | |
| (3, 8, 7) | | 442.0 + −18.0 + 90.0 + −128.0 + 134.0 + 0.0 + 157.0 = | | | | 677 | 7.65 | 1.390 | 2.22 | | | |
| (3, 8, 8) | | 442.0 + −18.0 + 90.0 + −128.0 + 134.0 + 0.0 + 167.0 = | | | | 687 | 6.69 | 0.991 | 1.58 | | | |
| | | AVERAGE | | | | 572 | 5.5 | 0.626 | TOTAL | 8 | 14 | |
| 4 | 34 | Isovaleric acid | 35.59 | 102.13 | 0.937 | | | | | | | |
| (4, 1, 1) | | | | | | 380 | 5.57 | 0.032 | 0.04 | 1 | 1 | |
| (4, 1, 2) | | 442.0 + −18.0 + 102.0 + −128.0 + 66.0 + 0.0 + 31.0 = | | | | 495 | 6.00 | 0.557 | 0.74 | | | |
| (4, 1, 3) | | 442.0 + −18.0 + 102.0 + −128.0 + 66.0 + 0.0 + 75.0 = | | | | 539 | 6.29 | 0.999 | 1.33 | | | |
| (4, 1, 4) | | 442.0 + −18.0 + 102.0 + −128.0 + 66.0 + 0.0 + 85.0 = | | | | 549 | 7.01 | 0.598 | 0.80 | | | |
| (4, 1, 5) | | 442.0 + −18.0 + 102.0 + −128.0 + 66.0 + 0.0 + 113.0 = | | | | 577 | 7.68 | 0.827 | 1.10 | | | |
| (4, 1, 6) | | 442.0 + −18.0 + 102.0 + −128.0 + 66.0 + 0.0 + 142.0 = | | | | 606 | 5.62 | 0.070 | 0.09 | 1 | 1 | |
| (4, 1, 7) | | 442.0 + −18.0 + 102.0 + −128.0 + 66.0 + 0.0 + 157.0 = | | | | 621 | 7.49 | 0.582 | 0.78 | | | |
| (4, 1, 8) | | 442.0 + −18.0 + 102.0 + −128.0 + 66.0 + 0.0 + 167.0 = | | | | 631 | 6.40 | 0.639 | 0.85 | | | |
| (4, 2, 1) | | | | | | 384 | 3.89 | 0.047 | 0.06 | 1 | 1 | |
| (4, 2, 2) | | 442.0 + −18.0 + 102.0 + −128.0 + 70.0 + 0.0 + 31.0 = | | | | 499 | 4.95 | 1.100 | 1.47 | | | |
| (4, 2, 3) | | 442.0 + −18.0 + 102.0 + −128.0 + 70.0 + 0.0 + 75.0 = | | | | 543 | 5.27 | 1.560 | 2.08 | | | |
| (4, 2, 4) | | 442.0 + −18.0 + 102.0 + −128.0 + 70.0 + 0.0 + 85.0 = | | | | 553 | 6.02 | 0.680 | 0.91 | | | |
| (4, 2, 5) | | 442.0 + −18.0 + 102.0 + −128.0 + 70.0 + 0.0 + 113.0 = | | | | 581 | 6.72 | 0.668 | 0.89 | | | |
| (4, 2, 6) | | 442.0 + −18.0 + 102.0 + −128.0 + 70.0 + 0.0 + 142.0 = | | | | 610 | 4.47 | 0.106 | 0.14 | | 1 | |
| (4, 2, 7) | | 442.0 + −18.0 + 102.0 + −128.0 + 70.0 + 0.0 + 157.0 = | | | | 625 | 6.61 | 0.569 | 0.76 | | | |
| (4, 2, 8) | | 442.0 + −18.0 + 102.0 + −128.0 + 70.0 + 0.0 + 167.0 = | | | | 635 | 5.54 | 0.889 | 1.19 | | | |
| (4, 3, 1) | | | | | | 396 | 6.32 | 0.081 | 0.11 | | 1 | |
| (4, 3, 2) | | 442.0 + −18.0 + 102.0 + −128.0 + 82.0 + 0.0 + 31.0 = | | | | 511 | 6.42 | 1.520 | 2.03 | | | |
| (4, 3, 3) | | 442.0 + −18.0 + 102.0 + −128.0 + 82.0 + 0.0 + 75.0 = | | | | 555 | 6.74 | 1.150 | 1.53 | | | |
| (4, 3, 4) | | 442.0 + −18.0 + 102.0 + −128.0 + 82.0 + 0.0 + 85.0 = | | | | 565 | 7.49 | 0.901 | 1.20 | | | |
| (4, 3, 5) | | 442.0 + −18.0 + 102.0 + −128.0 + 82.0 + 0.0 + 113.0 = | | | | 593 | 8.18 | 1.460 | 1.95 | | | |
| (4, 3, 6) | | 442.0 + −18.0 + 102.0 + −128.0 + 82.0 + 0.0 + 142.0 = | | | | 622 | 6.10 | 0.471 | 0.63 | | | |
| (4, 3, 7) | | 442.0 + −18.0 + 102.0 + −128.0 + 82.0 + 0.0 + 157.0 = | | | | 637 | 7.94 | 1.440 | 1.92 | | | |
| (4, 3, 8) | | 442.0 + −18.0 + 102.0 + −128.0 + 82.0 + 0.0 + 167.0 = | | | | 647 | 6.82 | 1.310 | 1.75 | | | |
| (4, 4, 1) | | | | | | 407 | 4.47 | 0.137 | 0.18 | | 1 | |
| (4, 4, 2) | | 442.0 + −18.0 + 102.0 + −128.0 + 93.0 + 0.0 + 31.0 = | | | | 522 | 5.11 | 1.340 | 1.79 | | | |
| (4, 4, 3) | | 442.0 + −18.0 + 102.0 + −128.0 + 93.0 + 0.0 + 75.0 = | | | | 566 | 5.38 | 1.310 | 1.75 | | | |
| (4, 4, 4) | | 442.0 + −18.0 + 102.0 + −128.0 + 93.0 + 0.0 + 85.0 = | | | | 576 | 6.02 | 0.696 | 0.93 | | | |
| (4, 4, 5) | | 442.0 + −18.0 + 102.0 + −128.0 + 93.0 + 0.0 + 113.0 = | | | | 604 | 6.61 | 0.868 | 1.16 | | | |
| (4, 4, 6) | | 442.0 + −18.0 + 102.0 + −128.0 + 93.0 + 0.0 + 142.0 = | | | | 633 | 4.77 | 0.117 | 0.16 | | 1 | |
| (4, 4, 7) | | 442.0 + −18.0 + 102.0 + −128.0 + 93.0 + 0.0 + 157.0 = | | | | 648 | 6.53 | 1.080 | 1.44 | | | |
| (4, 4, 8) | | 442.0 + −18.0 + 102.0 + −128.0 + 93.0 + 0.0 + 167.0 = | | | | 658 | 5.65 | 1.010 | 1.35 | | | |
| (4, 5, 1) | | | | | | 416 | 5.97 | 0.040 | 0.05 | 1 | 1 | |
| (4, 5, 2) | | 442.0 + −18.0 + 102.0 + −128.0 + 102.0 + 0.0 + 31.0 = | | | | 531 | 6.32 | 1.060 | 1.41 | | | |
| (4, 5, 3) | | 442.0 + −18.0 + 102.0 + −128.0 + 102.0 + 0.0 + 75.0 = | | | | 575 | 6.58 | 0.782 | 1.04 | | | |
| (4, 5, 4) | | 442.0 + −18.0 + 102.0 + −128.0 + 102.0 + 0.0 + 85.0 = | | | | 585 | 7.28 | 0.668 | 0.89 | | | |
| (4, 5, 5) | | 442.0 + −18.0 + 102.0 + −128.0 + 102.0 + 0.0 + 113.0 = | | | | 613 | 7.86 | 0.958 | 1.28 | | | |
| (4, 5, 6) | | 442.0 + −18.0 + 102.0 + −128.0 + 102.0 + 0.0 + 142.0 = | | | | 642 | 5.94 | 0.130 | 0.17 | | 1 | |
| (4, 5, 7) | | 442.0 + −18.0 + 102.0 + −128.0 + 102.0 + 0.0 + 157.0 = | | | | 657 | 7.73 | 1.020 | 1.36 | | | |
| (4, 5, 8) | | 442.0 + −18.0 + 102.0 + −128.0 + 102.0 + 0.0 + 167.0 = | | | | 667 | 6.66 | 0.561 | 0.75 | | | |
| (4, 6, 1) | | | | | | 430 | 6.82 | 0.031 | 0.04 | 1 | 1 | |
| (4, 6, 2) | | 442.0 + −18.0 + 102.0 + −128.0 + 116.0 + 0.0 + 31.0 = | | | | 545 | 6.34 | 0.844 | 1.13 | | | |
| (4, 6, 3) | | 442.0 + −18.0 + 102.0 + −128.0 + 116.0 + 0.0 + 75.0 = | | | | 589 | 6.61 | 0.598 | 0.80 | | | |
| (4, 6, 4) | | 442.0 + −18.0 + 102.0 + −128.0 + 116.0 + 0.0 + 85.0 = | | | | 599 | 7.30 | 0.725 | 0.97 | | | |
| (4, 6, 5) | | 442.0 + −18.0 + 102.0 + −128.0 + 116.0 + 0.0 + 113.0 = | | | | 627 | 7.92 | 0.918 | 1.22 | | | |
| (4, 6, 6) | | 442.0 + −18.0 + 102.0 + −128.0 + 116.0 + 0.0 + 142.0 = | | | | 656 | 6.02 | 0.047 | 0.06 | 1 | 1 | |
| (4, 6, 7) | | 442.0 + −18.0 + 102.0 + −128.0 + 116.0 + 0.0 + 157.0 = | | | | 671 | 7.70 | 1.050 | 1.40 | | | |
| (4, 6, 8) | | 442.0 + −18.0 + 102.0 + −128.0 + 116.0 + 0.0 + 167.0 = | | | | 681 | 6.72 | 0.610 | 0.81 | | | |
| (4, 7, 1) | | | | | | 442 | 4.61 | 0.121 | 0.16 | | 1 | |
| (4, 7, 2) | | 442.0 + −18.0 + 102.0 + −128.0 + 128.0 + 0.0 + 31.0 = | | | | 557 | 5.38 | 0.586 | 0.78 | | | |
| (4, 7, 3) | | 442.0 + −18.0 + 102.0 + −128.0 + 128.0 + 0.0 + 75.0 = | | | | 601 | 5.73 | 1.180 | 1.57 | | | |
| (4, 7, 4) | | 442.0 + −18.0 + 102.0 + −128.0 + 128.0 + 0.0 + 85.0 = | | | | 611 | 6.50 | 0.479 | 0.64 | | | |
| (4, 7, 5) | | 442.0 + −18.0 + 102.0 + −128.0 + 128.0 + 0.0 + 113.0 = | | | | 639 | 7.22 | 0.852 | 1.14 | | | |
| (4, 7, 6) | | 442.0 + −18.0 + 102.0 + −128.0 + 128.0 + 0.0 + 142.0 = | | | | 668 | 5.03 | 0.050 | 0.07 | 1 | 1 | |
| (4, 7, 7) | | 442.0 + −18.0 + 102.0 + −128.0 + 128.0 + 0.0 + 157.0 = | | | | 683 | 7.09 | 0.893 | 1.19 | | | |
| (4, 7, 8) | | 442.0 + −18.0 + 102.0 + −128.0 + 128.0 + 0.0 + 167.0 = | | | | 693 | 5.89 | 1.010 | 1.35 | | | |
| (4, 8, 1) | | | | | | 448 | 6.85 | 0.029 | 0.04 | 1 | 1 | |
| (4, 8, 2) | | 442.0 + −18.0 + 102.0 + −128.0 + 134.0 + 0.0 + 31.0 = | | | | 563 | 7.12 | 1.160 | 1.55 | | | |
| (4, 8, 3) | | 442.0 + −18.0 + 102.0 + −128.0 + 134.0 + 0.0 + 75.0 = | | | | 607 | 7.41 | 1.310 | 1.75 | | | |
| (4, 8, 4) | | 442.0 + −18.0 + 102.0 + −128.0 + 134.0 + 0.0 + 85.0 = | | | | 617 | 8.08 | 0.963 | 1.28 | | | |
| (4, 8, 5) | | 442.0 + −18.0 + 102.0 + −128.0 + 134.0 + 0.0 + 113.0 = | | | | 645 | 8.72 | 1.700 | 2.27 | | | |
| (4, 8, 6) | | 442.0 + −18.0 + 102.0 + −128.0 + 134.0 + 0.0 + 142.0 = | | | | 674 | 6.72 | 0.084 | 0.11 | | 1 | |
| (4, 8, 7) | | 442.0 + −18.0 + 102.0 + −128.0 + 134.0 + 0.0 + 157.0 = | | | | 689 | 8.45 | 1.740 | 2.32 | | | |
| (4, 8, 8) | | 442.0 + −18.0 + 102.0 + −128.0 + 134.0 + 0.0 + 167.0 = | | | | 699 | 7.44 | 0.979 | 1.31 | | | |
| | | AVERAGE | | | | 583 | 6.5 | 0.750 | TOTAL | 8 | 15 | |

TABLE G-continued

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| 5 | 31 | Hexadienoic acid, 2,4- | 36.61 | 112.13 | 1.000 | | | | | | | |
| (5, 1, 1) | | | | | | 380 | 5.62 | 0.033 | 0.09 | 1 | 1 | |
| (5, 1, 2) | | 442.0 + −18.0 + 112.0 + −128.0 + 66.0 + 0.0 + 31.0 = | | | | 505 | 6.05 | 0.311 | 0.85 | | | 2 |
| (5, 1, 3) | | 442.0 + −18.0 + 112.0 + −128.0 + 66.0 + 0.0 + 75.0 = | | | | 549 | 6.23 | 0.406 | 1.11 | | | |
| (5, 1, 4) | | 442.0 + −18.0 + 112.0 + −128.0 + 66.0 + 0.0 + 85.0 = | | | | 559 | 6.93 | 0.270 | 0.74 | | | |
| (5, 1, 5) | | 442.0 + −18.0 + 112.0 + −128.0 + 66.0 + 0.0 + 113.0 = | | | | 587 | 7.65 | 0.463 | 1.27 | | | |
| (5, 1, 6) | | 442.0 + −18.0 + 112.0 + −128.0 + 66.0 + 0.0 + 142.0 = | | | | 616 | 5.51 | 0.050 | 0.14 | | 1 | |
| (5, 1, 7) | | 442.0 + −18.0 + 112.0 + −128.0 + 66.0 + 0.0 + 157.0 = | | | | 631 | 7.46 | 0.520 | 1.42 | | | |
| (5, 1, 8) | | 442.0 + −18.0 + 112.0 + −128.0 + 66.0 + 0.0 + 167.0 = | | | | 641 | 6.34 | 0.393 | 1.07 | | | |
| (5, 2, 1) | | | | | | 384 | 3.97 | 0.031 | 0.08 | 1 | 1 | |
| (5, 2, 2) | | 442.0 + −18.0 + 112.0 + −128.0 + 70.0 + 0.0 + 31.0 = | | | | 509 | 6.98 | 0.532 | 1.45 | | | 2 |
| (5, 2, 3) | | 442.0 + −18.0 + 112.0 + −128.0 + 70.0 + 0.0 + 75.0 = | | | | 553 | 5.25 | 0.365 | 1.00 | | | |
| (5, 2, 4) | | 442.0 + −18.0 + 112.0 + −128.0 + 70.0 + 0.0 + 85.0 = | | | | 563 | 5.94 | 0.262 | 0.72 | | | |
| (5, 2, 5) | | 442.0 + −18.0 + 112.0 + −128.0 + 70.0 + 0.0 + 113.0 = | | | | 591 | 6.63 | 0.401 | 1.10 | | | |
| (5, 2, 6) | | 442.0 + −18.0 + 112.0 + −128.0 + 70.0 + 0.0 + 142.0 = | | | | 620 | 4.42 | 0.036 | 0.10 | | 1 | |
| (5, 2, 7) | | 442.0 + −18.0 + 112.0 + −128.0 + 70.0 + 0.0 + 157.0 = | | | | 635 | 6.53 | 0.356 | 0.97 | | | |
| (5, 2, 8) | | 442.0 + −18.0 + 112.0 + −128.0 + 70.0 + 0.0 + 167.0 = | | | | 645 | 5.49 | 0.397 | 1 08 | | | |
| (5, 3, 1) | | | | | | 396 | 6.07 | 0.073 | 0.20 | | | |
| (5, 3, 2) | | 442.0 + −18.0 + 112.0 + −128.0 + 82.0 + 0.0 + 31.0 = | | | | 521 | 6.45 | 0.602 | 1.64 | | | |
| (5, 3, 3) | | 442.0 + −18.0 + 112.0 + −128.0 + 82.0 + 0.0 + 75.0 = | | | | 565 | 6.66 | 0.573 | 1.57 | | | |
| (5, 3, 4) | | 442.0 + −18.0 + 112.0 + −128.0 + 82.0 + 0.0 + 85.0 = | | | | 575 | 7.41 | 0.324 | 0.89 | | | |
| (5, 3, 5) | | 442.0 + −18.0 + 112.0 + −128.0 + 82.0 + 0.0 + 113.0 = | | | | 603 | 8.16 | 0.692 | 1.89 | | | |
| (5, 3, 6) | | 442.0 + −18.0 + 112.0 + −128.0 + 82.0 + 0.0 + 142.0 = | | | | 632 | 5.91 | 0.078 | 0.21 | | | |
| (5, 3, 7) | | 442.0 + −18.0 + 112.0 + −128.0 + 82.0 + 0.0 + 157.0 = | | | | 647 | 7.92 | 0.905 | 2.47 | | | |
| (5, 3, 8) | | 442.0 + −18.0 + 112.0 + −128.0 + 82.0 + 0.0 + 167.0 = | | | | 657 | 6.74 | 0.836 | 2.28 | | | |
| (5, 4, 1) | | | | | | 407 | 4.50 | 0.143 | 0.39 | | | |
| (5, 4, 2) | | 442.0 + −18.0 + 112.0 + −128.0 + 93.0 + 0.0 + 31.0 = | | | | 532 | 5.22 | 0.344 | 0.94 | | | |
| (5, 4, 3) | | 442.0 + −18.0 + 112.0 + −128.0 + 93.0 + 0.0 + 75.0 = | | | | 576 | 5.33 | 0.463 | 1.27 | | | |
| (5, 4, 4) | | 442.0 + −18.0 + 112.0 + −128.0 + 93.0 + 0.0 + 85.0 = | | | | 586 | 5.94 | 0.266 | 0.73 | | | |
| (5, 4, 5) | | 442.0 + −18.0 + 112.0 + −128.0 + 93.0 + 0.0 + 113.0 = | | | | 614 | 6.53 | 0.352 | 0.96 | | | |
| (5, 4, 6) | | 442.0 + −18.0 + 112.0 + −128.0 + 93.0 + 0.0 + 142.0 = | | | | 643 | 4.71 | 0.051 | 0.14 | | 1 | |
| (5, 4, 7) | | 442.0 + −18.0 + 112.0 + −128.0 + 93.0 + 0.0 + 157.0 = | | | | 658 | 6.47 | 0.455 | 1.24 | | | |
| (5, 4, 8) | | 442.0 + −18.0 + 112.0 + −128.0 + 93.0 + 0.0 + 167.0 = | | | | 668 | 5.57 | 0.492 | 1.34 | | | |
| (5, 5, 1) | | | | | | 416 | 1.51 | 0.040 | 0.11 | | 1 | |
| (5, 5, 2) | | 442.0 + −18.0 + 112.0 + −128.0 + 102.0 + 0.0 + 31.0 = | | | | 541 | 6.34 | 0.430 | 1.17 | | | |
| (5, 5, 3) | | 442.0 + −18.0 + 112.0 + −128.0 + 102.0 + 0.0 + 75.0 = | | | | 585 | 6.50 | 0.385 | 1.05 | | | |
| (5, 5, 4) | | 442.0 + −18.0 + 112.0 + −128.0 + 102.0 + 0.0 + 85.0 = | | | | 595 | 7.17 | 0.251 | 0.69 | | | |
| (5, 5, 5) | | 442.0 + −18.0 + 112.0 + −128.0 + 102.0 + 0.0 + 113.0 = | | | | 623 | 7.84 | 0.508 | 1.39 | | | |
| (5, 5, 6) | | 442.0 + −18.0 + 112.0 + −128.0 + 102.0 + 0.0 + 142.0 = | | | | 652 | 5.14 | 0.307 | 0.84 | | | |
| (5, 5, 7) | | 442.0 + −18.0 + 112.0 + −128.0 + 102.0 + 0.0 + 157.0 = | | | | 667 | 7.70 | 0.737 | 2.01 | | | |
| (5, 5, 8) | | 442.0 + −18.0 + 112.0 + −128.0 + 102.0 + 0.0 + 167.0 = | | | | 677 | 6.58 | 0.414 | 1.13 | | | |
| (5, 6, 1) | | | | | | 430 | 6.07 | 0.057 | 0.15 | | 1 | |
| (5, 6, 2) | | 442.0 + −18.0 + 112.0 + −128.0 + 116.0 + 0.0 + 31.0 = | | | | 555 | 6.39 | 0.319 | 0.87 | | | 2 |
| (5, 6, 3) | | 442.0 + −18.0 + 112.0 + −128.0 + 116.0 + 0.0 + 75.0 = | | | | 599 | 6.55 | 0.418 | 1.14 | | | |
| (5, 6, 4) | | 442.0 + −18.0 + 112.0 + −128.0 + 116.0 + 0.0 + 85.0 = | | | | 609 | 7.20 | 0.217 | 0.59 | | | |
| (5, 6, 5) | | 442.0 + −18.0 + 112.0 + −128.0 + 116.0 + 0.0 + 113.0 = | | | | 637 | 7.84 | 0.430 | 1.17 | | | |
| (5, 6, 6) | | 442.0 + −18.0 + 112.0 + −128.0 + 116.0 + 0.0 + 142.0 = | | | | 666 | 5.94 | 0.034 | 0.09 | 1 | 1 | 2 |
| (5, 6, 7) | | 442.0 + −18.0 + 112.0 + −128.0 + 116.0 + 0.0 + 157.0 = | | | | 681 | 7.68 | 0.582 | 1.59 | | | |
| (5, 6, 8) | | 442.0 + −18.0 + 112.0 + −128.0 + 116.0 + 0.0 + 167.0 = | | | | 691 | 6.63 | 0.410 | 1.12 | | | |
| (5, 7, 1) | | | | | | 442 | 4.63 | 0.115 | 0.31 | | | |
| (5, 7, 2) | | 442.0 + −18.0 + 112.0 + −128.0 + 128.0 + 0.0 + 31.0 = | | | | 567 | 5.43 | 0.232 | 0.63 | | | |
| (5, 7, 3) | | 442.0 + −18.0 + 112.0 + −128.0 + 128.0 + 0.0 + 75.0 = | | | | 611 | 5.65 | 0.446 | 1.22 | | | |
| (5, 7, 4) | | 442.0 + −18.0 + 112.0 + −128.0 + 128.0 + 0.0 + 85.0 = | | | | 621 | 6.42 | 0.191 | 0.52 | | | |
| (5, 7, 5) | | 442.0 + −18.0 + 112.0 + −128.0 + 128.0 + 0.0 + 113.0 = | | | | 549 | 7.17 | 0.426 | 1.16 | | | |
| (5, 7, 6) | | 442.0 + −18.0 + 112.0 + −128.0 + 128.0 + 0.0 + 142.0 = | | | | 678 | 4.77 | 0.028 | 0.08 | 1 | 1 | |
| (5, 7, 7) | | 442.0 + −18.0 + 112.0 + −128.0 + 128.0 + 0.0 + 157.0 = | | | | 693 | 6.98 | 0.639 | 1.75 | | | |
| (5, 7, 8) | | 442.0 + −18.0 + 112.0 + −128.0 + 128.0 + 0.0 + 167.0 = | | | | 703 | 5.78 | 0.467 | 1.28 | | | |
| (5, 8, 1) | | | | | | 448 | 6.82 | 0.067 | 0.18 | | 1 | |
| (5, 8, 2) | | 442.0 + −18.0 + 112.0 + −128.0 + 134.0 + 0.0 + 31.0 = | | | | 573 | 7.12 | 0.594 | 1.62 | | | |
| (5, 8, 3) | | 442.0 + −18.0 + 112.0 + −128.0 + 134.0 + 0.0 + 75.0 = | | | | 617 | 7.33 | 0.487 | 1.33 | | | |
| (5, 8, 4) | | 442.0 + −18.0 + 112.0 + −128.0 + 134.0 + 0.0 + 85.0 = | | | | 627 | 8.02 | 0.426 | 1.16 | | | |
| (5, 8, 5) | | 442.0 + −18.0 + 112.0 + −128.0 + 134.0 + 0.0 + 113.0 = | | | | 655 | 8.69 | 0.733 | 2.00 | | | |
| (5, 8, 6) | | 442.0 + −18.0 + 112.0 + −128.0 + 134.0 + 0.0 + 142.0 = | | | | 684 | 6.71 | 0.035 | 0.09 | 1 | 1 | |
| (5, 8, 7) | | 442.0 + −18.0 + 112.0 + −128.0 + 134.0 + 0.0 + 157.0 = | | | | 699 | 8.45 | 0.827 | 2.26 | | | |
| (5, 8, 8) | | 442.0 + −18.0 + 112.0 + −128.0 + 134.0 + 0.0 + 167.0 = | | | | 709 | 7.38 | 0.696 | 1.90 | | | |
| | | AVERAGE | | | | 591 | 6.4 | 0.366 | TOTAL | 5 | 11 | |
| 6 | 33 | Isonicotinic acid | 40.20 | 123.11 | 1.000 | | | | | | | |
| (6, 1, 1) | | | | | | 380 | 5.60 | 0.044 | 0.10 | | 1 | |
| (6, 1, 2) | | 442.0 + −18.0 + 123.0 + −128.0 + 66.0 + 0.0 + 31.0 = | | | | 516 | 5.28 | 0.438 | 0.98 | | | |
| (6, 1, 3) | | 442.0 + −18.0 + 123.0 + −128.0 + 66.0 + 0.0 + 75.0 = | | | | 560 | 5.44 | 0.512 | 1.15 | | | |
| (6, 1, 4) | | 442.0 + −18.0 + 123.0 + −128.0 + 66.0 + 0.0 + 85.0 = | | | | 570 | 6.10 | 0.206 | 0.46 | | | |

TABLE G-continued

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| (6, 1, 5) | | 442.0 + −18.0 + 123.0 + −128.0 + 66.0 + 0.0 + 113.0 = | | | | 598 | 6.85 | 0.459 | 1.03 | | | |
| (6, 1, 6) | | 442.0 + −18.0 + 123.0 + −128.0 + 66.0 + 0.0 + 142.0 = | | | | 627 | 5.22 | 0.015 | 0.03 | 1 | 1 | |
| (6, 1, 7) | | 442.0 + −18.0 + 123.0 + −128.0 + 66.0 + 0.0 + 157.0 = | | | | 642 | 6.77 | 0.360 | 0.81 | | | |
| (6, 1, 8) | | 442.0 + −18.0 + 123.0 + −128.0 + 66.0 + 0.0 + 167.0 = | | | | 652 | 5.65 | 0.442 | 0.99 | | | |
| (6, 2, 1) | | | | | | 384 | 4.45 | 0.030 | 0.07 | 1 | 1 | 2 |
| (6, 2, 2) | | 442.0 + −18.0 + 123.0 + −128.0 + 70.0 + 0.0 + 31.0 = | | | | 520 | 3.30 | 0.319 | 0.72 | | | |
| (6, 2, 3) | | 442.0 + −18.0 + 123.0 + −128.0 + 70.0 + 0.0 + 75.0 = | | | | 564 | 3.83 | 0.565 | 1.27 | | | |
| (6, 2, 4) | | 442.0 + −18.0 + 123.0 + −128.0 + 70.0 + 0.0 + 85.0 = | | | | 574 | 5.01 | 0.553 | 1.24 | | | |
| (6, 2, 5) | | 442.0 + −18.0 + 123.0 + −128.0 + 70.0 + 0.0 + 113.0 = | | | | 602 | 5.78 | 0.532 | 1.19 | | | |
| (6, 2, 6) | | 442.0 + −18.0 + 123.0 + −128.0 + 70.0 + 0.0 + 142.0 = | | | | 631 | 2.98 | 0.029 | 0.06 | 1 | 1 | |
| (6, 2, 7) | | 442.0 + −18.0 + 123.0 + −128.0 + 70.0 + 0.0 + 157.0 = | | | | 646 | 5.73 | 0.377 | 0.85 | | | |
| (6, 2, 8) | | 442.0 + −18.0 + 123.0 + −128.0 + 70.0 + 0.0 + 167.0 = | | | | 656 | 4.55 | 0.606 | 1.36 | | | |
| (6, 3, 1) | | | | | | 396 | 6.08 | 0.053 | 0.12 | | 1 | 3 |
| (6, 3, 2) | | 442.0 + −18.0 + 123.0 + −128.0 + 82.0 + 0.0 + 31.0 = | | | | 532 | 5.73 | 0.717 | 1.61 | | | |
| (6, 3, 3) | | 442.0 + −18.0 + 123.0 + −128.0 + 82.0 + 0.0 + 75.0 = | | | | 576 | 5.97 | 0.905 | 2.03 | | | |
| (6, 3, 4) | | 442.0 + −18.0 + 123.0 + −128.0 + 82.0 + 0.0 + 85.0 = | | | | 586 | 6.61 | 0.844 | 1.89 | | | |
| (6, 3, 5) | | 442.0 + −18.0 + 123.0 + −128.0 + 82.0 + 0.0 + 113.0 = | | | | 614 | 7.41 | 1.040 | 2.33 | | | |
| (6, 3, 6) | | 442.0 + −18.0 + 123.0 + −128.0 + 82.0 + 0.0 + 142.0 = | | | | 643 | 5.76 | 0.042 | 0.09 | 1 | 1 | |
| (6, 3, 7) | | 442.0 + −18.0 + 123.0 + −128.0 + 82.0 + 0.0 + 157.0 = | | | | 658 | 7.25 | 0.799 | 1.79 | | | |
| (6, 3, 8) | | 442.0 + −18.0 + 123.0 + −128.0 + 82.0 + 0.0 + 167.0 = | | | | 668 | 6.10 | 0.750 | 1.68 | | | |
| (6, 4, 1) | | | | | | 407 | 4.47 | 0.108 | 0.24 | | | |
| (6, 4, 2) | | 442.0 + −18.0 + 123.0 + −128.0 + 93.0 + 0.0 + 31.0 = | | | | 543 | 2.37 | 0.754 | 1.69 | | | 3 |
| (6, 4, 3) | | 442.0 + −18.0 + 123.0 + −128.0 + 93.0 + 0.0 + 75.0 = | | | | 587 | 4.34 | 0.795 | 1.78 | | | |
| (6, 4, 4) | | 442.0 + −18.0 + 123.0 + −128.0 + 93.0 + 0.0 + 85.0 = | | | | 597 | 5.17 | 0.733 | 1.64 | | | |
| (6, 4, 5) | | 442.0 + −18.0 + 123.0 + −128.0 + 93.0 + 0.0 + 113.0 = | | | | 625 | 5.81 | 0.557 | 1.25 | | | |
| (6, 4, 6) | | 442.0 + −18.0 + 123.0 + −128.0 + 93.0 + 0.0 + 142.0 = | | | | 654 | 3.70 | 0.031 | 0.07 | 1 | 1 | |
| (6, 4, 7) | | 442.0 + −18.0 + 123.0 + −128.0 + 93.0 + 0.0 + 157.0 = | | | | 669 | 5.81 | 0.520 | 1.17 | | | |
| (6, 4, 8) | | 442.0 + −18.0 + 123.0 + −128.0 + 93.0 + 0.0 + 167.0 = | | | | 679 | 4.82 | 0.766 | 1.72 | | | |
| (6, 5, 1) | | | | | | 416 | 6.00 | 0.047 | 0.11 | | 1 | |
| (6, 5, 2) | | 442.0 + −18.0 + 123.0 + −128.0 + 102.0 + 0.0 + 31.0 = | | | | 552 | 5.73 | 0.295 | 0.66 | | | |
| (6, 5, 3) | | 442.0 + −18.0 + 123.0 + −128.0 + 102.0 + 0.0 + 75.0 = | | | | 596 | 5.92 | 0.483 | 1.08 | | | |
| (6, 5, 4) | | 442.0 + −18.0 + 123.0 + −128.0 + 102.0 + 0.0 + 85.0 = | | | | 606 | 6.50 | 0.516 | 1.16 | | | |
| (6, 5, 5) | | 442.0 + −18.0 + 123.0 + −128.0 + 102.0 + 0.0 + 113.0 = | | | | 634 | 7.17 | 0.606 | 1.36 | | | |
| (6, 5, 6) | | 442.0 + −18.0 + 123.0 + −128.0 + 102.0 + 0.0 + 142.0 = | | | | 663 | 5.70 | 0.037 | 0.08 | 1 | 1 | 2 |
| (6, 5, 7) | | 442.0 + −18.0 + 123.0 + −128.0 + 102.0 + 0.0 + 157.0 = | | | | 678 | 7.09 | 0.532 | 1.19 | | | |
| (6, 5, 8) | | 442.0 + −18.0 + 123.0 + −128.0 + 102.0 + 0.0 + 167.0 = | | | | 688 | 6.10 | 0.459 | 1.03 | | | |
| (6, 6, 1) | | | | | | 430 | 6.08 | 0.042 | 0.09 | 1 | 1 | |
| (6, 6, 2) | | 442.0 + −18.0 + 123.0 + −128.0 + 116.0 + 0.0 + 31.0 = | | | | 566 | 5.84 | 0.324 | 0.73 | | | |
| (6, 6, 3) | | 442.0 + −18.0 + 123.0 + −128.0 + 116.0 + 0.0 + 75.0 = | | | | 610 | 5.97 | 0.573 | 1.28 | | | |
| (6, 6, 4) | | 442.0 + −18.0 + 123.0 + −128.0 + 116.0 + 0.0 + 85.0 = | | | | 620 | 6.50 | 0.455 | 1.02 | | | |
| (6, 6, 5) | | 442.0 + −18.0 + 123.0 + −128.0 + 116.0 + 0.0 + 113.0 = | | | | 648 | 7.20 | 0.627 | 1.41 | | | |
| (6, 6, 6) | | 442.0 + −18.0 + 123.0 + −128.0 + 116.0 + 0.0 + 142.0 = | | | | 677 | 5.65 | 0.023 | 0.05 | 1 | 1 | |
| (6, 6, 7) | | 442.0 + −18.0 + 123.0 + −128.0 + 116.0 + 0.0 + 157.0 = | | | | 692 | 7.12 | 0.594 | 1.33 | | | |
| (6, 6, 8) | | 442.0 + −18.0 + 123.0 + −128.0 + 116.0 + 0.0 + 167.0 = | | | | 702 | 6.18 | 0.512 | 1.15 | | | |
| (6, 7, 1) | | | | | | 442 | 4.66 | 0.087 | 0.20 | | | |
| (6, 7, 2) | | 442.0 + −18.0 + 123.0 + −128.0 + 128.0 + 0.0 + 31.0 = | | | | 578 | 4.02 | 0.242 | 0.54 | | | |
| (6, 7, 3) | | 442.0 + −18.0 + 123.0 + −128.0 + 128.0 + 0.0 + 75.0 = | | | | 622 | 4.42 | 0.631 | 1.41 | | | |
| (6, 7, 4) | | 442.0 + −18.0 + 123.0 + −128.0 + 128.0 + 0.0 + 85.0 = | | | | 632 | 5.73 | 0.717 | 1.61 | | | |
| (6, 7, 5) | | 442.0 + −18.0 + 123.0 + −128.0 + 128.0 + 0.0 + 113.0 = | | | | 660 | 6.21 | 0.553 | 1.24 | | | |
| (6, 7, 6) | | 442.0 + −18.0 + 123.0 + −128.0 + 128.0 + 0.0 + 142.0 = | | | | 689 | 3.81 | 0.017 | 0.04 | 1 | 1 | |
| (6, 7, 7) | | 442.0 + −18.0 + 123.0 + −128.0 + 128.0 + 0.0 + 157.0 = | | | | 704 | 6.16 | 0.414 | 0.93 | | | |
| (6, 7, 6) | | 442.0 + −18.0 + 123.0 + −128.0 + 128.0 + 0.0 + 167.0 = | | | | 714 | 4.88 | 0.369 | 0.83 | | | |
| (6, 8, 1) | | | | | | 448 | 6.80 | 0.069 | 0.15 | | 1 | |
| (6, 8, 2) | | 442.0 + −18.0 + 123.0 + −128.0 + 134.0 + 0.0 + 31.0 = | | | | 584 | 6.64 | 0.647 | 1.45 | | | |
| (6, 8, 3) | | 442.0 + −18.0 + 123.0 + −128.0 + 134.0 + 0.0 + 75.0 = | | | | 628 | 6.80 | 0.770 | 1.73 | | | |
| (6, 8, 4) | | 442.0 + −18.0 + 123.0 + −128.0 + 134.0 + 0.0 + 85.0 = | | | | 638 | 7.41 | 0.455 | 1.02 | | | |
| (6, 8, 5) | | 442.0 + −18.0 + 123.0 + −128.0 + 134.0 + 0.0 + 113.0 = | | | | 666 | 8.10 | 0.877 | 1.97 | | | |
| (6, 8, 6) | | 442.0 + −18.0 + 123.0 + −128.0 + 134.0 + 0.0 + 142.0 = | | | | 695 | 6.80 | 0.030 | 0.07 | 1 | 1 | 2 |
| (6, 8, 7) | | 442.0 + −18.0 + 123.0 + −128.0 + 134.0 + 0.0 + 157.0 = | | | | 710 | 8.00 | 1.060 | 2.38 | | | |
| (6, 8, 8) | | 442.0 + −18.0 + 123.0 + −128.0 + 134.0 + 0.0 + 167.0 = | | | | 720 | 6.96 | 0.598 | 1.34 | | | |
| | | AVERAGE | | | | 601 | 5.8 | 0.446 | TOTAL | 10 | 14 | |
| 7 | 45 | Methoxyphenylacetic acid, 4- | 54.26 | 166.18 | 1.000 | | | | | | | |
| (7, 1, 1) | | | | | | 380 | 5.54 | 0.035 | 0.06 | 1 | 1 | |
| (7, 1, 2) | | 442.0 + −18.0 + 166.0 + −128.0 + 66.0 + 0.0 + 31.0 = | | | | 559 | 6.00 | 0.430 | 0.71 | | | |
| (7, 1, 3) | | 442.0 + −18.0 + 166.0 + −128.0 + 66.0 + 0.0 + 75.0 = | | | | 603 | 6.21 | 0.659 | 1.09 | | | |
| (7, 1, 4) | | 442.0 + −18.0 + 166.0 + −128.0 + 66.0 + 0.0 + 85.0 = | | | | 613 | 6.87 | 0.352 | 0.58 | | | |
| (7, 1, 5) | | 442.0 + −18.0 + 166.0 + −128.0 + 66.0 + 0.0 + 113.0 = | | | | 641 | 7.46 | 0.795 | 1.31 | | | |
| (7, 1, 6) | | 442.0 + −18.0 + 166.0 + −128.0 + 66.0 + 0.0 + 142.0 = | | | | 670 | 5.65 | 0.033 | 0.05 | 1 | 1 | |
| (7, 1, 7) | | 442.0 + −18.0 + 166.0 + −128.0 + 66.0 + 0.0 + 157.0 = | | | | 685 | 7.38 | 0.422 | 0.70 | | | |
| (7, 1, 8) | | 442.0 + −18.0 + 166.0 + −128.0 + 66.0 + 0.0 + 167.0 = | | | | 695 | 6.37 | 0.467 | 0.77 | | | |
| (7, 2, 1) | | | | | | 384 | 5.70 | 0.068 | 0.11 | | 1 | 2 |

TABLE G-continued

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| (7, 2, 2) | | 442.0 + −18.0 + 166.0 + −128.0 + 70.0 + 0.0 + 31.0 = | | | | 563 | 5.06 | 0.872 | 1.44 | | | |
| (7, 2, 3) | | 442.0 + −18.0 + 166.0 + −128.0 + 70.0 + 0.0 + 75.0 = | | | | 607 | 5.30 | 1.200 | 1.98 | | | |
| (7, 2, 4) | | 442.0 + −18.0 + 166.0 + −128.0 + 70.0 + 0.0 + 85.0 = | | | | 617 | 5.97 | 0.504 | 0.83 | | | |
| (7, 2, 5) | | 442.0 + −18.0 + 166.0 + −128.0 + 70.0 + 0.0 + 113.0 = | | | | 645 | 6.55 | 0.659 | 1.09 | | | |
| (7, 2, 6) | | 442.0 + −18.0 + 166.0 + −128.0 + 70.0 + 0.0 + 142.0 = | | | | 674 | 4.74 | 0.050 | 0.08 | 1 | 1 | |
| (7, 2, 7) | | 442.0 + −18.0 + 166.0 + −128.0 + 70.0 + 0.0 + 157.0 = | | | | 689 | 6.53 | 0.508 | 0.84 | | | |
| (7, 2, 8) | | 442.0 + −18.0 + 166.0 + −128.0 + 70.0 + 0.0 + 167.0 = | | | | 699 | 5.59 | 0.651 | 1.07 | | | |
| (7, 3, 1) | | | | | | 396 | 7.67 | 0.397 | 0.66 | | | |
| (7, 3, 2) | | 442.0 + −18.0 + 166.0 + −128.0 + 82.0 + 0.0 + 31.0 = | | | | 575 | 6.39 | 1.050 | 1.73 | | | |
| (7, 3, 3) | | 442.0 + −18.0 + 166.0 + −128.0 + 82.0 + 0.0 + 75.0 = | | | | 619 | 6.63 | 1.080 | 1.78 | | | |
| (7, 3, 4) | | 442.0 + −18.0 + 166.0 + −128.0 + 82.0 + 0.0 + 85.0 = | | | | 629 | 7.33 | 0.659 | 1.09 | | | |
| (7, 3, 5) | | 442.0 + −18.0 + 166.0 + −128.0 + 82.0 + 0.0 + 113.0 = | | | | 657 | 7.94 | 1.640 | 2.71 | | | |
| (7, 3, 6) | | 442.0 + −18.0 + 166.0 + −128.0 + 82.0 + 0.0 + 142.0 = | | | | 686 | 6.05 | 0.087 | 0.14 | | 1 | |
| (7, 3, 7) | | 442.0 + −18.0 + 166.0 + −128.0 + 82.0 + 0.0 + 157.0 = | | | | 701 | 7.78 | 1.390 | 2.29 | | | |
| (7, 3, 8) | | 442.0 + −18.0 + 166.0 + −128.0 + 82.0 + 0.0 + 167.0 = | | | | 711 | 6.74 | 0.495 | 0.82 | | | |
| (7, 4, 1) | | | | | | 407 | 4.45 | 0.161 | 0.27 | | | |
| (7, 4, 2) | | 442.0 + −18.0 + 166.0 + −128.0 + 93.0 + 0.0 + 31.0 = | | | | 586 | 5.19 | 0.651 | 1.07 | | | |
| (7, 4, 3) | | 442.0 + −18.0 + 166.0 + −128.0 + 93.0 + 0.0 + 75.0 = | | | | 630 | 5.41 | 0.991 | 1.64 | | | |
| (7, 4, 4) | | 442.0 + −18.0 + 166.0 + −128.0 + 93.0 + 0.0 + 85.0 = | | | | 640 | 6.00 | 0.537 | 0.89 | | | |
| (7, 4, 5) | | 442.0 + −18.0 + 166.0 + −128.0 + 93.0 + 0.0 + 113.0 = | | | | 668 | 6.47 | 0.717 | 1.18 | | | |
| (7, 4, 6) | | 442.0 + −18.0 + 166.0 + −128.0 + 93.0 + 0.0 + 142.0 = | | | | 697 | 4.90 | 0.043 | 0.07 | 1 | 1 | |
| (7, 4, 7) | | 442.0 + −18.0 + 166.0 + −128.0 + 93.0 + 0.0 + 157.0 = | | | | 712 | 6.47 | 0.647 | 1.07 | | | |
| (7, 4, 8) | | 442.0 + −18.0 + 166.0 + −128.0 + 93.0 + 0.0 + 167.0 = | | | | 722 | 5.65 | 0.766 | 1.26 | | | |
| (7, 5, 1) | | | | | | 416 | 5.97 | 0.050 | 0.08 | 1 | 1 | |
| (7, 5, 2) | | 442.0 + −18.0 + 166.0 + −128.0 + 102.0 + 0.0 + 31.0 = | | | | 595 | 6.26 | 0.680 | 1.12 | | | |
| (7, 5, 3) | | 442.0 + −18.0 + 166.0 + −128.0 + 102.0 + 0.0 + 75.0 = | | | | 639 | 6.47 | 0.713 | 1.18 | | | |
| (7, 5, 4) | | 442.0 + −18.0 + 166.0 + −128.0 + 102.0 + 0.0 + 85.0 = | | | | 649 | 7.11 | 0.590 | 0.97 | | | |
| (7, 5, 5) | | 442.0 + −18.0 + 166.0 + −128.0 + 102.0 + 0.0 + 113.0 = | | | | 677 | 7.65 | 1.050 | 1.73 | | | |
| (7, 5, 6) | | 442.0 + −18.0 + 166.0 + −128.0 + 102.0 + 0.0 + 142.0 = | | | | 706 | 5.91 | 0.060 | 0.10 | | 1 | |
| (7, 5, 7) | | 442.0 + −18.0 + 166.0 + −128.0 + 102.0 + 0.0 + 157.0 = | | | | 721 | 7.57 | 0.664 | 1.10 | | | |
| (7, 5, 8) | | 442.0 + −18.0 + 166.0 + −128.0 + 102.0 + 0.0 + 167.0 = | | | | 731 | 6.61 | 0.520 | 0.86 | | | |
| (7, 6, 1) | | | | | | 430 | 6.74 | 0.040 | 0.07 | 1 | 1 | |
| (7, 6, 2) | | 442.0 + −18.0 + 166.0 + −128.0 + 116.0 + 0.0 + 31.0 = | | | | 609 | 6.31 | 0.610 | 1.01 | | | |
| (7, 6, 3) | | 442.0 + −18.0 + 166.0 + −128.0 + 116.0 + 0.0 + 75.0 = | | | | 653 | 6.53 | 0.647 | 1.07 | | | |
| (7, 6, 4) | | 442.0 + −18.0 + 166.0 + −128.0 + 116.0 + 0.0 + 85.0 = | | | | 663 | 7.14 | 0.598 | 0.99 | | | |
| (7, 6, 5) | | 442.0 + −18.0 + 166.0 + −128.0 + 116.0 + 0.0 + 113.0 = | | | | 691 | 7.67 | 0.975 | 1.61 | | | |
| (7, 6, 6) | | 442.0 + −18.0 + 166.0 + −128.0 + 116.0 + 0.0 + 142.0 = | | | | 720 | 6.00 | 0.264 | 0.44 | | | |
| (7, 6, 7) | | 442.0 + −18.0 + 166.0 + −128.0 + 116.0 + 0.0 + 157.0 = | | | | 735 | 7.57 | 0.930 | 1.53 | | | |
| (7, 6, 8) | | 442.0 + −18.0 + 166.0 + −128.0 + 116.0 + 0.0 + 167.0 = | | | | 745 | 6.66 | 0.483 | 0.80 | | | |
| (7, 7, 1) | | | | | | 442 | 4.58 | 0.115 | 0.19 | | 1 | |
| (7, 7, 2) | | 442.0 + −18.0 + 166.0 + −128.0 + 128.0 + 0.0 + 31.0 = | | | | 621 | 5.43 | 0.442 | 0.73 | | | |
| (7, 7, 3) | | 442.0 + −18.0 + 166.0 + −128.0 + 128.0 + 0.0 + 75.0 = | | | | 665 | 5.70 | 0.975 | 1.61 | | | |
| (7, 7, 4) | | 442.0 + −18.0 + 166.0 + −128.0 + 128.0 + 0.0 + 85.0 = | | | | 675 | 6.42 | 0.315 | 0.52 | | | |
| (7, 7, 5) | | 442.0 + −18.0 + 166.0 + −128.0 + 128.0 + 0.0 + 113.0 = | | | | 703 | 7.01 | 0.844 | 1.39 | | | |
| (7, 7, 6) | | 442.0 + −18.0 + 166.0 + −128.0 + 128.0 + 0.0 + 142.0 = | | | | 732 | 5.09 | 0.020 | 0.03 | 1 | 1 | |
| (7, 7, 7) | | 442.0 + −18.0 + 166.0 + −128.0 + 128.0 + 0.0 + 157.0 = | | | | 747 | 6.93 | 0.848 | 1.40 | | | |
| (7, 7, 8) | | 442.0 + −18.0 + 166.0 + −128.0 + 128.0 + 0.0 + 167.0 = | | | | 757 | 5.89 | 0.627 | 1.03 | | | |
| (7, 8, 1) | | | | | | 448 | 6.82 | 0.049 | 0.08 | 1 | 1 | |
| (7, 8, 2) | | 442.0 + −18.0 + 166.0 + −128.0 + 134.0 + 0.0 + 31.0 = | | | | 627 | 7.06 | 0.987 | 1.63 | | | |
| (7, 8, 3) | | 442.0 + −18.0 + 166.0 + −128.0 + 134.0 + 0.0 + 75.0 = | | | | 671 | 7.27 | 1.390 | 2.29 | | | |
| (7, 8, 4) | | 442.0 + −18.0 + 166.0 + −128.0 + 134.0 + 0.0 + 85.0 = | | | | 681 | 7.89 | 0.786 | 1.30 | | | |
| (7, 8, 5) | | 442.0 + −18.0 + 166.0 + −128.0 + 134.0 + 0.0 + 113.0 = | | | | 709 | 8.45 | 1.380 | 2.28 | | | |
| (7, 8, 6) | | 442.0 + −18.0 + 166.0 + −128.0 + 134.0 + 0.0 + 142.0 = | | | | 738 | 6.71 | 0.054 | 0.09 | 1 | 1 | |
| (7, 8, 7) | | 442.0 + −18.0 + 166.0 + −128.0 + 134.0 + 0.0 + 157.0 = | | | | 753 | 8.26 | 1.360 | 2.24 | | | |
| (7, 8, 8) | | 442.0 + −18.0 + 166.0 + −128.0 + 134.0 + 0.0 + 167.0 = | | | | 763 | 7.35 | 0.725 | 1.20 | | | |
| | | AVERAGE | | | | 639 | 6.5 | 0.606 | TOTAL | 9 | 13 | |
| 8 | 49 | Methyl terephthalate, mono- | 58.82 | 180.16 | 1.000 | | | | | | | |
| (8, 1, 1) | | | | | | 380 | 5.60 | 0.023 | 0.04 | 1 | 1 | |
| (8, 1, 2) | | 442.0 + −18.0 + 180.0 + −128.0 + 66.0 + 0.0 + 31.0 = | | | | 573 | 6.00 | 0.442 | 0.78 | | | |
| (8, 1, 3) | | 442.0 + −18.0 + 180.0 + −128.0 + 66.0 + 0.0 + 75.0 = | | | | 617 | 6.10 | 0.676 | 1.19 | | | |
| (8, 1, 4) | | 442.0 + −18.0 + 180.0 + −128.0 + 66.0 + 0.0 + 85.0 = | | | | 627 | 6.74 | 0.389 | 0.69 | | | |
| (8, 1, 5) | | 442.0 + −18.0 + 180.0 + −128.0 + 66.0 + 0.0 + 113.0 = | | | | 655 | 7.33 | 0.688 | 1.22 | | | |
| (8, 1, 6) | | 442.0 + −18.0 + 180.0 + −128.0 + 66.0 + 0.0 + 142.0 = | | | | 684 | 5.57 | 0.050 | 0.09 | 1 | 1 | |
| (8, 1, 7) | | 442.0 + −18.0 + 180.0 + −128.0 + 66.0 + 0.0 + 157.0 = | | | | 699 | 7.17 | 0.492 | 0.87 | | | |
| (8, 1, 8) | | 442.0 + −18.0 + 180.0 + −128.0 + 66.0 + 0.0 + 167.0 = | | | | 709 | 6.18 | 0.500 | 0.88 | | | |
| (8, 2, 1) | | | | | | 384 | 5.62 | 0.063 | 0.11 | | 1 | 2 |
| (8, 2, 2) | | 442.0 + −18.0 + 180.0 + −128.0 + 70.0 + 0.0 + 31.0 = | | | | 577 | 5.17 | 0.864 | 1.53 | | | |
| (8, 2, 3) | | 442.0 + −18.0 + 180.0 + −128.0 + 70.0 + 0.0 + 75.0 = | | | | 621 | 5.28 | 0.713 | 1.26 | | | |
| (8, 2, 4) | | 442.0 + −18.0 + 180.0 + −128.0 + 70.0 + 0.0 + 85.0 = | | | | 631 | 5.92 | 0.578 | 1.02 | | | 2 |
| (8, 2, 5) | | 442.0 + −18.0 + 180.0 + −128.0 + 70.0 + 0.0 + 113.0 = | | | | 659 | 6.50 | 0.573 | 1.01 | | | |
| (8, 2, 6) | | 442.0 + −18.0 + 180.0 + −128.0 + 70.0 + 0.0 + 142.0 = | | | | 688 | 4.53 | 0.069 | 0.12 | | 1 | |

TABLE G-continued

Acid building blocks used in test library synthesis.
carboxylic acids 326.5 umol (50 eq)
Expected Mass Coding Scheme: (Acid, Alkyne, Amine) followed by mass calculations
Butyrolactone (aminolysis skip codon) compounds are common to each pool (italicized)

| BB # | Test # | Chemical Name | mg or uL acid | MW | d | Mass | Ret Time | LCMS Intensity | Rel Int | <10% Rel Int | <20% Rel Int | Mult Peaks |
|---|---|---|---|---|---|---|---|---|---|---|---|---|
| (8, 2, 7) | | 442.0 + −18.0 + 180.0 + −128.0 + 70.0 + 0.0 + 157.0 = | | | | 703 | 6.37 | 0.442 | 0.78 | | | |
| (8, 2, 8) | | 442.0 + −18.0 + 180.0 + −128.0 + 70.0 + 0.0 + 167.0 = | | | | 713 | 5.46 | 0.553 | 0.98 | | | |
| (8, 3, 1) | | | | | | 396 | 6.08 | 0.103 | 0.18 | | 1 | 2 |
| (8, 3, 2) | | 442.0 + −18.0 + 180.0 + −128.0 + 82.0 + 0.0 + 31.0 = | | | | 589 | 6.40 | 0.532 | 0.94 | | | |
| (8, 3, 3) | | 442.0 + −18.0 + 180.0 + −128.0 + 82.0 + 0.0 + 75.0 = | | | | 633 | 6.56 | 0.926 | 1.64 | | | |
| (8, 3, 4) | | 442.0 + −18.0 + 180.0 + −128.0 + 82.0 + 0.0 + 85.0 = | | | | 643 | 7.17 | 0.930 | 1.64 | | | |
| (8, 3, 5) | | 442.0 + −18.0 + 180.0 + −128.0 + 82.0 + 0.0 + 113.0 = | | | | 671 | 7.78 | 1.690 | 2.99 | | | |
| (8, 3, 6) | | 442.0 + −18.0 + 180.0 + −128.0 + 82.0 + 0.0 + 142.0 = | | | | 700 | 5.94 | 0.150 | 0.27 | | | |
| (8, 3, 7) | | 442.0 + −18.0 + 180.0 + −128.0 + 82.0 + 0.0 + 157.0 = | | | | 715 | 7.60 | 1.030 | 1.82 | | | |
| (8, 3, 8) | | 442.0 + −18.0 + 180.0 + −128.0 + 82.0 + 0.0 + 167.0 = | | | | 725 | 6.58 | 0.639 | 1.13 | | | |
| (8, 4, 1) | | | | | | 407 | 4.42 | 0.164 | 0.29 | | | |
| (8, 4, 2) | | 442.0 + −18.0 + 180.0 + −128.0 + 93.0 + 0.0 + 31.0 = | | | | 600 | 5.28 | 0.553 | 0.98 | | | |
| (8, 4, 3) | | 442.0 + −18.0 + 180.0 + −128.0 + 93.0 + 0.0 + 75.0 = | | | | 644 | 5.36 | 0.897 | 1.58 | | | |
| (8, 4, 4) | | 442.0 + −18.0 + 180.0 + −128.0 + 93.0 + 0.0 + 85.0 = | | | | 654 | 5.92 | 0.668 | 1.18 | | | |
| (8, 4, 5) | | 442.0 + −18.0 + 180.0 + −128.0 + 93.0 + 0.0 + 113.0 = | | | | 682 | 6.42 | 0.729 | 1.29 | | | |
| (8, 4, 6) | | 442.0 + −18.0 + 180.0 + −128.0 + 93.0 + 0.0 + 142.0 = | | | | 711 | 4.80 | 0.070 | 0.12 | | 1 | |
| (8, 4, 7) | | 442.0 + −18.0 + 180.0 + −128.0 + 93.0 + 0.0 + 157.0 = | | | | 726 | 6.34 | 0.676 | 1.19 | | | |
| (8, 4, 8) | | 442.0 + −18.0 + 180.0 + −128.0 + 93.0 + 0.0 + 167.0 = | | | | 736 | 5.54 | 0.627 | 1.11 | | | |
| (8, 5, 1) | | | | | | 416 | 5.97 | 0.052 | 0.09 | 1 | 1 | |
| (8, 5, 2) | | 442.0 + −18.0 + 180.0 + −128.0 + 102.0 + 0.0 + 31.0 = | | | | 609 | 6.29 | 0.532 | 0.94 | | | |
| (8, 5, 3) | | 442.0 + −18.0 + 180.0 + −128.0 + 102.0 + 0.0 + 75.0 = | | | | 653 | 6.40 | 0.430 | 0.76 | | | |
| (8, 5, 4) | | 442.0 + −18.0 + 180.0 + −128.0 + 102.0 + 0.0 + 85.0 = | | | | 663 | 6.96 | 0.668 | 1.18 | | | |
| (8, 5, 5) | | 442.0 + −18.0 + 180.0 + −128.0 + 102.0 + 0.0 + 113.0 = | | | | 691 | 7.52 | 1.010 | 1.78 | | | |
| (8, 5, 6) | | 442.0 + −18.0 + 180.0 + −128.0 + 102.0 + 0.0 + 142.0 = | | | | 720 | 5.86 | 0.088 | 0.16 | | 1 | |
| (8, 5, 7) | | 442.0 + −18.0 + 180.0 + −128.0 + 102.0 + 0.0 + 157.0 = | | | | 735 | 7.38 | 0.733 | 1.30 | | | |
| (8, 5, 8) | | 442.0 + −18.0 + 180.0 + −128.0 + 102.0 + 0.0 + 167.0 = | | | | 745 | 6.45 | 0.299 | 0.53 | | | |
| (8, 6, 1) | | | | | | 430 | 6.02 | 0.068 | 0.12 | | 1 | 2 |
| (8, 6, 2) | | 442.0 + −18.0 + 180.0 + −128.0 + 116.0 + 0.0 + 31.0 = | | | | 623 | 6.40 | 0.291 | 0.51 | | | |
| (8, 6, 3) | | 442.0 + −18.0 + 180.0 + −128.0 + 116.0 + 0.0 + 75.0 = | | | | 667 | 6.50 | 0.668 | 1.18 | | | |
| (8, 6, 4) | | 442.0 + −18.0 + 180.0 + −128.0 + 116.0 + 0.0 + 85.0 = | | | | 677 | 7.04 | 0.786 | 1.39 | | | |
| (8, 6, 5) | | 442.0 + −18.0 + 180.0 + −128.0 + 116.0 + 0.0 + 113.0 = | | | | 705 | 7.62 | 0.979 | 1.73 | | | |
| (8, 6, 6) | | 442.0 + −18.0 + 180.0 + −128.0 + 116.0 + 0.0 + 142.0 = | | | | 734 | 6.00 | 0.050 | 0.09 | 1 | 1 | |
| (8, 6, 7) | | 442.0 + −18.0 + 180.0 + −128.0 + 116.0 + 0.0 + 157.0 = | | | | 749 | 7.46 | 0.795 | 1.40 | | | |
| (8, 6, 8) | | 442.0 + −18.0 + 180.0 + −128.0 + 116.0 + 0.0 + 167.0 = | | | | 759 | 6.58 | 0.332 | 0.59 | | | |
| (8, 7, 1) | | | | | | 442 | 4.56 | 0.117 | 0.21 | | | |
| (8, 7, 2) | | 442.0 + −18.0 + 180.0 + −128.0 + 128.0 + 0.0 + 31.0 = | | | | 635 | 5.44 | 0.389 | 0.69 | | | |
| (8, 7, 3) | | 442.0 + −18.0 + 180.0 + −128.0 + 128.0 + 0.0 + 75.0 = | | | | 679 | 0.56 | 1.020 | 1.80 | | | |
| (8, 7, 4) | | 442.0 + −18.0 + 180.0 + −128.0 + 128.0 + 0.0 + 85.0 = | | | | 689 | 6.24 | 0.459 | 0.81 | | | |
| (8, 7, 5) | | 442.0 + −18.0 + 180.0 + −128.0 + 128.0 + 0.0 + 113.0 = | | | | 717 | 6.88 | 0.987 | 1.74 | | | |
| (8, 7, 6) | | 442.0 + −18.0 + 180.0 + −128.0 + 128.0 + 0.0 + 142.0 = | | | | 746 | 4.85 | 0.030 | 0.05 | 1 | 1 | |
| (8, 7, 7) | | 442.0 + −18.0 + 180.0 + −128.0 + 128.0 + 0.0 + 157.0 = | | | | 761 | 6.69 | 0.553 | 0.98 | | | |
| (8, 7, 8) | | 442.0 + −18.0 + 180.0 + −128.0 + 128.0 + 0.0 + 167.0 = | | | | 771 | 5.68 | 0.516 | 0.91 | | | |
| (8, 8, 1) | | | | | | 448 | 6.77 | 0.120 | 0.21 | | | |
| (8, 8, 2) | | 442.0 + −18.0 + 180.0 + −128.0 + 134.0 + 0.0 + 31.0 = | | | | 641 | 7.12 | 0.938 | 1.66 | | | |
| (8, 8, 3) | | 442.0 + −18.0 + 180.0 + −128.0 + 134.0 + 0.0 + 75.0 = | | | | 685 | 7.25 | 1.160 | 2.05 | | | |
| (8, 8, 4) | | 442.0 + −18.0 + 180.0 + −128.0 + 134.0 + 0.0 + 85.0 = | | | | 695 | 7.84 | 0.979 | 1.73 | | | |
| (8, 8, 5) | | 442.0 + −18.0 + 180.0 + −128.0 + 134.0 + 0.0 + 113.0 = | | | | 723 | 8.37 | 1.290 | 2.28 | | | |
| (8, 8, 6) | | 442.0 + −18.0 + 180.0 + −128.0 + 134.0 + 0.0 + 142.0 = | | | | 752 | 6.72 | 0.056 | 0.10 | | 1 | 2 |
| (8, 8, 7) | | 442.0 + −18.0 + 180.0 + −128.0 + 134.0 + 0.0 + 157.0 = | | | | 767 | 8.16 | 1.180 | 2.08 | | | |
| (8, 8, 8) | | 442.0 + −18.0 + 180.0 + −128.0 + 134.0 + 0.0 + 167.0 = | | | | 777 | 7.28 | 0.602 | 1.06 | | | |
| | | AVERAGE | | | | 651 | 6.3 | 0.557 | TOTAL | 5 | 12 | |
| | | SUBTOTAL | | | | | | | | 58 | 97 | |
| | | less redundant butyrolactone misses | | | | | | | | −20 | −41 | |
| | | GRAND TOTAL | | | | | | | | 38 | 56 | |
| | | total compounds | | | | | | | | 456 | 456 | |
| | | % HITS | | | | | | | | 91.7 | 87.7 | |

VII. Large Library Synthesis:

With the three critical "quality control" experiments complete (Demonstration Compound synthesis, Building Block Testing, and Test Library Synthesis), we were prepared to execute the synthesis of a large library of compounds derived from the iodobenzyl tetracycles, 30 alkynes, 62 amines, and 62 carboxylic acids reacting with generally greater than or equal to 90% conversion and purity in Building Block Testing were selected for inclusion in library synthesis (FIG. 4, Tables H–K). When an additional skip codon is added at each position, these numbers allow optimum use of library encoding tags ($2^n$-1 building blocks where n=number of tags at a given position) leaving the "all 0" code unused at each position.

2 spacers+skip codon=3 building blocks at Position 1

2-epoxycyclohexenol enantiomers=2 building blocks at Position 2

3-iodobenzylnitrone isomers=3 building blocks at Position 3

30 alkynes+skip codon 31 building blocks at Position 4

62 amines+skip codon=63 building blocks at Position 5

62 acids+skip codon=63 building blocks at Position 6

Figure 58:
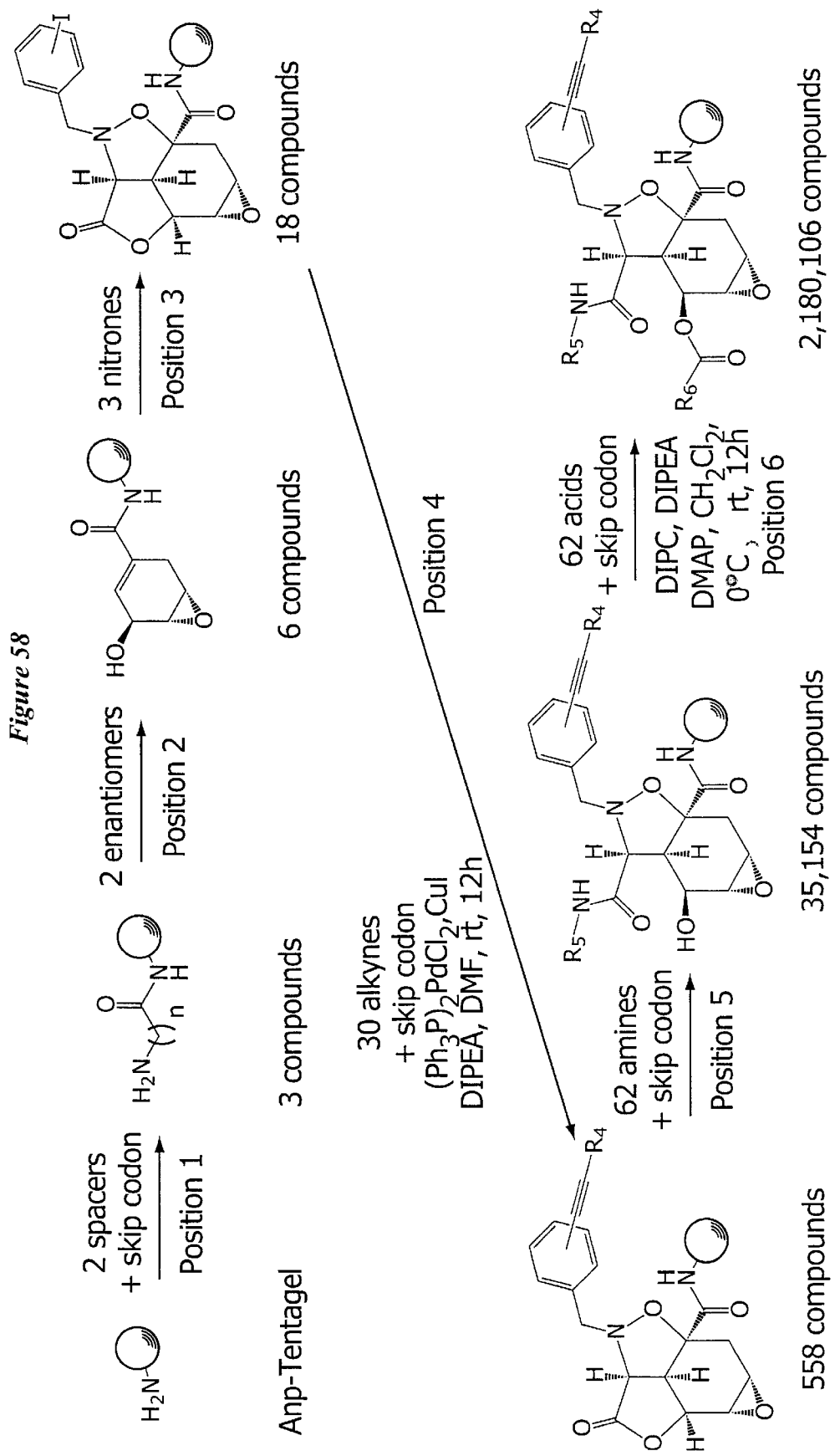
FIG. 58 depicts a synthetic scheme and compound numbers for large library synthesis.

Noting that compounds resulting from the Position 5 amine skip codon with intact butyrolactones would not react with the acids at Position 6, the library was calculated to contain 2, 180, 106 members (FIG. 58). To avoid overrepresentation of lactone-closed compounds, the Position 5 skip codon pool was $\frac{1}{63}^{rd}$ the size of the other 63 pools.

3×2×3×31×1 (×1)=558 lactone-closed compounds

3×2×3×31×62×63=2, 179, 548 lactone-opened compounds

558+2, 179, 548=2, 180, 106 total compounds

We set out to synthesize three copies of the library as it has been calculated that this number is required during screening to ensure 95% confidence that each of the 2, 180, 106 expected compounds is represented at lease once (see http://www.stanford.edu/group/nolan/FACSsern.html on the WWW). 90 $\mu$m Tentagel S $NH_2$ has been estimated to contain 2, 860, 000 beads per gram (Rapp, W. E. Presented at the IBC International Conference on Miniaturization Technologies, Squaw Valley, Calif., February 1998). Thus, 2.2868 g of Tentagel S $NH_2$ was required for the synthesis. Coupling of the ANP photolinker adds mass to the resin and reduces both the effective loading level and the number of beads per gram. The indicated loading level of the Tentagel S $NH_2$ resin used was 0.29 meq/g while the $H_2N$-Anp-Tentagel synthesized above had a calculated loading level of 0.2745 meq/g. Since the loading level is directly proportional to the number of beads per gram, 2.4159 g of $H_2N$-Anp-Tentagel was calculated to contain the same number of beads as 2.2868 g of Tentagel S $NN_2$.

3×2, 180, 106=6, 450, 318 beads 6, 540, 318 beads/2, 860, 000 beads per gram=2.2868 g Tentagel S $NH_2$ 2.2868 g×(0.29/0.2745)=2.4159 g $H_2N$-Anp-Tentagel To allow for resin losses during synthesis and tag verification, 2.5 g of H2N-Anp-Tentagel was used for synthesis of the library.

Methods. Pooling steps were performed by rinsing all of the resin portions into a silanized 50 mL fritted glass tube followed by thorough mixing by $N_2$ bubbling in $CH_2Cl_2$. The resin was then slurried in $CH_2Cl_2$ and transferred via Gilson P5000 pipetteman to a PD-10 column (placed under high vacuum for 30 min then tared) with drainage provided by a VacMan manifold. The resin was washed several times with dist $CH_2Cl_2$, allowed to dry several minutes by drawing air through the tube, then washed down with additional dist $CH_2Cl_2$. The entire tube was then placed under high vacuum for 30 min and reweighed. Splitting steps were accomplished by weighing aliquots of the pooled resin into the appropriate vessels. The last portion of resin was removed from the pooling tube via vacuum cannula transfer to the appropriate vessel. Tagging reactions were performed before each coupling step as described in IX. Binary Encoding below. Coupling reactions for Positions 4–6 were performed in sets of seven to facilitate washing after the reactions. PD-10 and BioSpin® columns were capped at both ends and sealed with teflon tape and parafilm.

Position 1-Spacer Coupling and Deprotection. In each of six PD-10 columns was placed $H_2N$-Anp-Tentagel (416.7 mg, 114.4 $\mu$mol, 1.0 eq) synthesized as above. After tagging, to two of each of the six resin portions was added Fmoc-Gly-OH (102 mg, 343.2 $\mu$mol, 3.0 eq) or Fmoc-Aca-OH (121 mg, 343.2 $\mu$mol, 3.0 eq). The remaining two portions were set aside as the Position 1 skip codon. PyBOP (179 mg, 343.2 $\mu$mol, 3.0 eq) was added to each of the four tubes being coupled. NMP (5 mL) and DIPEA (99.6 $\mu$L, 572.0 mmol, 5.0 eq) were added to each tube with brief vortexing between each addition. After mixing for 80 min, the resin portions were washed with 5×NMP, 5×$CH_2Cl_2$ and a small sample of each treated with the Kaiser ninhydrin test to verify complete coupling. The portions were then treated with 20% piperidine in DMF for 2×15 min, washed as above, and the deprotection reaction verified by Kaiser ninhydrin test.

Position 2-Epoxycyclohexenol Coupling. After pooling, the spacer resins were split into two equal portions in silanized 50 mL fitted glass tubes and tagged. Subsequently, both of the resin portions (1.25 g, 0.27 meq/g avg, 337.5 $\mu$mol, 1.0 eq) were washed with 1×20% DIPEA in $CH_2Cl_2$, 3×$CH_2Cl_2$ and 1×anh NMP. The resin was then bubbled in minimal dist $CH_2Cl_2$ and the appropriate epoxycyclohexenol carboxylic acid, 2 (58 mg, 371.3 $\mu$mol, 1.1 eq) and PyBOP (193.2 mg, 371.3 $\mu$mol, 1.1 eq) were added to each vessel followed by NMP (25 mL). DIPEA (176.4 $\mu$L, 1.01 mmol, 3.0 eq) was added to each tube and the reactions allowed to proceed with $N_2$ bubbling for 9 h. The resins were washed with 5×NMP, 5×$CH_2Cl_2$ and complete conversion verified by Kaiser ninhydrin test.

Position 3-Nitrone Tandem Reaction. After pooling, the epoxycyclohexenol resins were split into six equal portions in PD-10 columns and tagged. To two each of the six tagged resin portions (429 mg, 0.26 meq/g avg, 111.8 $\mu$mol, 1.0 eq, dried under high vacuum) was added the appropriate nitrone carboxylic acid, 7a-c (68.2 mg, 223.6 $\mu$mol, 2.0 eq) and PyBroP (104.2 mg, 223.6 $\mu$mol, 2.0 eq). The tubes were flushed with Ar and cooled to 0° C. in an ice bath. $CH_2Cl_2$ (4 mL), DIPEA (77.9 $\mu$L, 447 $\mu$mol, 4.0 eq), and solid DMAP (15.0 mg, 123.0 $\mu$mol, 1.1 eq) were added in succession with immediate vortexing and recooling to 0° C. between each addition. The tubes were then transferred to a Labquake at 4° C., for 2 h, then warmed to rt and mixed for 2–10 h. After the standard wash (Method B), approx 1 mg of resin was removed from each tube and photolyzed in 30 μL CH$_3$CN for 2 h. Percent conversion was then analyzed by TLC (17:3 CH$_2$Cl$_2$/MeOH and 1:1 CH$_2$Cl$_2$/THF). The process was repeated until no epoxycyclohexenol carboxamides could be detected. LC-MS analysis of photocleaved samples from each of the six pools indicated the presence of all three of the expected tetracycles for each pool.

Position 4-Alkyne Coupling. After pooling, the iodobenzyl tetracycle resins were split into 31 equal portions in 2 mL BioSpin columns and tagged. To each tagged resin portion (86 mg, 0.24 meq/g, 20.85 μmol, 1.0 eq) was added CuI (8.7 mg, 45.87 μmol, 2.2 eq) and (Ph$_3$P)$_2$PdCl$_2$ (16.1 mg, 22.94 μmol, 1.1 eq) or (Ph3P)4Pd (26.5 mg, 22.94 μmol, 1.1 eq). DMF (860 μL) as added and the tubes flushed with Ar and vortexed briefly. DIPEA (monoalkynes: 109 μL, 625.5 μmol, 30 eq; bisalkynes: 254.3 μL, 1.460 μmol, 70 eq) was added followed immediately by the appropriate alkyne (monoalkynes: 417 μmol, 20 eq; bisalkynes 1.043 μmol, 50 eq; see Table H). The tubes were vortexed briefly and mixed for 2 h followed by the standard wash procedure (Method B).

Position 5-Amine Coupling. After pooling, the alkynylbenzyl tetracycle resins were split into 63 portions in 2 mL BioSpin columns such that the 63$^{rd}$ portion was ⅟63$^{rd}$ the weight of the other equal 62 portions. Following the tag coupling, the 63$^{rd}$ position was set aside and to each of the remaining resin portions (40.45 mg, 0.24 meq/g, 9.82 μmol, 1.0 eq) was added 2-hydroxypyriding (non-α-branched amines: 4.67 mg, 49.09 1 mol, 5 eq; α-branched amines; 9.34 mg, 98.17 μmol, 10 eq) as a 404.5 μL stock solution in THF (normal amines) or 3:2 CH$_2$Cl$_2$/DMF (amine hydrochloride salts). The tubes were flushed with Ar and appropriate amine (non-α-branched amines: 245.43 μmol, 25 eq; α-branched amines 490.86 μmol, 50 eq; see Table I) was added to each tube followed by DIPEA (85.5 μL, 490.86 1mol, 50 eq) where appropriate. The tubes were vortexed briefly and mixed for 15 h followed by the standard wash procedure (Method A).

Position 6-Acid Coupling. The first 62 resin portions above were pooled and split into 63 equal portions in 2 mL BioSpin® columns and tagged. The 63$^{rd}$ (amine skip codon) portion above was kept aside. After tagging, to each of the resin portions (37.14 mg, 0.235 meq/g, 8.72 μmol, 1.09 eq) was added 150 μL CH$_2$Cl$_2$. The tubes were flushed with Ar and cooled to 0° C. in an ice bath. The appropriate acids (871.8 μmol, 100 eq, see Table J) were placed in oven-dried 8 mL teflon-capped vials and dissolved in 532 μL CH$_2$Cl$_2$. DIPC (68.5 μL, 435.9 μmol, 50 eq) was added and the mixture stirred for 2 min. DIPEA (75.9 μL, 435.9 μmmol, 50 eq) was added and the mixture stirred another 3 min. Half of each preactivated acid mixture was added to the appropriate BioSpin® column, the tube vortexed briefly and returned to 0° C. DMAP (5.325 mg, 43.58 μmol, 5 eq) was added to each tube as a 50 μL stock solution in CH$_2$Cl$_2$, the tubes vortexed briefly and returned to the ice bath for 30 min. The tubes were warmed to rt, sealed and mixed for 11 h followed by the standard wash procedure (Method A) with an additional 3×20% DIPEA in CH$_2$Cl$_2$ wash.

TABLE H

| BB# | Chemical Name |
|---|---|
| \multicolumn{2}{c}{Spacer, epoxycyclohexenol, and nitrone building blocks used in library synthesis.} | |

| BB# | Chemical Name |
|---|---|
| | Spacer Postion 1 |
| 1 | SKIP CODON |
| 2 | Glycine |
| 3 | 6-Aminocaproic acid |
| | Epoxycyclohexenol Position 2 |
| 1 | (+)-Epoxycyclohexenol |
| 2 | (−)-Epoxycyclohexenol |
| | Nitrone Position 3 |
| 1 | 2-Iodobenzyl nitrone |
| 2 | 3-Iodobenzyl nitrone |
| 3 | 4-Iodobenzyl nitrone |

TABLE I

Alkyne building blocks used in library synthesis.

mono terminal alkyne 417.0 umol alkyne
bis terminal alkyne (italicized) 1042.6 umol alkyne

* BB #23 was tested separately in an NMR scale reaciton (data not shown)

| BB # | Test # | Chemical Name | mg or uL alkyne | MW | d | Vendor | Catalog # | Size |
|---|---|---|---|---|---|---|---|---|
| 1 | ±1 | Acetaldehyde ethyl propargyl acetal | | 128.17 | 0.898 | Aldrich | 33,482-0 | 25 g |
| 2 | ±2 | Butyl 1-methyl-2-propynyl ether, tert- | | 126.20 | 0.795 | Aldrich | 38,425-9 | 100 mL |
| 3 | 3 | Butyl)phenylacetylene, 4-(tert- | | 158.00 | 0.889 | GFS | 115730 | 10 g |
| 4 | ±5,43 | Butynloxy)tetrahydro-2H-pyran, 2-(3- | | 154.21 | 0.984 | Aldrich | 30,586-3 | 5 g |
| 5 | 6 | Chloro-4-ethynylbenzene, 1- | | 136.58 | 1.000 | Aldrich | 20,647-4 | 1 g |
| 6 | 8 | Decadiyne, 1,5- | | 134.22 | 1.000 | GFS | 126706 | 10 g |
| 7 | 10 | *Diethynylbenzene, m-* | | *126.15* | *1.000* | *GFS* | *130100* | *5 g* |
| 8 | 11 | Dimethy-1-butyne, 3,3- | | 82.15 | 0.677 | Aldrich | 24,439-2 | 5 g |
| 9 | 12 | Dimethylamino-2-propyne, 1- | | 83.13 | 0.772 | Aldrich | 14,306-5 | 5 g |
| 10 | 13 | Dodecyne, 1- | | 166.31 | 0.778 | Aldrich | 24,440-6 | 5 g |
| 11 | 46 | Ethynyl-1-cyclohexanol, 1- | | 124.18 | 0.967 | Aldrich | E5,140-6 | 5 mL |
| 12 | 47 | Ethynyl-4-fluorobenzene, 1- | | 120.13 | 1.048 | Aldrich | 40,433-0 | 500 mg |
| 13 | 48 | Ethynyl-9-fluorenol, 9- | | 206.25 | 1.000 | GFS | 143705 | 10 g |
| 14 | 17 | Ethynylcyclohexene, 1- | | 106.17 | 0.903 | Aldrich | 31,657-1 | 5 g |
| 15 | 49 | Ethynylcyclopentanol, 1- | | 110.16 | 0.962 | Aldrich | 13,086-9 | 5 g |
| 16 | 18 | Ethynylestradiol 3-methyl ether | | 310.44 | 1.000 | Aldrich | 85,587-1 | 5 g |
| 17 | 19 | Ethynylpyridine, 2- | | 103.12 | 0.940 | GFS | 143907 | 1 g |
| 18 | 20 | Ethynyltoluene, 4- | | 116.16 | 0.916 | Aldrich | 20,650-4 | 5 g |
| 19 | 22 | Hexyne, 1- | | 82.15 | 0.715 | Aldrich | 24,442-2 | 25 mL |
| 20 | 23 | Hexynenitrile, 5- | | 93.13 | 0.889 | Aldrich | 27,134-9 | 5 g |
| 21 | 24 | Methyl propargyl ether | | 70.09 | 0.830 | Aldrich | 17,719-9 | 10 g |
| 22 | 25 | Methyl-1-buten-3-yne, 2- | | 66.10 | 0.695 | Aldrich | M3,280-1 | 5 g |
| 23 | - | Methyl-3-butyn-2-ol, 2- | | 84.12 | 0.868 | Aldrich | 12,976-3 | 5 mL |
| 24 | 26 | Methyl-N-propargylbenzylamine, N- | | 159.23 | 0.944 | Aldrich | M7,425-3 | 5 g |
| 25 | 27 | *Nonadiyne, 1,8-* | | *120.20* | *0.799* | *Aldrich* | *16,130-6* | *10 g* |
| 26 | 28 | Pentyne, 1- | | 68.12 | 0.691 | Aldrich | 25,656-0 | 5 g |
| 27 | 29 | Phenyl-1-butyne, 4- | | 130.19 | 0.926 | GFS | 184701 | 5 g |
| 28 | 30 | Phenyl-1-propyne, 3- | | 116.16 | 0.934 | Aldrich | 37,684-1 | 5 g |
| 29 | 31 | Phenylacetylene | | 102.14 | 0.930 | Aldrich | 11,770-6 | 25 mL |
| 30 | 37,53 | Propiolaldehyde diethyl acetal | | 128.17 | 0.894 | Aldrich | 30,360-7 | 5 g |
| 31 | | SKIP CODON | | 127.90 | - | | | |
| | | | AVERAGE | 123.85 | | | | |

TABLE J

Amine building blocks used in library synthesis.

beta-branched or greater (mult = 1)  245.43 umol amine (25 eq)
alpha-branched (mult = 2)  490.86 umol amine (50 eq)
2-hydroxypyridine (2-pyr)  1.0  49.09 umol (5 eq) in THF
stock solutions  1.1  49.09 umol (5 eq) in 3:2 CH2Cl2/DMF
 2.0  98.17 umol (10 eq) in THF

| BB # | Test # | Chemical Name | 2-pyr | mg or uL req'd | uL DIPEA | MW | d | mult | salt Aldrich Catalog # | Size |
|---|---|---|---|---|---|---|---|---|---|---|
| 1 | 1 | Allylamine | 1.0 | 18.4 | | 57.10 | 0.761 | 1 | 24,107-5 | 50 mL |
| 2 | 5 | Aminoacetaldehyde diethyl acetal | 1.0 | 35.7 | | 133.19 | 0.916 | 1 | A3,720-0 | 25 mL |
| 3 | 6 | Aminoacetaldehyde dimethyl acetal | 1.0 | 26.7 | | 105.14 | 0.965 | 1 | 12,196-7 | 25 mL |
| 4 | 8 | Aminoethyl)benzenesulfonamide, 4-(2- | 1.0 | 49.1 | | 200.26 | 1.000 | 1 | 27,524-7 | 25 g |
| 5 | 9 | Aminoethyl)morpholine, 4-(2- | 1.0 | 32.2 | | 130.19 | 0.992 | 1 | A5,500-4 | 5 g |
| 6 | 78 | Aminoethyl)pyridine, 2-(2- | 1.0 | 29.4 | | 122.17 | 1.021 | 1 | A5,530-6 | 10 g |
| 7 | 11 | Aminoethyl)pyrrolidine, 1-(2- | 1.0 | 31.1 | | 114.19 | 0.901 | 1 | A5,535-7 | 5 g |
| 8 | 13 | Aminoindan, (R)-(-)-1- | 2.0 | 63.0 | | 133.19 | 1.038 | 2 | 44,534-7 | 1 g |
| 9 | 14 | Aminoindan, (S)-(+)-1- | 2.0 | 63.0 | | 133.19 | 1.038 | 2 | 44,535-5 | 1 g |
| 10 | ±15 | Aminomethyl)-15-crown-5, 2-( | 1.0 | 54.0 | | 249.31 | 1.134 | 1 | 38,841-6 | 1 g |
| 11 | 17 | Aminomethyl)cyclopropane, ( | 1.0 | 21.3 | | 71.12 | 0.820 | 1 | 35,952-1 | 1 mL |
| 12 | 10 | Aminomethyl)pyridine, 2-( | 1.0 | 25.0 | | 108.14 | 1.062 | 1 | A6,540-9 | 5 g |
| 13 | 19,79 | Aminomethyl)pyridine, 3-( | 1.0 | 25.0 | | 108.14 | 1.062 | 1 | A6,540-9 | 5 g |
| 14 | 20 | Aminomethyl)pyridine, 4-( | 1.0 | 24.9 | | 108.14 | 1.065 | 1 | A6,560-3 | 25 g |
| 15 | 23 | Aminopropyl)imidazole, 1-(3- | 1.0 | 29.3 | | 125.18 | 1.049 | 1 | 27,226-4 | 50 g |
| 16 | 24 | Aminopropyltrimethoxysilane, 3- | 1.0 | 42.8 | | 179.29 | 1.027 | 1 | 28,177-8 | 5 mL |
| 17 | 28 | Benzylamine | 1.0 | 26.8 | | 107.16 | 0.981 | 1 | 18,570-1 | 5 g |
| 18 | 30 | Bornylamine, (R)-(+)- | 2.0 | 75.2 | | 153.27 | 1.000 | 2 | 35,993-9 | 500 mg |
| 19 | 31 | Butylamine | 1.0 | 24.3 | | 73.14 | 0.740 | 1 | 23,991-7 | 50 g |
| 20 | 80 | Butylamine, (R)-(-)-sec- | 2.0 | 49.1 | | 73.14 | 0.731 | 2 | 29,664-3 | 1 g |
| 21 | 81 | Butylamine, (S)-(+)-sec- | 2.0 | 49.1 | | 73.14 | 0.731 | 2 | 29,665-1 | 1 g |
| 22 | 32 | Cyclobutylamine | 2.0 | 41.9 | | 71.12 | 0.833 | 2 | 25,518-5 | 1 g |
| 23 | 34 | Cyclohexylamine | 2.0 | 56.2 | | 99.18 | 0.867 | 2 | 24,064-8 | 5 mL |
| 24 | 82 | Cyclohexylethylamine, (R)-(-)-1- | 2.0 | 73.0 | | 127.33 | 0.856 | 2 | 33,650-5 | 5 g |
| 25 | 83 | Cyclohexylethylamine, (S)-(+)-1- | 2.0 | 73.0 | | 127.33 | 0.856 | 2 | 33,651-3 | 5 g |
| 26 | 35 | Cyclopentylamine | 2.0 | 48.4 | | 85.15 | 0.863 | 2 | C11,500-2 | 5 g |
| 27 | 36 | Cyclopropylamine | 2.0 | 34.0 | | 57.10 | 0.824 | 2 | 12,550-4 | 10 g |
| 28 | 38 | Diethoxymethylsilyl)propylamine, 3-( | 1.0 | 51.3 | | 191.35 | 0.916 | 1 | 37,189-0 | 50 mL |
| 29 | 39 | Dimethoxyphenethylamine, 3,4- | 1.0 | 41.4 | | 181.24 | 1.074 | 1 | D13,620-4 | 25 g |
| 30 | 41 | Dimethylaminopropylamine, 3- | 1.0 | 30.9 | | 102.18 | 0.812 | 1 | 24,005-2 | 50 mL |
| 31 | 43 | Ethylamine (2.0M in THF) | 1.0 | 122.7 | | 500.00 | 1.000 | 1 | 39,507-2 | 100 mL |
| 32 | 49 | Fluorobenzylamine, 3- | 1.0 | 28.0 | | 125.15 | 1.097 | 1 | | |
| 33 | 46 | Fluorophenethylamine, 4- | 1.0 | 32.2 | | 139.17 | 1.061 | 1 | 36,182-8 | 10 g |
| 34 | 48 | Geranylamine | 1.0 | 45.4 | | 153.27 | 0.829 | 1 | 41,264-3 | 5 g |
| 35 | 50 | Isopinocampheylamine, (1R,2R,3R,5S)-(-)- | 2.0 | 82.8 | | 153.27 | 0.909 | 2 | 39,165-4 | 5 g |

TABLE J-continued

Amine builing blocks used in library synthesis.

| beta-branched or greater (mult = 1) | | 245.43 umol amine (25 eq) | |
|---|---|---|---|
| alpha-branched (mult = 2) | | 490.86 umol amine (50 eq) | |
| 2-hydroxypyridine (2-pyr) | | 1.0 | 49.09 umol (5 eq) in THF |
| stock solutions | | 1.1 | 49.09 umol (5 eq) in 3:2 CH2Cl2/DMF |
| | | 2.0 | 98.17 umol (10 eq) in THF |

| | | | | | | | | | |
|---|---|---|---|---|---|---|---|---|---|
| 36 | 51 | Isopinocampheylamine, (1S,2S,3S,5R)-(+)- | | | 153.27 | 0.909 | 2 | | 39,166-2 | 5 g |
| 37 | 52 | Isopropylamine | | | 59.11 | 0.694 | 2 | | 10,906-1 | 25 mL |
| 38 | 53 | Methoxybenzylamine, 2- | | | 137.18 | 1.051 | 1 | | 15,988-3 | 5 g |
| 39 | 54 | Methoxybenzylamine, 4- | | | 137.18 | 1.050 | 1 | | M1,110-3 | 25 g |
| 40 | 55 | Methoxyethylamine, 2- | | | 75.11 | 0.864 | 1 | | 24,106-7 | 50 mL |
| 41 | 56 | Methoxyphenethylamine, 2- | | | 151.21 | 1.033 | 1 | | 37,359-1 | 5 g |
| 42 | 57 | Methoxyphenethylamine, 3- | | | 151.21 | 1.038 | 1 | | 27,022-9 | 5 g |
| 43 | 58 | Methoxyphenethylamine, 4- | | | 151.21 | 1.033 | 1 | | 18,730-5 | 5 g |
| 44 | 59 | Methoxypropylamine, 3- | | | 89.14 | 0.874 | 1 | | M2,500-7 | 25 mL |
| 45 | 60 | Methylamine (2.0M in THF) | | | 500.00 | 1.000 | 1 | | 39,505-6 | 100 mL |
| 46 | 85 | Methylbenzylamine, (R)-(+)-a- | | | 121.18 | 0.940 | 2 | | 42,193-6 | 5 mL |
| 47 | 61 | Myrtanylamine, (-)-cis- | | | 153.27 | 0.915 | 1 | | 18,080-7 | 10 g |
| 48 | 86 | Napthyl)ethylamine, (S)-(-)-1-(1- | | | 171.25 | 1.060 | 2 | | 27,745-0 | 5 g |
| 49 | 62 | Napthylenemethylamine, 1- | | | 157.22 | 1.073 | 1 | | 12,703-5 | 5 g |
| 50 | 63 | Nitrobenzylamine hydrochloride, 3- | | | 188.62 | 1.000 | 1 | 1 | 19,166-3 | 5 g |
| 51 | 65 | Octylamine | | | 129.25 | 0.782 | 1 | | O-580-2 | 100 g |
| 52 | 66 | Phenethylamine | | | 121.18 | 0.965 | 1 | | 40,726-7 | 100 mL |
| 53 | 69 | Piperonylamine | | | 151.17 | 1.214 | 1 | | P4,950-3 | 25 g |
| 54 | 70 | Propargyl amine | | | 55.08 | 0.803 | 1 | | P5,090-0 | 5 g |
| 55 | 71 | Tetrahydrofurfurylamine, (R)-(-)- | | | 101.15 | 0.980 | 1 | | 41,293-7 | 1 g |
| 56 | 72 | Tetrahydrofurfurylamine, (S)-(+)- | | | 101.15 | 0.980 | 1 | | 41,294-5 | 1 g |
| 57 | 73 | Tetramethyl-1,3-propanediamine, N,N,2,2- | | | 130.24 | 0.818 | 1 | | 22,741-2 | 25 g |
| 58 | 74 | Thiopheneethylamine, 2- | | | 127.21 | 1.087 | 1 | | 42,327-0 | 5 g |
| 59 | 87 | Trifluoromethoxy)benzylamine, 4-( | | | 191.15 | 1.252 | 1 | | 34,098-7 | 1 g |
| 60 | 88 | Trifluoromethyl)benzylamine, 3-( | | | 175.16 | 1.222 | 1 | | 26,349-4 | 5 g |
| 61 | 76 | Tryptamine | | | 160.22 | 1.000 | 1 | | 19,374-7 | 10 g |
| 62 | 77 | Veratrylamine | | | 167.21 | 1.109 | 1 | | V130-9 | 5 g |
| 63 | | SKIP CODON | | | | | | | | |
| | | | | AVERAGE | 139.95 | | | | | |

TABLE K

Acid building blocks used in library synthesis.

carboxylic acid 871.77 umol (2 × 50 eq)

| BB # | Test # | Chemical Name | mg or uL acid | MW | d | Aldrich Catalog # | Size |
|---|---|---|---|---|---|---|---|
| 1 | 1 | Acetic acid | 49.9 | 60.05 | 1.049 | 33,882-6 | 25 mL |
| 2 | 85 | Acetoxyacetic acid | 102.9 | 118.09 | 1.000 | 30,234-1 | 5 g |
| 3 | 5 | Anisic acid, m- | 132.6 | 152.15 | 1.000 | 11,771-4 | 25 g |
| 4 | 86 | Benzofurancarboxylic acid, 2- | 141.3 | 162.14 | 1.000 | 30,727-0 | 5 g |
| 5 | 8 | Benzoic acid | 106.5 | 122.12 | 1.000 | 24,238-1 | 25 g |
| 6 | 9 | Butynoic acid, 2- | 73.3 | 84.07 | 1.000 | 30,366-6 | 5 g |
| 7 | 11 | Chloropropionic acid, 3- | 94.6 | 108.52 | 1.000 | 13,269-1 | 5 g |
| 8 | 87 | Cinnoline-4-carboxlic acid | 151.8 | 174.16 | 1.000 | C8,215-9 | 1 g |
| 9 | 12 | Crotonic acid | 75.1 | 86.09 | 1.000 | 23,956-9 | 50 g |
| 10 | 14 | Cyanobenzoic acid, 3- | 128.3 | 147.13 | 1.000 | 15,716-3 | 1 g |
| 11 | 15 | Cyanobenzoic acid, 4- | 128.3 | 147.13 | 1.000 | C8,980-3 | 5 g |
| 12 | 16 | Cyclohexanecarboxylic acid | 108.2 | 128.17 | 1.033 | 10,183-4 | 5 g |
| 13 | 17 | Cyclopentanecarboxylic acid | 94.5 | 114.14 | 1.053 | C11,200-3 | 5 g |
| 14 | 18 | Cyclopentylacetic acid | 109.3 | 128.17 | 1.022 | 12,549-0 | 5 g |
| 15 | 19 | Cyclopropanecarboxylic acid | 69.0 | 86.09 | 1.088 | C11,660-2 | 25 g |
| 16 | 20 | Dihydro-2,2-dimethyl-4-oxo-2H-pyran-6-carboxylic acid, 3,4- | 148.3 | 170.16 | 1.000 | 19,572-3 | 5 g |
| 17 | 21 | Dihydro-2-methylbenzoic acid, 1,4- | 120.5 | 138.17 | 1.000 | 30,035-7 | 5 g |
| 18 | 89 | Dimethylacrylic acid, 3,3- | 87.3 | 100.12 | 1.000 | D13,860-6 | 5 g |
| 19 | 25 | Ferroceneacetic acid | 212.8 | 244.08 | 1.000 | 33,504-5 | 500 mg |
| 20 | 27 | Furanacrylic acid, trans-3- | 120.4 | 138.12 | 1.000 | 33,638-6 | 5 g |
| 21 | 28 | Furoic acid, 2- | 97.7 | 112.08 | 1.000 | F2,050-5 | 5 g |
| 22 | 29 | Furoic acid, 3- | 97.7 | 112.08 | 1.000 | 16,339-2 | 5 g |
| 23 | 31 | Hexadienoic acid, 2,4-(Sorbic acid) | 97.8 | 112.13 | 1.000 | 24,010-9 | 50 g |
| 24 | 32 | Isobutyric acid | 80.9 | 88.11 | 0.950 | 24,016-8 | 50 mL |
| 25 | 33 | Isonicotinic acid | 107.3 | 123.11 | 1.000 | I-1,750-8 | 5 g |
| 26 | 34 | Isovaleric acid | 95.0 | 102.13 | 0.937 | 12,954-2 | 5 mL |
| 27 | 35 | Levulinic acid | 89.3 | 116.12 | 1.134 | L200-9 | 50 g |
| 28 | 36 | Linolenic acid | 265.6 | 278.44 | 0.914 | 85,601-0 | 5 g |
| 29 | 37 | Menthoxyacetic acid, (+)- | 183.2 | 214.31 | 1.020 | 44,869-7 | 5 mL |
| 30 | 38 | Menthoxyacetic acid, (-)- | 183.2 | 214.31 | 1.020 | M300-0 | 10 g |
| 31 | 39 | Methacrylic acid | 73.9 | 86.09 | 1.015 | 39,537-4 | 5 mL |
| 32 | 91 | Methoxy-1-indanone-3-acetic acid, 5- | 192.0 | 220.23 | 1.000 | 22,528-2 | 1g |
| 33 | 40 | Methoxyacetic acid | 66.9 | 90.08 | 1.174 | 19,455-7 | 50 g |
| 34 | 41 | Methoxyphenylacetic acid, (R)-(-)-a- | 144.9 | 166.18 | 1.000 | 24,896-7 | 1 g |
| 35 | 43 | Methoxyphenylacetic acid, 2- | 144.9 | 166.18 | 1.000 | 18,065-3 | 5 g |
| 36 | 44 | Methoxyphenylacetic acid, 3- | 144.9 | 166.18 | 1.000 | M1,900-7 | 5 g |
| 37 | 45 | Methoxyphenylacetic acid, 4- | 144.9 | 166.18 | 1.000 | M1,920-1 | 5 g |
| 38 | 46 | Methyl (1S,2R)-(+)-cis-1,2,3,6-tetrahydrophthalate, 1- | 160.6 | 184.19 | 1.000 | 36,728-1 | 1 g |
| 39 | 47 | Methyl glutarate, mono- | 111.9 | 146.14 | 1.139 | M4,735-3 | 5 g |
| 40 | 48 | Methyl phthalate, mono- | 157.1 | 180.16 | 1.000 | 31,764-0 | 25 g |
| 41 | 49 | Methyl terephthalate, mono- | 157.1 | 180.16 | 1.000 | 32,838-3 | 5 g |
| 42 | 92 | Methyl-2-pyrrolecarboxylic acid, 1- | 109.1 | 125.13 | 1.000 | 15,314-1 | 5 g |

| | | | | | | | |
|---|---|---|---|---|---|---|---|
| 43 | 53 | Methylenedioxy)phenylacetic acid, 3,4-( | | 180.16 | 1.000 | 32,967-3 | 5 g |
| 44 | 54 | Methylindole-2-carboxylic acid, 1- | | 175.19 | 1.000 | 13,415-5 | 5 g |
| 45 | 55 | Nicotinic acid | | 123.11 | 1.000 | N785-0 | 5 g |
| 46 | 60 | Norbornaneacetic acid, 2- | | 154.21 | 1.065 | 12,726-4 | 5 g |
| 47 | 62 | Oxo-4-phenyl-3-oxazolidineacetic acid, (S)-(+)-2- | | 221.21 | 1.000 | 39,134-4 | 1 g |
| 48 | 63 | Oxotricyclo[2.2.1.0(2,6)]heptane-7-carboxylic acid, anti-3- | | 152.15 | 1.000 | 32,285-7 | 1 g |
| 49 | 64 | Phenylacetic acid | | 136.15 | 1.081 | P1,662-1 | 5 g |
| 50 | 67 | Picolinic acid | | 123.11 | 1.000 | P4,280-0 | 5 g |
| 51 | 68 | Propionic acid | | 74.08 | 0.993 | 40,290-7 | 100 mL |
| 52 | 69 | Pyrazinecarboxylic acid, 2- | | 124.10 | 1.000 | P5,610-0 | 25 g |
| 53 | 94 | Pyridyl)acrylic acid, trans-3-(3- | | 149.15 | 1.000 | P6,620-3 | 5 g |
| 54 | ±75 | Tetrahydro-2-furoic acid | | 116.12 | 1.209 | 34,151-7 | 5 g |
| 55 | ±76 | Tetrahydro-3-furoic acid | | 116.12 | 1.214 | 33,995-4 | 5 g |
| 56 | 95 | Thienyl)acrylic acid, 3-(2- | | 154.19 | 1.000 | 13,058-3 | 5 g |
| 57 | 80 | Thiophenecarboxylic acid, 2- | | 128.15 | 1.000 | T3,260-3 | 25 g |
| 58 | 81 | Thiophenecarboxylic acid, 3- | | 128.15 | 1.000 | 24,776-6 | 5 g |
| 59 | 96 | Trifluoro-m-toluic acid, a,a,a- | | 190.12 | 1.000 | 18,834-4 | 5 g |
| 60 | 97 | Trifluoro-o-toluic acid, a,a,a- | | 190.12 | 1.000 | 19,688-6 | 5 g |
| 61 | 98 | Trifluoro-p-toluic acid, a,a,a- | | 190.12 | 1.000 | 19,689-4 | 5 g |
| 62 | 84 | Vinylacetic acid | | 86.09 | 1.013 | 13,471-6 | 25 g |
| 63 | | SKIP CODON | | - | - | - | - |
| | | AVERAGE | | 143.07 | | | |

VIII. Binary Encoding:

In our hands, the published procedures (Nestler, H. P.; Bartlett, P. A.; Still, W. C. *J. Org. Chem.* 1994, 59, 4723–4724) gave inconsistent and unsatisfactory results. Substitution of the rhodium bis(trifluoroacetate) catalyst with the bulky rhodium bis(triphenylacetate) catalyst (Callot, J. J.; Metz, F. *Tetrahedron* 1985, 41, 4495–4501) suppressed diazoketone dimerization and substantially improved tag incorporation. The optimized tagging, cleavage, and analysis procedures are presented below.

Methods. HPLC grade CH$_3$CN, spectrophotometric grade DMF, and 99+% decane (Aldrich) were used in bead picking and tag cleavage procedures. DMF and decane were stored over activated 4 Å MS during use. N,O-Bistriinethylsilylacetamide (BSA, Pierce, Rockford, Ill.; 38836) was obtained in ampules and stored as stocks at –20° C. Solvent and BSA aliquots were prepared fresh daily. Ammonium cerium nitrate (CAN, Aldrich, 136 mg) was dissolved in 0.5 mL distd THF and 0.5 mL ddH$_2$O and used within 2 h of preparation.

Sonication was performed in an Ultrasonic Cleaner water bath (Cole-Parmer, Vernon Hills, Ill.; 8892). Centrifugation was performed at 2000×g with a National Labnet C-1200 Mini Centrifuge (VWR 20668-212). EC-GC analysis was performed on a Hewlett-Packard 5890E Series II Plus gas chromatograph equipped with an Ultra-1 crosslinked methyl siloxane 25 m×0.2 mm×0.33 μm film thickness capillary column (HP 19091A-102) and a [63]Ni electron capture detector (HP 19233-69576).

Tag Coupling. The resin to be tagged was washed with 5×distd CH$_2$Cl$_2$. Resins containing free amine functionalities were washed further with 5×0.2% TFA in distd CH$_2$Cl$_2$. Rhodium triphenylacetate prepared as previously described (Callot et al. *Tetrahedron* 1985, 41, 4495) (180 nmol per 100 mg resin) was dissolved in distd EtOAc (1 mL per 100 mg resin) by sonication for 20 sec and added to the resin. The mixture was agitated for 10 min by N$_2$ bubbling, 360° rotation, or gentle vortexing as appropriate for the reaction vessel.

The diazoketone tags synthesized as previously described (Ohlmeyer et al. *Proc. Natl. Acad. Sci. USA* 1993, 90, 10922; Nestler et al. *J. Org. Chem.* 1994, 59, 4723) were dissolved in EtOAc at a concentration of approximately 24 mM. The appropriate stock solutions (500 μL per 100 mg resin) were combined to generate the binary code for each building block (see Supporting Information). The combined stock solution was added to the resin in four equal portions at 30 min intervals. 2 h after the final addition, the resin was drained and the procedure repeated. The second coupling reaction was allowed to proceed overnight, then the resin was washed with 5×CH$_2$Cl$_2$ and 5×CH$_3$CN. Beads from every pool were analyzed for tag incorporation.

Tag Cleavage and Analysis. Several beads were removed from each reaction tube with the aid of a flame-pulled capillary tube and placed on a glass 25×75 mm microscope slide (VWR 48300-025). CH$_3$CN was added to the plate and a "Microliter 705" 50 μL syringe (Hamilton, Reno, Nev.; 80530) with a 22s gauge removeable needle (Hamilton 80464) was used to pick single beads with the aid of an Olympus CK2 microscope. The beads were transferred to 1.1–1.2 I.D.×100 mm glass capillary tubes (Corning, Corning, N.Y.; 9530-2) which had been cut to approximately 3 cm. The tubes were centrifuged briefly, the CH$_3$CN was removed with a "Microliter 701" 10 μL syringe (Hamilton 80330) with a stainless steel taper needle for 320 μm columns (HP 5182-0831), and the tubes were centrifuged again. 2 μL CAN solution then 3 μL decane were added with centrifugation after each addition. The tubes were allowed to stand for 10 min, sonicated for 1 min, then centrifuged. The 10 μL syringe was rinsed with 3×CH₃CN, 3×DMF, 3×decane, and 2 μL neat BSA. The syringe barrel was coated with the BSA plug, which was then ejected. The top decane layer from the capillary tube was drawn into the syringe and the sample plug drawn up and down in the BSA-coated portion of the barrel. The sample was allowed to stand for 1 min inside the syringe, then analyzed by EC-GC using the published method (Ohlmeyer et al. *Proc. Natl. Acad. Sci. USA* 1993, 90, 10922) EC-GC analysis of single bead cleavage samples from all tagged resin portions indicated satisfactory tag incorporation with clearly defined peaks. Complete data (165 pages) are available upon request. To avoid overburdening, a representative example is shown in FIG. 59.

TABLE L

Binary encoding scheme for diazoketone tags.

| Building Block # | Spacer | | Epoxyol | | Nitrone | | Alkyne | | | | | Amine | | | | | | Acid | | | | | |
|---|---|---|---|---|---|---|---|---|---|---|---|---|---|---|---|---|---|---|---|---|---|---|---|
| | 1C | 2C | 1B | 1D | 2B | 2D | 3B | 3D | 4B | 4D | 5D | 6D | 7D | 8B | 8D | 9B | 9D | 10B | 10D | 7A | 8A | 9A | 10A |
| 1 | 0 | 1 | 0 | 1 | 0 | 1 | 0 | 0 | 0 | 0 | 1 | 0 | 0 | 0 | 0 | 0 | 1 | 0 | 0 | 0 | 0 | 0 | 1 |
| 2 | 1 | 0 | 1 | 0 | 1 | 0 | 0 | 0 | 0 | 1 | 0 | 0 | 0 | 0 | 0 | 1 | 0 | 0 | 0 | 0 | 0 | 1 | 0 |
| 3 | 1 | 1 | 1 | 1 | 1 | 1 | 0 | 0 | 0 | 1 | 1 | 0 | 0 | 0 | 0 | 1 | 1 | 0 | 0 | 0 | 0 | 1 | 1 |
| 4 | 1 | 1 | 1 | 1 | 1 | 1 | 0 | 0 | 1 | 0 | 0 | 0 | 0 | 1 | 0 | 0 | 0 | 0 | 0 | 0 | 1 | 0 | 0 |
| 5 | 1 | 1 | 1 | 1 | 1 | 1 | 0 | 0 | 1 | 0 | 1 | 0 | 0 | 0 | 1 | 0 | 1 | 0 | 0 | 0 | 1 | 0 | 1 |
| 6 | 1 | 1 | 1 | 1 | 1 | 1 | 0 | 0 | 1 | 1 | 0 | 0 | 0 | 0 | 1 | 1 | 0 | 0 | 0 | 0 | 1 | 1 | 0 |
| 7 | 1 | 1 | 1 | 1 | 1 | 1 | 0 | 0 | 1 | 1 | 1 | 0 | 0 | 0 | 1 | 1 | 1 | 0 | 0 | 0 | 1 | 1 | 1 |
| 8 | 1 | 1 | 1 | 1 | 1 | 1 | 0 | 1 | 0 | 0 | 0 | 0 | 0 | 1 | 0 | 0 | 0 | 0 | 0 | 1 | 0 | 0 | 0 |
| 9 | 1 | 1 | 1 | 1 | 1 | 1 | 0 | 1 | 0 | 0 | 1 | 0 | 0 | 1 | 0 | 0 | 1 | 0 | 0 | 1 | 0 | 0 | 1 |
| 10 | 1 | 1 | 1 | 1 | 1 | 1 | 0 | 1 | 0 | 1 | 0 | 0 | 0 | 1 | 0 | 1 | 0 | 0 | 0 | 1 | 0 | 1 | 0 |
| 11 | 1 | 1 | 1 | 1 | 1 | 1 | 0 | 1 | 0 | 1 | 1 | 0 | 0 | 1 | 0 | 1 | 1 | 0 | 0 | 1 | 0 | 1 | 1 |
| 12 | 1 | 1 | 1 | 1 | 1 | 1 | 0 | 1 | 1 | 0 | 0 | 0 | 0 | 1 | 1 | 0 | 0 | 0 | 0 | 1 | 1 | 0 | 0 |
| 13 | 1 | 1 | 1 | 1 | 1 | 1 | 0 | 1 | 1 | 0 | 1 | 0 | 0 | 1 | 1 | 0 | 1 | 0 | 0 | 1 | 1 | 0 | 1 |
| 14 | 1 | 1 | 1 | 1 | 1 | 1 | 0 | 1 | 1 | 1 | 0 | 0 | 0 | 1 | 1 | 1 | 0 | 0 | 0 | 1 | 1 | 1 | 0 |
| 15 | 1 | 1 | 1 | 1 | 1 | 1 | 0 | 1 | 1 | 1 | 1 | 0 | 0 | 1 | 1 | 1 | 1 | 0 | 0 | 1 | 1 | 1 | 1 |
| 16 | 1 | 1 | 1 | 1 | 1 | 1 | 1 | 0 | 0 | 0 | 0 | 1 | 0 | 0 | 0 | 0 | 0 | 1 | 0 | 0 | 0 | 0 | 0 |
| 17 | 1 | 1 | 1 | 1 | 1 | 1 | 1 | 0 | 0 | 0 | 1 | 1 | 0 | 0 | 0 | 0 | 1 | 1 | 0 | 0 | 0 | 0 | 1 |
| 18 | 1 | 1 | 1 | 1 | 1 | 1 | 1 | 0 | 0 | 1 | 0 | 1 | 0 | 0 | 0 | 1 | 0 | 1 | 0 | 0 | 0 | 1 | 0 |
| 19 | 1 | 1 | 1 | 1 | 1 | 1 | 1 | 0 | 0 | 1 | 1 | 1 | 0 | 0 | 0 | 1 | 1 | 1 | 0 | 0 | 0 | 1 | 1 |
| 20 | 1 | 1 | 1 | 1 | 1 | 1 | 1 | 0 | 1 | 0 | 0 | 1 | 0 | 0 | 1 | 0 | 0 | 1 | 0 | 0 | 1 | 0 | 0 |
| 21 | 1 | 1 | 1 | 1 | 1 | 1 | 1 | 0 | 1 | 0 | 1 | 1 | 0 | 0 | 1 | 0 | 1 | 1 | 0 | 0 | 1 | 0 | 1 |
| 22 | 1 | 1 | 1 | 1 | 1 | 1 | 1 | 0 | 1 | 1 | 0 | 1 | 0 | 0 | 1 | 1 | 0 | 1 | 0 | 0 | 1 | 1 | 0 |
| 23 | 1 | 1 | 1 | 1 | 1 | 1 | 1 | 0 | 1 | 1 | 1 | 1 | 0 | 0 | 1 | 1 | 1 | 1 | 0 | 0 | 1 | 1 | 1 |
| 24 | 1 | 1 | 1 | 1 | 1 | 1 | 1 | 1 | 0 | 0 | 0 | 1 | 1 | 0 | 0 | 0 | 0 | 1 | 1 | 0 | 0 | 0 | 0 |
| 25 | 1 | 1 | 1 | 1 | 1 | 1 | 1 | 1 | 0 | 0 | 1 | 1 | 1 | 0 | 0 | 0 | 1 | 1 | 1 | 0 | 0 | 0 | 1 |
| 26 | 1 | 1 | 1 | 1 | 1 | 1 | 1 | 1 | 0 | 1 | 0 | 1 | 1 | 0 | 0 | 1 | 0 | 1 | 1 | 0 | 0 | 1 | 0 |
| 27 | 1 | 1 | 1 | 1 | 1 | 1 | 1 | 1 | 0 | 1 | 1 | 1 | 1 | 0 | 0 | 1 | 1 | 1 | 1 | 0 | 0 | 1 | 1 |
| 28 | 1 | 1 | 1 | 1 | 1 | 1 | 1 | 1 | 1 | 0 | 0 | 1 | 1 | 0 | 1 | 0 | 0 | 1 | 1 | 0 | 1 | 0 | 0 |
| 29 | 1 | 1 | 1 | 1 | 1 | 1 | 1 | 1 | 1 | 0 | 1 | 1 | 1 | 0 | 1 | 0 | 1 | 1 | 1 | 0 | 1 | 0 | 1 |
| 30 | 1 | 1 | 1 | 1 | 1 | 1 | 1 | 1 | 1 | 1 | 0 | 1 | 1 | 0 | 1 | 1 | 0 | 1 | 1 | 0 | 1 | 1 | 0 |
| 31 | 1 | 1 | 1 | 1 | 1 | 1 | 1 | 1 | 1 | 1 | 1 | 1 | 1 | 0 | 1 | 1 | 1 | 1 | 1 | 0 | 1 | 1 | 1 |

TABLE L-continued

Binary encoding scheme for diazoketone tags.

| # | | | | | | | | | | | | | | | | | |
|---|---|---|---|---|---|---|---|---|---|---|---|---|---|---|---|---|---|
| 32 | 1 | 1 | 1 | 1 | 1 | 1 | 1 | 1 | 1 | 1 | 1 | 0 | 0 | 0 | 0 | 0 | 1 | 0 | 0 | 0 | 0 | 0 |
| 33 | 1 | 1 | 1 | 1 | 1 | 1 | 1 | 1 | 1 | 1 | 1 | 0 | 0 | 0 | 0 | 1 | 1 | 0 | 0 | 0 | 0 | 1 |
| 34 | 1 | 1 | 1 | 1 | 1 | 1 | 1 | 1 | 1 | 1 | 1 | 0 | 0 | 0 | 1 | 0 | 1 | 0 | 0 | 0 | 1 | 0 |
| 35 | 1 | 1 | 1 | 1 | 1 | 1 | 1 | 1 | 1 | 1 | 1 | 0 | 0 | 0 | 1 | 1 | 1 | 0 | 0 | 0 | 1 | 1 |
| 36 | 1 | 1 | 1 | 1 | 1 | 1 | 1 | 1 | 1 | 1 | 1 | 0 | 0 | 1 | 0 | 0 | 1 | 0 | 0 | 1 | 0 | 0 |
| 37 | 1 | 1 | 1 | 1 | 1 | 1 | 1 | 1 | 1 | 1 | 1 | 0 | 0 | 1 | 0 | 1 | 1 | 0 | 0 | 1 | 0 | 1 |
| 38 | 1 | 1 | 1 | 1 | 1 | 1 | 1 | 1 | 1 | 1 | 1 | 0 | 0 | 1 | 1 | 0 | 1 | 0 | 0 | 1 | 1 | 0 |
| 39 | 1 | 1 | 1 | 1 | 1 | 1 | 1 | 1 | 1 | 1 | 1 | 0 | 0 | 1 | 1 | 1 | 1 | 0 | 0 | 1 | 1 | 1 |
| 40 | 1 | 1 | 1 | 1 | 1 | 1 | 1 | 1 | 1 | 1 | 1 | 0 | 1 | 0 | 0 | 0 | 1 | 0 | 1 | 0 | 0 | 0 |
| 41 | 1 | 1 | 1 | 1 | 1 | 1 | 1 | 1 | 1 | 1 | 1 | 0 | 1 | 0 | 0 | 1 | 1 | 0 | 1 | 0 | 0 | 1 |
| 42 | 1 | 1 | 1 | 1 | 1 | 1 | 1 | 1 | 1 | 1 | 1 | 0 | 1 | 0 | 1 | 0 | 1 | 0 | 1 | 0 | 1 | 0 |
| 43 | 1 | 1 | 1 | 1 | 1 | 1 | 1 | 1 | 1 | 1 | 1 | 0 | 1 | 0 | 1 | 1 | 1 | 0 | 1 | 0 | 1 | 1 |
| 44 | 1 | 1 | 1 | 1 | 1 | 1 | 1 | 1 | 1 | 1 | 1 | 0 | 1 | 1 | 0 | 0 | 1 | 0 | 1 | 1 | 0 | 0 |
| 45 | 1 | 1 | 1 | 1 | 1 | 1 | 1 | 1 | 1 | 1 | 1 | 0 | 1 | 1 | 0 | 1 | 1 | 0 | 1 | 1 | 0 | 1 |
| 46 | 1 | 1 | 1 | 1 | 1 | 1 | 1 | 1 | 1 | 1 | 1 | 0 | 1 | 1 | 1 | 0 | 1 | 0 | 1 | 1 | 1 | 0 |
| 47 | 1 | 1 | 1 | 1 | 1 | 1 | 1 | 1 | 1 | 1 | 1 | 0 | 1 | 1 | 1 | 1 | 1 | 0 | 1 | 1 | 1 | 1 |
| 48 | 1 | 1 | 1 | 1 | 1 | 1 | 1 | 1 | 1 | 1 | 1 | 1 | 0 | 0 | 0 | 0 | 1 | 1 | 0 | 0 | 0 | 0 |
| 49 | 1 | 1 | 1 | 1 | 1 | 1 | 1 | 1 | 1 | 1 | 1 | 1 | 0 | 0 | 0 | 1 | 1 | 1 | 0 | 0 | 0 | 1 |
| 50 | 1 | 1 | 1 | 1 | 1 | 1 | 1 | 1 | 1 | 1 | 1 | 1 | 0 | 0 | 1 | 0 | 1 | 1 | 0 | 0 | 1 | 0 |
| 51 | 1 | 1 | 1 | 1 | 1 | 1 | 1 | 1 | 1 | 1 | 1 | 1 | 0 | 0 | 1 | 1 | 1 | 1 | 0 | 0 | 1 | 1 |
| 52 | 1 | 1 | 1 | 1 | 1 | 1 | 1 | 1 | 1 | 1 | 1 | 1 | 0 | 1 | 0 | 0 | 1 | 1 | 0 | 1 | 0 | 0 |
| 53 | 1 | 1 | 1 | 1 | 1 | 1 | 1 | 1 | 1 | 1 | 1 | 1 | 0 | 1 | 0 | 1 | 1 | 1 | 0 | 1 | 0 | 1 |
| 54 | 1 | 1 | 1 | 1 | 1 | 1 | 1 | 1 | 1 | 1 | 1 | 1 | 0 | 1 | 1 | 0 | 1 | 1 | 0 | 1 | 1 | 0 |
| 55 | 1 | 1 | 1 | 1 | 1 | 1 | 1 | 1 | 1 | 1 | 1 | 1 | 0 | 1 | 1 | 1 | 1 | 1 | 0 | 1 | 1 | 1 |
| 56 | 1 | 1 | 1 | 1 | 1 | 1 | 1 | 1 | 1 | 1 | 1 | 1 | 1 | 0 | 0 | 0 | 1 | 1 | 1 | 0 | 0 | 0 |
| 57 | 1 | 1 | 1 | 1 | 1 | 1 | 1 | 1 | 1 | 1 | 1 | 1 | 1 | 0 | 0 | 1 | 1 | 1 | 1 | 0 | 0 | 1 |
| 58 | 1 | 1 | 1 | 1 | 1 | 1 | 1 | 1 | 1 | 1 | 1 | 1 | 1 | 0 | 1 | 0 | 1 | 1 | 1 | 0 | 1 | 0 |
| 59 | 1 | 1 | 1 | 1 | 1 | 1 | 1 | 1 | 1 | 1 | 1 | 1 | 1 | 0 | 1 | 1 | 1 | 1 | 1 | 0 | 1 | 1 |
| 60 | 1 | 1 | 1 | 1 | 1 | 1 | 1 | 1 | 1 | 1 | 1 | 1 | 1 | 1 | 0 | 0 | 1 | 1 | 1 | 1 | 0 | 0 |
| 61 | 1 | 1 | 1 | 1 | 1 | 1 | 1 | 1 | 1 | 1 | 1 | 1 | 1 | 1 | 0 | 1 | 1 | 1 | 1 | 1 | 0 | 1 |
| 62 | 1 | 1 | 1 | 1 | 1 | 1 | 1 | 1 | 1 | 1 | 1 | 1 | 1 | 1 | 1 | 0 | 1 | 1 | 1 | 1 | 1 | 0 |
| 63 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |

Note that tags 5B, 6B, and 7B were not used.

Example 6

Experimentals for Isoquinuclidine-based Library

General Methods: All reactions were performed on Tentagel polystyrene resin purchased from Rapp Polymere, Germany. In addition to standard polyethylene glycol spacers, the resin was charged with a photocleavable linker element. Cleavage of compounds from solid phase at any step of synthesis was carried out by placing resin in a minimal amount of acetonitrile followed by exposure to UV (300 nm) for approximately 1 hour. All reactions were carried out at room temperature unless otherwise noted.

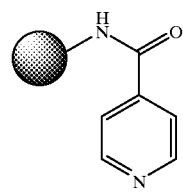

Isonicotinamide. 1 g Tentagel resin (0.24 mmol/g) was placed in a 10 mL reaction barrel and allowed to swell in dry $CH_2Cl_2$. Isonicotinoyl chloride hydrochloride was added (213.61 mg, 5 eq) and the resulting suspension mixed well. Freshly distilled diisopropylethylamine was slowly added (0.641 mL, 15 eq) resulting in dissolution of any remaining insoluble acid chloride. The reaction was shaken and allowed to proceed for 15 min., after which the resin was drained of reactants and washed well with $CH_2Cl_2$, THF, and iPrOH 3 times. The resin was given a final wash with trimethylorthoformate (TMOF) followed by anhydrous THF, and dried under a nitrogen stream. $^1$H NMR: δ 8.77 (dd, J=4.46, 1.68 Hz, 2 H), 7.65 (dd, J=4.42, 1.72, 2H), 6.08 (d, J=107 Hz, 2H); $^{13}$C NMR: δ 167.22, 150.73, 140.43, 121.07; IR (NaCl plate): 3327.6, 3059.4, 1682.1, 1622.3 cm$^{-1}$.

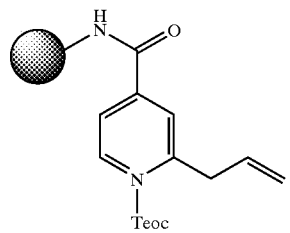

1 g resin (approx. 0.24 mmol/g) was swelled with dry CH$_2$Cl$_2$ in a 10 mL reaction barrel. Allyltributyltin was added (1.86 mL, 25 eq) and the resulting solution shaken well and cooled to 0° C. Teoc-Cl (trimethylsilylethoxycarbonylc chloride) was then added (1.08 mL, 25 eq), the reaction barrel vented, and shaken for 6 hours, warning to room temperature after the first hour. The reaction vessel was then drained and the resin washed with alternating solutions of anhydrous hexane and CH$_2$Cl$_2$, THF, DMF, MeCN, and iPrOH (3×). The final wash of TMOF followed by THF dried the resin, which was stored under N$_2$. The product generated in this step is vulnerable to UV-induced photorearrangement; the data shown below pertain to desired product only. $^1$H NMR: δ 6.90, 6.78, (d, J=15.5 Hz), 6.22 (m), 5.95–5.55 (m), 5.09, 5.01, 4.95 (m), 4.45, 4.40 (m), 2.35 (dm), 1.05 (m), 0.05. HPLC ret (reverse phase): 2.488 min. MS: M$^+$=309.

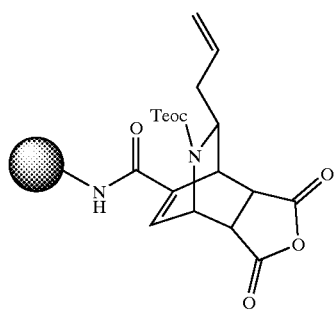

1 g resin (approx.0.24 mmol/g) was placed dry into a 20 mL screw top glass vial. Anhydrous toluene (8 mL) was then added, and the solution shaken to disperse the resin uniformly. 3 eq maleic anhydride (70 mg) were dissolved in a minimal amount of anhydrous acetonitrile, and added to the resin. The vial threads were sealed with teflon tape, the reaction heated to 80° C. for 12 hr, and the vessel shaken well every 3 hours. The resin was filtered into a fritted reaction vessel and the glass vial washed with CH$_2$Cl$_2$ to remove any adherent beads. The resin was washed 3× with CH$_2$Cl$_2$, THF, DMF, MeCN, and iPrOH. TMOF and THF solutions were used to dry the resin, which was stored under N$_2$. $^1$H NMR: δ 7.15, 7.05 (d), 6.31, 5.79 (m), 5.49, 5.37 (t), 5.17–5.05 (m), 4.26 (m), 3.91, 3.31 (dd), 3.21, 3.11, 2.59, 2.49, 1.86 (m), 1.69, 1.39, 1.05 (m), 0.07. HPLC ret. (reverse phase): 2.224 min. MS: M$^+$=407.

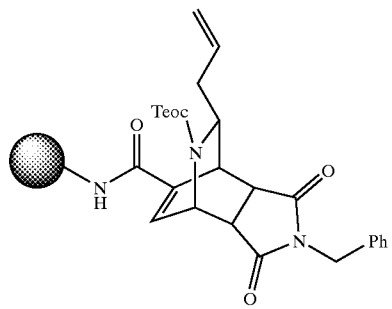

1 g resin (approx. 0.24 mmol/g) was placed dry into a 20 mL screw top glass vial. Anhydrous toluene (8 mL) was then added, and the solution shaken to disperse the resin uniformly. 5 eq benzylamine (0.131 mL) was then added to the resin. The vial threads were sealed with teflon tape, the reaction heated to 80° C. for 12 hr., and the vessel shaken well every 3 hours. The resin was filtered into a fritted reaction vessel and the glass vial washed with CH$_2$Cl$_2$ to remove any adherent beads. The resin was washed 3× with CH$_2$Cl$_2$, THF, DMF, MeCN, and iPrOH. TMOF and THF solutions were used to dry the resin, which was stored under N$_2$. HPLC ret (reverse phase): 2.545 min. MS: M$^+$+Na=518.

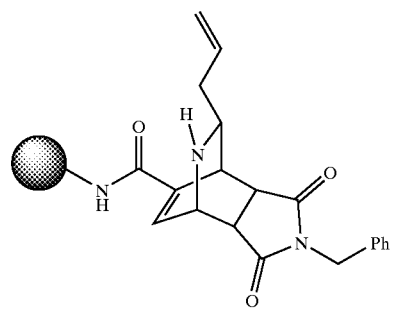

1 g resin (approx. 0.24 mmol/g) was swelled with CH$_2$Cl$_2$ in a 10 mL reaction vessel. The resin was drained and CH$_2$Cl$_2$ sufficient to cover the resin added. Approximately 2 mL TFA was added, the reaction vessel shaken, and vented. Shaking was continued for 10 min, after which the solution was drained, and the TFA treatment repeated for 15 min. The resin was drained, fresh CH$_2$Cl$_2$ added, and approximately 1 mL DIPEA (diisopropylethylamine) added to neutralize any residual TFA. The resin was washed with CH$_2$Cl$_2$, THF, DMF, MeCN, and iPrOH (3 times). TMOF and THF solutions were used to dry the resin, which was stored under N$_2$. $^1$H NMR: δ 7.35 (m), 7.13 (d), 6.80 (d), 6.05 (m), 5.75 (m), 5.65 (m), 5.03 (m), 4.7–4.45 (d), 3.6 (d), 3.25 (dd), 3.11 (td), 3.08 (dd), 2.80 (m), 1.90 (m), 1.79 (dm), 1.37 (m). HPLC ret (reverse phase): 1.808 min. MS: M$^+$=352.

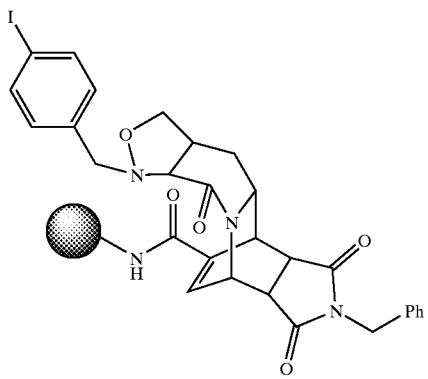

1 g resin (approx. 0.24 mmol/g) was swelled with 7 mL CH$_2$Cl$_2$ in a 10 mL reaction vessel. 25 eq. p-iodobenzylnitrone (1.82 g) was added and the vessel shaken to dissolve the solid material. 25 eq. PyBroP (2.79 g) was then added, and the mixture shaken again. Upon dissolution of all solid reagents, the vessel was cooled to −20° C. for 6 hr. Subsequent washing was performed 3× with CH$_2$Cl$_2$, THF, DMF, MeCN, and iPrOH. TMOF and THF solutions were used to dry the resin, which was then stored under N$_2$. $^1$H NMR: δ 7.91 (d), 7.54 (d), 7.30 (m), 7.02 (t), 6.53 (dd), 5.75 (dd), 5.09 (t), 4.60 (t), 4.07 (t), 3.81, 3.76 (m), 3.65 (d), 3.4–3.3 (m), 3.14, 1.95 (m), 1.78. HPLC ret. (reverse phase): 2.182 min. MS: M$^+$=639.

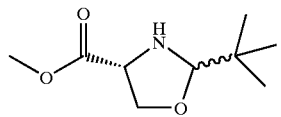

Methyl(4R)-2-(t-butyl)-3-(1,3)-oxazolidine-4-carboxylate. (Dieter Seebach and Johannes D. Aebi, *Tetrahedron Letters*, Vol. 25, No. 24, pp. 2545–2548) To a 100 mL round bottomed flask equipped with a stir bar and Dean Stark trap and purged with N$_2$ was added D-serine methyl ester hydrochloride (6.2 g, 40 mmol, 1 eq.) followed by n-pentane (50 mL). Pivaldehyde (8.8 mL, 80 mmol, 2 eq) was added to the mixture followed by triethylamine (6.1 mL, 44 mmol, 1.1 eq). The mixture was heated to reflux for 16 h with removal of water. The mixture was cooled to 23° C., filtered, washed with ether (50 mL) and concentrated to an oil which was used without further purification in the next step.

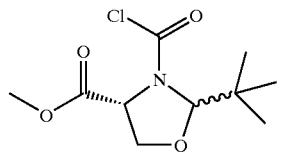

Methyl(2S,4R)-2-(t-butyl)-3-chlorocarbonyl-(1,3)-oxazolidine-4-carboxylate. Jaques Streith, Arnaud Boiron, Thierry Sifferlen, Christiane Strehler, Theophile Tschamber, Tetrahedron Letters, Vol. 35, No. 23, pp. 3927–3930). To a stirred solution of oxazolidine (7.02 g, 37.5 mmol, 1 eq) in CH$_2$Cl$_2$ (141 ml) at −15° C. was added a 1.93 M solution of phosgene in toluene (29 ml, 56 mmol, 1.5 eq) dropwise. Triethyl amine (6.7 mL, 48 mmol, 1.3 eq) was added dropwise and the reaction was allowed to warm to 23° C. After 2 h N$_2$ was bubbled through the reaction mixture in order to remove excess phosgene. The solvents were evaporated and the residue was slurried with AcOEt/cyclohexane (3:7) and the mixture was filtered. The filtrate was concentrated and purified by flash chromatography (rf=). Recrystallization from pentane yielded Methyl(2S,4R)-2-(t-butyl)-3-chlorocarbonyl-(1,3)-oxazolidine-4-carboxylate (7.9 g, 85%), m.p.=78° C. NMR (400 MHz, CDCl$_3$): δ 5.17 (s, 1H, C2-H), 4.89 (dd, 1H, J=7.9, 4.8, C4-H), 4.39 (dd, 1H, J=8.8, 4.5, C5-Hβ), 4.22 (dd, 1H, J=8.8, 8.1, C5-Hα), 3.81 (s, 3H, CO$_2$CH$_3$), 0.97 (s, 9H, C(CH$_3$)$_3$).

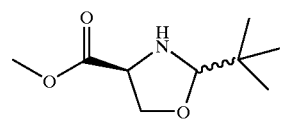

Methyl(4S)-2-(t-butyl)-3-(1,3)-oxazolidine-4-carboxylate. (Dieter Seebach and Johannes D. Aebi, *Tetrahedron Letters*, Vol. 25, No. 24, pp. 2545–2548). To a 100 mL round-bottomed flask equipped with stir bar and Dean Stark trap and purged with N$_2$ was added L-serine methyl ester hydrochloride (6.2 g, 40 mmol, 1 eq) followed by n-pentane (50 mL). Privaldehyde (8.8 mL, 80 mmol, 2 eq) was added to the mixture followed by triethylamine (6.1 mL, 44 mmol, 1.1 eq). The mixture was heated to reflux for 16 h with removal of water. The mixture was cooled to 23° C., filtered, washed with ether (50 mL) and concentrated to an oil which was used without further purification in the next step.

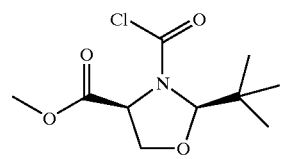

Methyl(2R,4S)-2-(t-butyl)-3-chlorocarbonyl-(1,3)-oxazolidine-4-carboxylate. (Jacques Streith, Arnaud Boiron, Thierry Sifferlen, Christiane Strehler, Theophile Tschamber *Tetrahedron Letters*, Vol. 35, No. 23, pp. 3927–3930). To a stirred solution of oxazolidine (7.02 g, 37.5 mmol, 1 eq) in CH$_2$Cl$_2$ (141 ml) at −15° C. was added a 1.93 M solution of phosgene in toluene (29 mL, 56 mmol, 1.5 eq) dropwise. Triethyl amine (6.7 mL, 48 mmol, 1.3 eq) was added dropwise and the reaction was allowed to warm to 23° C. After 2 h N$_2$ was bubbled through the reaction mixture in order to remove excess phosgene. The solvents were evaporated and the residue was slurried with AcOEt/cyclohexane (3:7) and the mixture was filtered. The filtrate was concentrated and purified by flash chromatography (rf=). Recrystallization from pentane yielded Methyl(2R,4S)-2-(t-butyl)-3-chlorocarbonyl-(1,3)-oxazolidine-4-carboxylate (7.9 g, 85%), m.p.=78° C. $^1$H NMR (400 MHz, CDCl$_3$): d 5.17 (s, 1H, C2-H), 4.89 (dd, 1H, J=7.9, 4.8, C4-H), 4.39 (dd, 1H, J=8.8, 4.5, C5-Hβ), 4.22 (dd, 1H, J=8.8, 8.1, C5-Hα), 3.81 (s, 3H, CO$_2$CH$_3$), 0.97 (s, 9H, C(CH$_3$)$_3$).

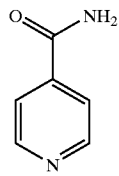

Isonicotinamide. 3-Amino-3-(2'-nitrophenyl)-2,2-dimethylproponylcarboxamide-Tentagel resin (200 mg, 0.27 meq/g, 54 µmol, 1 eq) was placed in a PD-10 column. Isonicotinoylchloride hydrochloride (48 mg, 270 µmol, 5 eq), distilled $CH_2Cl_2$ (2.4 mL), and DIPEA (141 µl, 810 µmol, 15 eq) were added in sequence. After 1 h the resin was washed 3×DMF, 3×IPA, 3×DMF, 3×$CH_2Cl_2$, 3×DMF, 3×$CH_3CN$, 3×THF, 3×$CH_2Cl_2$ to yield isonictinoyl-3-Amino-3-(2'-nitrophenyl)-2,2-dimethylproponylcarboxamide-Tentagel resin which was negative to Kaiser ninhydrin test. Photolysis of the resin yielded the crude isonicotinamide, as a yellow oil. IR (NaCl) 3175, 1684, 1554, 1506, 1412, 612 cm$^{-1}$; $^1$H NMR (500 MHz, $CD_3CN$): δ 8.70 (br m, 2H), 7.65 (dd, J=4.4, 1.7, 2H). EI-MS (Direct) m/z (rel int): 122 (M), 100). 106 (33).

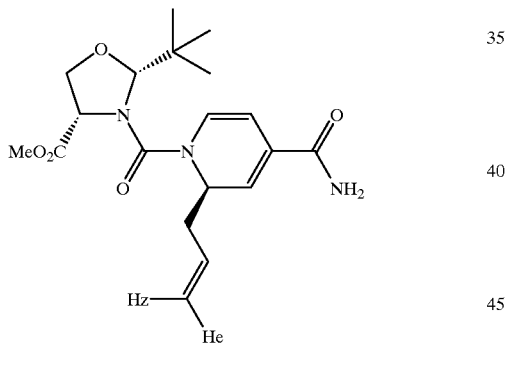

Methyl(2R,2'R,4'S)-3'-[2-allyl-4-carboxamide-1,2-dihydro-1-pyridinyl]-carbonyl-2'-t-butyl-(1,3)-oxazoline-4-carboxylate. Isonicotinamide resin (80 mg, 0.27 meq/g, 21.6 µmol, 1 eq) was placed in a new PD-10 column along with methyl(2R,4S)-2-(t-butyl)-3-chlorocarbonyl-(1,3)-oxazolidine-4-carboxylate (54 mg, 216 µmol, 10 eq), NaI (65 mg, 432 µmol, 20 eq) and toluene (800 µl). The mixture was agitated by 360 rotation for 5 days during which time the resin changed colors from tan to burgundy, the resin was filtered and washed with toluene 10×1 mL, resuspended in toluene (900 µL), cooled to 0° C. and treated with allyl-tributyltin (860 µl, 2.8 mmol, 130 eq). The mixture was agitated by 360 rotation for 1 day. The resin washed with hexanes 50×1 mL, $CH_2Cl_2$ 50×1 mL.

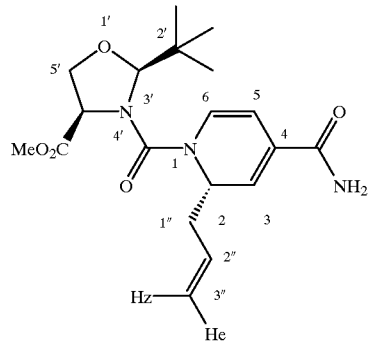

Methyl(2S,2'S,4'R)-3'-[2-allyl-4-carboxamide-1,2-dihydro-1-pyridinyl]-carbonyl-2'-t-butyl-(1,3)-oxazoline-4-carboxylate. Isonicotinamide resin (80 mg, 0.27 meq/g, 21.6 umol, 1 eq) was placed in a new PD-10 column along with methyl(2S,4R)-2-(t-butyl)-3-chlorocarbonyl-(1,3)-oxazoline-4-carboxylate (54 mg, 216 µmol, 10 eq), NaI (65 mg, 432 ummol, 20 eq) and toluene (800 µl). The mixture was agitated by 360 rotation for 5 days during which time the resin. changed colors from tan to burgundy. The resin was filtered and washed with toluene 10×1 mL, resuspended in toluene (900 µL), cooled to 0° C. and treated with allyltributyltin (860 µl, 2.8 mmol, 130 eq). The mixture was agitated by 360 rotation for 1 day. The resin was washed with hexanes 50×1 mL, $CH_2Cl_2$ 50×1 mL.

Solution Phase Studies

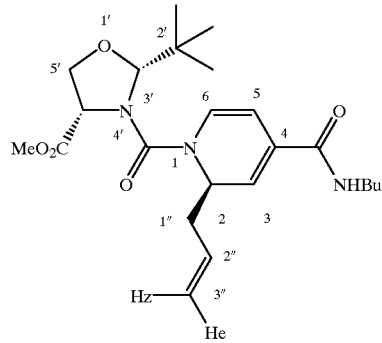

Methyl(2R,2'R,4'S)-3'-[2-allyl-4-butylcarboxamide-1,2-dihydro-1-pyridinyl]-carbonyl-2'-t-butyl-(1,3)-oxazoline-4-carboxylate. To a flame dried 5 mL round-bottomed flask equipped with stir bar and purged with $N_2$ was added N-butyl isonicotinamde (50 mg, 280 µmol, 1 eq), Methyl (2R,4S)-2-(t-butyl)3-chlorocarbonyl-(1,3)-oxazolidine-4-carboxylate (70 mg, 280 µmol, 1 eq), NaI (84 mg, 560 µmol, 2 eq) and toluene (1.2 mL). The flask was capped with a glass-stopper, sealed with parafilm, and stirred for 5 days. The flask was then fitted with a nitrogen inlet and cooled to 0° C. Allyltributyltin (86 µl, 308 µmol, 1.1 eq) was added and the flask was allowed to warm to 23° C. with stirring ovemite. The mixture was filtered, concentrated and purified by column chromatography ($SiO_2$, 10% MeOH/$CHCl_3$) to afford 109 mg, 90% of Methyl(2R,2'R,4'S)-3'-[2-allyl-4- butylcarboxamide-1,2-dihydro-1-pyridinyl]carbonyl-2'-t-butyl-(1,3)-oxazoline-4-carboxylate. $^1$H NMR (400 MHz, CDCl$_3$): 6.99 (d, 1H, J=7.6, C5-H), 6.17 (d, 1H, J=6.2, C6-H), 5.8 (m, 1H, C1"-H), 5.72 (t, 1H, NH), 5.67 (dd, 1H, J=7.6, 1.7, C3-H), 5.43 (s, 1H, C2'-H), 5.05 (m, 1H, C3"-H$_c$), 5.01 (br s, 1H, C3"-H$_\alpha$), 4.74 (dd, 1H, J=6.3, C4'-H), 4.36 9d, 1H, J=8.8, C5'-H$_\alpha$), 4.09 (d, 1H, J=6.03, C5'-H$_\beta$), 3.79 (m, 1H, C2-H), 3.75 (s, 3H, CO$_2$CH$_3$), 3.32 (m, 2H, NHCH$_2$), 2.4–2.3 (m, 2H, C1"-H), 1.4–1.2 (m, 4H, (CH$_2$)$_2$), 0.97 (s, 9H, C2'-t-Bu), 0.96 (t, 3H, CH$_3$).

What we claim is:

1. A library of compounds having the structure:

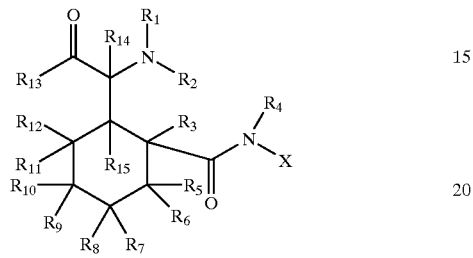

wherein $R_1$, $R_4$–$R_7$, $R_{10}$, $R_{11}$, $R_{14}$ and $R_{15}$ are each independently hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine, or substituted or unsubstituted heterocycle wherein said heterocycle is substituted with 1–5 substituents selected from the group consisting: of lower alkyl, halo, hydroxy, amino, thio, lower alkoxy, lower alkylthio, lower alkylamino, nitro, phenoxy, and benzyloxy;

wherein $R_2$ and $R_3$ taken together comprise —O— whereby a N—O linkage is generated, or alternatively, $R_2$ is hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, and benzyloxy; and $R_3$ is $OR_{16}$, wherein $R_{16}$ is hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, and benzyloxy;

wherein $R_8$ and $R_9$ taken together comprise an epoxide moiety, or alternatively, $R_8$ is hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulflhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, benzyloxy, and $R_9$ is $OR_{17}$, wherein $R_{17}$ is hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, and benzyloxy;

wherein $R_{12}$ and $R_{13}$ taken together is —O— whereby a γ-lactone is generated, or alternatively, $R_{12}$ is hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, and benzyloxy, and $R_{13}$ is $OR_{18}$ or $NHR_{18}$, wherein $R_{18}$ is hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, and benzyloxy; and wherein X is a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine, substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, and benzyloxy, or is hydrogen, solid support unit, or polymer.

2. The library of claim 1 produced by the method comprising:

(a) synthesizing one or more expoxyol templates having the following structure:

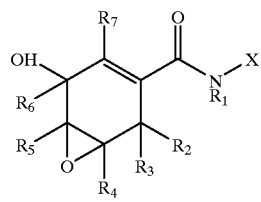

wherein R₁–R₇ each independently comprises hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, benzyloxy; and wherein X is any of the above, hydrogen, a solid support unit or a polymer;

(b) reacting one or more nitrone carboxylic acids with said one or more expoxyol templates to yield one or more diversifiable tetracyclic scaffolds having the following structure:

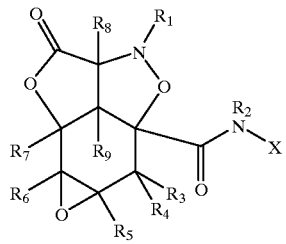

wherein R₁–R₉ independently comprises hydrogen or a linear or branched, substituted or unsubstituted alkyl, aryl, alkenyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, alkynyl, halogen, cyano, sulfhydryl, carbamoyl, nitro, trifluoromethyl, phosphine or substituted or unsubstituted heterocycle wherein said heterocycle is substituted with 1–5 substituents selected from the group consisting of lower alkyl, halo, hydroxy, amino, thio, lower alkoxy, lower alkylthio, lower alkylamino, nitro, phenoxy, and benzyloxy; and wherein X is any of the above, hydrogen, a solid support unit or a polymer;

(c) diversifying said one or more tetracyclic scaffold structures at one or more reactive moieties with one or more reagents, to generate a library having one or more compounds.

3. The library of claim 1, wherein the library has the structure:

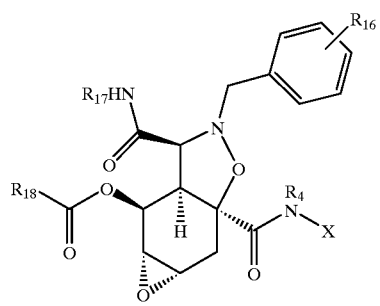

wherein R₄ is hydrogen; X is a solid support unit or polymer; R₁₆ is a halogen or an alkyne substituted with a linear or branched, substituted or unsubstituted alkyl, cycloalkyl, aryl, alkenyl, alkynyl, alkoxy, thioalkyl, heteroaryl, heterocycle, polycycle, sulfoxide, trialkylsilyl, dialkylarylsilyl, diarylalkylsilyl, triarylsilyl, trialkoxysilyl, amino, phosphine, cyano, hydroxy, or thio; R₁₇ is hydrogen or a linear or branched, substituted or unsubstituted alkyl, cycloalkyl, aryl, alkenyl, alkynyl, heteroaryl, heterocycle, polycycle, sulfoxide, trialkylsilyl, dialkylarylsilyl, diarylalkylsilyl, triarylsilyl, trialkoxysilyl, amino, phosphine, cyano, hydroxy, or thio; R₁₈ is hydrogen or a linear or branched, substituted or unsubstituted alkyl, cycloalkyl, aryl, alkenyl, alkynyl, heteroaryl, heterocycle, polycycle, sulfoxide, trialkylsilyl, dialkylarylsilyl, diaryl alkylsilyl, triarylsilyl, trialkoxysilyl, amino, phosphine, cyano, hydroxy, thio, or ferrocene.

4. The library of claim 3, produced by the method comprising:

(a) synthesizing one or more eopoxyol templates having the structure:

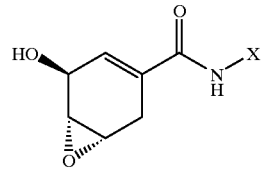

wherein X is hydrogen, a solid support unit, or polymer;

(b) reacting one or more nitrone carboxylic acids with said one or more epoxyol templates to yield one or more diversifiable tetracyclic scaffolds having the structure:

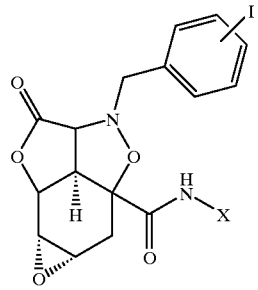

wherein X is hydrogen, a solid support unit, or a polymer;

(c) diversifying said one or more tetracyclic scaffold structures at one or more reactive moieties with one or more reagents to generate a library having one or more compounds.

5. The library of claim 4, wherein the step of diversifying further comprises: reacting the iodoaryl group with one or more terminal alkynes selected from the group consisting of acetaldehyde ethyl propargyl acetal, tert-butyl 1-methyl-2-propynyl ether, 4-(tert-butyl)phenylacetylene, tert-butyldimethylsilyl acetylene, 2-(3-butynloxy)tetrahydro-2H-pyran, 1-chloro-4-ethynylbenzene, 1,4-decadiyne (50% in hexane), 1,5-decadiyne, 3-dibutylamino-1-propyne, m-diethynylbenzene, 3,3-dimethyl-1-butyne, 1-dimethylamino-2-propyne, 1-dodecyne, ethyl ethynyl ether (50% in hexanes), ethynyl p-tolyl sulfone, 1-ethynyl-4-fluorobenzene, 1-ethynylcyclohexene, ethynylestradiol 3-methyl ether, 2-ethynylpyridine, 4-ethynyltoluene, 1,5-hexadiyne (50% in hexane), 1-hexyne, 5-hexynenitrile, methyl propargyl ether, 2-methyl-1-buten-3-yne, methyl-N-propargylbenzylamine, 1,8-nonadiyne, 1-pentyne, 4-phenyl-1-butyne, 3-phenyl-1-propyne, phenylacetylene, propargyl ether, propargyn-1 H-benzotriazole, N-(propargyloxy) phthalimide, N-propargylphthalimide, propargyltriphenylphosphonium bromide, proiolaldehyde diethyl acetal, tetrahydro-2-(2-propynyloxy)-2H-pyran, triethylsilylacetylene, tripropargylamine, 2-(3-butynloxy)tetrahydro-2H-pyran, 3,5-dimethyl-1-hexyn-3-ol, 1,1-diphenyl-2-propyn-1-ol, 1-ethynyl-1-cyclohexanol, 1-ethynyl-4-fluorobenzene, 9-ethynyl-9-fluorenol, 1-ethynylcyclopentanol, 1-heptyne, 3-methyl-1-pentyn-3-ol, 2-phenyl-3-butyn-2-ol, and propiolaldehyde diethyl acetal;

reacting the lactone functionality with one more amines selected from the group consisting of allylamine, 2-amino-1-propene-1,1,3-tricarbonitrile, 3-amino-1H-isoindole hydrochloride, 3-amino-5-methylisoxazole, aminoacetaldehyde diethyl acetal, aminoacetaldehyde dimethyl acetal, aminoacetonitrile bisulfate, 4-(2-aminoethyl)benzenesulfonamide, 4-(2-aminoethyl) morpholine, 2-(2-aminomethyl)pyridine, 1-(2-aminoethyl)pyrrolidine, 2-aminoindan hydroxchloride, (R)-(-)-1-aminoindan, (S)-(+)-1-aminoindan, 2-(aminomethyl)-15-crown- 5,4-(aminomethyl) benzenesulfonamide hydrochloride, (aminomethyl) cyclopropane, 2-pyrenemethylamine hydrochloride, 3-(aminomethyl)pyridine, 4-(aminomethyl)pyridine, 3-aminopropionitrile fumarate, 1-(3-aminopropyl)-2-pyrrolidinone, 1-(3-aminopropyl)imidazole, 3-aminopropyltrimethoxysilane, (R)-(+)-3-aminoquinuclidine dihydrochloride, (S)-(-)-3-aminoquinuclidine dihydrochloride, ammonia (0.5 M in dioxane), benzylamine, S-benzylcysteamine hydrochloride, (R)-(+)-bomylamine, butylamine, cyclobutylamine, cyclohexanemethylamine, cyclohexylamine, cyclopentylamine, cyclopropylamine, (R)-(+)-cycloserine, 3-(diethoxymethylsilyl)propylamine, 3,4-dimethoxyphenethylamine, 4-(dimethylamino) benzylamine dihydrochloride, 3-dimethylaminopropylamine, N,N-dimethylethylenediamine, ethylamine (2.0 M in THF), 1-ethylpropylamine, 2-fluoroethylamine hydrochloride, 4-fluorophenethylamine, furfurylamine, geranylamine, 3-fluorobenzylamine, (1R,2R,3R,5S)-(-)-isopinocampheylamine, (1S,2S,3S,5R)-(+)-isopinocampheylamine, isopropylamine, 2-methoxybenzylamine, 4-methoxybenzylamine, 2-methoxyethylamine, 2-methoxyphenethylamine, 3-methoxyphenethylamine, 4-methoxyphenethylamine, 3-methoxypropylamine, methylamine (2.0M in THF), (-)-cis-myrtanylamine, 1-napthylenemethylamine, 3-nitrobenzylamine hydrochloride, 4-nitrophenethylamine hydrochloride, octylamine, phenethylamine, trans-2phenylcyclopropylamine hydrochloride, 2-phenylglycinonitrile hydrochloride, piperonylamine, propargyl amine, (R)-(-)-tetrahydrofurfurylamine, (S)-(+)-tetrahydrofurfurylamine, N,N,2,2-tetramethyl-1,3-propanediamine, 2-thiopheneethylamine, 2,2,2-trifluoroethylamine, tryptamine, veratrylamine, 2-(2-aminoethyl)pyridine, 3-(aminomethyl)pyridine, (R)-(-)-sec-butylamine, (S)-(+)-sec-butylamine, (R)-(-)-1-cyclohexylethylamine, (S)-(+)-1-cyclohexylethylamine, isoamylamine, (R)-(+)-a-methylbenzylamine, (S)-(-)-1-(1-napthyl)ethylamine, 4-(trifluoromethyoxy)benzylamine, and 3-(trifluoromethyl)benzylamine; and reacting the hydroxyl generated upon opening of the lactone with one or more acids selected from the group consisting of acetic acid, 4-acetoxybenzoic acid, acetylsalicyclic acid, acrylic acid, m-anisic acid, o-anisic acid, p-anisic acid, benzoic acid, 2-butynoic acid, ( 3-carboxypropyl)trimethylammonium chloride, 3-chloropropionic acid, crotonic acid, cyanoacetic acid, 3-cyanobenzoic acid, 4-cyanobenzoic acid, cyclohexanecarboxylic acid, cyclopentanecarboxylic acid, cyclopentylacetic acid, cyclopropanecarboxylic acid, 3,4-dihydro-2,2-dimethyl-4-oxy-2H-pyran-6-carboxylic acid, 1,4-dihydro-2-methylbenzoic acid, 3-dimethylaminobenzoic acid, 4-dimethylaminobenzoic acid, N,N-dimethylglycine, ferroceneacetic acid, formic acid, trans-3-furanacrylic acid, 2-furoic acid, 3-furoic acid, furylacrylic acid, 2,4-hexadienoic acid (Sorbic acid), isobutyric acid, isonicotinic acid, isovaleric acid, levulinic acid, linolenic acid, (+)-merithoxyacetic acid, (-)-menthoxyacetic acid, methacrylic acid, methoxyacetic acid, (R)-(-)-amethoxyphenylacetic acid, (S)-(+)-a-methoxyphenylacetic acid, 2-methoxyphenylacetic acid, 3-methoxyphenylacetic acid, 4-methoxyphenylacetic acid, 1-methyl(1S,2R)-(+)-cis-1,2,3,6-tetrahydrophthalate, mono-methyl glutarate, mono-methyl phthalate, mono-methyl terephthalate, [1R-(1-α,2b,3a)]-(+)-3-methyl-2-(nitromethyl)-5-oxocyclopentaneacetic acid, 4-(3-methyl-5-oxo-2-pyrazolin-1-yl)benzoic acid, 6-methylchromone-2-carboxylic acid, 3,4-(methylenedioxy)phenylacetic acid, 1-methylindole-2-carboxylic acid, nicotinic acid, 5-nitro-2-furoic acid, 4-nitrobenzoic acid, 4-nitrophenylacetic acid, 3-nitropropionic acid, 2-norbomaneacetic acid, orotic acid monohydrate, (S)-(+)-2-oxo-4-phenyl-3-oxazolidineacetic acid, anti-3-oxotricyclo[2.2.1.0(2,6)]heptane-7-carboxylic acid, phenylacetic acid, phenylpropiolic acid, phthalylsulfathiazole, picolinic acid, propionic acid, 2-pyrazinecarboxylic acid, 2-pyridylacetic acid hydrochloride, 3-pyridylacetic acid hydrochloride, 4-pyridylacetic acid hydrochloride, (2-pyrimidylthio) acetic acid, pyruvic acid, tetrahydro-2-furoic acid, tetrahydro-3-furoic acid, thioctic acid, 2-thiopheneacetic acid, 3-thiopheneacetic acid, 2-thiophenecarboxylic acid, 3-thiophenecarboxylic acid, 2-thiopheneglyoxylic acid, ($\alpha,\alpha,\alpha$-trifluoro-p-tolyl)acetic acid, vinylacetic acid, acetoxyacetic acid, 2-benzofurancarboxylic acid, cinnoline-4-carboxylic acid, 3,5-diido-4-pyridone-1-acetic acid, 3,3-dimethylacrylic acid, ferrocenecarboxylic acid, 5-methoxy-1-indanone-3-acetic acid, 1-methyl-2-pyrrolecarboxylic acid, 3-oxo-1-indancarboxylic acid, trans-3-(3-pyridyl)acrylic acid, 3-(2-thienyl)acrylic acid, $\alpha,\alpha,\alpha$-trifluoro-m-toluic acid, $\alpha,\alpha,\alpha$-trifluoro-o-toluic acid, and $\alpha,\alpha,\alpha$-trifluoro-p-toluic acid.

6. The library of claim 3, wherein the library has at least 450 library members.

7. The library of claim 3, wherein the library has at least 1 million library members.

8. A kit for determining biological activity of one or more library members comprising:

a binding reagent; and a library of one or more compounds, wherein said library of one or more compounds is the library of claim 1 or claim 3.

\* \* \* \* \*